United States Patent
King et al.

(10) Patent No.: US 9,499,632 B2
(45) Date of Patent: Nov. 22, 2016

(54) HUMAN ANTIBODIES THAT BIND CD22 AND USES THEREOF

(71) Applicant: E. R. SQUIBB & SONS, L. L. C., Princeton, NJ (US)

(72) Inventors: David John King, Solana Beach, CA (US); Alison Witte, Rogue River, OR (US); Heidi N. Leblanc, Mountain View, CA (US); Richard Theolis, Santa Cruz, CA (US); Asna Masood, Saratoga, CA (US); Mark Yamanaka, Pleasanton, CA (US); Kyra D. Zens, San Mateo, CA (US); Sarah R. Reed, Santa Cruz, CA (US); Tim Sproul, Livermore, CA (US); Chetana Rao-Naik, Walnut Creek, CA (US); David Passmore, Mountain View, CA (US); Dawn M. Tanamachi, San Carlos, CA (US); Kristopher Toy, San Jose, CA (US)

(73) Assignee: E.R. Squibb & Sons, L.L.C., Princeton, NJ (US)

( * ) Notice: Subject to any disclaimer, the term of this patent is extended or adjusted under 35 U.S.C. 154(b) by 609 days.

(21) Appl. No.: 13/772,063

(22) Filed: Feb. 20, 2013

(65) Prior Publication Data

US 2013/0230530 A1 Sep. 5, 2013

Related U.S. Application Data

(62) Division of application No. 12/517,183, filed as application No. PCT/US2007/086152 on Nov. 30, 2007, now Pat. No. 8,481,683.

(60) Provisional application No. 60/868,231, filed on Dec. 1, 2006.

(51) Int. Cl.

| | |
|---|---|
| *A61K 39/40* | (2006.01) |
| *A61K 39/42* | (2006.01) |
| *A61K 39/395* | (2006.01) |
| *C07K 16/30* | (2006.01) |
| *A61K 47/48* | (2006.01) |
| *A61K 51/10* | (2006.01) |
| *C07K 16/28* | (2006.01) |
| *A61K 45/06* | (2006.01) |
| *C07K 16/00* | (2006.01) |
| *A61K 39/00* | (2006.01) |

(52) U.S. Cl.
CPC ..... *C07K 16/3061* (2013.01); *A61K 39/39558* (2013.01); *A61K 45/06* (2013.01); *A61K 47/48561* (2013.01); *A61K 51/1027* (2013.01); *C07K 16/2803* (2013.01); *A61K 2039/505* (2013.01); *C07K 2317/21* (2013.01); *C07K 2317/41* (2013.01); *C07K 2317/565* (2013.01); *C07K 2317/70* (2013.01); *C07K 2317/732* (2013.01); *C07K 2317/734* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,484,892 | A | 1/1996 | Tedder et al. |
| 5,545,806 | A | 8/1996 | Lonberg et al. |
| 6,699,473 | B2 | 3/2004 | Raisch et al. |
| 7,641,901 | B2 | 1/2010 | Goldenberg et al. |
| 7,829,086 | B2 | 11/2010 | Hilbert et al. |
| 2003/0039649 | A1 | 2/2003 | Foote |
| 2003/0175884 | A1 | 9/2003 | Umana et al. |
| 2004/0120948 | A1 | 6/2004 | Mikayama et al. |
| 2005/0118182 | A1 | 6/2005 | Pastan et al. |
| 2006/0269543 | A1 | 11/2006 | Chu |
| 2010/0143368 | A1 | 6/2010 | King et al. |

FOREIGN PATENT DOCUMENTS

| | | |
|---|---|---|
| WO | WO 96/04925 | 2/1996 |
| WO | WO 98/42378 | 10/1998 |
| WO | WO 00/67795 | 11/2000 |
| WO | WO 00/74718 | 12/2000 |
| WO | WO 01/97858 | 12/2001 |
| WO | WO 03/027135 | 4/2003 |
| WO | WO 03/072736 | 9/2003 |
| WO | WO 03/074567 | 9/2003 |
| WO | WO 03/092623 | 11/2003 |
| WO | WO 03/093320 | 11/2003 |
| WO | WO 03/105782 | 12/2003 |
| WO | WO 2004/110390 | 12/2004 |
| WO | WO 2005/052006 | 6/2005 |

(Continued)

OTHER PUBLICATIONS

Walker et al. Immunology 2007, 123:314-325.*

(Continued)

*Primary Examiner* — Chun Dahle
(74) *Attorney, Agent, or Firm* — Ashton J. Delauney; Z. Angela Guo

(57) ABSTRACT

The present disclosure provides isolated monoclonal antibodies that specifically bind to CD22 with high affinity, particularly human monoclonal antibodies. Nucleic acid molecules encoding the antibodies of this disclosure, expression vectors, host cells and methods for expressing the antibodies of this disclosure are also provided. Antibody-partner molecule conjugates, bispecific molecules and pharmaceutical compositions comprising the antibodies of this disclosure are also provided. This disclosure also provides methods for detecting CD22, as well as methods for treating various cancers and inflammatory and autoimmune disorders using an anti-CD22 antibody of this disclosure.

42 Claims, 44 Drawing Sheets

(56) References Cited

FOREIGN PATENT DOCUMENTS

| WO | WO 2007/103470 | 9/2007 |
|---|---|---|
| WO | WO 2007/140371 | 12/2007 |

OTHER PUBLICATIONS

Yang et al. Blood 107;9:3639-3646.*
Hirano et al. Cancer Research 2005, 65;3:1090-1096.*
Reuben et al. Cancer 2006, 106;11:2437-2444.*
Bofill, M. et al., Human B Cell Development—II. Subpopulations in the Human Fetus, The Journal of Immunology, vol. 134, No. 3, pp. 1531-1538 (1985).
Campana, D. et al., "Human B Cell Development—I. Phenotypic Differences of B Lymphocytes in the Bone Marrow and Peripheral Lymphoid Tissue", The Journal of Immunology, vol. 134, No. 3, pp. 1524-1530 (1985).
Cesano, A. et al., "CD22 as a Target of Passive Immunotherapy", Seminars in Oncology, vol. 30, No. 2, pp. 253-257 (2003).
Coleman, M. et al., "Epratuzumab—Targeting B-Cell Malignancies through CD22l", Clinical Cancer Research, 9:3991S-3994S, pp. 1-5 (2003).
Pezzutto, A. et al., "Amplification of Human B Cell Activation by a Monoclonal Antibody to the B Cell-Specific Antigen CD22, Bp 130/140", The Journal of Immunology, vol. 138, No. 1, pp. 98-103 (1987).
Steinfeld, S.D. et al., "Epratuzumab (humanised anti-CD22 antibody) in autoimmune diseases", Expert Opin. Biol. Ther., vol. 6, No. 9, pp. 943-949 (2006).
Wilson, G.L. et al., "cDNA Cloning of the B Cell Membrane Protein CD22: A Mediator of B-B Cell Interactions", The Journal of Experimental Medicine, vol. 173, pp. 137-146 (1991).
DiJoseph et al., "Antibody-targeted Chemotherapy with CMC-544; a CD22-targeted Immunoconjugate of Calicheamicin for the Treatment of B-Lymphoid Malignancies," Blood, Mar. 2004, 103(5), pp. 1807-1814.
Carnahan, et al., "Epratuzumab, a CD22 Targeting Recombinant Humanized Antibody With a Different Mode of Action From Rituximab," Molecular Immunology, Jun. 2006, 44, pp. 1331-1341.
Chen, et al., "CD22 Attenuates Calcium Signaling by Potentiating Plasma Membrane Calcium ATPase Activity," Nature Immunology, Jun. 2004, 5(6), pp. 651-657.
Ho, M., et al., "Isolation of anti-CD22 Fv with high affinity by Fv display on human cells" *Proceedings of the National Academy of Sciences of the United State of America*, vol. 103, No. 25, pp. 9637-9642, Jun. 20, 2006.
Ho, M., et al., "Corrections and Retraction: Isolation of anti-CD22 Fv with high affinity by Fv display on human cells" *Proceedings of the National Academy of Sciences of the United State of America*, vol. 104, No. 36, p. 14543, Sep. 4, 2007.
Leonard, J., et al. "Preclinical and clinical evaluation of epratuzumab (anti-CD22 IgG) in B-cell malignancies", ONCO-GENE, vol. 26, No. 25, May 2007, pp. 3704-3713 (ISSN: 0950-9232).
European Office Action issued Apr. 4, 2013.

* cited by examiner

Anti-CD22 12C5 VH

V segment:    7-4.1
    D segment:    3-3
    J segment:    JH6b

```
         Q   V   Q   L   V   Q   S   G   S   E   L   K   K   P   G   A   S   V
     1  CAG GTG CAG CTG GTC CAA TCT GCG TCT GAG TTG AAG AAG CCT GGG GCC TCA GTG
                                                                          CDR1
                                                                  -------------------
         K   V   S   C   K   A   S   G   Y   T   F   T   S   Y   A   M   N   W
    55  AAG GTT TCC TGC AAG GCT TCT GGA TAC ACC TTC ACT AGT TAT GCT ATG AAT TGG
                                                                          CDR2
                                                              -------------------
         V   R   Q   A   P   G   Q   G   L   E   W   M   G   W   I   N   T   N
   109  GTG CGA CAG GCC CCT GGA CAA GGG CTT GAG TGG ATG GGA TGG ATC AAC ACC AAC
                    CDR2
         -----------------------------------------
         T   G   N   P   T   Y   A   Q   G   F   T   G   R   F   V   F   S   L
   163  ACT GGG AAC CCA ACG TAT GCC CAG GGC TTC ACA GGA CGG TTT GTC TTC TCC TTG

D   T   S   V   S   T   A   Y   L   Q   I   S   S   L   K   A   E   D
   217  GAC ACC TCT GTC AGC ACG GCA TAT CTG CAG ATC AGC AGC CTA AAG GCT GAG GAC
                                                                      CDR3
                                                  ---------------------------------
         T   A   V   Y   Y   C   A   R   L   F   Y   Y   Y   F   G   M   D   V
   271  ACT GCC GTG TAT TAC TGT GCT AGG TTA TTC TAC TAC TAC TTC GGT ATG GAC GTC

W   G   Q   G   T   T   V   T   V   S   S
   325  TGG GGC CAA GGG ACC ACG GTC ACC GTC TCC TCA
```

FIGURE 1A

Anti-CD22 12C5 Vλ

V segment:    3b2
    J segment:    JL2

```
         Q   S   A   L   T   Q   P   A   S   V   S   G   S   P   G   Q   S   I
    1  CAG TCT GCC CTG ACT CAG CCT GCC TCC GTG TCT GGG TCT CCT GGA CAG TCG ATC
                                                          CDR1
                                        ----------------------------------------
         T   I   S   C   T   G   T   S   S   D   V   G   S   Y   N   L   V   S
   55  ACC ATC TCC TGC ACT GGA ACC AGT AGT GAT GTT GGG AGT TAT AAC CTT GTC TCC
                                                                          CDR2
                                                                        --------
         W   Y   Q   L   H   P   G   K   A   P   K   L   M   I   Y   E   V   S
  109  TGG TAC CAA CTC CAC CCA GGC AAA GCC CCC AAA CTC ATG ATT TAT GAG GTC AGT
            CDR2
        --------
         K   R   P   S   G   V   S   N   R   F   S   G   S   K   S   G   N   T
  163  AAG CGG CCC TCA GGG GTT TCT AAT CGC TTC TCT GGC TCC AAG TCT GGC AAC ACG
         A   S   L   T   I   S   G   L   Q   A   E   D   E   A   D   Y   Y   C
  217  GCC TCC CTG ACA ATC TCT GGG CTC CAG GCT GAG GAC GAG GCT GAT TAT TAC TGC
                        CDR3
                    ------------------------------------
         C   S   Y   A   N   S   S   T   L   V   F   G   G   G   T   K   L   T
  271  TGC TCA TAT GCA AAT AGT AGC ACT TTG GTA TTC GGC GGA GGG ACC AAG CTG ACC
         V   L
  325  GTC CTA
```

FIGURE 1B

Anti-CD22 19A3 VH
Anti-CD22 CD22.1 VH

V segment:    4-34
    D segment:    3-9
    J segment:    JH4b

Q   V   Q   L   Q   Q   W   G   A   G   L   L   K   P   S   E   T   L
      1  CAG GTG CAG CTA CAG CAG TGG GGC GCA GGA CTG TTG AAG CCT TCG GAG ACC CTG

CDR1
                                                   ------------------------------
         S   L   T   C   A   V   Y   G   R   S   F   S   S   Y   Y   W   S   W
     55  TCC CTC ACC TGC GCT GTC TAT GGT AGG TCC TTC AGT AGT TAC TAC TGG AGC TGG

CDR2
                                                           -------------------------
         I   R   Q   P   P   G   K   G   L   E   W   I   G   D   I   N   H   S
    109  ATC CGC CAG CCC CCA GGG AAG GGG CTG GAG TGG ATT GGG GAC ATC AAT CAT AGT

CDR2
         ---------------------------------------
         G   S   T   N   Y   N   P   S   L   K   S   R   V   T   I   S   V   D
    163  GGA AGC ACC AAC TAC AAC CCG TCC CTC AAG AGT CGA GTC ACC ATA TCA GTA GAC

T   S   K   N   Q   F   S   L   K   L   S   S   V   T   A   A   D   T
    217  ACG TCC AAG AAC CAG TTC TCC CTG AAG CTG AGC TCT GTG ACC GCC GCA GAC ACG

CDR3
                                    -----------------------------------------
         A   V   Y   Y   C   A   G   T   F   Y   D   I   L   T   G   Y   Y   P
    271  GCT GTG TAT TAC TGT GCG GGA ACG TTT TAC GAT ATT TTG ACT GGT TAT TAT CCC

CDR3
         ------------
         L   G   Y   W   G   P   G   T   L   V   T   V   S   S
    325  CTT GGG TAC TGG GGC CCG GGA ACC CTG GTC ACC GTC TCC TCA

FIGURE 2A

Anti- CD22 19A3 VK
Anti- CD22 CD22.1 VK
Anti- CD22 CD22.2 VK

V segment:    L6
   J segment:    JK1

E   I   V   L   T   Q   S   P   A   T   L   S   L   S   P   G   E   R
     1  GAA ATT GTG TTG ACA CAG TCT CCA GCC ACC CTG TCT TTG TCT CCA GGG GAA AGA

CDR1
                                ------------------------------------------------
          A   T   L   S   C   R   A   S   Q   S   V   S   S   Y   L   A   W   Y
     55 GCC ACC CTC TCC TGC AGG GCC AGT CAG AGT GTT AGC AGC TAC TTA GCC TGG TAC

CDR2
                                                                     ----------
          Q   Q   K   P   G   Q   A   P   R   L   L   I   Y   D   A   S   N   R
    109 CAA CAG AAA CCT GGC CAG GCT CCC AGG CTC CTC ATC TAT GAT GCA TCC AAC AGG

CDR2
        ----
          A   T   G   I   P   A   R   F   S   G   S   G   S   G   T   D   F   T
    163 GCC ACT GGC ATC CCA GCC AGG TTC AGT GGC AGT GGG TCT GGG ACA GAC TTC ACT

CDR3
                                                                     ----------
          L   T   I   S   S   L   E   P   E   D   F   A   V   Y   Y   C   Q   Q
    217 CTC ACC ATC AGC AGC CTA GAG CCT GAA GAT TTT GCA GTT TAT TAC TGT CAG CAG

CDR3
        ----------
          R   S   N   W   P   T   F   G   Q   G   T   K   V   E   I   K
    271 CGT AGC AAC TGG CCT ACG TTC GGC CAA GGG ACC AAG GTG GAA ATC AAA

FIGURE 2B

Anti-CD22 CD22.2 VH

V segment:    4-34
    D segment:    3-9
    J segment:    JH4b

```
       Q   V   Q   L   Q   Q   W   G   A   G   L   L   K   P   S   E   T   L
  1   CAG GTG CAG CTA CAG CAG TGG GGC GCA GGA CTG TTG AAG CCT TCG GAG ACC CTG
                                                                        CDR1
                                                                        ----------------------
       S   L   T   C   A   V   Y   G   S   S   F   S   S   Y   Y   W   S   W
 55   TCC CTC ACC TGC GCT GTC TAT GGT AGC TCC TTC AGT AGT TAC TAC TGG AGC TGG
                                                                        CDR2
                                                                        ----------------------
       I   R   Q   P   P   G   K   G   L   E   W   I   G   D   I   Q   H   S
109   ATC CGC CAG CCC CCA GGG AAG GGG CTG GAG TGG ATT GGG GAC ATC CAA CAT AGT
      CDR2
      ----------------------------------------------
       G   S   T   N   Y   N   P   S   L   K   S   R   V   T   I   S   V   D
163   GGA AGC ACC AAC TAC AAC CCG TCC CTC AAG AGT CGA GTC ACC ATA TCA GTA GAC

T   S   K   N   Q   F   S   L   K   L   S   S   V   T   A   A   D   T
217   ACG TCC AAG AAC CAG TTC TCC CTG AAG CTG AGC TCT GTG ACC GCC GCG GAC ACG
                                                       CDR3
                                                       ----------------------
       A   V   Y   Y   C   A   G   T   F   Y   D   I   L   T   G   Y   Y   P
271   GCT GTG TAT TAC TGT GCG GGA ACG TTT TAC GAT ATT TTG ACT GGT TAT TAT CCC
      CDR3
      ----------
       L   G   Y   W   G   P   G   T   L   V   T   V   S   S
325   CTT GGG TAC TGG GGC CCG GGA ACC CTG GTC ACC GTC TCC TCA
```

FIGURE 2C

Anti-CD22 16F7 VH

V segment:    5-51
    D segment:    3-10
    J segment:    JH3b

E   V   Q   L   V   Q   S   G   A   E   V   K   P   G   E   S   L
      1  GAG GTC CAG CTG GTG CAG TCT GGA GCA GAG GTG AAA AAG CCC GGG GAG TCT CTG

CDR1
                                                      ------------------------------
         K   I   S   C   K   G   S   G   Y   N   F   T   S   Y   W   I   G   W
     55  AAG ATC TCC TGT AAG GGT TCT GGA TAC AAC TTT ACC AGC TAC TGG ATC GGC TGG

CDR2
                                                      ------------------------------
         V   R   Q   M   P   G   K   G   L   E   W   M   G   I   I   Y   P   G
    109  GTG CGC CAG ATG CCC GGG AAA GGC CTG GAG TGG ATG GGG ATC ATC TAT CCT GGT

CDR2
         -----------------------------------
         D   S   D   T   R   Y   S   P   S   F   Q   G   Q   V   T   I   S   A
    163  GAC TCT GAT ACC AGA TAC AGC CCG TCC TTC CAA GGC CAG GTC ACC ATC TCA GCC

D   K   S   I   S   T   A   Y   L   Q   W   S   S   L   K   A   S   D
    217  GAC AAG TCC ATC AGC ACC GCC TAC CTG CAG TGG AGC AGC CTG AAG GCC TCG GAC

CDR3
                                              -------------------------------------
         T   A   M   Y   Y   C   A   T   P   T   Y   Y   F   G   S   V   A   F
    271  ACC GCC ATG TAT TAC TGT GCG ACC CCG ACC TAT TAC TTT GGT TCC GTG GCT TTT

CDR3
         -----------
         D   I   W   G   Q   G   T   M   V   T   V   S   S
    325  GAT ATT TGG GGC CAA GGG ACA ATG GTC ACC GTC TCT TCA

FIGURE 3A

Anti-CD22 16F7 VK1

V segment: A27
J segment: JK1

```
          E   I   V   L   T   Q   S   P   G   T   L   S   L   S   P   G   E   R
      1 GAA ATT GTG TTG ACG CAG TCT CCA GGC ACC CTG TCT TTG TCT CCA GGG GAA AGA
                                              CDR1
                                    ------------------------------------------
          A   T   L   S   C   R   A   S   Q   S   V   S   S   Y   L   A   W
     55 GCC ACC CTC TCC TGC AGG GCC AGT CAG AGT GTT AGC AGC TAC TTA GCC TGG
                                                                        CDR2
                                                                  ------------
          Y   Q   Q   K   P   G   Q   A   P   R   L   L   I   Y   G   A   S
    109 TAC CAG CAG AAA CCT GGC CAG GCT CCC AGG CTC CTC ATC TAT GGT GCA TCC

CDR2
    -------
          P   A   T   G   I   P   D   R   F   S   G   S   G   S   G   T   D   F
    163 AGC GCC ACT GGC ATC CCA GAC AGG TTC AGT GGC AGT GGG TCT GGG ACA GAC TTC

CDR3
    -------
          T   L   T   I   S   R   L   E   P   E   D   F   A   V   Y   Y   C   Q
    217 ACT CTC ACC ATC AGC AGA CTG GAG CCT GAA GAT TTT GCA GTG TAT TAC TGT CAG
                   CDR3
          ------------------------------------------
          Q   Y   G   S   S   P   P   T   F   G   Q   G   T   K   V   E   I   K
    271 CAG TAT GGT AGC TCA CCT CCG ACG TTC GGC CAA GGG ACC AAG GTG GAA ATC AAA
```

FIGURE 3B

Anti-CD22 16F7 VK2

V segment:     A10
   J segment:     JK2

```
          E   I   V   L   T   Q   S   P   D   F   Q   S   V   T   P   E   E   K
     1  GAA ATT GTG CTG ACT CAG TCT CCA GAC TTT CAG TCT GTG ACT CCA AAG GAG AAA

CDR1
                                ------------------------------------------------
          V   T   I   T   C   R   A   S   Q   S   I   G   S   S   L   H   W   Y
     55 GTC ACC ATC ACC TGC CGG GCC AGT CAG AGC ATT GGT AGT AGC TTA CAC TGG TAC

CDR2
                                                                   --------------
          Q   Q   K   P   D   Q   S   P   K   L   L   I   K   Y   A   S   Q   S
    109 CAG CAG AAA CCA GAT CAG TCT CCA AAG CTC CTC ATC AAG TAT GCT TCC CAG TCC

CDR2
        ---------
          F   S   G   V   P   S   R   F   S   G   S   G   S   G   T   D   F   T
    163 TTC TCA GGG GTC CCC TCG AGG TTC AGT GGC AGT GGA TCT GGG ACA GAT TTC ACT

CDR3
                                                                        --------
          L   T   I   N   S   L   E   A   E   D   A   A   A   Y   Y   C   H   Q
    217 CTC ACC ATC AAT AGC CTG GAA GCT GAA GAT GCT GCA GCG TAT TAC TGT CAT CAG

CDR3
        -----------------
          S   S   S   L   P   Y   T   F   G   Q   G   T   K   L   E   I   K
    271 AGT AGT AGT TTA CCG TAC ACT TTT GGC CAG GGG ACC AAG CTG GAG ATC AAA
```

FIGURE 3C

Anti-CD22 23C6 VH

V segment:    1-69
    D segment:    2-15
    J segment:    JH6b

```
       Q   V   Q   L   V   Q   S   G   A   E   V   K   K   T   G   S   S   V
    1  CAG GTC CAG CTG GTG CAG TCT GGG GCT GAG GTG AAA AAG ACT GGG TCC TCG GTG

CDR 1
                                                           --------------------
       K   V   S   C   K   A   S   G   G   T   F   S   S   Y   G   I   N   W
   55  AAG GTC TCC TGC AAG GCT TCT GGA GCC ACC TTC AGC AGC TAT GGT ATC AAC TGG

CDR 2
                                                                 --------------
       V   R   Q   A   P   G   Q   G   L   E   W   M   G   E   I   I   P   I
  109  GTG CGA CAG GCC CCT GGA CAA GGG CTT GAA TGG ATG GGA GAG ATC ATC CCT ATC

CDR 2
       --------------------------------------------
       F   G   T   A   N   Y   A   Q   K   F   Q   G   R   V   T   I   T   A
  163  TTT GGT ACA GCA AAC TAC GCA CAG AAG TTC CAG GGC AGA GTC ACG ATT ACC GCG

D   E   S   T   S   T   V   Y   M   E   L   S   S   L   R   S   E   D
  217  GAC GAA TCC ACG AGC ACA GTC TAC ATG GAG CTG AGC AGC CTG AGA TCT GAG GAC

CDR 3
                                                      -----------------------
       T   A   V   Y   Y   C   A   R   D   Q   G   V   V   V   V   A   A   T
  271  ACG GCC GTG TAT TAC TGT GCG AGA GAT CAG GGT GTA GTG GTG GTA GCT GCA ACC

CDR 3
       ------------------------------------
       H   Y   Y   Y   Y   G   M   D   V   W   G   Q   G   T   T   V   T   V
  325  CAC TAC TAC TAC TAC GGT ATG GAC GTC TGG GGC CAA GGG ACC ACG GTC ACC GTC

S   S
  379  TCC TCA
```

FIGURE 4A

Anti-CD22 23C6 VK1

V segment:     L6
J segment:     JK1

```
            E   I   V   L   T   Q   S   P   A   T   L   S   L   S   P   G   E   R
  1   GAA ATT GTG TTG ACA CAG TCT CCA GCC ACC CTG TCT TTG TCT CCA GGG GAA AGA

CDR 1
                                     -------------------------------------------
            A   T   L   S   C   R   A   S   Q   S   V   S   S   Y   L   A   W   Y
 55   GCC ACC CTC TCC TGC AGG GCC AGT CAG AGT GTT AGC AGT TAC TTA GCC TGG TAC

CDR 2
                                                                    ---------------
            Q   Q   K   P   G   Q   A   P   R   L   L   I   Y   D   A   S   N   R
109   CAA CAG AAA CCT GGC CAG GCT CCT AGG CTC CTC ATC TAT GAT GCA TCC AAC AGG

CDR 2
     -----------
            A   T   G   I   P   A   R   F   S   G   S   G   S   G   T   D   F   T
163   GCC ACT GGC ATC CCA GCC AGG TTC AGT GGC AGT GGG TCT GGG ACA GAC TTC ACT

CDR 3
                                                                    ---------
            L   T   I   S   S   L   E   P   E   D   F   A   V   Y   Y   C   Q   Q
217   CTC ACC ATC AGC AGC CTA GAG CCT GAA GAT TTT GCA GTT TAT TAC TGT CAG CAG

CDR 3
     ----------------------------
            R   S   N   W   P   W   T   F   G   Q   G   T   K   V   E   I   K
271   CGT AGC AAC TGG CCG TGG ACG TTC GGC CAA GGG ACC AAG GTG GAA ATC AAA
```

FIGURE 4B

Anti-CD22 23C6 VK3

V segment:    L6
J segment:    JK1

```
      E   I   V   L   T   Q   S   P   A   T   L   S   L   S   P   G   E   R
  1  GAA ATT GTG TTG ACA CAG TCT CCA GCC ACC CTG TCT TTG TCT CCA GGG GAA AGA
                                          CDR 1
                                          ----------------------------------
      A   T   L   S   C   R   A   S   Q   S   V   S   N   F   L   A   W   Y
  55 GCC ACC CTC TCC TGC AGG GCC AGT CAG AGT GTT AGC AAC TTC TTA GCC TGG TAC
                                                                 CDR 2
                                                                 -----------
      Q   Q   K   P   G   Q   A   P   R   L   L   I   Y   D   A   S   N   R
 109 CAA CAG AAA CCT GGC CAG GCT CCC AGG CTC CTC ATC TAT GAT GCA TCC AAC AGG
      CDR 2
      ---------
      A   T   G   I   P   A   R   F   S   G   S   G   S   G   T   D   F   T
 163 GCC ACT GGC ATC CCA GCC AGG TTC AGT GGC AGT GGG TCT GGG ACA GAC TTC ACT
                                                                 CDR 3
                                                                 -----------
      L   T   I   S   S   L   E   P   E   D   F   A   V   Y   Y   C   Q   Q
 217 CTC ACC ATC AGC AGC CTA GAG CCT GAA GAT TTT GCA GTT TAT TAC TGT CAG CAG
          CDR 3
      ------------------------
      R   S   N   W   P   P   T   F   G   Q   G   T   K   V   E   I   K
 271 CGT AGC AAC TGG CCT CCG ACG TTC GGC CAA GGG ACC AAG GTG GAA ATC AAA
```

FIGURE 4C

```
Anti-CD22 12C5 VH 7-4.1 germline        QVQLVQSGSELKKPGASVKVSCKASGYTFTSYAMNWVK
12C5 VH               Q...................................

7-4.1 germline        QAPGQGLEWMGWINTMTGNPTYAQGFTGRFVFSLDTS
12C5 VH                                    CDR2
                      Q...................................

7-4.1 germline        STAYLQISSLKAEDTAVYYCAR
JH6b germline                                       YYYYGMDVWGQGTT
12C5 VH               .....................         CDR3
                                                    LF.YYYYGMDVWGQGTT JH6b germline         VTVSS
12C5 VH               .....
```

```
                                                          CDR1
Anti-CD22 19A3 VH      Q V Q L Q Q W G A G L L K P S E T L S L T C A V Y G G S P S G Y Y W S W
Anti-CD22.1 VH         - - - - - - - - - - - - - - - - - - - - - - - - - - R - - S - - - - -

4-34 germline          Q V Q L Q Q W G A G L L K P S E T L S L T C A V Y G G S F S G Y Y W S W
19A3 VH                - - - - - - - - - - - - - - - - - - - - - - - - - - - - P - - - - - -

CDR2
4-34 germline          I R Q P P G K G L E W I G E I N H S G S T N Y N P S L K S R V T I S V D
19A3 VH                - - - - - - - - - - - - - - - Q - - - - - - - - - - - - - - - - - - -

4-34 germline          T S K N Q F S L K L S S V T A A D T A V Y Y C A R
19A3 VH                - - - - - - - - - - - - - - - - - - - - - - - - -
                                                               CDR3
JH4b germline                                            G T F Y D I L T G Y Y P
19A3 VH                                                  - - - - - - - - - - - -

JH4b germline          L D Y W G Q G T L V T V S S
19A3 VH                - - - - - - - - - - - - - -
```

FIGURE 6A

```
Anti- CD22 19A3 VK
Anti- CD22 CD22.1 VK
Anti- CD22 CD22.2 VK

CDR1
L6 germline      EIVLTQSPATLSLSPGERATLSCRASQSVSS ,
19A3 VK          ,                              , CDR2
L6 germline      YLAWYQQKPGQAPRLLIYDASNRATGIPARF ,
19A3 VK          ,                              , CDR3
L6 germline      SGSGSGTDFTLTISSLEPEDFAVYYCQQRSN ,
19A3 VK          ,                              , L6 germline      WP                             ,
JK1 germline        TFGQGTKVEIK                 ,
19A3 VK          ,                              ,
```

FIGURE 6B

```
Anti-CD22 19A3 N57Q VH (CD22.2)

V segment:    4-34
D segment:    3-9
J segment:    JH4b 4-34 germline    Q V Q L Q Q W G A G L L K P S E T L
CD22.2 VH        - - - - - - - - - - - - - - - - -

CDR1
4-34 germline    S L T C A V Y G G S F S G Y Y W S W
CD22.2 VH        - - - - - - - - R - - - S - - - - -

CDR2
4-34 germline    I R Q P P G K G L E W I G E I N H S
CD22.2 VH        - - - - - - - - - - - - - D - Q - -

___CDR2_____
4-34 germline    G S T N Y N P S L K S R V T I S V D
CD22.2 VH        - - - - - - - - - - - - - - - - - -

4-34 germline    T S K N Q F S L K L S S V T A A D T
CD22.2 VH        - - - - - - - - - - - - - - - - - -

___CDR3_____
4-34 germline    A V Y Y C A R
CD22.2 VH        - - - - - - - G T F Y D I L T G Y Y P JH4b germline    D Y W G Q G T L V T V S S
CD22.2 VH        L G - - P - - - - - - -
```

FIGURE 6C

Anti-CD22 16F7 VH 5-51 germline          EVQLVQSGAEVKKPGESLKISCKGSGYSFT
16F7 VH                                                 :
                              CDR1
5-51 germline          SYWIG WVRQMPGKGLEWMG IIYPGDSDTRY
16F7 VH                    :                    CDR2   :

5-51 germline          SPSFQGQVTISADKSISTAYLQWSSLKASD
16F7 VH                                                :
                                    CDR3
5-51 germline          TAMYYCAR               APDIWGQGTMVTVSS
JH3b germline
16F7 VH                         TPTVVFGSV

FIGURE 7A

```
Anti-CD22 16F7 VK1

CDR1
A27 germline        ETVLTQSPGTLSLSPGERATLSCRASQSVSSSYLAWYQ
16F7 VK1            : : : : : : : : : : : : : : : : : : : : : : : : : : : : : : : : : : : : : :

CDR2
A27 germline        QKPGQAPRLLIYGASSRATGIPDRFSGSGSGTDFTLTI
16F7 VK1            : : : : : : : : : : : : : : : : : : : : : : : : : : : : : : : : : : : : : :

CDR3
A27 germline        SRLEPEDFAVYYCQQYGSSPP         TFGQGTKVEIS
JK1 germline                                     TFGQGTKVEIS
16F7 VK1            : : : : : : : : : : : : : : : : : : : : : : : : : : : : :
```

FIGURE 7B

```
Anti-CD22 16F7 VK2

CDR1
A10 germline      D I V L T Q S P D F Q S V T P K E K V T I T C R A S Q S I G S :
16F7 VK2          . . . . . . . . . . . . . . . . . . . . . . . . . . . . . . . :

CDR2
A10 germline      S L H W Y Q Q K P D Q S P K L L I K Y A S Q S F S G V P S R :
16F7 VK2          . . . . . . . . . . . . . . . . . . . . . . . . . . . . . . :

CDR3
A10 germline      S G S G S G T D F T L T I N S L E A E D A A T Y Y C H Q S S :
16F7 VK2          . . . . . . . . . . . . . . . . . . . . . . . . . . . . A . :

A10 germline      L P     Y T F G Q G T K L E I K :
JK2 germline      . .     . . . . . . . . . . . . :
16F7 VK3          . .     . . . . . . . . . . . . :
```

FIGURE 7C

```
Anti-CD22 23C6 VH      QVQLVQSGAEVKKPGSSVKVSCKASGGTFSSYAISW
1-69 germline          ----------------------------------- CDR1
23C6 VH                ----------------------------------T-G-N 1-69 germline          VRQAPGQGLEWMGGIIPIFGTANYAQKFQG RVTITA
23C6 VH                ----------------B--------------

CDR2
1-69 germline          DESTSTAYMELSSLRSEDTAVYYCAR
2-15 germline VH       -------------------A------
23C6 VH CDR3                         CDR3
                       YYYGMDVWGQGTTVTVSS           DIVVVAAT
JH6b germline          -----------------                 
23C6 VH                H----------------            DQG-----T
```

FIGURE 8A

Anti-CD22 23C6 VKl/VK2

```
                      CDR1
                      _____
L6 germline    EIVLTQSPATLSLSPGERATLSCRASQSVSS..N
23C6 VK1       . . . . . . . . . . . . . . . . . . . . . . . . . . . . . . .
23C6 VK2       . . . . . . . . . . . . . . . . . . . . . . . . . . . . . . .

CDR2
                              _____
L6 germline    YLAWYQQKPGQAPRLLIYDASNRATGIPARF
23C6 VK1       . . . . . . . . . . . . . . . . . . . . . . . . . . . . . . .
23C6 VK2       R . . . . . . . . . . . . . . . . . . . . . . . . . . . . . .

CDR3
                                         _____
L6 germline    SGSGSGTDFTLTISSLEPEDFAVYYCQQYGSSN
23C6 VK1       . . . . . . . . . . . . . . . . . . . . . . . . . . . . . . . . .
23C6 VK2       . . . . . . . . . . . . . . . . . . . . . . . . . . . . . . . . .

L6 germline    WP.TFGQGTKVEIK
JK1 germline   . . . . . . . . . . . . . .
23C6 VK1       . . . . . . . . . . . . . .
23C6 VK2       . . B . . . . . . . . . . .
```

FIGURE 8B

Anti-CD22 4G6 VH

V segment:    1-69
    D segment:    7-27
    J segment:    JH4b

```
      Q   V   Q   L   V   Q   S   G   A   E   V   K   K   P   G   S   S   V
   1  CAG GTC CAG TTG GTG CAG TCT GGG GCT GAG GTG AAG AAG CCT GGG TCC TCG GTG
                                                              CDR1
                                                         ------------------------
      K   V   S   C   K   P   S   G   D   T   F   S   N   Y   A   I   S   W
  55  AAG GTC TCC TGC AAG CCT TCT GGA GAC ACC TTC AGC AAC TAT GCT ATC AGC TGG
                                                                   CDR2
                                                              ---------------------
      V   R   Q   A   P   G   Q   G   L   E   W   M   G   R   I   I   P   I
 109  GTG CGA CAG GCC CCT GGA CAA GGG CTT GAG TGG ATG GGA AGG ATC ATC CCT ATC
              CDR2
      ---------------------------------------
      L   G   M   A   I   Y   A   P   K   F   Q   G   R   V   T   I   T   A
 163  CTT GGT ATG GCT ATC TAC GCA CCG AAG TTC CAG GGC AGA GTT ACG ATT ACC GCG

D   K   S   T   N   T   A   F   M   D   L   T   S   L   Y   F   D   D
 217  GAC AAA TCC ACG AAC ACA GCC TTC ATG GAT CTT ACC AGC CTG TAT TTT GAC GAC
                                                                 CDR3
                                                         -------------------------
      T   A   V   Y   Y   C   A   R   A   P   T   Y   W   G   S   K   D   Y
 271  ACG GCC GTG TAT TAC TGT GCG AGA GCC CCA ACT TAC TGG GGA TCG AAG GAC TAC
          CDR3
      -------------
      F   D   Y   W   G   Q   G   T   L   V   T   V   S   S
 325  TTT GAC TAC TGG GGC CAG GGA ACC CTG GTC ACC GTC TCC TCA
```

FIGURE 17A

Anti-CD22 4G6 VK1

V segment: L18
J segment: JK2

```
        A   I   Q   L   T   Q   S   P   S   S   L   S   A   S   V   G   D   R
   1    GCT ATC CAG TTG ACC CAG TCT CCA TCC TCC CTG TCT GCA TCT GTA GGA GAC AGA
                                                CDR1
                                    ------------------------------------------
        V   T   I   T   C   R   A   S   Q   D   I   S   S   G   L   A   W   Y
   55   GTC ACC ATC ACT TGC CGT GCA AGT CAG GAC ATT AGC AGT GGT TTA GCC TGG TAT
                                                                     CDR2
                                                                     ---------
        Q   Q   K   P   G   T   A   P   K   L   L   I   Y   D   A   S   S   L
   109  CAG CAG AAA CCA GGG ACA GCT CCT AAG CTC CTG ATC TAT GAT GCC TCC AGT TTG
        CDR2
        ---------
        E   S   G   V   P   S   R   F   S   G   S   G   S   G   T   D   F   T
   163  GAA AGT GGG GTC CCA TCA AGG TTC AGC GGC AGT GGA TCT GGG ACA GAT TTC ACT
                                                                         CDR3
                                                                         -----
        L   T   I   S   S   L   Q   P   D   D   F   A   T   Y   Y   C   Q   Q
   217  CTC ACC ATC AGC AGC CTG CAG CCT GAC GAT TTT GCA ACT TAT TAC TGT CAA CAG
              CDR3
        -----------------------
        F   N   S   F   P   Y   T   F   G   Q   G   T   K   L   E   I   K
   271  TTT AAT AGT TTC CCG TAC ACT TTT GGC CAG GGG ACC AAG CTG GAG ATC AAA
```

FIGURE 17B

Anti-CD22 4G6 VK2

V segment:    A27
    J segment:    JK4

```
       E   I   V   L   T   Q   S   P   G   T   L   S   L   S   P   G   E   R
  1  GAA ATT GTG TTG ACG CAG TCT CCA GGC ACC CTG TCT TTG TCT CCA GGG GAA AGA
                                                  CDR1
                                        -----------------------------------------
       A   T   L   S   C   R   A   S   Q   S   V   S   S   S   Y   L   A   W
 55  GCC ACC CTC TCC TGC AGG GCC AGT CAG AGT GTT AGC AGC AGC TAC TTA GCC TGG
                                                                        CDR2
                                                                  ---------------
       Y   Q   Q   K   P   G   Q   A   P   R   L   L   I   Y   G   A   S   S
109  TAC CAG CAG AAA CCT GGC CAG GCT CCC AGG CTC CTC ATC TAT GGT GCA TCC AGC
         CDR2
     ------------
       R   A   T   G   I   P   D   R   F   S   G   S   G   S   G   T   D   F
163  AGG GCC ACT GGC ATC CCA GAC AGG TTC AGT GGC AGT GGG TCT GGG ACA GAC TTC
                                                                        CDR3
                                                                        ----
       T   L   T   I   S   R   L   E   P   E   D   F   A   V   Y   Y   C   Q
217  ACT CTC ACC ATC AGC AGA CTG GAG CCT GAA GAT TTT GCA GTG TAT TAC TGT CAG
         CDR3
     ----------------------------
       Q   Y   G   S   S   P   T   F   G   G   G   T   K   V   E   I   K
271  CAG TAT GGT AGC TCA CCC ACT TTC GGC GGA GGG ACC AAG GTG GAG ATC AAA
```

FIGURE 17C

Anti-CD22 21F6 VH1

V segment:     4-34
D segment:     3-9
J segment:     JH4b

```
        Q   V   Q   L   Q   Q   W   G   A   G   L   L   K   P   S   E   T   L
    1 CAG GTC CAG CTA CAG CAG TGG GGC GCA GGA CTG TTG AAG CCT TCG GAG ACC CTG

CDR1
                                                      ---------------------------
        S   L   T   C   A   V   Y   G   G   S   F   S   G   H   Y   W   S   W
   55 TCC CTC ACC TGC GCT GTC TAT GGT GGG TCC TTC AGT GGT CAC TAC TGG AGC TGG

CDR2
                                                         ---------------------------
        I   R   Q   S   P   G   K   G   L   E   W   I   G   E   T   D   H   S
  109 ATC CGC CAG TCC CCA GGG AAG GGG CTG GAG TGG ATT GGG GAA ACC GAT CAT AGT

CDR2
    -------------------------------------------------
        G   S   T   N   Y   N   P   S   L   K   S   R   V   T   I   S   I   D
  163 GGA AGC ACC AAC TAC AAT CCG TCC CTC AAG AGT CGA GTC ACC ATA TCA ATA GAC

T   S   K   N   Q   F   S   L   K   L   S   S   V   T   A   A   D   T
  217 ACG TCC AAG AAT CAG TTC TCC CTG AAG CTG AGC TCT GTG ACC GCC GCG GAC ACG

CDR3
                                    ---------------------------------------------
        A   V   Y   Y   C   A   R   T   Y   Y   D   I   L   T   D   Y   Y   P
  271 GCT GTG TAT TAC TGT GCG AGG ACT TAT TAC GAT ATT TTG ACT GAT TAT TAC CCC

CDR3
    ---------------
        F   D   S   W   G   Q   G   T   L   V   T   V   S   S
  325 TTT GAC TCC TGG GGC CAG GGA ACC CTG GTC ACC GTC TCT TCA
```

FIGURE 18A

Anti-CD22 21F6 VH2

V segment:    4-34
    D segment:    3-9
    J segment:    JH4b

```
      Q   V   Q   L   Q   Q   W   G   A   G   L   L   K   P   S   E   T   L
  1  CAG GTG CAG CTA CAG CAG TGG GCT GCA GGA CTG TTG AAG CCT TCG GAG ACC CTG

CDR1
                                                            ----------------------
      S   L   T   C   A   V   Y   G   G   S   F   S   G   H   Y   W   S   W
 55  TCC CTC ACC TGC GCT GTC TAT GGT GGG TCC TTC AGT GGT CAC TAC TGG AGC TGG

CDR2
                                                            ----------------------
      I   R   Q   S   P   G   K   G   L   E   W   I   G   E   I   D   H   S
109  ATC CGC CAG TCC CCA GGG AAG GGA CTG GAG TGG ATT GGG GAA ATC GAT CAT AGT

CDR2
     ----------------------------------------------
      G   S   T   N   Y   N   P   S   L   K   S   R   V   T   I   S   V   D
163  GGA AGC ACC AAC TAC AAT CCG TCC CTC AAG AGT CGA GTC ACC ATA TCA GTA GAC

T   S   K   N   Q   F   S   L   K   L   S   S   V   T   A   A   D   T
217  ACG TCC AAG AAC CAG TTC TCC CTG AAG CTG AGC TCT GTG ACC GCC GCG GAC ACG

CDR3
                                            ------------------------------------
      A   M   Y   Y   C   A   R   T   Y   Y   D   I   L   T   D   Y   Y   P
271  GCT ATG TAT TAC TGT GCG AGG ACG TAT TAC GAT ATT TTG ACT GAT TAT TAC CCC

CDR3
     --------------
      F   D   S   W   G   Q   G   T   L   V   T   V   S   S
325  TTT GAC TCC TGG GGC CAG GGA ACC CTG GTC ACC GTC TCC TCA
```

FIGURE 18B

Anti-CD22 21F6 VK

V segment:     L6
J segment:     JK4

```
       E   I   V   L   T   Q   S   P   A   T   L   S   L   S   P   G   E   R
  1  GAA ATT GTG TTG ACA CAG TCT CCA GCC ACC CTG TCT TTG TCT CCA GGG GAA AGA
                                      CDR1
                          ----------------------------------------------------
       A   T   L   S   C   R   A   S   Q   S   V   S   G   Y   L   A   W   Y
 55  GCC ACC CTC TCC TGC AGG GCT AGT CAG AGT GTT AGC GGC TAC TTA GCC TGG TAC
                                                                 CDR2
                                                       ---------------------
       Q   Q   K   P   G   Q   A   P   R   L   L   I   Y   D   V   S   Y   R
109  CAA CAG AAA CCT GGC CAG GCT CCC AGG CTC CTC ATC TAT GAT GTA TCC TAC AGG
     CDR2
     -------
       A   T   G   I   L   V   R   F   S   G   S   G   S   G   T   D   F   T
163  GCC ACT GGC ATC CTA GTC AGG TTC AGT GGC AGT GGG TCT GGG ACA GAC TTC ACT
                                                                      CDR3
                                                                  ---------
       L   T   I   S   S   L   E   P   E   D   F   A   V   Y   Y   C   Q   Q
217  CTC ACC ATC AGC AGC CTA GAG CCT GAA GAT TTT GCA GTT TAT TAC TGT CAG CAG
             CDR3
     -----------------------
       R   S   N   W   P   I   T   F   G   G   G   T   K   V   E   I   K
271  CGT AGT AAC TGG CCC ATC ACT TTC GGC GGA GGG ACC AAG GTG GAG ATC AAA
```

FIGURE 18C

Anti-CD22 4G6 VH

V segment: 1-69
D segment: 7-27
J segment: JH4b

```
                                                              CDR1
1-69 germline    Q V Q L V Q S G A E V K K P G S S V K V S C K A S G G T F S S Y A I S M
4G6 VH           - - - - - - - - - - - - - - - - - - - - - - - - - - - - - - - - N - -

CDR2
1-69 germline    V R Q A P G Q G L E W M G R I I P I L G I A N Y A Q K F Q G R V T I T A
4G6 VH           - - - - - - - - - - - - - - - - - - - - - - - M - I - P - - - - - - -

CDR3
1-69 germline    D K S T S T A Y M E L S S L R S E D T A V Y Y C A R           A P T Y W G S K D Y
JH4b germline
4G6 VH           - - - - - - - - - - N - F - D - F - Y R - - - - - -           - - - - - - - - -

JH4b germline    F D Y W G Q G T L V T V S S
4G6 VH           - - - - - - - - - A - - - -
```

FIGURE 19A

Anti-CD22 4G6 VK1

V segment: L18
J segment: JK3

```
                                          CDR1
L18 germline     A I Q L T Q S P S S L S A S V G D R V T I T C R A S Q G I S S A L A W Y Q Q K
4G6 VK1          : : : : : : : : : : : : : : : : : : : : : : : : : : : : : : : : : : : : : : :

CDR2
L18 germline     P G E A P K L L I Y D A S S L R S G V P S R F S G S G S G T D F T L T I S S L
4G6 VK1          : : : : : : : : : : T : : : : : : : : : : : : : : : : : : : : : : : : : : : :

CDR3
L18 germline     Q P E D F A T Y Y C Q Q F N S         Y T F G Q G T K L E I K
JK3 germline                                 F P :
4G6 VK1          : : : : : : : : : : : D : :           : : : : : : : : : : :
```

FIGURE 19B

```
Anti-CD22 4G6 VK2

V segment:    A27
J segment:    JK4

A27 germline     E I V L T Q S P G T L S L S P G E R
4G6 VK2          - - - - - - - - - - - - - - - - - -

CDR1
A27 germline     A T L S C R A S Q S V S S S Y L A W
4G6 VK2          - - - - - - - - - - - - - - - - - -

CDR2
A27 germline     Y Q Q K P G Q A P R L L I Y G A S S
4G6 VK2          - - - - - - - - - - - - - - - - - -

A27 germline     R A T G I P D R F S G S G S G T D F
4G6 VK2          - - - - - - - - - - - - - - - - - -

A27 germline     T L T I S R L E P E D F A V Y Y C Q
4G6 VK2          - - - - - - - - - - - - - - - - - -

CDR3
A27 germline     Q Y G S S P
JK4 germline                 T F G G G T K V E I K
4G6 VK2          - - - - - - - - - - - - - - - - -
```

FIGURE 19C

Anti-CD22 21F6 VH1

```
4-34 germline    Q V Q L Q Q W G A G L L K P S E T L
21F6 VH1         - - - - - - - - - - - - - - - - - -
```

```
                                               CDR1
4-34 germline    S L T C A V Y G G S F S G Y Y W S W
21F6 VH1         - - - - - - - - - - - - - H - - - -
```

```
                                               CDR2
4-34 germline    I R Q P P G K G L E W I G E I N H S
21F6 VH1         - - - S - - - - - - - - - - T D - -
```

```
        CDR2
4-34 germline    G S T N Y N P S L K S R V T I S V D
21F6 VH1         - - - - - - - - - - - - - - - I -
```

```
4-34 germline    T S K N Q F S L K L S S V T A A D T
21F6 VH1         - - - - - - - - - - - - - - - - - -
```

```
                               CDR3
4-34 germline    A V Y Y C A R
21F6 VH1         - - - - - - - T Y Y D I L T D Y Y F
```

```
JH4b germline    F D Y W G Q G T L V T V S S
21F6 VH1         - - S - - - - - - - - - -
```

FIGURE 20A

Anti-CD22 21F6 VH2

```
4-34 germline    Q V Q L Q Q W G A G L L K P S E T L
21F6 VH2         - - - - - - - - - - - - - - - - - -

CDR1
4-34 germline    S L T C A V Y G G S F S G Y Y W S W
21F6 VH2         - - - - - - - - - - - - - H - - - -

CDR2
4-34 germline    I R Q P P G K G L E W I G E I N H S
21F6 VH2         - - - S - - - - - - - - - - D - -

CDR2
4-34 germline    G S T N Y N P S L K S R V T I S V D
21F6 VH2         - - - - - - - - - - - - - - - - - -

4-34 germline    T S K N Q F S L K L S S V T A A D T
21F6 VH2         - - - - - - - - - - - - - - - - - -

CDR3
4-34 germline    A V Y Y C A R
21F6 VH2         - M - - - - - T Y Y D I L T D Y Y P JH4b germline    F D Y W G Q G T L V T V S S
21F6 VH2         - - G - - - - - - - - - -
```

FIGURE 20B

Anti-CD22 21F6 VK

```
                              CDR1
L6 germline         DIVLTQSPATLSLSPGERATLSCRASQSVSG
21F6 VK1            ...............................

CDR2
L6 germline         YLAWYQQKPGQAPRLLIYDASNRATGIPARF
21F6 VK1            ....................Y.....A..L.

CDR3
L6 germline         SGSGSGTDFTLTISSLEPEDFAVYYCQQRSN
21F6 VK1            ...........................C...

L6 germline         WP
JK4 germline          TFGGGTKVEIK
21F6 VK1            ..I..........
```

FIGURE 20C

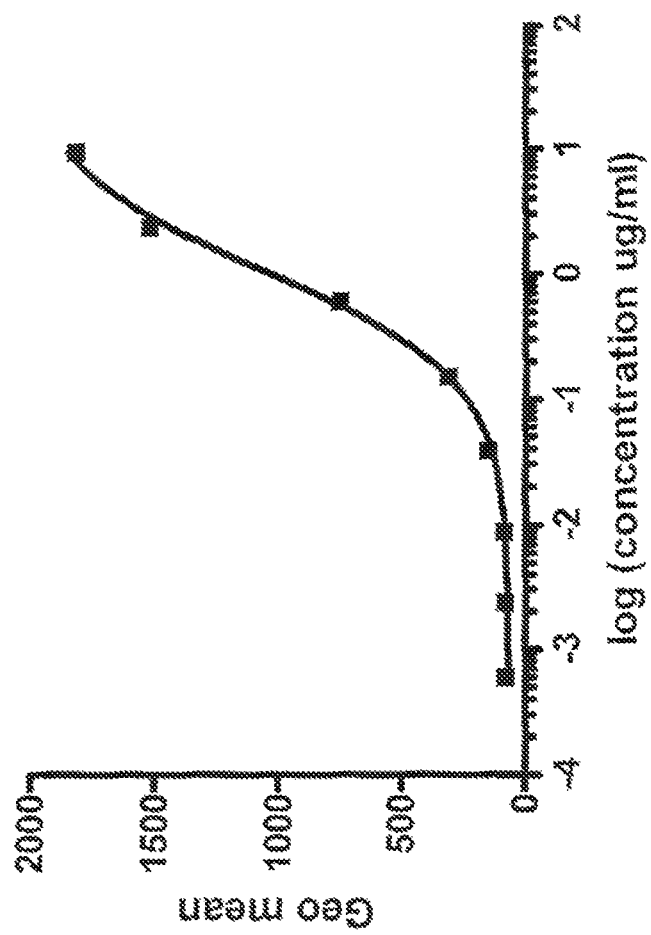

HUMAN ANTIBODIES THAT BIND CD22 AND USES THEREOF

CROSS-REFERENCE TO RELATED APPLICATIONS

This application is a Divisional of U.S. application Ser. No. 12/517,183, filed Feb. 17, 2010, which is a national stage of International Application Serial No. PCT/US2007/086152, filed Nov. 30, 2007, which claims priority of U.S. Provisional Application Ser. No. 60/868,231, filed on Dec. 1, 2006, each of which is herein incorporated by reference.

BACKGROUND

CD22 is a cell-surface type I glycoprotein of the sialoadhesin family. CD22 is also known in the art as BL-CAM, B3, Leu-14 and Lyb-8, among other names. CD22 was initially characterized by the antibodies anti-S—HCL-1 (Schwarting, R. et al. (1985) *Blood* 65:974-983), HD39 (Dorken, B. et al. (1986) *J. Immunol.* 136:4470-4479) and RFB4 (Campana, D. et al. (1985) *J. Immunol.* 134:1524-1530). CD22 has been established as a lectin-like adhesion molecule that binds alpha-2,6-linked sialic acid-bearing ligands and as a regulator of B cell antigen receptor (BCR) signaling. Structurally, there are several splice variants of CD22 that exist, but the predominant form in humans has an extracellular region containing seven immunoglobulin-like domains.

CD22 has been shown to be specifically expressed by B lymphocytes and is functionally important as a negative regulator of B lymphocyte activation (reviewed by Nitschke, L. (2005) *Curr. Opin. Immunol.* 17:290-297 and Tedder, T. F. et al (2005) *Adv. Immunol.* 88:1-50). In studies that utilized gene-targeted mice that expressed mutant CD22 molecules that do not interact with alpha-2,6-linked sialic acid ligands, it was determined that certain functions (such as expression of cell surface CD22, IgM and MHC Class II on mature B cells, maintenance of marginal zone B cell populations, optimal B cell antigen receptor-induced proliferation and B cell turnover rates) were regulated by CD22 ligand binding, whereas other functions (such as CD22 phosphorylation, CD22 negative regulation of calcium mobilization after BCR ligation, recruitment of SHP-1 to CD22 and B cell migration) did not require ligand engagement (Poe, J. C. et al. (2004) *Nat. Immunol.* 5:1078-1087).

CD22 is considered to be an inhibitory co-receptor that downmodulates BCR signalling by setting a signalling threshold that prevents overstimulation of B cells. Activation of such an inhibitory co-receptor occurs by phosphorylation on cytoplasmic ITIMs (immunoreceptor tyrosine-based inhibition motifs), followed by recruitment of the tyrosine phosphatase SHP-1 or the lipid phosphatase SHIIP (reviewed in by Nitschke, L. (2005) *Curr. Opin. Immunol.* 17:290-297). Additionally, CD22 has been found to play a central role in a regulatory loop controlling the CD19/CD21-Src-family protein tyrosine kinase (PTK) amplification pathway that regulates basal signaling thresholds and intensifies Src-family kinase activation after BCR ligation (reviewed in Tedder, T. F. et al (2005) *Adv. Immunol.* 88:1-50).

Approximately 60-80% of B cell malignancies express CD22, thereby making it a potential target for passive immunotherapy (see e.g., Cesano, A. and Gayko, U. (2003) *Semin. Oncol.* 30:253-257). Moreover, selective modulation of B cell activity via targeting of CD22 has been suggested as a means for treatment of autoimmune diseases (see e.g., Steinfeld, S. D. and Youinou, P. (2006) *Expert. Opin. Biol. Ther.* 6:943-949). A humanized anti-CD22 monoclonal antibody, epratuzumab, has been described (Coleman, M. et al. (2003) *Clin. Cancer Res.* 9:3991 S-3994S). However, additional anti-CD22 reagents are still needed.

SUMMARY

The present disclosure provides isolated monoclonal antibodies, in particular human monoclonal antibodies, that bind to human CD22 and that exhibit numerous desirable properties. These properties include high affinity binding to CD22, the ability to internalize into CD22+ cells, the ability to mediate antibody dependent cellular cytotoxicity (ADCC), the ability to enhance cell death of Ramos cells induced by B cell receptor (BCR) stimulation, and/or inhibits growth of CD22-expressing cells in vivo when conjugated to a cytotoxin. The antibodies of the invention can be used, for example, to treat CD22+ B cell malignancies and/or to treat various inflammatory or autoimmune disorders.

In one aspect, the instant disclosure pertains to an isolated human monoclonal antibody, or an antigen-binding portion thereof, wherein the antibody binds to human CD22 and exhibits at least one of the following properties:

(a) internalizes into CD22$^+$ cells;

(b) exhibits antibody dependent cellular cytotoxicity (ADCC) against CD22$^+$ cells;

(c) enhances cell death of Ramos cells induced by B cell receptor (BCR) stimulation; and (d) inhibits growth of CD22-expressing cells in vivo when conjugated to a cytotoxin.

In another embodiment, the antibody exhibits at least two of properties (a), (b), (c) and (d). In yet another embodiment, the antibody exhibits three of properties (a), (b), (c) and (d). In another embodiment, the antibody exhibits all four of properties (a), (b), (c), and (d). In certain embodiments, the antibody does not have a direct anti-proliferative effect on Ramos cells. In certain embodiments, the antibody does not induce calcium flux in Ramos cells. In certain embodiments, the antibody does not mediate complement dependent cytotoxicity (CDC) on Ramos cells. Preferably, the antibody binds to human CD22 with high affinity, e.g., with a $K_D$ of $1\times10^{-7}$ M or less or a $K_D$ of $1\times10^{-8}$ M or less or a $K_D$ of $1\times10^{-9}$ M or less or a $K_D$ of $1\times10^{-10}$ or less or a KD of $7\times10^{-11}$ or less.

In another aspect, the invention pertains to an isolated human monoclonal antibody, or antigen binding portion thereof, wherein the antibody cross-competes for binding to CD22 with a reference antibody, wherein the reference antibody comprises:

(a) a heavy chain variable region comprising the amino acid sequence of SEQ ID NO:31 and a light chain variable region comprising the amino acid sequence of SEQ ID NO:35; or (b) a heavy chain variable region comprising the amino acid sequence of SEQ ID NO:32 or 61 and a light chain variable region comprising the amino acid sequence of SEQ ID NO:36; or (c) a heavy chain variable region comprising the amino acid sequence of SEQ ID NO:33 and a light chain variable region comprising the amino acid sequence of SEQ ID NO:37 or 38; or (d) a heavy chain variable region comprising the amino acid sequence of SEQ ID NO:34 and a light chain variable region comprising the amino acid sequence of SEQ ID NO:39 or 40; or (e) a heavy chain variable region comprising the amino acid sequence of SEQ ID NO:81 and a light chain variable region comprising the amino acid sequence of SEQ ID NO:84 or 85; or (f) a heavy chain variable region comprising the amino acid sequence of SEQ ID NO:82 or 83 and a light chain variable region comprising the amino acid sequence of SEQ ID NO:86.
wherein the antibody specifically binds human CD22

In yet another aspect, the invention pertains to an isolated monoclonal antibody, or an antigen-binding portion thereof, comprising a heavy chain variable region that is the product of or derived from a human $V_H$ 7-4.1 gene, a human $V_H$ 4-34 gene, a human $V_H$ 5-51 gene, or a human VH 1-69 gene, wherein the antibody specifically binds human CD22. In yet another aspect, the invention pertains to an isolated monoclonal antibody, or an antigen-binding portion thereof, comprising a light chain variable region that is the product of or derived from a human $V_\lambda$ 2b2 gene, a human $V_K$ L6 gene, a human $V_K$ A27 gene, a human $V_K$ A10 gene, or a human L18 gene, wherein the antibody specifically binds human CD22. In still another aspect, the invention pertains to an isolated antibody, or antigen-binding portion thereof, comprising:

(a) a heavy chain variable region that is the product of or derived from a human $V_H$ 7-4.1 gene and a light chain variable region that is the product of or derived from a human $V_\lambda$ 2b2 gene; or (b) a heavy chain variable region that is the product of or derived from a human $V_H$ 4-34 gene and a light chain variable region that is the product of or derived from a human $V_K$ L6 gene; or (c) a heavy chain variable region that is the product of or derived from a human $V_H$ 5-51 gene and a light chain variable region that is the product of or derived from a human $V_K$ A27 or A10 gene;

(d) a heavy chain variable region that is the product of or derived from a human $V_H$ 1-69 gene and a light chain variable region that is the product of or derived from a human $V_K$ L6 gene; or (e) a heavy chain variable region that is the product of or derived from a human $V_H$ 1-69 gene and a light chain variable region that is the product of or derived from a human $V_K$ L18 or A27 gene;
wherein the antibody specifically binds human CD22.

In another aspect, this disclosure provides an isolated monoclonal antibody, or antigen binding portion thereof, comprising:
 a heavy chain variable region that comprises CDR1, CDR2, and CDR3 sequences; and a light chain variable region that comprises CDR1, CDR2, and CDR3 sequences, wherein:

(a) the heavy chain variable region CDR3 sequence comprises an amino acid sequence selected from the group consisting of amino acid sequences of SEQ ID NOs: 9-12 and 69-71, and conservative modifications thereof;

(b) the light chain variable region CDR3 sequence comprises an amino acid sequence selected from the group consisting of amino acid sequence of SEQ ID NOs: 25-30, 78-80, and conservative modifications thereof; and (c) the antibody binds to human CD22.

In preferred embodiments, this antibody also has one or more of the following characteristics: internalizes into CD22+ cells, mediates ADCC activity and/or enhances cell death of Ramos cells induced by BCR stimulation, and/or inhibits growth of CD22-expressing cells in vivo when conjugated to a cytotoxin.

Preferably, the heavy chain variable region CDR2 sequence comprises an amino acid sequence selected from the group consisting of amino acid sequences of SEQ ID NOs: 5-8, 60, 66-68, and conservative modifications thereof; and the light chain variable region CDR2 sequence comprises an amino acid sequence selected from the group consisting of amino acid sequences of SEQ ID NOs: 19-24, 75-77, and conservative modifications thereof.

Preferably, the heavy chain variable region CDR1 sequence comprises an amino acid sequence selected from the group consisting of amino acid sequences of SEQ ID NOs: 1-4, 63-65, and conservative modifications thereof; and the light chain variable region CDR1 sequence comprises an amino acid sequence selected from the group consisting of amino acid sequences of SEQ ID NOs: 13-18, 72-74, and conservative modifications thereof.

A preferred combination comprises:
(a) a heavy chain variable region CDR1 comprising SEQ ID NO:1;
(b) a heavy chain variable region CDR2 comprising SEQ ID NO:5;
(c) a heavy chain variable region CDR3 comprising SEQ ID NO:9;
(d) a light chain variable region CDR1 comprising SEQ ID NO:13;
(e) a light chain variable region CDR2 comprising SEQ ID NO:19; and
(f) a light chain variable region CDR3 comprising SEQ ID NO:25.

Another preferred combination comprises:
(a) a heavy chain variable region CDR1 comprising SEQ ID NO:2;
(b) a heavy chain variable region CDR2 comprising SEQ ID NO:6 or 60;
(c) a heavy chain variable region CDR3 comprising SEQ ID NO:10;
(d) a light chain variable region CDR1 comprising SEQ ID NO:14;
(e) a light chain variable region CDR2 comprising SEQ ID NO:20; and
(f) a light chain variable region CDR3 comprising SEQ ID NO:26.

Another preferred combination comprises:
(a) a heavy chain variable region CDR1 comprising SEQ ID NO:3;
(b) a heavy chain variable region CDR2 comprising SEQ ID NO:7;
(c) a heavy chain variable region CDR3 comprising SEQ ID NO:11;
(d) a light chain variable region CDR1 comprising SEQ ID NO:15 or 16;
(e) a light chain variable region CDR2 comprising SEQ ID NO:21 or 22; and
(f) a light chain variable region CDR3 comprising SEQ ID NO:27 or 28.

Another preferred combination comprises:
(a) a heavy chain variable region CDR1 comprising SEQ ID NO:4;
(b) a heavy chain variable region CDR2 comprising SEQ ID NO:8;
(c) a heavy chain variable region CDR3 comprising SEQ ID NO:12;
(d) a light chain variable region CDR1 comprising SEQ ID NO:17 or 18;
(e) a light chain variable region CDR2 comprising SEQ ID NO:23 or 24; and (f) a light chain variable region CDR3 comprising SEQ ID NO:29 or 30.

Another preferred combination comprises:
(a) a heavy chain variable region CDR1 comprising SEQ ID NO:63;
(b) a heavy chain variable region CDR2 comprising SEQ ID NO:66;
(c) a heavy chain variable region CDR3 comprising SEQ ID NO:69;
(d) a light chain variable region CDR1 comprising SEQ ID NO:72 or 73;
(e) a light chain variable region CDR2 comprising SEQ ID NO:75 or 76; and
(f) a light chain variable region CDR3 comprising SEQ ID NO:78 or 79.

Another preferred combination comprises:
(a) a heavy chain variable region CDR1 comprising SEQ ID NO:64 or 65;
(b) a heavy chain variable region CDR2 comprising SEQ ID NO:67 or 68;
(c) a heavy chain variable region CDR3 comprising SEQ ID NO:70 or 71;
(d) a light chain variable region CDR1 comprising SEQ ID NO:74;
(e) a light chain variable region CDR2 comprising SEQ ID NO:77; and
(f) a light chain variable region CDR3 comprising SEQ ID NO:80.

Other preferred antibodies of this disclosure, or antigen binding portions thereof, comprise:
(a) a heavy chain variable region comprising an amino acid sequence selected from the group consisting of SEQ ID NOs: 31-34, 61 and 81-83; and
(b) a light chain variable region comprising an amino acid sequence selected from the group consisting of SEQ ID NOs: 35-40 and 84-86; wherein the antibody specifically binds human CD22.

A preferred combination comprises: (a) a heavy chain variable region comprising the amino acid sequence of SEQ ID NO:31; and (b) a light chain variable region comprising the amino acid sequence of SEQ ID NO:35.

Another preferred combination comprises: (a) a heavy chain variable region comprising the amino acid sequence of SEQ ID NOS:32 or 61; and (b) a light chain variable region comprising the amino acid sequence of SEQ ID NO:36.

Another preferred combination comprises: (a) a heavy chain variable region comprising the amino acid sequence of SEQ ID NO:33; and (b) a light chain variable region comprising the amino acid sequence of SEQ ID NO:37 or 38.

Another preferred combination comprises: (a) a heavy chain variable region comprising the amino acid sequence of SEQ ID NO:34; and (b) a light chain variable region comprising the amino acid sequence of SEQ ID NO:39 or 40.

Another preferred combination comprises: (a) a heavy chain variable region comprising the amino acid sequence of SEQ ID NO:81; and (b) a light chain variable region comprising the amino acid sequence of SEQ ID NO:84 or 85.

Another preferred combination comprises: (a) a heavy chain variable region comprising the amino acid sequence of SEQ ID NO:82 or 83; and (b) a light chain variable region comprising the amino acid sequence of SEQ ID NO:86.

In another aspect of this disclosure, antibodies, or antigen-binding portions thereof, are provided that compete for binding to CD22 with any of the aforementioned antibodies.

The antibodies of this disclosure can be, for example, full-length antibodies, for example of an IgG1 or IgG4 isotype. Alternatively, the antibodies can be antibody fragments, such as Fab, Fab' or Fab'2 fragments, or single chain antibodies.

This disclosure also provides an immunoconjugate comprising an antibody of this disclosure, or antigen-binding portion thereof, linked to a therapeutic agent, such as a cytotoxin or a radioactive isotope. In a particularly preferred embodiment, the invention provides an immunoconjugate comprising an antibody of this disclosure, or antigen-binding portion thereof, linked to the compound "Cytotoxin A" (e.g., via a thiol linkage). This disclosure also provides a bispecific molecule comprising an antibody, or antigen-binding portion thereof, of this disclosure, linked to a second functional moiety having a different binding specificity than said antibody, or antigen binding portion thereof.

Compositions comprising an antibody, or antigen-binding portion thereof, or immunoconjugate or bispecific molecule of this disclosure and a pharmaceutically acceptable carrier are also provided.

Nucleic acid molecules encoding the antibodies, or antigen-binding portions thereof, of this disclosure are also encompassed by this disclosure, as well as expression vectors comprising such nucleic acids and host cells comprising such expression vectors. Methods for preparing anti-CD22 antibodies using the host cells comprising such expression vectors are also provided and may include the steps of (i) expressing the antibody in the host cell and (ii) isolating the antibody from the host cell.

Another aspect of this disclosure pertains to methods of inhibiting growth of a CD22-expressing tumor cell. The method comprises contacting the CD22-expressing tumor cell with an antibody, or antigen-binding portion thereof, of the invention such that growth of the CD22-expressing tumor cell is inhibited. The tumor cell can be, for example, a B cell lymphoma, such as a non-Hodgkin's lymphoma. In certain embodiments, the antibody, or antigen-binding portion thereof, is conjugated to a therapeutic agent, such as a cytotoxin.

Another aspect of this disclosure pertains to methods of treating an inflammatory or autoimmune disorder in a subject. The method comprises administering to the subject an antibody, or antigen-binding portion thereof, of the invention such that the inflammatory or autoimmune disorder in the subject is treated. The autoimmune disorder can be, for example, systemic lupus erythematosus or rheumatoid arthritis.

The present disclosure also provides isolated anti-CD22 antibody-partner molecule conjugates that specifically bind to CD22 with high affinity, particularly those comprising human monoclonal antibodies. Certain of such antibody-partner molecule conjugates are capable of being internalized into CD22-expressing cells and are capable of mediating antibody dependent cellular cytotoxicity. This disclosure also provides methods for treating cancers, such as a B cell lymphoma, such as a non-Hodgkin's lymphoma, using an anti-CD22 antibody-partner molecule conjugate disclosed herein.

In another aspect, the invention provides a method of treating an inflammatory or autoimmune disorder in a subject. The method comprises administering to the subject an antibody, or antigen-binding portion thereof, of the invention such that the inflammatory or autoimmune disorder in the subject is treated. Non-limiting examples of preferred autoimmune disorders include systemic lupus erythematosus and rheumatoid arthritis. Other examples of autoimmune disorders include inflammatory bowel disease (including ulcerative colitis and Crohn's disease), Type I diabetes, multiple sclerosis, Sjogren's syndrome, autoimmune thyroiditis (including Grave's disease and Hashimoto's thyroiditis), psoriasis and glomerulonephritis.

Compositions comprising an antibody, or antigen-binding portion thereof, conjugated to a partner molecule of this disclosure are also provided. Partner molecules that can be advantageously conjugated to an antibody in an antibody partner molecule conjugate as disclosed herein include, but are not limited to, molecules as drugs, toxins, marker molecules (e.g., radioisotopes), proteins and therapeutic agents. Compositions comprising antibody-partner molecule conjugates and pharmaceutically acceptable carriers are also disclosed herein.

In one aspect, such antibody-partner molecule conjugates are conjugated via chemical linkers. In some embodiments, the linker is a peptidyl linker, and is depicted herein as (L4)p-F-(L1)m. Other linkers include hydrazine and disulfide linkers, and is depicted herein as (L4)p-H-(L1)m or (L4)p-J-(L1)m, respectively. In addition to the linkers being attached to the partner, the present invention also provides cleavable linker arms that are appropriate for attachment to essentially any molecular species.

In another aspect, the invention pertains to a method of inhibiting growth of a CD22-expressing tumor cell. The method comprises contacting the CD22-expressing tumor cell with an antibody-partner molecule conjugate of the disclosure such that growth of the CD22-tumor cell is inhibited. In a preferred embodiment, the partner molecule is a therapeutic agent, such as a cytotoxin. Particularly preferred CD22-expressing tumor cells are B cell lymphomas, such as non-Hodgkin's lymphoma. Other types of CD22-expressing tumor cells include Burkitt's lymphomas and B cell chronic lymphocytic leukemias. In still other embodiments, the CD22-expressing tumor cell is from a cancer selected from the group consisting of Burkitt's lymphomas and B cell chronic lymphocytic leukemias.

In another aspect, the invention pertains to a method of treating cancer in a subject. The method comprises administering to the subject an antibody-partner molecule conjugate of the disclosure such that the cancer is treated in the subject. In a preferred embodiment, the partner molecule is a therapeutic agent, such as a cytotoxin. Particularly preferred cancers for treatment are B cell lymphomas, such as a non-Hodgkin's lymphoma. Other types of cancers include Burkitt's lymphomas and B cell chronic lymphocytic leukemias.

Other features and advantages of the instant disclosure will be apparent from the following detailed description and examples, which should not be construed as limiting. The contents of all references, Genbank entries, patents and published patent applications cited throughout this application are expressly incorporated herein by reference.

BRIEF DESCRIPTION OF THE DRAWINGS

FIG. 1A shows the nucleotide sequence (SEQ ID NO:41) and amino acid sequence (SEQ ID NO:31) of the heavy chain variable region of the 12C5 human monoclonal antibody. The CDR1 (SEQ ID NO:1), CDR2 (SEQ ID NO:5) and CDR3 (SEQ ID NO:9) regions are delineated and the V, D and J germline derivations are indicated.

FIG. 1B shows the nucleotide sequence (SEQ ID NO:45) and amino acid sequence (SEQ ID NO:35) of the lambda light chain variable region of the 12C5 human monoclonal antibody. The CDR1 (SEQ ID NO:13), CDR2 (SEQ ID NO:19) and CDR3 (SEQ ID NO:25) regions are delineated and the V and J germline derivations are indicated.

FIG. 2A shows the nucleotide sequence (SEQ ID NO:42) and amino acid sequence (SEQ ID NO:32) of the heavy chain variable region of the 19A3 human monoclonal antibody, and the nucleotitde sequence and aminio acid sequence of the heavy chain variable region of the CD22.1 recombinant antibody. The sequences of the heavy chain variable region of 19A3 are identical to that of CD22.1. The CDR1 (SEQ ID NO:2), CDR2 (SEQ ID NO:6) and CDR3 (SEQ ID NO:10) regions are delineated and the V, D and J germline derivations are indicated.

FIG. 2B shows the nucleotide sequence (SEQ ID NO:46) and amino acid sequence (SEQ ID NO:36) of the kappa light chain variable region of the 19A3 human monoclonal antibody, and the nucleotide and amino acid sequences of the kappa light chain variable region of the CD22.1 recombinant human monoclonal antibody. The sequences of the kappa light chain variable region of both CD22.1 and CD22.2 are identical to those of 19A3. The CDR1 (SEQ ID NO:14), CDR2 (SEQ ID NO:20) and CDR3 (SEQ ID NO:26) regions are delineated and the V and J germline derivations are indicated.

FIG. 2C shows the nucleotide sequence (SEQ ID NO:62) and amino acid sequence (SEQ ID NO:61) of the heavy chain variable region variable region of the CD22.2 recombinant human monoclonal antibody. The CDR1 (SEQ ID NO:2), CDR2 (SEQ ID NO:60) and CDR3 (SEQ ID NO:10) regions are delineated and the V and J germline derivations are indicated.

FIG. 3A shows the nucleotide sequence (SEQ ID NO:43) and amino acid sequence (SEQ ID NO:33) of the heavy chain variable region of the 16F7 human monoclonal antibody. The CDR1 (SEQ ID NO:3), CDR2 (SEQ ID NO:7) and CDR3 (SEQ ID NO:11) regions are delineated and the V, D and J germline derivations are indicated.

FIG. 3B shows the nucleotide sequence (SEQ ID NO:47) and amino acid sequence (SEQ ID NO:37) of the $V_K.1$ kappa light chain variable region of the 16F7 human monoclonal antibody. The CDR1 (SEQ ID NO:15), CDR2 (SEQ ID NO21:) and CDR3 (SEQ ID NO27:) regions are delineated and the V and J germline derivations are indicated.

FIG. 3C shows the nucleotide sequence (SEQ ID NO:48) and amino acid sequence (SEQ ID NO:38) of the $V_K.2$ kappa light chain variable region of the 16F7 human monoclonal antibody. The CDR1 (SEQ ID NO:16), CDR2 (SEQ ID NO:22) and CDR3 (SEQ ID NO:28) regions are delineated and the V and J germline derivations are indicated.

FIG. 4A shows the nucleotide sequence (SEQ ID NO:44) and amino acid sequence (SEQ ID NO:34) of the heavy chain variable region of the 23C6 human monoclonal antibody. The CDR1 (SEQ ID NO:4), CDR2 (SEQ ID NO:8) and CDR3 (SEQ ID NO:12) regions are delineated and the V, D and J germline derivations are indicated.

FIG. 4B shows the nucleotide sequence (SEQ ID NO:49) and amino acid sequence (SEQ ID NO:39) of the $V_K.1$ kappa light chain variable region of the 23C6 human monoclonal antibody. The CDR1 (SEQ ID NO:17), CDR2 (SEQ ID NO:23) and CDR3 (SEQ ID NO:29) regions are delineated and the V and J germline derivations are indicated.

FIG. 4C shows the nucleotide sequence (SEQ ID NO:50) and amino acid sequence (SEQ ID NO:40) of the $V_K.2$ kappa light chain variable region of the 23C6 human monoclonal antibody. The CDR1 (SEQ ID NO:18), CDR2 (SEQ ID NO:24) and CDR3 (SEQ ID NO:30) regions are delineated and the V and J germline derivations are indicated.

FIG. 5A shows the alignment of the amino acid sequence of the heavy chain variable regions of 12C5 (SEQ ID NO:31) with the human germline $V_H$ 7-4.1 amino acid sequence (SEQ ID NO:51).

FIG. 5B shows the alignment of the amino acid sequence of the light chain variable region of 12C5 (SEQ ID NO:35) with the human germline $V_\lambda$ 2b2 amino acid sequence (SEQ ID NO:55).

FIG. 6A shows the alignment of the amino acid sequence of the heavy chain variable regions of 19A3/CD22.1 (SEQ ID NO:32) with the human germline $V_H$ 4-34 amino acid sequence (SEQ ID NO:52).

FIG. 6B shows the alignment of the amino acid sequence of the light chain variable regions of 19A3/CD22.1/CD22.2 (SEQ ID NO:36) with the human germline $V_K$ L6 amino acid sequence (SEQ ID NO:56).

FIG. 6C shows the alignment of the amino acid sequence of the heavy chain variable region of CD22.2 (SEQ ID NO:61) with the human germline $V_H$ 4-34 amino acid sequence (SEQ ID NO:52).

FIG. 7A shows the alignment of the amino acid sequence of the heavy chain variable regions of 16F7 (SEQ ID NO:33) with the human germline $V_H$ 5-51 amino acid sequence (SEQ ID NO:53).

FIG. 7B shows the alignment of the amino acid sequence of the $V_K$.1 light chain variable region of 16F7 (SEQ ID NO:37) with the human germline $V_K$ A27 amino acid sequence (SEQ ID NO:57).

FIG. 7C shows the alignment of the amino acid sequence of the $V_K$.2 light chain variable region of 16F7 (SEQ ID NO:38) with the human germline $V_K$ A10 amino acid sequence (SEQ ID NO:57).

FIG. 8A shows the alignment of the amino acid sequence of the heavy chain variable regions of 23C6 (SEQ ID NO:34) with the human germline $V_H$ 1-69 amino acid sequence (SEQ ID NO:54).

FIG. 8B shows the alignment of the amino acid sequence of the $V_K$.1 light chain variable region of 23C6 (SEQ ID NO:39) and the $V_K$.2 light chain variable region of 23C6 (SEQ ID NO:40) with the human germline $V_K$ L6 amino acid sequence (SEQ ID NO:56).

FIG. 17A shows the nucleotide sequence (SEQ ID NO:87) and amino acid sequence (SEQ ID NO:81) of the 4G6 human antibody. The CDR1 (SEQ ID NO:63), CDR2 (SEQ ID NO:66) and CDR3 (SEQ ID NO:69) regions are delineated and the V, D and J germline derivations are indicated.

FIG. 17B shows the nucleotide sequence (SEQ ID NO:90) and amino acid sequence (SEQ ID NO:84) of the $V_K$1 kappa light chain variable region of the 4G6 human monoclonal antibody. The CDR1 (SEQ ID NO:72), CDR2 (SEQ ID NO:75) and CDR3 (SEQ ID NO:78) regions are delineated and the V and J germline derivations are indicated.

FIG. 17C shows the nucleotide sequence (SEQ ID NO:91) and amino acid sequence (SEQ ID NO:85) of the $V_K$2 kappa light chain variable region of the 4G6 human monoclonal antibody. The CDR1 (SEQ ID NO:73), CDR2 (SEQ ID NO:76) and CDR3 (SEQ ID NO:79) regions are delineated and the V and J germline derivations are indicated.

FIG. 18A shows the nucleotide sequence (SEQ ID NO:88) and amino acid sequence (SEQ ID NO:82) of the $V_H$1 heavy chain variable region of the 21F6 human monoclonal antibody. The CDR1 (SEQ ID NO:64), CDR2 (SEQ ID NO:67) and CDR3 (SEQ ID NO:70) regions are delineated and the V, D and J germline derivations are indicated.

FIG. 18B shows the nucleotide sequence (SEQ ID NO:89) and amino acid sequence (SEQ ID NO:83) of the $V_H$2 heavy chain variable region of the 21F6 human monoclonal antibody. The CDR1 (SEQ ID NO:65), CDR2 (SEQ ID NO:68) and CDR3 (SEQ ID NO:71) regions are delineated and the V, D and J germline derivations are indicated.

FIG. 18C shows the nucleotide sequence (SEQ ID NOs: 92) and amino acid sequence (SEQ ID NO:86) of the kappa light chain variable region of the 21F6 human monoclonal antibody. The CDR1 (SEQ ID NO:74), CDR2 (SEQ ID NO:77) and CDR3 (SEQ ID NO:80) regions are delineated and the V and J germline derivations are indicated.

FIG. 19A shows the alignment of the amino acid sequence of the heavy chain variable regions of 4G6 (SEQ ID NO:81) with the human germline $V_H$ 1-69 amino acid sequence (SEQ ID NO:54).

FIG. 19B shows the alignment of the amino acid sequence of the $V_K$1 kappa light chain variable region of 4G6 (SEQ ID NO:84) with the human germline $V_K$ L18 amino acid sequence (SEQ ID NO:93).

FIG. 19C shows the alignment of the amino acid sequence of the $V_K$2 kappa light chain variable region of 4G6 (SEQ ID NO:85) with the human germline $V_K$ A27 amino acid sequence (SEQ ID NO:57).

FIG. 20A shows the alignment of the amino acid sequence of the $V_H$1 heavy chain variable regions of 21F6 (SEQ ID NO:82) with the human germline $V_H$ 4-34-amino acid sequence (SEQ ID NO:52).

FIG. 20B shows the alignment of the amino acid sequence of the $V_H$2 heavy chain variable regions of 21F6 (SEQ ID NO:83) with the human germline $V_H$ 4-34 amino acid sequence (SEQ ID NO:52).

FIG. 20C shows the alignment of the amino acid sequence of the kappa light chain variable region of 21F6 (SEQ ID NO:86) with the human germline $V_K$ L6 amino acid sequence (SEQ ID NO:56).

FIG. 21 is a graph showing binding of CD22 expressed on the surface of CHO cells by the anti-CD22 human antibody 4G6.

DETAILED DESCRIPTION OF THIS DISCLOSURES

Figure 9:
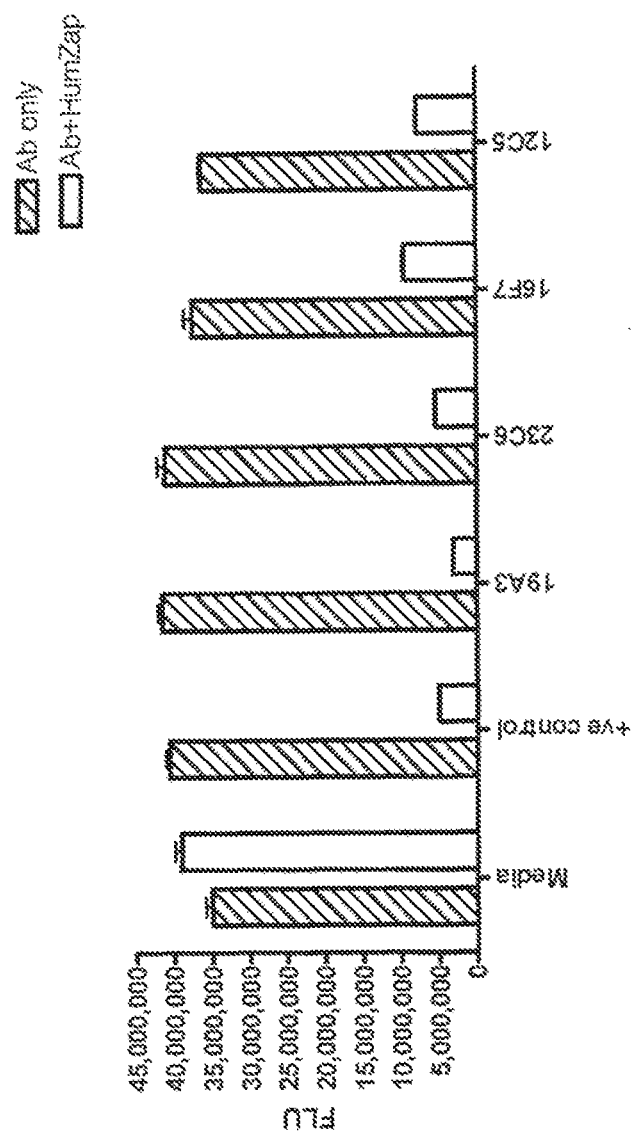
FIG. 9 is a bar graph showing the internalization of anti-CD22 human antibodies 12C5, 19A3, 16F7 and 23C6 into Raji cells.

The present disclosure relates to isolated monoclonal antibodies, particularly human monoclonal antibodies that bind specifically to human CD22 with high affinity. In certain embodiments, the antibodies of this disclosure are derived from particular heavy and light chain germline sequences and/or comprise particular structural features such as CDR regions comprising particular amino acid sequences. This disclosure provides isolated antibodies, immuno-partner molecule conjugates, bispecific molecules, affibodies, domain antibodies, nanobodies and unibodies, methods of making said molecules, and pharmaceutical compositions comprising said molecules and pharmaceutical carriers. The invention also relates to methods of using the molecules, such as to detect CD22, as well as to modulate B cell activity in diseases or disorders associated with expression of CD22 or involving B cell regulation, such as CD22+ tumors and inflammatory or autoimmune disorders. This disclosure also provides methods of using the anti-CD22 antibodies of this invention to inhibit the growth of CD22+ tumor cells, for example, to treat B cell lymphomas. Additionally, this disclosure provides methods of using the anti-CD22 antibodies of this disclosure to treat inflammatory or autoimmune disorders.

In order that the present invention may be more readily understood, certain terms are first defined. Additional definitions are set forth throughout the detailed description.

The terms "CD22," "BL-CAM," "B3," "Leu-14" and "Lyb-8" are used interchangeably, and include variants, isoforms, and species homologs of CD22. Accordingly, human antibodies of this disclosure may, in certain cases, cross-react with CD22 from species other than human. In certain embodiments, the antibodies may be completely specific for human CD22 and may not exhibit species or other types of non-human cross-reactivity. The complete amino acid sequence of an exemplary human CD22 has Genbank accession number NP_001762 (SEQ ID NO:59).

The human CD22 sequence may differ from human CD22 of SEQ ID NO:59 by having, for example, conserved mutations or mutations in non-conserved regions and the CD22 has substantially the same biological function as the human CD22 of SEQ ID NO:59. For example, a biological function of human CD22 is having an epitope in the extracellular domain of CD22 that is specifically bound by an antibody of the instant disclosure or a biological function of human CD22 is modulation of BCR signalling.

A particular human CD22 sequence will generally be at least 90% identical in amino acids sequence to human CD22 of SEQ ID NO:59 and contains amino acid residues that identify the amino acid sequence as being human when compared to CD22 amino acid sequences of other species (e.g., murine). In certain cases, a human CD22 may be at least 95%, or even at least 96%, 97%, 98%, or 99% identical in amino acid sequence to CD22 of SEQ ID NO:59. In certain embodiments, a human CD22 sequence will display no more than 10 amino acid differences from the CD22 of SEQ ID NO:59. In certain embodiments, the human CD22 may display no more than 5, or even no more than 4, 3, 2, or 1 amino acid difference from the CD22 of SEQ ID NO:59. Percent identity can be determined as described herein.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present disclosure is the CD22 protein.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., CD22). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, Fundamental Immunology (Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii)

an isolated complementarity determining region (CDR); and (viii) a nanobody, a heavy chain variable region containing a single variable domain and two constant domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The abbreviation "$V_K$", as used herein, refers to the variable domain of a kappa light chain, whereas the abbreviation "$V_\lambda$", as used herein, refers to the variable domain of a lambda light chain. The abbreviation "$V_L$", as used herein, refers to the variable domain of an immunoglobulin light chain and thus encompasses both $V_K$ and $V_\lambda$ light chains.

An "isolated antibody", as used herein, is intended to refer to an antibody that is substantially free of other antibodies having different antigenic specificities (e.g., an isolated antibody that specifically binds CD22 is substantially free of antibodies that specifically bind antigens other than CD22). An isolated antibody that specifically binds CD22 may, however, have cross-reactivity to other antigens, such as CD22 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of this disclosure may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity, which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "antibody mimetic" is intended to refer to molecules capable of mimicking an antibody's ability to bind an antigen, but which are not limited to native antibody structures. Examples of such antibody mimetics include, but are not limited to, Affibodies, DARPins, Anticalins, Avimers, and Versabodies, all of which employ binding structures that, while they mimic traditional antibody binding, are generated from and function via distinct mechanisms.

As used herein, the term "partner molecule" refers to the entity which is conjugated to an antibody in an antibody-partner molecule conjugate. Examples of partner molecules include drugs, toxins, marker molecules (including, but not limited to peptide and small molecule markers such as fluorochrome markers, as well as single atom markers such as radioisotopes), proteins and therapeutic agents.

As used herein, an antibody that "specifically binds to human CD22" is intended to refer to an antibody that binds to human CD22 (and possibly CD22 from one or more non-human species) but does not substantially bind to non-CD22 proteins. In certain embodiments, an antibody of the instant disclosure specifically binds to human CD22 of SEQ ID NO:59 or a variant thereof. Preferably, the antibody binds to human CD22 with a $K_D$ of $1\times10^{-7}$ M or less, more preferably $1\times10^{-8}$ M or less, more preferably $5\times10^{-9}$ M or less, more preferably $1\times10^{-9}$ M or less, even more preferably $5\times10^{-10}$ M or less, and even more preferably $7\times10^{-11}$ or less.

The term "does not substantially bind" to a protein or cells, as used herein, means does not bind or does not bind with a high affinity to the protein or cells, i.e. binds to the protein or cells with a $K_D$ of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The term "$K_{assoc}$" or "$K_a$", as used herein, is intended to refer to the association rate of a particular antibody-antigen interaction, whereas the term "Ic$_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $1\times10^{-7}$ M or less, more preferably $5\times10^{-8}$ M or less, even more preferably $1\times10^{-8}$ M or less, even more preferably $5\times10^{-9}$ M or less and even more preferably $1\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

The symbol "-", whether utilized as a bond or displayed perpendicular to a bond, indicates the point at which the displayed moiety is attached to the remainder of the molecule, solid support, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "het-eroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, and S, and wherein the nitrogen, carbon and sulfur atoms may optionally be oxidized and the nitrogen heteroatom may optionally be quaternized. The heteroatom(s) O, N, S, and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). The terms "heteroalkyl" and "heteroalkylene" encompass poly(ethylene glycol) and its derivatives (see, for example, Shearwater Polymers Catalog, 2001). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The term "lower" in combination with the terms "alkyl" or "heteroalkyl" refers to a moiety having from 1 to 6 carbon atoms.

The terms "alkoxy," "alkylamino," "alkylsulfonyl," and "alkylthio" (or thioalkoxy) are used in their conventional sense, and refer to those alkyl groups attached to the remainder of the molecule via an oxygen atom, an amino group, an $SO_2$ group or a sulfur atom, respectively. The term "arylsulfonyl" refers to an aryl group attached to the remainder of the molecule via an $SO_2$ group, and the term "sulfhydryl" refers to an SH group.

In general, an "acyl substituent" is also selected from the group set forth above. As used herein, the term "acyl substituent" refers to groups attached to, and fulfilling the valence of a carbonyl carbon that is either directly or indirectly attached to the polycyclic nucleus of the compounds of the present invention.

The terms "cycloalkyl" and "heterocycloalkyl", by themselves or in combination with other terms, represent, unless otherwise stated, cyclic versions of substituted or unsubstituted "alkyl" and substituted or unsubstituted "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The heteroatoms and carbon atoms of the cyclic structures are optionally oxidized.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a substituted or unsubstituted polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen, carbon and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Aryl" and "heteroaryl" also encompass ring systems in which one or more non-aromatic ring systems are fused, or otherwise bound, to an aryl or heteroaryl system.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroalkyl substituents," respectively, and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R'" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R'"' groups when more than one of these groups is present. When R' and R" are attached to the same nitrogen atom, they can be combined with the nitrogen atom to form a 5, 6, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, the aryl substituents and heteroaryl substituents are generally referred to as "aryl substituents" and "heteroaryl substituents," respectively, and are varied and selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R'" are preferably independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. When a compound of the invention includes more than one R group, for example, each of the R groups is independently selected as are each R', R", R'" and R'" groups when more than one of these groups is present.

Two of the aryl substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$-$C_6$) alkyl.

As used herein, the term "diphosphate" includes but is not limited to an ester of phosphoric acid containing two phosphate groups. The term "triphosphate" includes but is not limited to an ester of phosphoric acid containing three phosphate groups. For example, particular drugs having a diphosphate or a triphosphate include:

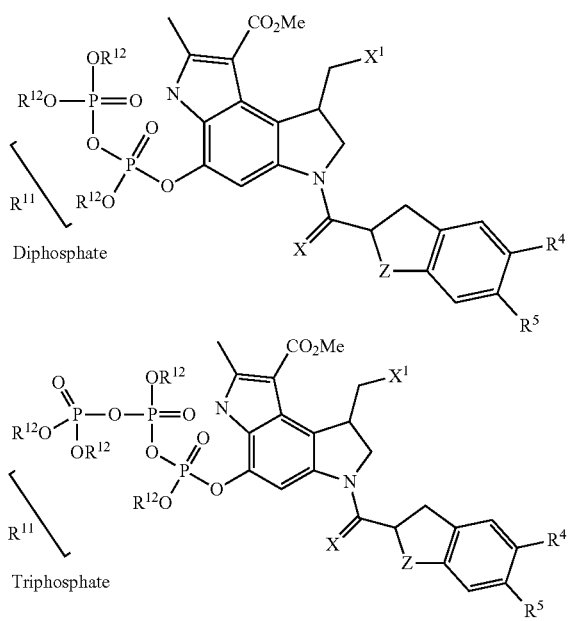

Diphosphate

Triphosphate

As used herein, the term "heteroatom" includes oxygen (O), nitrogen (N), sulfur (S) and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

Various aspects of this disclosure are described in further detail in the following subsections.

Anti-CD22 Antibodies

The antibodies of this disclosure are characterized by particular functional features or properties of the antibodies. For example, the antibodies bind specifically to human CD22. Preferably, an antibody of the invention binds to CD22 with high affinity, for example with a $K_D$ of $1 \times 10^{-7}$ M or less.

The anti-CD22 antibodies of this disclosure preferably exhibit one or more of the following characteristics:

(a) internalizing into $CD22^+$ cells;

(b) exhibiting antibody dependent cellular cytotoxicity (ADCC) against $CD22^+$ cells;

(c) enhancing cell death of Ramos cells induced by B cell receptor (BCR) stimulation, and (d) inhibits growth of CD22-expressing cells in vivo when conjugated to a cytotoxin.

In preferred embodiments, the antibody exhibits at least two of properties (a), (b), (c) and (d). In yet another embodiment, the antibody exhibits three of properties (a), (b), (c) and (d). In another embodiment, the antibody exhibits all four of properties (a), (b), (c), and (d).

While the anti-CD22 antibodies of the invention exhibit certain functional properties, in certain embodiments another feature of the antibodies is that they do not exhibit other particular functional properties. For example, in certain embodiments, the antibody does not have a direct anti-proliferative effect on Ramos cells. In other embodiments, the antibody does not induce calcium flux in Ramos cells. In yet other embodiments, the antibody does not mediate complement dependent cytotoxicity (CDC) on Ramos cells.

It is noted that it has been reported that a humanized anti-CD22 antibody, epratuzumab, lacked a direct anti-proliferative effect and CDC activity against non-Hodgkin's lymphoma cell lines yet the antibody did mediate cytotoxic effects against the cell lines by other means (see Carnahan, J. et al. (2006) *Mol. Immunol.* 44:1331-1341).

Preferably, an antibody of this disclosure binds to human CD22 with a $K_D$ of $1 \times 10^{-7}$ M or less, binds to human CD22 with a $K_D$ of $1 \times 10^{-8}$ M or less, binds to human CD22 with a $K_D$ of $5 \times 10^{-9}$ M or less, binds to human CD22 with a $K_D$ of $3 \times 10^{-9}$ M or less, binds to human CD22 with a $K_D$ of $1 \times 10^{-9}$ M or less, or binds to human CD22 with a $K_D$ of $5 \times 10^{-10}$ M or less, or binds to human CD22 with a $K_D$ of $1 \times 10^{-10}$ or binds to human CD22 with a $K_D$ of $7 \times 10^{-11}$ M or less.

Standard assays to evaluate the binding affinity of the antibodies toward human CD22 are known in the art, including for example, ELISA and BIAcore analysis with recombinant CD22 (see Example 3). The Examples also provide detailed descriptions of suitable assays for evaluating antibody internalization (Example 4), ADCC activity (Example 5), enhancement of cell death induced by BCR stimulation (Example 7), direct anti-proliferative effects of antibodies (Example 8), induction of calcium flux (Example 6), and CDC activity (Example 9), and anti-proliferative effects of antibody-drug immunoconjugates on solid tumor cell proliferation in vivo (Example 10).

Monoclonal Antibodies 12C5, 19A3, CD22.1, CD22.2, 16F7, 23C6, 4G6 and 21F6

Preferred antibodies of this disclosure are the human monoclonal antibodies 12C5, 19A3, 16F7, 23C6, 4G6 and 21F6, and the recombinant human monoclonal antibodies CD22.1, CD22.2, all of which were isolated and structurally characterized as described in Examples 1 and 2.

The $V_H$ amino acid sequences of 12C5, 19A3, CD22.1, CD22.2, 16F7, 23C6, 4G6 and 21F6 are shown in SEQ ID NOs: 31, 32, 61, 33, 34, 81, 82 and 83, respectively, wherein the heavy chains of 19A3 and CD22.1 are identical and correspond to SEQ ID NO:32 and the $V_H$ heavy chain of 21F6 correspond to either SEQ ID NO:82 or 83

The $V_L$ amino acid sequences of 12C5, 19A3, CD22.1, CD22.2, 16F7, 23C6, 4G6 and 21F6 are shown in SEQ ID NOs:35, 36, 37, 38, 39, 40, 84, 85 and 86, respectively, wherein the kappa light chains of 19A3, CD22.1 and CD22.2 are identical and correspond to SEQ ID NO:36, the kappa light chain of 16F7 corresponds to either SEQ ID NO:37 or 38, the kappa light chain of 23C6 corresponds to either SEQ ID NO:39 or 40, and the kappa light chain of 4G6 corresponds to either SEQ ID NO: 84 or 85.

Given that each of these antibodies can bind to CD22, the $V_H$ and $V_L$ sequences can be "mixed and matched" to create other anti-CD22 binding molecules of this disclosure. CD22 binding of such "mixed and matched" antibodies can be tested using the binding assays described above and in the Examples (e.g., ELISA or flow cytometry). Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one aspect, this disclosure provides an isolated monoclonal antibody, or antigen binding portion thereof comprising:

(a) a heavy chain variable region comprising an amino acid sequence selected from the group consisting of SEQ ID NOs:31-34, 61 and 81-83; and (b) a light chain variable region comprising an amino acid sequence selected from the group consisting of SEQ ID NOs:35-40 and 84-86;

wherein the antibody specifically binds CD22, preferably human CD22.

Preferred heavy and light chain combinations include:
(a) a heavy chain variable region comprising the amino acid sequence of SEQ ID NO:31 and a light chain variable region comprising the amino acid sequence of SEQ ID NO:35; or
(b) a heavy chain variable region comprising the amino acid sequence of SEQ ID NO:32 or 61, and a light chain variable region comprising the amino acid sequence of SEQ ID NO:36; or
(c) a heavy chain variable region comprising the amino acid sequence of SEQ ID NO:33 and a light chain variable region comprising the amino acid sequence of SEQ ID NO:37 or 38; or
(d) a heavy chain variable region comprising the amino acid sequence of SEQ ID NO:34 and a light chain variable region comprising the amino acid sequence of SEQ ID NO:39 or 40; or
(e) a heavy chain variable region comprising the amino acid sequence of SEQ ID NO:81 and a light chain variable region comprising the amino acid sequence of SEQ ID NO:84 or 85; or
(f) a heavy chain variable region comprising the amino acid sequence of SEQ ID NO:82 or 83 or and a light chain variable region comprising the amino acid sequence of SEQ ID NO:86.

In another aspect, this disclosure provides antibodies that comprise the heavy chain and light chain CDR1s, CDR2s and CDR3s of 12C5, 19A3, CD22.1, CD22.2, 16F7, 23C6, 4G6, 21F6, or combinations thereof.

The amino acid sequences of the $V_H$ CDR1s of 12C5, 19A3, CD22.1, CD22.2, 16F7, 23C6, 4G6 and 21F6 are shown in SEQ ID NOs: 1-4 and 63-65, respectively (wherein the CDR1s of the $V_H$ sequences of 19A3, CD22.1 and CD22.2 are identical and are shown in SEQ ID NO:2, and the CDR1s of the $V_H$1 and $V_H$2 sequences of 21F6 are identical and are shown in SEQ ID NOs: 64 and 65, respectively.

The amino acid sequences of the $V_H$ CDR2s of 12C5, 19A3, CD22.1, 16F7, 23C6, CD22.2, 4G6 and 21F6 are shown in SEQ ID NOs: 5-8, 60, and 66-68, respectively (wherein the CDR2s of the $V_H$ sequences of 19A3 and CD22.1 are identical and are shown in SEQ ID NO:6, the CDR2 of the $V_H$ sequence of CD22.2 is shown in SEQ ID NO:60, and the CDR2s of the $V_H$1 and $V_H$2 sequences of 21F6 are shown in SEQ ID NOs:67 and 68).

The amino acid sequences of the $V_H$ CDR3s of 12C5, 19A3, CD22.1, CD22.2, 16F7, 23C6, 4G6 and 21F6 are shown in SEQ ID NOs: 9-12 and 69-71, respectively (wherein the CDR3s of the $V_H$ sequences of 19A3, CD22.1 and CD22.2 are identical and are shown in SEQ ID NO:10, and the CDR3s of the $V_H$1 and $V_H$2 sequences of 21F6 are shown in SEQ ID NOs:70 and 71).

The amino acid sequences of the $V_L$ CDR1s of 12C5, 19A3, CD22.1, CD22.2, 16F7, 23C6, 4G6 and 21F6 are shown in SEQ ID NOs: 13-18 and 72-74, respectively (wherein the CDR1s of the $V_K$ sequences of 19A3, CD22.1 and CD22.2 are identical, and are shown in SEQ ID NO:14, the CDR1s of the $V_K$.1 and $V_K$.2 sequences of 16F7 are shown in SEQ ID NOs: 15 and 16, the CDR1s of the $V_K$.1 and $V_K$.2 sequences of 23C6 are shown in SEQ ID NOs: 17 and 18, and the CDR1s of the $V_K$.1 and $V_K$.2 sequences of 4G6 are shown in SEQ ID NOs 72 and 73).

The amino acid sequences of the $V_L$ CDR2s of 12C5, 19A3, CD22.1, CD22.2, 16F7, 23C6, 4G6 and 21F6 are shown in SEQ ID NOs: 19-24 and 75-77, respectively (wherein the CDR2s of the $V_K$ sequences of 19A3, CD22.1 and CD22.2 are identical, and are shown in SEQ ID NO:20, the CDR2s of the $V_K$.1 and $V_K$.2 sequences of 16F7 are shown in SEQ ID NOs: 21 and 22, the CDR2s of the $V_K$.1 and $V_K$.2 sequences of 23C6 are shown in SEQ ID NOs: 23 and 24, and the CDR2s of the $V_K$.1 and $V_K$.2 sequences of 4G6 are shown in SEQ ID NOs: 75 and 76).

The amino acid sequences of the $V_L$ CDR1s of 12C5, 19A3, CD22.1, CD22.2, 16F7, 23C6, 4G6 and 21F6 are shown in SEQ ID NOs: 25-30 and 78-80, respectively (wherein the CDR3s of the $V_K$ sequences of 19A3, CD22.1 and CD22.2 are identical, and are shown in SEQ ID NO:26, the CDR3s of the $V_K$.1 and $V_K$.2 sequences of 16F7 are shown in SEQ ID NOs: 27 and 28, the CDR3s of the $V_K$.1 and $V_K$.2 sequences of 23C6 are shown in SEQ ID NOs: 29 and 30, and the CDR3s of the $V_K$.1 and $V_K$.2 sequences of 4G6 are shown in SEQ ID NOs: 78 and 79).

The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to CD22 and that antigen-binding specificity is provided primarily by the CDR1, CDR2, and CDR3 regions, the $V_H$ CDR1, CDR2, and CDR3 sequences and $V_L$ CDR1, CDR2, and CDR3 sequences can be "mixed and matched" (i.e., CDRs from different antibodies can be mixed and match, although each antibody must contain a $V_H$ CDR1, CDR2, and CDR3 and a $V_L$ CDR1, CDR2, and CDR3) to create other anti-CD22 binding molecules of this disclosure. CD22 binding of such "mixed and matched" antibodies can be tested using the binding assays described above and in the Examples (e.g., ELISAs, Biacore® analysis). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_L$ CDR sequences are mixed and matched, the CDR1, CDR2 and/or CDR3 sequence from a particular $V_L$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies antibodies CDR1s of 12C5, 19A3, CD22.1, CD22.2, 16F7, 23C6, 4G6 and 21F6.

Accordingly, in another aspect, this disclosure provides an isolated monoclonal antibody, or antigen binding portion thereof comprising:
(a) a heavy chain variable region CDR1 comprising an amino acid sequence selected from the group consisting of SEQ ID NOs: 1-4 and 63-65;
(b) a heavy chain variable region CDR2 comprising an amino acid sequence selected from the group consisting of SEQ ID NOs: 5-8, 60 and 66-68;
(c) a heavy chain variable region CDR3 comprising an amino acid sequence selected from the group consisting of SEQ ID NOs: 9-12 and 69-71;
(d) a light chain variable region CDR1 comprising an amino acid sequence selected from the group consisting of SEQ ID NOs: 13-18 and 72-74;
(e) a light chain variable region CDR2 comprising an amino acid sequence selected from the group consisting of SEQ ID NOs: 19-24 and 75-77; and (f) a light chain variable region CDR3 comprising an amino acid sequence selected from the group consisting of SEQ ID NOs: 25-30 and 78-80;

wherein the antibody specifically binds CD22, preferably human CD22.

In a preferred embodiment, the antibody comprises:
(a) a heavy chain variable region CDR1 comprising SEQ ID NO:1;
(b) a heavy chain variable region CDR2 comprising SEQ ID NO:5;
(c) a heavy chain variable region CDR3 comprising SEQ ID NO:9;
(d) a light chain variable region CDR1 comprising SEQ ID NO:13;
(e) a light chain variable region CDR2 comprising SEQ ID NO:19; and
(f) a light chain variable region CDR3 comprising SEQ ID NO:25.

In another preferred embodiment, the antibody comprises:
(a) a heavy chain variable region CDR1 comprising SEQ ID NO:2;
(b) a heavy chain variable region CDR2 comprising SEQ ID NO:6 or 60;
(c) a heavy chain variable region CDR3 comprising SEQ ID NO:10;
(d) a light chain variable region CDR1 comprising SEQ ID NO:14;
(e) a light chain variable region CDR2 comprising SEQ ID NO:20; and
(f) a light chain variable region CDR3 comprising SEQ ID NO:26.

In another preferred embodiment, the antibody comprises:
(a) a heavy chain variable region CDR1 comprising SEQ ID NO:3;
(b) a heavy chain variable region CDR2 comprising SEQ ID NO:7;
(c) a heavy chain variable region CDR3 comprising SEQ ID NO:11;
(d) a light chain variable region CDR1 comprising SEQ ID NO:15 or 16;
(e) a light chain variable region CDR2 comprising SEQ ID NO:21 or 22; and
(f) a light chain variable region CDR3 comprising SEQ ID NO:27 or 28.

In another preferred embodiment, the antibody comprises:
(a) a heavy chain variable region CDR1 comprising SEQ ID NO:4;
(b) a heavy chain variable region CDR2 comprising SEQ ID NO:8;
(c) a heavy chain variable region CDR3 comprising SEQ ID NO:12;
(d) a light chain variable region CDR1 comprising SEQ ID NO:17 or 18;
(e) a light chain variable region CDR2 comprising SEQ ID NO:23 or 24; and
(f) a light chain variable region CDR3 comprising SEQ ID NO:29 or 30.

In another preferred embodiment, the antibody comprises:
(a) a heavy chain variable region CDR1 comprising SEQ ID NO:63;
(b) a heavy chain variable region CDR2 comprising SEQ ID $NO_{66}$;
(c) a heavy chain variable region CDR3 comprising SEQ ID NO:69;
(d) a light chain variable region CDR1 comprising SEQ ID NO:72 or 73;
(e) a light chain variable region CDR2 comprising SEQ ID NO:75 or 76; and
(f) a light chain variable region CDR3 comprising SEQ ID NO:78 or 79.

In another preferred embodiment, the antibody comprises:
(a) a heavy chain variable region CDR1 comprising SEQ ID NO:64 or 65;
(b) a heavy chain variable region CDR2 comprising SEQ ID NO:67 or 68;
(c) a heavy chain variable region CDR3 comprising SEQ ID NO:70 or 71;
(d) a light chain variable region CDR1 comprising SEQ ID NO:74;
(e) a light chain variable region CDR2 comprising SEQ ID NO:77; and
(f) a light chain variable region CDR3 comprising SEQ ID NO:80.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al., *British J. of Cancer* 83(2):252-260 (2000) (describing the production of a humanized anti-CD30 antibody using only the heavy chain variable domain CDR3 of murine anti-CD30 antibody Ki-4); Beiboer et al., *J. Mol. Biol.* 296:833-849 (2000) (describing recombinant epithelial glycoprotein-2 (EGP-2) antibodies using only the heavy chain CDR3 sequence of the parental murine MOC-31 anti-EGP-2 antibody); Rader et al., *Proc. Natl. Acad. Sci. U.S.A.* 95:8910-8915 (1998) (describing a panel of humanized anti-integrin $\alpha_v\beta_3$ antibodies using a heavy and light chain variable CDR3 domain of a murine anti-integrin $\alpha_v\beta_3$ antibody LM609 wherein each member antibody comprises a distinct sequence outside the CDR3 domain and capable of binding the same epitope as the parent muring antibody with affinities as high or higher than the parent murine antibody); Barbas et al., *J. Am. Chem. Soc.* 116:2161-2162 (1994) (disclosing that the CDR3 domain provides the most significant contribution to antigen binding); Barbas et al., *Proc. Natl. Acad. Sci. U.S.A.* 92:2529-2533 (1995) (describing the grafting of heavy chain CDR3 seqeunces of three Fabs (SI-1, SI-40, and SI-32) against human placental DNA onto the heavy chain of an anti-tetanus toxoid Fab thereby replacing the existing heavy chain CDR3 and demonstrating that the CDR3 domain alone conferred binding specificity); Ditzel et al., *J. Immunol.* 157:739-749 (1996) (describing grafting studies wherein transfer of only the heavy chain CDR3 of a parent polyspecific Fab LNA3 to a heavy chain of a monospecific IgG tetanus toxoid-binding Fab p313 antibody was sufficient to retain binding specificity of the parent Fab); Berezov et al., *BIAjournal* 8:Scientific Review 8 (2001) (describing peptide mimetics based on the CDR3 of an anti-HER2 monoclonal antibody; Igarashi et al., *J. Biochem (Tokyo)* 117:452-7 (1995) (describing a 12 amino acid synthetic polypeptide corresponding to the CDR3 domain of an anti-phosphatidylserine antibody); Bourgeois et al., *J. Virol* 72:807-10 (1998) (showing that a single peptide derived form the heavy chain CDR3 domain of an anti-respiratory syncytial virus (RSV) antibody was capable of neutralizing the virus in vitro); Levi et al., *Proc. Natl. Acad. Sci. U.S.A.* 90:4374-8 (1993) (describing a peptide based on the heavy chain CDR3 domain of a murine anti-HIV antibody); Polymenis and Stoller, *J. Immunol.* 152:5218-5329 (1994) (describing enabling binding of an scFv by grafting the heavy chain CDR3 region of a Z-DNA-binding antibody) and Xu and Davis, *Immunity* 13:37-45 (2000) (describing that diversity at the heavy chain CDR3 is sufficient to permit otherwise identical IgM molecules to distinguish between a variety of hapten and protein antigens). See also, U.S. Pat. Nos. 6,951,646; 6,914,128; 6,090,382; 6,818,216; 6,156,313; 6,827,925; 5,833,943; 5,762,905 and 5,760,185, describing patented antibodies defined by a single CDR domain. Each of these references is hereby incorporated by reference in its entirety.

Accordingly, the present disclosure provides monoclonal antibodies comprising one or more heavy and/or light chain CDR3 domains from an antibody derived from a human or non-human animal, wherein the monoclonal antibody is capable of specifically binding to CD22. Within certain aspects, the present disclosure provides monoclonal antibodies comprising one or more heavy and/or light chain CDR3 domain from a non-human antibody, such as a mouse or rat antibody, wherein the monoclonal antibody is capable of specifically binding to CD22. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

Within other aspects, the present disclosure provides monoclonal antibodies comprising one or more heavy and/or light chain CDR3 domain from a human antibody, such as, for example, a human antibody obtained from a non-human animal, wherein the human antibody is capable of specifically binding to CD22. Within other aspects, the present disclosure provides monoclonal antibodies comprising one or more heavy and/or light chain CDR3 domain from a first human antibody, such as, for example, a human antibody obtained from a non-human animal, wherein the first human antibody is capable of specifically binding to CD22 and wherein the CDR3 domain from the first human antibody replaces a CDR3 domain in a human antibody that is lacking binding specificity for CD22 to generate a second human antibody that is capable of specifically binding to CD22. Within some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody.

Antibodies Having Particular Germline Sequences

In certain embodiments, an antibody of this disclosure comprises a heavy chain variable region from a particular germline heavy chain immunoglobulin gene and/or a light chain variable region from a particular germline light chain immunoglobulin gene.

For example, in a preferred embodiment, this disclosure provides an isolated monoclonal antibody, or an antigen-binding portion thereof, comprising a heavy chain variable region that is the product of or derived from a human $V_H$ 7-4.1 gene, a human $V_H$ 4-34 gene, a human $V_H$ 5-51 gene, or a human $V_H$ 1-69 gene, wherein the antibody specifically binds CD22.

In another preferred embodiment, this disclosure provides an isolated monoclonal antibody, or an antigen-binding portion thereof, comprising a light chain variable region that is the product of or derived from a human V), 2b2 gene, a human $V_K$ L6 gene, a human $V_K$ A27 gene, a human $V_K$ A10 gene, or a human $V_K$ L18 gene, wherein the antibody specifically binds CD22.

In yet another preferred embodiment, this disclosure provides an isolated monoclonal antibody, or antigen-binding portion thereof, wherein the antibody comprises a heavy chain variable region that is the product of or derived from a human $V_H$ 7-4.1 gene and comprises a light chain variable region that is the product of or derived from a human $V_\lambda$ 2b2 gene, wherein the antibody specifically binds to CD22, preferably human CD22.

In yet another preferred embodiment, this disclosure provides an isolated monoclonal antibody, or antigen-binding portion thereof, wherein the antibody comprises a heavy chain variable region that is the product of or derived from a human $V_H$ 4-34 gene and comprises a light chain variable region that is the product of or derived from a human $V_K$ L6 gene, wherein the antibody specifically binds to CD22, preferably human CD22.

In yet another preferred embodiment, this disclosure provides an isolated monoclonal antibody, or antigen-binding portion thereof, wherein the antibody comprises a heavy chain variable region that is the product of or derived from a human $V_H$ 5-51 gene and comprises a light chain variable region that is the product of or derived from a human $V_K$ A27 or A10 gene, wherein the antibody specifically binds to CD22, preferably human CD22.

In yet another preferred embodiment, this disclosure provides an isolated monoclonal antibody, or antigen-binding portion thereof, wherein the antibody comprises a heavy chain variable region that is the product of or derived from a human $V_H$ 1-69 gene and comprises a light chain variable region that is the product of or derived from a human $V_K$ L6 gene, wherein the antibody specifically binds to CD22, preferably human CD22.

In yet another preferred embodiment, this disclosure provides an isolated monoclonal antibody, or antigen-binding portion thereof, wherein the antibody comprises a heavy chain variable region that is the product of or derived from a human $V_H$ 1-69 gene and comprises a light chain variable region that is the product of or derived from a human $V_K$ A27 or L18 gene, wherein the antibody specifically binds to CD22, preferably human CD22.

Such antibodies also may possess one or more of the functional characteristics described in detail above, such as internalization into CD22+ cells, ADCC activity against CD22+ cells and/or enahancement of cell death of Ramos cells induced by BCR stimulationa cytotoxin.

An example of an antibody having $V_H$ and $V_L$ of $V_H$ 7-4.1 and V), 2b2, respectively, is the 12C5 antibody. An example of an antibody having $V_H$ and $V_L$ of $V_H$ 4-34 and $V_K$ L6, respectively, is the 19A3 antibody. Another example of an antibody having $V_H$ and $V_L$ of $V_H$ 4-34 and $V_K$ L6, respectively, is the CD22.1 antibody. Another example of an antibody having $V_H$ and $V_L$ of $V_H$ 4-34 and $V_K$ L6, respectively, wherein the $V_H$ chain includes an N57Q mutation, is the CD22.2 antibody. Another example of an antibody having $V_H$ and $V_L$ of $V_H$ 4-34 and $V_K$ L6 germline, respectively, is the 21F6 antibody. An example of an antibody having $V_H$ and $V_L$ of $V_H$ 5-51 and $V_K$ A27 or A10, respectively, is the 16F7 antibody. An example of an antibody having $V_H$ and $V_L$ of $V_H$ 1-69 and $V_K$ L6, respectively, is the 23C6 antibody. An example of an antibody having $V_H$ and $V_L$ of $V_H$ 1-69 and $V_K$ A27 or L18, respectively, is the 4G6 antibody.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of this disclosure comprises heavy and light chain variable regions comprising amino acid sequences that are homologous to the amino acid sequences of the preferred antibodies described herein, and wherein the antibodies retain the desired functional properties of the anti-CD22 antibodies of this disclosure.

For example, this disclosure provides an isolated monoclonal antibody, or antigen binding portion thereof, comprising a heavy chain variable region and a light chain variable region, wherein:

(a) the heavy chain variable region comprises an amino acid sequence that is at least 80% homologous to an amino acid sequence selected from the group consisting of SEQ ID NOs:31-34, 61 and 81-83;

(b) the light chain variable region comprises an amino acid sequence that is at least 80% homologous to an amino acid sequence selected from the group consisting of SEQ ID NOs:35-40 and 84-86;

(c) the antibody specifically binds to human CD22.

Additionally or alternatively, the antibody may possess one or more of the following functional properties: (a) binds to human CD22 with a $K_D$ of $1\times10^{-7}$ M or less; (b) internalizes into CD22+ cells; (c) exhibits ADCC activity on CD22+ cells; (d) enhances cell death of Ramos cells induced by, for example, BCR stimulation; and/or (e) inhibits growth of CD22-expressing cells in vivo when conjugated to a cytotoxin.

In various embodiments, the antibody can be, for example, a human antibody, a humanized antibody or a chimeric antibody.

In other embodiments, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding SEQ ID NOs:41-44, 62, or 87-89, or SEQ ID NOs:45-50 or 90-92, followed by testing of the encoded altered antibody for retained function (i.e., the functions set forth above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appi. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present disclosure can further be used as a "query sequence" to perform a search against public databases to, for example, to identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of this disclosure. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) are useful. See www.ncbi.nlm.nih.gov.

Antibodies with Conservative Modifications

In certain embodiments, an antibody of this disclosure comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 12C5, 19A3, CD22.1, CD22.2, 16F7, 23C6, 4G6 and 21F6), or conservative modifications thereof, and wherein the antibodies retain the desired functional properties of the anti-CD22 antibodies of this disclosure. It is understood in the art that certain conservative sequence modification can be made which do not remove antigen binding. See, for example, Brummell et al. (1993) *Biochem* 32:1180-8 (describing mutational analysis in the CDR3 heavy chain domain of antibodies specific for *Salmonella*); de Wildt et al. (1997) *Prot. Eng.* 10:835-41

(describing mutation studies in anti-UA 1 antibodies); Komissarov et al. (1997) *J. Biol. Chem.* 272:26864-26870 (showing that mutations in the middle of HCDR3 led to either abolished or diminished affinity); Hall et al. (1992) *J. Immunol.* 149:1605-12 (describing that a single amino acid change in the CDR3 region abolished binding activity); Kelley and O'Connell (1993) *Biochem.* 32:6862-35 (describing the contribution of Tyr residues in antigen binding); Adib-Conquy et al. (1998) *Int. Immunol.* 10:341-6 (describing the effect of hydrophobicity in binding) and Beers et al. (2000) *Clin. Can. Res.* 6:2835-43 (describing HCDR3 amino acid mutants).

Accordingly, this disclosure provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of amino acid sequences of SEQ ID NOs: 9-12, 69-71 and conservative modifications thereof;

(b) the light chain variable region CDR3 sequence comprises an amino acid sequence selected from the group consisting of amino acid sequence of SEQ ID NOs: 25-30, 79-80, and conservative modifications thereof; and (c) the antibody specifically binds to human CD22.

Additionally or alternatively, the antibody may possess one or more of the following functional properties: (a) binds to human CD22 with a $K_D$ of $1 \times 10^{-7}$ M or less; (b) internalizes into CD22+ cells; (c) exhibits ADCC activity on CD22+ cells; and/or (d) enhances cell death of Ramos cells induced by BCR stimulation; and/or (e) inhibits growth of CD22-expressing cells in vivo when conjugated to a cytotoxin.

In a preferred embodiment, the heavy chain variable region CDR2 sequence comprises an amino acid sequence selected from the group consisting of amino acid sequences of SEQ ID NOs:5-8, 60, 66-68, and conservative modifications thereof; and the light chain variable region CDR2 sequence comprises an amino acid sequence selected from the group consisting of amino acid sequences of SEQ ID NOs:19-24, 75-77, and conservative modifications thereof. In another preferred embodiment, the heavy chain variable region CDR1 sequence comprises an amino acid sequence selected from the group consisting of amino acid sequences of SEQ ID NOs:1-4, 63-65, and conservative modifications thereof; and the light chain variable region CDR1 sequence comprises an amino acid sequence selected from the group consisting of amino acid sequences of SEQ ID NOs:13-18, 72-74, and conservative modifications thereof.

In various embodiments, the antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of this disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of this disclosure can be replaced with other amino acid residues from the same side chain family and the altered antibody can be tested for retained function (i.e., the functions set forth above) using the functional assays described herein.

Antibodies that Bind to the Same Epitope as Anti-CD22 Antibodies

In another embodiment, this disclosure provides antibodies that bind to the same epitope on human CD22 that are recognized by any of the anti-CD22 monoclonal antibodies of this disclosure (i.e., antibodies that have the ability to cross-compete for binding to CD22 with any of the monoclonal antibodies of this disclosure). In preferred embodiments, the reference antibody for cross-competition studies can be the monoclonal antibody 12C5 (having $V_H$ and $V_L$ sequences as shown in SEQ ID NOs:31 and 35, respectively), or the monoclonal antibody 19A3 or the monoclonal antibody CD22.1 or the monoclonal antibody CD22.2 (having $V_H$ and $V_L$ sequences as shown in SEQ ID NOs:32/61 and 36, respectively) or the monoclonal antibody 16F7 (having $V_H$ and $V_L$ sequences as shown in SEQ ID NOs:33 and 37/38, respectively) or the monoclonal antibody 23C6 (having $V_H$ and $V_L$ sequences as shown in SEQ ID NOs:34 and 39/40, respectively), or the monoclonal antibody 4G6 (having $V_H$ and $V_L$ sequences as shown in SEQ ID NOs:81 and 84/85, respectively) or the monoclonal antibody 21F6 (having $V_H$ and $V_L$ sequences as shown in SEQ ID NOs: 82/83 and 86, respectively).

Such cross-competing antibodies can be identified based on their ability to cross-compete with 12C5, 19A3, CD22.1, CD22.2, 16F7, 23C6, 4G6 and 21F6 in standard CD22 binding assays. For example, standard ELISA assays can be used in which recombinant CD22 is immoblized on the plate, one of the antibodies is fluorescently labeled and the ability of non-labeled antibodies to compete off the binding of the labeled antibody is evaluated. Additionally or alternatively, BIAcore analysis can be used to assess the ability of the antibodies to cross-compete, as described in Example 3 (regarding the epitope grouping of 12C5, 19A3, CD22.1, CD22.2, 16F7, 23C6, 4G6 and 21F6). The ability of a test antibody to inhibit the binding of, for example, 12C5, 19A3, CD22.1, CD22.2, 16F7, 23C6, 4G6 and 21F6 to human CD22 demonstrates that the test antibody can compete with 12C5, 19A3, CD22.1, CD22.2, 16F7, 23C6, 4G6 and 21F6 for binding to human CD22 and thus binds to the same epitope on human CD22 as is recognized by 12C5, 19A3, CD22.1, CD22.2, 16F7, 23C6, 4G6 and 21F6. As described in detail in Example 3, the antibodies 12C5, 19A3, CD22.1, CD22.2, 16F7, 23C6, 4G6 and 21F6, each bind to a distinct epitope on CD22 and thus belong to distinct epitope groups. In a preferred embodiment, the antibody that binds to the same epitope on 12C5, 19A3, CD22.1, CD22.2, 16F7, 23C6, 4G6 and 21F6 is a human monoclonal antibody. Such human monoclonal antibodies can be prepared and isolated as described in the Examples.

Engineered and Modified Antibodies

An antibody of this disclosure further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of this disclosure pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs:1-4 and 63-65, SEQ ID NOs:5-8, 60, and 66-68, and SEQ ID NOs:9-12 and 69-71, respectively; and a light chain variable region comprising CDR1, CDR2, and CDR3 sequences comprising an amino acid sequence selected from the group consisting of SEQ ID NOs:13-18 and 72-74, SEQ ID NOs:19-24 and 75-77, and SEQ ID NOs:25-30 and 78-80, respectively. Thus, such antibodies contain the $V_H$ and $V_L$ CDR sequences of monoclonal antibodies 12C5, 19A3, CD22.1, CD22.2, 16F7, 23C6, 4G6 and 21F6, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank accession numbers: 1-69 (NG_0010109, NT_024637 and BC070333), 3-33 (NG_0010109 and NT_024637) and 3-7 (NG_0010109 and NT_024637). As another example, the following heavy chain germline sequences found in the HCo12 HuMAb mouse are available in the accompanying Genbank accession numbers: 1-69 (NG_0010109, NT_024637 and BC070333), 5-51 (NG_0010109 and NT_024637), 4-34 (NG_0010109 and NT_024637), 3-30.3 (CAJ556644) and 3-23 (AJ406678).

Antibody protein sequences are compared against a compiled protein sequence database using one of the sequence similarity searching methods called the Gapped BLAST (Altschul et al. (1997) *Nucleic Acids Research* 25:3389-3402), which is well known to those skilled in the art. BLAST is a heuristic algorithm in that a statistically significant alignment between the antibody sequence and the database sequence is likely to contain high-scoring segment pairs (HSP) of aligned words. Segment pairs whose scores cannot be improved by extension or trimming is called a hit. Briefly, the nucleotide sequences of VBASE origin (http://vbase.mrc-cpe.cam.ac.uk/vbase1/list2.php) are translated and the region between and including FR1 through FR3 framework region is retained. The database sequences have an average length of 98 residues. Duplicate sequences which are exact matches over the entire length of the protein are removed. A BLAST search for proteins using the program blastp with default, standard parameters except the low complexity filter, which is turned off, and the substitution matrix of BLOSUM62, filters for top 5 hits yielding sequence matches. The nucleotide sequences are translated in all six frames and the frame with no stop codons in the matching segment of the database sequence is considered the potential hit. This is in turn confirmed using the BLAST program tblastx, which translates the antibody sequence in all six frames and compares those translations to the VBASE nucleotide sequences dynamically translated in all six frames.

The identities are exact amino acid matches between the antibody sequence and the protein database over the entire length of the sequence. The positives (identities+substitution match) are not identical but amino acid substitutions guided by the BLOSUM62 substitution matrix. If the antibody sequence matches two of the database sequences with same identity, the hit with most positives would be decided to be the matching sequence hit.

Preferred framework sequences for use in the antibodies of this disclosure are those that are structurally similar to the framework sequences used by selected antibodies of this disclosure, e.g., similar to the $V_H$ 7-4.1 (SEQ ID NO:51), $V_H$ 4-34 (SEQ ID NO:52), $V_H$ 5-51 (SEQ ID NO:53), or $V_H$ 1-69 (SEQ ID NO:54) framework sequences and/or the $V_\lambda$ 2b2 (SEQ ID NO:55), $V_K$ L6 (SEQ ID NO:56), $V_K$ A27 (SEQ ID NO:57), $V_K$ A10 (SEQ ID NO:58), or $V_K$ L18 (SEQ ID NO:93) framework sequences used by preferred monoclonal antibodies of this disclosure. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the instant disclosure provides isolated anti-CD22 monoclonal antibodies, or antigen binding portions thereof, comprising a heavy chain variable region comprising: (a) a $V_H$ CDR1 region comprising an amino acid sequence selected from the group consisting of SEQ ID NOs: 1-4 or 63-65, or an amino acid sequence having one, two, three, four or five amino acid substitutions, deletions or additions as compared to SEQ ID NOs:1-4 or 63-65; (b) a $V_H$ CDR2 region comprising an amino acid sequence selected from the group consisting of SEQ ID NOs:5-8, 60 or 66-68, or an amino acid sequence having one, two, three, four or five amino acid substitutions, deletions or additions as compared to SEQ ID NOs:5-8, 60 or 66-68; (c) a $V_H$ CDR3 region comprising an amino acid sequence selected from the group consisting of SEQ ID NOs:9-12 or 69-71, or an amino acid sequence having one, two, three, four or five amino acid substitutions, deletions or additions as compared to SEQ ID NOs:9-12 or 69-71; (d) a $V_L$ CDR1 region comprising an amino acid sequence selected from the group consisting of SEQ ID NOs:13-18 or 72-74, or an amino acid sequence having one, two, three, four or five amino acid substitutions, deletions or additions as compared to SEQ ID NOs:13-18 or 72-74; (e) a $V_L$ CDR2 region comprising an amino acid sequence selected from the group consisting of SEQ ID NOs:19-24 or 75-77, or an amino acid sequence having one, two, three, four or five amino acid substitutions, deletions or additions as compared to SEQ ID NOs:19-24 or 75-77; and (f) a $V_L$ CDR3 region comprising an amino acid sequence selected from the group consisting of SEQ ID NOs:25-30 or 78-80, or an amino acid sequence having one, two, three, four or five amino acid substitutions, deletions or additions as compared to SEQ ID NOs:25-30 or 78-80.

Engineered antibodies of this disclosure include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

For example, for the12C5 $V_\lambda$ region, framework region amino acid positions 40 and 68 (using the Kabat numbering system) differ from germline. One or both of these positions can be backmutated to germline sequences by making one or both of the following substitutions: L40Q and R68K.

Furthermore, for the 19A3 and the CD22.1 $V_H$ regions, framework region amino acid position 27 (using the Kabat numbering system) differs from germline. This position can be backmutated to the germline sequence by making the following substitution: R27G.

Furthermore, for the CD22.2 $V_H$ region, framework region amino acid positions 27 and 57 (using the Kabat numbering system) differs from germline. This position can be backmutated to the germline sequence by making the following substitutions: R27G and Q57N.

Furthermore, for the 16F7 $V_H$ region, framework region amino acid position 28 (using the Kabat numbering system) differs from germline. This position can be backmutated to the germline sequence by making the following substitution: N28S.

Furthermore, for the 16F7 $V_K$.2 region, framework region amino acid position 85 (using the Kabat numbering system) differs from germline. This position can be backmutated to the germline sequence by making the following substitution: A85T.

Furthermore, for the 23C6 $V_H$ region, framework region amino acid positions 14, 79 and 88 (using the Kabat numbering system) differ from germline. One, two or all three of these positions can be backmutated to germline sequences by making one, two or all three of the following substitutions: T14P, V79A and A88S.

Furthermore, for the 4G6 $V_H$ region, framework region amino acid positions P, D, F, D, T, Y and F (using the Kabat numbering system) differs from germline. This position can be backmutated to the germline sequence by making one, two, three, four, five, six or all seven of the following substitution: P?A; D?G; N?S; F?Y; D?E; T?S; Y?R; F?S. NEED INPUT RE: KABAT NUMBERING.

Furthermore, for the 4G6 $V_K$1 region framework region amino acid positions T and D (using the Kabat numbering system) differs from germline. These positions can be backmutated to the germline sequence by making one or two of the following substitution: T?K and D?E.

Furthermore, for the 21F6 $V_H$1 region, framework region amino acid position S and I (using the Kabat numbering system) differs from germline. These positions can be backmutated to the germline sequence by making the following substitution: S?P and I?V.

Furthermore, for the 21F6 $V_H$2 region framework region amino acid positions S and M (using the Kabat numbering system) differs from germline. These positions can be backmutated to the germline sequence by making the following substitution: S?P and M?V.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 2003/0153043 by Carr et al.

In addition or alternative to modifications made within the framework or CDR regions, antibodies of this disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of this disclosure may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 to Co et al. Additional approaches for altering glycosylation are described in further detail in U.S. Pat. No. 7,214,775 to Hanai et al., U.S. Pat. No. 6,737,056 to Presta, U.S. Pub No. 20070020260 to Presta, PCT Publication No. WO/2007/084926 to Dickey et al., PCT Publication No. WO/2006/089294 to Zhu et al., and PCT Publication No. WO/2007/055916 to Ravetch et al., each of which is hereby incorporated by reference in its entirety.

In one exemplary embodiment, a glycosylation site in the CDR2 region of the $V_H$ chain of the 19A3 anitbody was eliminated by introducing an N57Q mutation (see Example 1), to give the recombinant antibody CD22.2 having the $V_H$ amino acid sequence shown in SEQ ID NO:61.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of this disclosure to thereby produce an antibody with altered glycosylation. For example, the cell lines Ms704, Ms705, and Ms709 lack the fucosyltransferase gene, FUT8 (alpha (1.6) fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1.6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). Antibodies with a modified glycosylation profile can also be produced in chicken eggs, as described in US Patent Application No. PCT/US06/05853. Alternatively, antibodies with a modified glycosylation profile can be produced in plant cells, such as Lemna. Methods for production of antibodies in a plant system are disclosed in the U.S. Patent application corresponding to Alston & Bird LLP, filed on Aug. 11, 2006. PCT Publication WO 99/54342 by Umana et al. describes cell lines engineered to express glycoprotein-modifying glycosyl transferases (e.g., beta(1.4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) *Biochem.* 14:5516-23).

Additionally or alternatively, an antibody can be made that has an altered type of glycosylation, wherein that alteration relates to the level of sialyation of the antibody. Such alterations are described in PCT Publication No. WO/2007/084926 to Dickey et al, and PCT Publication No. WO/2007/055916 to Ravetch et al., both of which are incoporated by reference in their entirety. For example, one may employ an enzymatic reaction with sialidase, such as, for example, *Arthrobacter* ureafacens sialidase. The conditions of such a reaction are generally described in the U.S. Pat. No. 5,831,077, which is hereby incorporated by reference in its entirety. Other non-limiting examples of suitable enzymes are neuraminidase and N-Glycosidase F, as described in Schloemer et al., J. Virology, 15(4), 882-893 (1975) and in Leibiger et al., Biochem J., 338, 529-538 (1999), respectively. Desialylated antibodies may be further purified by using affinity chromatography. Alternatively, one may employ methods to increase the level of sialyation, such as by employing sialytransferase enzymes. Conditions of such a reaction are generally described in Basset et al., Scandinavian Journal of Immunology, 51(3), 307-311 (2000).

Another modification of the antibodies herein that is contemplated by this disclosure is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of this disclosure. See for example, EP 0 154 316 by Nishimura et al. and EP 0 401 384 by Ishikawa et al.

Antibody Fragments and Antibody Mimetics

The instant invention is not limited to traditional antibodies and may be practiced through the use of antibody fragments and antibody mimetics. As detailed below, a wide variety of antibody fragment and antibody mimetic technologies have now been developed and are widely known in the art. While a number of these technologies, such as domain antibodies, Nanobodies, and UniBodies make use of fragments of, or other modifications to, traditional antibody structures, there are also alternative technologies, such as Affibodies, DARPins, Anticalins, Avimers, and Versabodies that employ binding structures that, while they mimic traditional antibody binding, are generated from and function via distinct mechanisms.

Domain Antibodies (dAbs) are the smallest functional binding units of antibodies, corresponding to the variable regions of either the heavy (VH) or light (VL) chains of human antibodies. Domain Antibodies have a molecular weight of approximately 13 kDa. Domantis has developed a series of large and highly functional libraries of fully human VH and VL dAbs (more than ten billion different sequences in each library), and uses these libraries to select dAbs that are specific to therapeutic targets. In contrast to many conventional antibodies, Domain Antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; U.S. Serial No. 2004/0110941; European patent application No. 1433846 and European Patents 0368684 & 0616640; WO05/035572, WO04/101790, WO04/081026, WO04/058821, WO04/003019 and WO03/002609, each of which is herein incorporated by reference in its entirety.

Nanobodies are antibody-derived therapeutic proteins that contain the unique structural and functional properties of naturally-occurring heavy-chain antibodies. These heavy-chain antibodies contain a single variable domain (VHH) and two constant domains (CH2 and CH3). Importantly, the cloned and isolated VHH domain is a perfectly stable polypeptide harbouring the full antigen-binding capacity of the original heavy-chain antibody. Nanobodies have a high homology with the VH domains of human antibodies and can be further humanized without any loss of activity. Importantly, Nanobodies have a low immunogenic potential, which has been confirmed in primate studies with Nanobody lead compounds.

Nanobodies combine the advantages of conventional antibodies with important features of small molecule drugs. Like conventional antibodies, Nanobodies show high target specificity, high affinity for their target and low inherent toxicity. However, like small molecule drugs they can inhibit enzymes and readily access receptor clefts. Furthermore, Nanobodies are extremely stable, can be administered by means other than injection (see, e.g., WO 04/041867, which is herein incorporated by reference in its entirety) and are easy to manufacture. Other advantages of Nanobodies include recognizing uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts, e.g., *E. coli* (see, e.g., U.S. Pat. No. 6,765,087, which is herein incorporated by reference in its entirety), molds (for example *Aspergillus* or *Trichoderma*) and yeast (for example *Saccharomyces, Kluyveromyces, Hansenula* or *Pichia*) (see, e.g., U.S. Pat. No. 6,838,254, which is herein incorporated by reference in its entirety). The production process is scalable and multi-kilogram quantities of Nanobodies have been produced. Because Nanobodies exhibit a superior stability compared with conventional antibodies, they can be formulated as a long shelf-life, ready-to-use solution.

The Nanoclone method (see, e.g., WO 06/079372, which is herein incorporated by reference in its entirety) is a proprietary method for generating Nanobodies against a desired target, based on automated high-throughout selection of B-cells and could be used in the context of the instant invention.

UniBodies are another antibody fragment technology, however this one is based upon the removal of the hinge region of IgG4 antibodies. The deletion of the hinge region results in a molecule that is essentially half the size of traditional IgG4 antibodies and has a univalent binding region rather than the bivalent binding region of IgG4 antibodies. It is also well known that IgG4 antibodies are inert and thus do not interact with the immune system, which may be advantageous for the treatment of diseases where an immune response is not desired, and this advantage is passed onto UniBodies. For example, UniBodies may function to inhibit or silence, but not kill, the cells to which they are bound. Additionally, UniBody binding to cancer cells do not stimulate them to proliferate. Furthermore, because UniBodies are about half the size of traditional IgG4 antibodies, they may show better distribution over larger solid tumors with potentially advantageous efficacy. UniBodies are cleared from the body at a similar rate to whole IgG4 antibodies and are able to bind with a similar affinity for their antigens as whole antibodies. Further details of UniBodies may be obtained by reference to patent application WO2007/059782, which is herein incorporated by reference in its entirety.

Affibody molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, Gunneriusson E, Ringdahl J, Stahl S, Uhlen M, Nygren P A, Binding proteins selected from combinatorial libraries of an α-helical bacterial receptor domain, Nat Biotechnol 1997; 15:772-7. Ronmark J, Gronlund H, Uhlen M, Nygren P A, Human immunoglobulin A (IgA)-specific ligands from combinatorial engineering of protein A, Eur J Biochem 2002; 269:2647-55). The simple, robust structure of Affibody molecules in combination with their low molecular weight (6 kDa), make them suitable for a wide variety of applications, for instance, as detection reagents (Ronmark J, Hansson M, Nguyen T, et al, Construction and characterization of affibody-Fc chimeras produced in *Escherichia coli*, J Immunol Methods 2002; 261:199-211) and to inhibit receptor interactions (Sandstorm K, Xu Z, Forsberg G, Nygren P A, Inhibition of the CD28-CD80 co-stimulation signal by a CD28-binding Affibody ligand developed by combinatorial protein engineering, Protein Eng 2003; 16:691-7). Further details of Affibodies and methods of production thereof may be obtained by reference to U.S. Pat. No. 5,831,012 which is herein incorporated by reference in its entirety.

Labelled Affibodies may also be useful in imaging applications for determining abundance of Isoforms.

DARPins (Designed Ankyrin Repeat Proteins) are one example of an antibody mimetic DRP (Designed Repeat Protein) technology that has been developed to exploit the binding abilities of non-antibody polypeptides. Repeat proteins such as ankyrin or leucine-rich repeat proteins, are ubiquitous binding molecules, which occur, unlike antibodies, intra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated. This strategy includes the consensus design of self-compatible repeats displaying variable surface residues and their random assembly into repeat domains.

DARPins can be produced in bacterial expression systems at very high yields and they belong to the most stable proteins known. Highly specific, high-affinity DARPins to a broad range of target proteins, including human receptors, cytokines, kinases, human proteases, viruses and membrane proteins, have been selected. DARPins having affinities in the single-digit nanomolar to picomolar range can be obtained.

DARPins have been used in a wide range of applications, including ELISA, sandwich ELISA, flow cytometric analysis (FACS), immunohistochemistry (1HC), chip applications, affinity purification or Western blotting. DARPins also proved to be highly active in the intracellular compartment for example as intracellular marker proteins fused to green fluorescent protein (GFP). DARPins were further used to inhibit viral entry with IC50 in the pM range. DARPins are not only ideal to block protein-protein interactions, but also to inhibit enzymes. Proteases, kinases and transporters have been successfully inhibited, most often an allosteric inhibition mode. Very fast and specific enrichments on the tumor and very favorable tumor to blood ratios make DARPins well suited for in vivo diagnostics or therapeutic approaches.

Additional information regarding DARPins and other DRP technologies can be found in U.S. Patent Application Publication No. 2004/0132028 and International Patent Application Publication No. WO 02/20565, both of which are hereby incorporated by reference in their entirety.

Anticalins are an additional antibody mimetic technology, however in this case the binding specificity is derived from lipocalins, a family of low molecular weight proteins that are naturally and abundantly expressed in human tissues and body fluids. Lipocalins have evolved to perform a range of functions in vivo associated with the physiological transport and storage of chemically sensitive or insoluble compounds. Lipocalins have a robust intrinsic structure comprising a highly conserved β-barrel which supports four loops at one terminus of the protein. These loops form the entrance to a binding pocket and conformational differences in this part of the molecule account for the variation in binding specificity between individual lipocalins.

While the overall structure of hypervariable loops supported by a conserved β-sheet framework is reminiscent of immunoglobulins, lipocalins differ considerably from antibodies in terms of size, being composed of a single polypeptide chain of 160-180 amino acids which is marginally larger than a single immunoglobulin domain.

Lipocalins are cloned and their loops are subjected to engineering in order to create Anticalins. Libraries of structurally diverse Anticalins have been generated and Anticalin display allows the selection and screening of binding function, followed by the expression and production of soluble protein for further analysis in prokaryotic or eukaryotic systems. Studies have successfully demonstrated that Anticalins can be developed that are specific for virtually any human target protein can be isolated and binding affinities in the nanomolar or higher range can be obtained.

Anticalins can also be formatted as dual targeting proteins, so-called Duocalins. A Duocalin binds two separate therapeutic targets in one easily produced monomeric protein using standard manufacturing processes while retaining target specificity and affinity regardless of the structural orientation of its two binding domains.

Modulation of multiple targets through a single molecule is particularly advantageous in diseases known to involve more than a single causative factor. Moreover, bi- or multivalent binding formats such as Duocalins have significant potential in targeting cell surface molecules in disease, mediating agonistic effects on signal transduction pathways or inducing enhanced internalization effects via binding and clustering of cell surface receptors. Furthermore, the high intrinsic stability of Duocalins is comparable to monomeric Anticalins, offering flexible formulation and delivery potential for Duocalins.

Additional information regarding Anticalins can be found in U.S. Pat. No. 7,250,297 and International Patent Application Publication No. WO 99/16873, both of which are hereby incorporated by reference in their entirety.

Another antibody mimetic technology useful in the context of the instant invention are Avimers. Avimers are evolved from a large family of human extracellular receptor domains by in vitro exon shuffling and phage display, generating multidomain proteins with binding and inhibitory properties. Linking multiple independent binding domains has been shown to create avidity and results in improved affinity and specificity compared with conventional single-epitope binding proteins. Other potential advantages include simple and efficient production of multitarget-specific molecules in *Escherichia coli*, improved thermostability and resistance to proteases. Avimers with sub-nanomolar affinities have been obtained against a variety of targets.

Additional information regarding Avimers can be found in U.S. Patent Application Publication Nos. 2006/0286603, 2006/0234299, 2006/0223114, 2006/0177831, 2006/0008844, 2005/0221384, 2005/0164301, 2005/0089932, 2005/0053973, 2005/0048512, 2004/0175756, all of which are hereby incorporated by reference in their entirety.

Versabodies are another antibody mimetic technology that could be used in the context of the instant invention. Versabodies are small proteins of 3-5 kDa with >15% cysteines, which form a high disulfide density scaffold, replacing the hydrophobic core that typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T-cell epitopes, because the residues that contribute most to MHC presentation are hydrophobic. All four of these properties are well-known to affect immunogenicity, and together they are expected to cause a large decrease in immunogenicity.

The inspiration for Versabodies comes from the natural injectable biopharmaceuticals produced by leeches, snakes, spiders, scorpions, snails, and anemones, which are known to exhibit unexpectedly low immunogenicity. Starting with selected natural protein families, by design and by screening the size, hydrophobicity, proteolytic antigen processing, and epitope density are minimized to levels far below the average for natural injectable proteins.

Given the structure of Versabodies, these antibody mimetics offer a versatile format that includes multi-valency, multi-specificity, a diversity of half-life mechanisms, tissue targeting modules and the absence of the antibody Fc region.

Furthermore, Versabodies are manufactured in *E. coli* at high yields, and because of their hydrophilicity and small size, Versabodies are highly soluble and can be formulated to high concentrations. Versabodies are exceptionally heat stable (they can be boiled) and offer extended shelf-life.

Additional information regarding Versabodies can be found in U.S. Patent Application Publication No. 2007/0191272 which is hereby incorporated by reference in its entirety.

The detailed description of antibody fragment and antibody mimetic technologies provided above is not intended to be a comprehensive list of all technologies that could be used in the context of the instant specification. For example, and also not by way of limitation, a variety of additional technologies including alternative polypeptide-based technologies, such as fusions of complimentary determining regions as outlined in Qui et al., Nature Biotechnology, 25 (8) 921-929 (2007), which is hereby incorporated by reference in its entirety, as well as nucleic acid-based technologies, such as the RNA aptamer technologies described in U.S. Pat. Nos. 5,789,157, 5,864,026, 5,712,375, 5,763,566, 6,013,443, 6,376,474, 6,613,526, 6,114,120, 6,261,774, and 6,387,620, all of which are hereby incorporated by reference, could be used in the context of the instant invention.

Antibody Physical Properties

The antibodies of the present disclosure may be further characterized by the various physical properties of the anti-CD22 antibodies. Various assays may be used to detect and/or differentiate different classes of antibodies based on these physical properties.

In some embodiments, antibodies of the present disclosure may contain one or more glycosylation sites in either the light or heavy chain variable region. The presence of one or more glycosylation sites in the variable region may result in increased immunogenicity of the antibody or an alteration of the pK of the antibody due to altered antigen binding (Marshall et al (1972) *Annu Rev Biochem* 41:673-702; Gala F A and Morrison S L (2004) *J Immunol* 172:5489-94; Wallick et al (1988) *J Exp Med* 168:1099-109; Spiro R G (2002) *Glycobiology* 12:43 R-56R; Parekh et al (1985) *Nature* 316:452-7; Mimura et al. (2000) *Mol Immunol* 37:697-706). Glycosylation has been known to occur at motifs containing an N—X—S/T sequence. Variable region glycosylation may be tested using a Glycoblot assay, which cleaves the antibody to produce a Fab, and then tests for glycosylation using an assay that measures periodate oxidation and Schiff base formation. Alternatively, variable region glycosylation may be tested using Dionex light chromatography (Dionex-LC), which cleaves saccharides from a Fab into monosaccharides and analyzes the individual saccharide content. In some instances, it is preferred to have an anti-CD22 antibody that does not contain variable region glycosylation. This can be achieved either by selecting antibodies that do not contain the glycosylation motif in the variable region or by mutating residues within the glycosylation motif using standard techniques well known in the art.

In a preferred embodiment, the antibodies of the present disclosure do not contain asparagine isomerism sites. A deamidation or isoaspartic acid effect may occur on N-G or D-G sequences, respectively. The deamidation or isoaspartic acid effect results in the creation of isoaspartic acid which decreases the stability of an antibody by creating a kinked structure off a side chain carboxy terminus rather than the main chain. The creation of isoaspartic acid can be measured using an iso-quant assay, which uses a reverse-phase HPLC to test for isoaspartic acid.

Each antibody will have a unique isoelectric point (pI), but generally antibodies will fall in the pH range of between 6 and 9.5. The pI for an IgG1 antibody typically falls within the pH range of 7-9.5 and the pI for an IgG4 antibody typically falls within the pH range of 6-8. Antibodies may have a pI that is outside this range. Although the effects are generally unknown, there is speculation that antibodies with a pI outside the normal range may have some unfolding and instability under in vivo conditions. The isoelectric point may be tested using a capillary isoelectric focusing assay, which creates a pH gradient and may utilize laser focusing for increased accuracy (Janini et al (2002) *Electrophoresis* 23:1605-11; Ma et al. (2001) *Chromatographia* 53:S75-89; Hunt et al (1998) *J Chromatogr A* 800:355-67). In some instances, it is preferred to have an anti-CD22 antibody that contains a pI value that falls in the normal range. This can be achieved either by selecting antibodies with a pI in the normal range, or by mutating charged surface residues using standard techniques well known in the art.

Each antibody will have a melting temperature that is indicative of thermal stability (Krishnamurthy R and Manning MC (2002) *Curr Pharm Biotechnol* 3:361-71). A higher thermal stability indicates greater overall antibody stability in vivo. The melting point of an antibody may be measure using techniques such as differential scanning calorimetry (Chen et al (2003) *Pharm Res* 20:1952-60; Ghirlando et al (1999) *Immunol Lett* 68:47-52). $T_{M1}$ indicates the temperature of the initial unfolding of the antibody. $T_{M2}$ indicates the temperature of complete unfolding of the antibody. Generally, it is preferred that the $T_{M1}$ of an antibody of the present disclosure is greater than 60° C., preferably greater than 65° C., even more preferably greater than 70° C. Alternatively, the thermal stability of an antibody may be measure using circular dichroism (Murray et al. (2002) *J. Chromatogr Sci* 40:343-9).

In a preferred embodiment, antibodies are selected that do not rapidly degrade. Fragmentation of an anti-CD22 antibody may be measured using capillary electrophoresis (CE) and MALDI-MS, as is well understood in the art (Alexander A J and Hughes D E (1995) *Anal Chem* 67:3626-32).

In another preferred embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC), and light scattering to identify monomers, dimers, trimers or multimers.

Methods of Engineering Antibodies

As discussed above, the anti-CD22 antibodies having $V_H$ and $V_L$ sequences disclosed herein can be used to create new anti-CD22 antibodies by modifying the $V_H$ and/or $V_L$ sequences, or the constant region(s) attached thereto. Thus, in another aspect of this disclosure, the structural features of an anti-CD22 antibody of this disclosure, e.g. 12C5, 19A3, CD22.1, CD22.2, 16F7, 23C6, 4G6 and 21F6, are used to create structurally related anti-CD22 antibodies that retain at least one functional property of the antibodies of this disclosure, such as binding to human CD22. For example, one or more CDR regions of 12C5, 19A3, CD22.1, CD22.2, 16F7, 23C6, 4G6 and 21F6, or mutations thereof, can be combined recombinantly with known framework regions and/or other CDRs to create additional, recombinantly-engineered, anti-CD22 antibodies of this disclosure, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, this disclosure provides a method for preparing an anti-CD22 antibody comprising:

(a) providing: (i) a heavy chain variable region antibody sequence comprising a CDR1 sequence selected from the group consisting of SEQ ID NOs: 1-4 and 63-65; a CDR2 sequence selected from the group consisting of SEQ ID NOs: 5-8, 60, and 66-68 and/or a CDR3 sequence selected from the group consisting of SEQ ID NOs: 9-12 and 69-71; and/or (ii) a light chain variable region antibody sequence comprising a CDR1 sequence selected from the group consisting of SEQ ID NOs: 13-18 and 72-74; a CDR2 sequence selected from the group consisting of SEQ ID NOs: 19-24 and 75-77; and/or a CDR3 sequence selected from the group consisting of SEQ ID NOs: 25-30 and 78-80;

(b) altering at least one amino acid residue within the heavy chain variable region antibody sequence and/or the light chain variable region antibody sequence to create at least one altered antibody sequence; and (c) expressing the altered antibody sequence as a protein.

For example, standard molecular biology techniques can be used to prepare and express the altered antibody sequence.

Preferably, the antibody encoded by the altered antibody sequence(s) is one that retains one, some or all of the functional properties of the anti-CD22 antibodies described herein, which functional properties include, but are not limited to:

(a) internalizing into CD22+ cells;
(b) exhibiting ADCC activity on CD22+ cells;
(c) enhancing cell death of Ramos cells induced by BCR stimulation;
(d) not having a direct anti-proliferative effect on Ramos cells;
(d) not inducing calcium flux in Ramos cells;
(e) not mediating CDC activity on Ramos cells; and/or
(f) inhibits growth of CD22-expressing cells in vivo when conjugated to a cytotoxin The functional properties of the altered antibodies can be assessed using standard assays available in the art and/or described herein, such as those set forth in the Examples.

In certain embodiments of the methods of engineering antibodies of this disclosure, mutations can be introduced randomly or selectively along all or part of an anti-CD22 antibody coding sequence and the resulting modified anti-CD22 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of this Disclosure

Another aspect of this disclosure pertains to nucleic acid molecules that encode the antibodies of this disclosure. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of this disclosure can be, for example, DNA or RNA and may or may not contain intronic sequences. In a preferred embodiment, the nucleic acid is a cDNA molecule.

Nucleic acids of this disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of this disclosure are those encoding the $V_H$ and $V_L$ sequences of the 12C5, 19A3, CD22.1, CD22.2, 16F7, 23C6, 4G6 and 21F6 monoclonal antibodies. DNA sequences encoding the $V_H$ sequences of 12C5, 19A3, CD22.1, 16F7, 23C6, CD22.2, 4G6 and 21F6 are shown in SEQ ID NOs: 41-44, 62 and 87-89, respectively (wherein the heavy chains of 19A3 and CD22.1 are identical and correspond to SEQ ID NO:42; the heavy chain of CD22.2 corresponds to SEQ ID NO:62; and the heavy chains of 21F6 correspond to SEQ ID NOs:82 and 83). DNA sequences encoding the $V_L$ sequences of 12C5, 19A3, CD22.1, CD22.2, 16F7, 23C6, 4G6 and 21F6 are shown in SEQ ID NOs: 45-50 and 90-92, respectively (wherein the kappa light chains of 19A3, CD22.1 and CD22.2 are identical and correspond to SEQ ID NO:46, the kappa light chain of 16F7 corresponds to either SEQ ID NO:47 or 48, the kappa light chain of 23C6 corresponds to either SEQ ID NO:49 or 50, and the kappa light chain of 4G6 corresponds to either SEQ ID NO:90 or 91).

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgQ1, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence $(Gly_4\text{-}Ser)_3$, such that the $V_H$ and $V_L$ sequences can be expressed as a contiguous single-chain protein, with the $V_L$ and $V_H$ regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Production of Monoclonal Antibodies of this Disclosure

Monoclonal antibodies (mAbs) of the present disclosure can be produced by a variety of techniques, including conventional monoclonal antibody methodology e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure Immunization protocols and techniques for isolation of immunized splenocytes for fusion are known in the art. Fusion partners (e.g., murine myeloma cells) and fusion procedures are also known.

Chimeric or humanized antibodies of the present disclosure can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al). To create a humanized antibody, murine CDR regions can be inserted into a human framework using methods known in the art (see e.g., U.S. Pat. No. 5,225,539 to Winter, and U.S. Pat. Nos. 5,530,101; 5,585, 089; 5,693,762 and 6,180,370 to Queen et al.).

In a preferred embodiment, the antibodies of this disclosure are human monoclonal antibodies. Such human monoclonal antibodies directed against CD22 can be generated using transgenic or transchromosomic mice carrying parts of the human immune system rather than the mouse system. These transgenic and transchromosomic mice include mice referred to herein as the HuMAb Mouse® and KM Mouse®, respectively, and are collectively referred to herein as "human Ig mice."

The HuMAb Mouse® (Medarex®, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). Preparation and use of the HuMAb Mouse®, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al., (1994) J. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of this disclosure can be raised using a mouse that carries human immunoglobulin sequences on transgenes and transchomosomes, such as a mouse that carries a human heavy chain transgene and a human light chain transchromosome. This mouse is referred to herein as a "KM Mouse®" and is described in detail in PCT Publication WO 02/43478 to Ishida et al.

Still further, alternative transgenic animal systems expressing human immunoglobulin genes are available in the art and can be used to raise anti-CD22 antibodies of this disclosure. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-CD22 antibodies of this disclosure. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (e.g., Kuroiwa et al. (2002) Nature Biotechnology 20:889-894 and PCT application No. WO 2002/092812) and can be used to raise anti-CD22 antibodies of this disclosure.

Human monoclonal antibodies of this disclosure can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of this disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In another embodiment, human anti-CD22 antibodies are prepared using a combination of human Ig mouse and phage display techniques, as described in U.S. Pat. No. 6,794,132 by Buechler et al. More specifically, the method first involves raising an anti-CD22 antibody response in a human Ig mouse (such as a HuMab mouse or KM mouse as described above) by immunizing the mouse with a CD22 antigen, followed by isolating nucleic acids encoding human antibody chains from lymphatic cells of the mouse and introducing these nucleic acids into a display vector (e.g., phage) to provide a library of display packages. Thus, each library member comprises a nucleic acid encoding a human antibody chain and each antibody chain is displayed from the display package. The library then is screened with a CD22 antigen to isolate library members that specifically bind CD22. Nucleic acid inserts of the selected library members then are isolated and sequenced by standard methods to determine the light and heavy chain variable sequences of the selected CD22 binders. The variable regions can be converted to full-length antibody chains by standard recombinant DNA techniques, such as cloning of the variable regions into an expression vector that carries the human heavy and light chain constant regions such that the $V_H$ region is operatively linked to the $C_H$ region and the $V_L$ region is operatively linked to the $C_L$ region.

Immunization of Human Ig Mice

When human Ig mice are used to raise human antibodies of this disclosure, such mice can be immunized with a purified or enriched preparation of CD22 antigen and/or recombinant CD22, or cells expressing CD22, or a CD22 fusion protein, as described by Lonberg, N. et al. (1994) Nature 368(6474): 856-859; Fishwild, D. et al. (1996) Nature Biotechnology 14: 845-851; and PCT Publication WO 98/24884 and WO 01/14424. Preferably, the mice will be 6-16 weeks of age upon the first infusion. For example, a purified or recombinant preparation (5-50 μg) of CD22 antigen can be used to immunize the human Ig mice intraperitoneally. Most preferably, the immunogen used to raise the antibodies of this disclosure is a combination of recombinant human CD22 extracellular domain and CHO cells engineered to express full-length human CD22 on the cell surface (described further in Example 1).

Detailed procedures to generate fully human monoclonal antibodies to CD22 are described in Example 1 below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-CD22 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12). Alternatively or additionally, the KM Mouse® and/or KM-XHAC strains can be used, as described in Example 1.

Generation of Hybridomas Producing Human Monoclonal Antibodies of this Disclosure To generate hybridomas producing human monoclonal antibodies of this disclosure, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Alternatively, the single cell suspension of splenic lymphocytes from immunized mice can be fused using an electric field based electrofusion method, using a CytoPulse large chamber cell fusion electroporator (CytoPulse Sciences, Inc., Glen Burnie Md.). Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

Generation of Transfectomas Producing Monoclonal Antibodies of this Disclosure

Antibodies of this disclosure also can be produced in a host cell transfectoma using, for example, a combination of recombinant DNA techniques and gene transfection methods as is well known in the art (e.g., Morrison, S. (1985) *Science* 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used.

The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of this disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of this disclosure may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all to Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of this disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of this disclosure include Chinese Hamster Ovary (CHO cells) (including dhfr− CHO cells, described in Urlaub and ChasM, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular, for use with NSO myeloma cells, another preferred expression system is the GS gene expression system disclosed in WO 87/04462 (to Wilson), WO 89/01036 (to Bebbington) and EP 338,841 (to Bebbington). When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of the invention can be tested for binding to CD22 by, for example, standard ELISA. Briefly, microtiter plates are coated with purified and/or recombinant CD22 (e.g., CD22 ECD as described in Example 1) at 0.25 µg/ml in PBS, and then blocked with 5% bovine serum albumin in PBS. Dilutions of antibody (e.g., dilutions of plasma from CD22-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice that develop the highest titers will be used for fusions.

An ELISA assay as described above can also be used to screen for hybridomas that show positive reactivity with CD22 immunogen. Hybridomas that bind with high avidity to CD22 are subcloned and further characterized. One clone from each hybridoma, which retains the reactivity of the parent cells (by ELISA), can be chosen for making a 5-10 vial cell bank stored at −140° C., and for antibody purification.

To purify anti-CD22 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected anti-CD22 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using CD22 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4° C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-CD22 human IgGs can be further tested for reactivity with CD22 antigen by Western blotting. Briefly, CD22 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

The binding specificity of an antibody of this disclosure may also be determined by monitoring binding of the antibody to cells expressing CD22, for example by flow cytometry. A cell line that naturally expresses CD22, such as Daudi cells or Raji cells, may be used or a cell line, such as a CHO cell line, may be transfected with an expression vector encoding a transmembrane form of CD22. The transfected protein may comprise a tag, such as a myc-tag, preferably at the N-terminus, for detection using an antibody to the tag. Binding of an antibody of this disclosure to CD22 may be determined by incubating the transfected cells with the antibody, and detecting bound antibody. Binding of an antibody to the tag on the transfected protein may be used as a positive control.

Bispecific Molecules

In another aspect, the present disclosure features bispecific molecules comprising an anti-CD22 antibody, or a fragment thereof, of this disclosure. An antibody of this disclosure, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of this disclosure may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of this disclosure, an antibody of this disclosure can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present disclosure includes bispecific molecules comprising at least one first binding specificity for CD22 and a second binding specificity for a second target epitope. In a particular embodiment of this disclosure, the second target epitope is an Fc receptor, e.g., human FcγRI (CD64) or a human Fcα receptor (CD89). Therefore, this disclosure includes bispecific molecules capable of binding both to FcγR or FcαR expressing effector cells (e.g., monocytes, macrophages or polymorphonuclear cells (PMNs)), and to target cells expressing CD22. These bispecific molecules target CD22 expressing cells to effector cell and trigger Fc receptor-mediated effector cell activities, such as phagocytosis of CD22 expressing cells, antibody dependent cell-mediated cytotoxicity (ADCC), cytokine release, or generation of superoxide anion.

In an embodiment of this disclosure in which the bispecific molecule is multispecific, the molecule can further include a third binding specificity, in addition to an anti-Fc binding specificity and an anti-CD22 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of this disclosure comprise as a binding specificity at least one antibody, or an antibody fragment thereof, including, e.g., an Fab, Fab', F(ab')$_2$, Fv, Fd, dAb or a single chain Fv. The antibody may also be a light chain or heavy chain dimer, or any minimal fragment thereof such as a Fv or a single chain construct as described in U.S. Pat. No. 4,946,778 to Ladner et al., the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII(CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ M$^{-1}$).

The production and characterization of certain preferred anti-Fcγ monoclonal antibodies are described in PCT Publication WO 88/00052 and in U.S. Pat. No. 4,954,617 to Fanger et al., the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this disclosure are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) *J. Immunol* 155 (10): 4996-5002 and PCT Publication WO 94/10332 to Tempest et al. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcγRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcγRI has medium affinity ($\approx 5 \times 10^7$ M$^{-1}$) for both IgA1 and IgA2, which is increased upon exposure to cytokines such as G-CSF or GM-CSF (Morton, H. C. et al. (1996) *Critical Reviews in Immunology* 16:423-440). Four FcγRI-specific monoclonal antibodies, identified as A3, A59, A62 and A77, which bind FcγRI outside the IgA ligand binding domain, have been described (Monteiro, R. C. et al. (1992) *J. Immunol.* 148:1764).

FcαRI and FcγRI are preferred trigger receptors for use in the bispecific molecules of this disclosure because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); and (4) mediate enhanced antigen presentation of antigens, including self-antigens, targeted to them.

While human monoclonal antibodies are preferred, other antibodies which can be employed in the bispecific molecules of this disclosure are murine, chimeric and humanized monoclonal antibodies.

The bispecific molecules of the present disclosure can be prepared by conjugating the constituent binding specificities, e.g., the anti-FcR and anti-CD22 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) *J. Exp. Med.* 160:1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83, and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand x Fab fusion protein. A bispecific molecule of this disclosure can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858, all of which are expressly incorporated herein by reference.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ-counter or a scintillation counter or by autoradiography.

Linkers

The present invention provides for antibody-partner conjugates where the antibody is linked to the partner through a chemical linker. In some embodiments, the linker is a peptidyl linker, and is depicted herein as $(L^4)_p$-F-$(L^1)_m$.

Other linkers include hydrazine and disulfide linkers, and is depicted herein as $(L^4)_p$-H-$(L^1)_m$ or $(L^4)_p$-J-$(L^1)_m$, respectively. In addition to the linkers being attached to the partner, the present invention also provides cleavable linker arms that are appropriate for attachment to essentially any molecular species. The linker arm aspect of the invention is exemplified herein by reference to their attachment to a therapeutic moiety. It will, however, be readily apparent to those of skill in the art that the linkers can be attached to diverse species including, but not limited to, diagnostic agents, analytical agents, biomolecules, targeting agents, detectable labels and the like.

The use of peptidyl and other linkers in antibody-partner conjugates is described in U.S. Provisional Patent Application Ser. Nos. 60/295,196; 60/295,259; 60/295,342; 60/304,908; 60/572,667; 60/661,174; 60/669,871; 60/720,499; 60/730,804; 60/735,657; 60/891,028; and U.S. patent application Ser. Nos. 10/160,972; 10/161,234; 11/134,685; 11/134,826; and 11/398,854 and U.S. Pat. No. 6,989,452 and PCT Patent Application No. PCT/US2006/37793, all of which are incorporated herein by reference.

Additional linkers are described in U.S. Pat. No. 6,214,345 (Bristol-Myers Squibb), U.S. Pat. Appl. 2003/0096743 and U.S. Pat. Appl. 2003/0130189 (both to Seattle Genetics), de Groot et al., J. Med. Chem. 42, 5277 (1999); de Groot et al. J. Org. Chem. 43, 3093 (2000); de Groot et al., J. Med. Chem. 66, 8815, (2001); WO 02/083180 (Syntarga); Carl et al., J. Med. Chem. Lett. 24, 479, (1981); Dubowchik et al., Bioorg & Med. Chem. Lett. 8, 3347 (1998).

In one aspect, the present invention relates to linkers that are useful to attach targeting groups to therapeutic agents and markers. In another aspect, the invention provides linkers that impart stability to compounds, reduce their in vivo toxicity, or otherwise favorably affect their pharmacokinetics, bioavailability and/or pharmacodynamics. It is generally preferred that in such embodiments, the linker is cleaved, releasing the active drug, once the drug is delivered to its site of action. Thus, in one embodiment of the invention, the linkers of the invention are traceless, such that once removed from the therapeutic agent or marker (such as during activation), no trace of the linker's presence remains.

In another embodiment of the invention, the linkers are characterized by their ability to be cleaved at a site in or near the target cell such as at the site of therapeutic action or marker activity. Such cleavage can be enzymatic in nature. This feature aids in reducing systemic activation of the therapeutic agent or marker, reducing toxicity and systemic side effects. Preferred cleavable groups for enzymatic cleavage include peptide bonds, ester linkages, and disulfide linkages. In other embodiments, the linkers are sensitive to pH and are cleaved through changes in pH.

An important aspect of the current invention is the ability to control the speed with which the linkers cleave. Often a linker that cleaves quickly is desired. In some embodiments, however, a linker that cleaves more slowly may be preferred. For example, in a sustained release formulation or in a formulation with both a quick release and a slow release component, it may be useful to provide a linker which cleaves more slowly. WO 02/096910 provides several specific ligand-drug complexes having a hydrazine linker. However, there is no way to "tune" the linker composition dependent upon the rate of cyclization required, and the particular compounds described cleave the ligand from the drug at a slower rate than is preferred for many drug-linker conjugates. In contrast, the hydrazine linkers of the current invention provide for a range of cyclization rates, from very fast to very slow, thereby allowing for the selection of a particular hydrazine linker based on the desired rate of cyclization.

For example, very fast cyclization can be achieved with hydrazine linkers that produce a single 5-membered ring upon cleavage. Preferred cyclization rates for targeted delivery of a cytotoxic agent to cells are achieved using hydrazine linkers that produce, upon cleavage, either two 5-membered rings or a single 6-membered ring resulting from a linker having two methyls at the geminal position. The gem-dimethyl effect has been shown to accelerate the rate of the cyclization reaction as compared to a single 6-membered ring without the two methyls at the geminal position. This results from the strain being relieved in the ring. Sometimes, however, substitutents may slow down the reaction instead of making it faster. Often the reasons for the retardation can be traced to steric hindrance. For example, the gem dimethyl substitution allows for a much faster cyclization reaction to occur compared to when the geminal carbon is a $CH_2$.

It is important to note, however, that in some embodiments, a linker that cleaves more slowly may be preferred. For example, in a sustained release formulation or in a formulation with both a quick release and a slow release component, it may be useful to provide a linker which cleaves more slowly. In certain embodiments, a slow rate of cyclization is achieved using a hydrazine linker that produces, upon cleavage, either a single 6-membered ring, without the gem-dimethyl substitution, or a single 7-membered ring.

The linkers also serve to stabilize the therapeutic agent or marker against degradation while in circulation. This feature provides a significant benefit since such stabilization results in prolonging the circulation half-life of the attached agent or marker. The linker also serves to attenuate the activity of the attached agent or marker so that the conjugate is relatively benign while in circulation and has the desired effect, for example is toxic, after activation at the desired site of action. For therapeutic agent conjugates, this feature of the linker serves to improve the therapeutic index of the agent.

The stabilizing groups are preferably selected to limit clearance and metabolism of the therapeutic agent or marker by enzymes that may be present in blood or non-target tissue and are further selected to limit transport of the agent or marker into the cells. The stabilizing groups serve to block degradation of the agent or marker and may also act in providing other physical characteristics of the agent or marker. The stabilizing group may also improve the agent or marker's stability during storage in either a formulated or non-formulated form.

Ideally, the stabilizing group is useful to stabilize a therapeutic agent or marker if it serves to protect the agent or marker from degradation when tested by storage of the agent or marker in human blood at 37° C. for 2 hours and results in less than 20%, preferably less than 10%, more preferably less than 5% and even more preferably less than 2%, cleavage of the agent or marker by the enzymes present in the human blood under the given assay conditions.

The present invention also relates to conjugates containing these linkers. More particularly, the invention relates to prodrugs that may be used for the treatment of disease, especially for cancer chemotherapy. Specifically, use of the linkers described herein provide for prodrugs that display a high specificity of action, a reduced toxicity, and an improved stability in blood relative to prodrugs of similar structure.

The linkers of the present invention as described herein may be present at a variety of positions within the partner molecule.

Thus, there is provided a linker that may contain any of a variety of groups as part of its chain that will cleave in vivo, e.g., in the blood stream, at a rate which is enhanced relative to that of constructs that lack such groups. Also provided are conjugates of the linker arms with therapeutic and diagnostic agents. The linkers are useful to form prodrug analogs of therapeutic agents and to reversibly link a therapeutic or diagnostic agent to a targeting agent, a detectable label, or a solid support. The linkers may be incorporated into complexes that include the cytotoxins of the invention.

In addition to the cleavable peptide, hydrazine, or disulfide group, one or more self-immolative linker groups $L^1$ are optionally introduced between the cytoCytotoxin And the targeting agent. These linker groups may also be described as spacer groups and contain at least two reactive functional groups. Typically, one chemical functionality of the spacer group bonds to a chemical functionality of the therapeutic agent, e.g., cytotoxin, while the other chemical functionality of the spacer group is used to bond to a chemical functionality of the targeting agent or the cleavable linker. Examples of chemical functionalities of spacer groups include hydroxy, mercapto, carbonyl, carboxy, amino, ketone, and mercapto groups.

The self-immolative linkers, represented by $L^1$, are generally a substituted or unsubstituted alkyl, substituted or unsubstituted aryl, substituted or unsubstituted heteroaryl or substituted or unsubstituted heteroalkyl group. In one embodiment, the alkyl or aryl groups may comprise between 1 and 20 carbon atoms. They may also comprise a polyethylene glycol moiety.

Exemplary spacer groups include, for example, 6-aminohexanol, 6-mercaptohexanol, 10-hydroxydecanoic acid, glycine and other amino acids, 1,6-hexanediol, β-alanine, 2-aminoethanol, cysteamine (2-aminoethanethiol), 5-aminopentanoic acid, 6-aminohexanoic acid, 3-maleimidobenzoic acid, phthalide, α-substituted phthalides, the carbonyl group, aminal esters, nucleic acids, peptides and the like.

The spacer can serve to introduce additional molecular mass and chemical functionality into the cytotoxin-targeting agent complex. Generally, the additional mass and functionality will affect the serum half-life and other properties of the complex. Thus, through careful selection of spacer groups, cytotoxin complexes with a range of serum half-lives can be produced.

The spacer(s) located directly adjacent to the drug moiety is also denoted as $(L^1)m$, wherein m is an integer selected from 0, 1, 2, 3, 4, 5, and 6. When multiple $L^1$ spacers are present, either identical or different spacers may be used. $L^1$ may be any self-immolative group.

$L^4$ is a linker moiety that preferably imparts increased solubility or decreased aggregation properties to conjugates utilizing a linker that contains the moiety or modifies the hydrolysis rate of the conjugate. The $L^4$ linker does not have to be self immolative. In one embodiment, the $L^4$ moiety is substituted alkyl, unsubstituted alkyl, substituted aryl, unsubstituted aryl, substituted heteroalkyl, or unsubstituted heteroalkyl, any of which may be straight, branched, or cyclic. The substitutions may be, for example, a lower ($C^1$-$C^6$) alkyl, alkoxy, alkylthio, alkylamino, or dialkylamino. In certain embodiments, $L^4$ comprises a non-cyclic moiety. In another embodiment, $L^4$ comprises any positively or negatively charged amino acid polymer, such as polylysine or polyargenine. $L^4$ can comprise a polymer such as a polyethylene glycol moiety. Additionally the $L^4$ linker can comprise, for example, both a polymer component and a small chemical moiety.

In a preferred embodiment, $L^4$ comprises a polyethylene glycol (PEG) moiety. The PEG portion of $L^4$ may be between 1 and 50 units long. Preferably, the PEG will have 1-12 repeat units, more preferably 3-12 repeat units, more preferably 2-6 repeat units, or even more preferably 3-5 repeat units and most preferably 4 repeat units. $L^4$ may consist solely of the PEG moiety, or it may also contain an additional substituted or unsubstituted alkyl or heteroalkyl. It is useful to combine PEG as part of the $L^4$ moiety to enhance the water solubility of the complex. Additionally, the PEG moiety reduces the degree of aggregation that may occur during the conjugation of the drug to the antibody.

In some embodiments, $L^4$ comprises

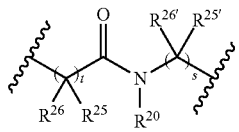

directly attached to the N-terminus of $(AA^1)_c$. $R^{20}$ is a member selected from H, substituted or unsubstituted alkyl, substituted or unsubstituted heteroalkyl, and acyl. Each $R^{25}$, $R^{25'}$, $R^{26}$, and $R^{26'}$ is independently selected from H, substituted or unsubstituted alkyl, substituted or unsubstituted heteroalkyl, substituted or unsubstituted aryl, substituted or unsubstituted heteroaryl, and substituted or unsubstituted heterocycloalkyl; and s and t are independently integers from 1 to 6. Preferably, $R^{20}$, $R^{25}$, $R^{25'}$, $R^{26}$ and $R^{26'}$ are hydrophobic. In some embodiments, $R^{20}$ is H or alkyl (preferably, unsubstituted lower alkyl). In some embodiments, $R^{25}$, $R^{25'}$, $R^{26}$ and $R^{26'}$ are independently H or alkyl (preferably, unsubstituted $C^1$ to $C^4$ alkyl). In some embodiments, $R^{25}$, $R^{25'}$, $R^{26}$ and $R^{26'}$ are all H. In some embodiments, t is 1 and s is 1 or 2.

Peptide Linkers (F)

As discussed above, the peptidyl linkers of the invention can be represented by the general formula: $(L^4)_p$-F-$(L^1)_m$, wherein F represents the linker portion comprising the peptidyl moiety. In one embodiment, the F portion comprises an optional additional self-immolative linker(s), $L^2$, and a carbonyl group. In another embodiment, the F portion comprises an amino group and an optional spacer group(s), $L^3$.

Accordingly, in one embodiment, the conjugate comprising the peptidyl linker comprises a structure of the following formula (a):

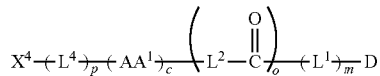

In this embodiment, $L^1$ is a self-immolative linker, as described above, and $L^4$ is a moiety that preferably imparts increased solubility, or decreased aggregation properties, or modifies the hydrolysis rate, as described above. $L^2$ represents a self-immolative linker(s). In addition, m is 0, 1, 2, 3, 4, 5, or 6; and o and p are independently 0 or 1. $AA^1$ represents one or more natural amino acids, and/or unnatural α-amino acids; c is an integer from 1 and 20. In some embodiments, c is in the range of 2 to 5 or c is 2 or 3.

In the peptide linkers of the invention of the above formula (a), $AA^1$ is linked, at its amino terminus, either directly to $L^4$ or, when $L^4$ is absent, directly to the $X^4$ group (i.e., the targeting agent, detectable label, protected reactive functional group or unprotected reactive functional group). In some embodiments, when $L^4$ is present, $L^4$ does not comprise a carboxylic acyl group directly attached to the N-terminus of $(AA^1)_c$. Thus, it is not necessary in these embodiments for there to be a carboxylic acyl unit directly between either $L^4$ or $X^4$ and $AA^1$, as is necessary in the peptidic linkers of U.S. Pat. No. 6,214,345.

In another embodiment, the conjugate comprising the peptidyl linker comprises a structure of the following formula (b):

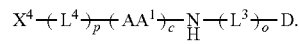

In this embodiment, $L^4$ is a moiety that preferably imparts increased solubility, or decreased aggregation properties, or modifies the hydrolysis rate, as described above; $L^3$ is a spacer group comprising a primary or secondary amine or a carboxyl functional group, and either the amine of $L^3$ forms an amide bond with a pendant carboxyl functional group of D or the carboxyl of $L^3$ forms an amide bond with a pendant amine functional group of D; and o and p are independently 0 or 1. $AA^1$ represents one or more natural amino acids, and/or unnatural α-amino acids; c is an integer from 1 and 20. In this embodiment, $L^1$ is absent (i.e., m is 0 in the general formula).

In the peptide linkers of the invention of the above formula (b), $AA^1$ is linked, at its amino terminus, either directly to $L^4$ or, when $L^4$ is absent, directly to the $X^4$ group (i.e., the targeting agent, detectable label, protected reactive functional group or unprotected reactive functional group). In some embodiments, when $L^4$ is present, $L^4$ does not comprise a carboxylic acyl group directly attached to the N-terminus of $(AA^1)$. Thus, it is not necessary in these embodiments for there to be a carboxylic acyl unit directly between either $L^4$ or $X^4$ and $AA^1$, as is necessary in the peptidic linkers of U.S. Pat. No. 6,214,345.

The Self-Immolative Linker $L^2$

The self-immolative linker $L^2$ is a bifunctional chemical moiety which is capable of covalently linking together two spaced chemical moieties into a normally stable tripartate molecule, releasing one of said spaced chemical moieties from the tripartate molecule by means of enzymatic cleavage; and following said enzymatic cleavage, spontaneously cleaving from the remainder of the molecule to release the other of said spaced chemical moieties. In accordance with the present invention, the self-immolative spacer is covalently linked at one of its ends to the peptide moiety and covalently linked at its other end to the chemically reactive site of the drug moiety whose derivatization inhibits pharmacological activity, so as to space and covalently link together the peptide moiety and the drug moiety into a tripartate molecule which is stable and pharmacologically inactive in the absence of the target enzyme, but which is enzymatically cleavable by such target enzyme at the bond covalently linking the spacer moiety and the peptide moiety to thereby effect release of the peptide moiety from the tripartate molecule. Such enzymatic cleavage, in turn, will activate the self-immolating character of the spacer moiety and initiate spontaneous cleavage of the bond covalently linking the spacer moiety to the drug moiety, to thereby effect release of the drug in pharmacologically active form.

The self-immolative linker $L^2$ may be any self-immolative group. Preferably $L^2$ is a substituted alkyl, unsubstituted alkyl, substituted heteroalkyl, unsubstituted heteroalkyl, unsubstituted heterocycloalkyl, substituted heterocycloalkyl, substituted and unsubstituted aryl, and substituted and unsubstituted heteroaryl.

One particularly preferred self-immolative spacer $L^2$ may be represented by the formula (c):

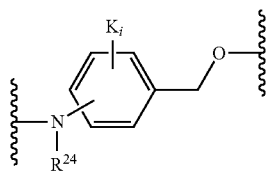

The aromatic ring of the aminobenzyl group may be substituted with one or more "K" groups. A "K" group is a substituent on the aromatic ring that replaces a hydrogen otherwise attached to one of the four non-substituted carbons that are part of the ring structure. The "K" group may be a single atom, such as a halogen, or may be a multi-atom group, such as alkyl, heteroalkyl, amino, nitro, hydroxy, alkoxy, haloalkyl, and cyano. Each K is independently selected from the group consisting of substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, halogen, $NO_2$, $NR^{21}R^{22}$, $NR^{21}COR^{22}$, $OCONR^{21}R^{22}$, $OCOR^{21}$, and $OR^{21}$, wherein $R^{21}$ and $R^{22}$ are independently selected from the group consisting of H, substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl and unsubstituted heterocycloalkyl. Exemplary K substituents include, but are not limited to, F, Cl, Br, I, $NO_2$, OH, $OCH_3$, $NHCOCH_3$, $N(CH_3)_2$, $NHCOCF_3$ and methyl. For "$K_i$", i is an integer of 0, 1, 2, 3, or 4. In one preferred embodiment, i is 0.

The ether oxygen atom of the structure shown above is connected to a carbonyl group. The line from the $NR^{24}$ functionality into the aromatic ring indicates that the amine functionality may be bonded to any of the five carbons that both form the ring and are not substituted by the $—CH_2—O—$ group. Preferably, the $NR^{24}$ functionality of X is covalently bound to the aromatic ring at the para position relative to the $—CH_2—O—$ group. $R^{24}$ is a member selected from the group consisting of H, substituted alkyl, unsubstituted alkyl, substituted heteroalkyl, and unsubstituted heteroalkyl. In a specific embodiment, $R^{24}$ is hydrogen.

In one embodiment, the invention provides a peptide linker of formula (a) above, wherein F comprises the structure:

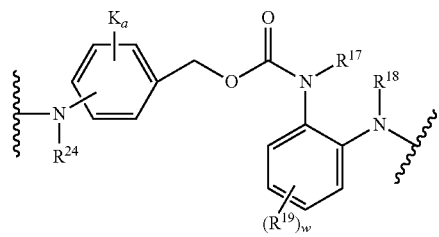

where $R^{24}$ is selected from the group consisting of H, substituted alkyl, unsubstituted alkyl, substituted heteroalkyl, and unsubstituted heteroalkyl. Each K is a member independently selected from the group consisting of substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, halogen, $NO_2$, $NR^{21}R^{22}$, $NR^{21}COr^{22}$, $OCONR^{21}R^{22}$, $OCOR^{21}$, and $OR^{21}$ where $R^{21}$ and $R^{22}$ are independently selected from the group consisting of H, substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl; and i is an integer of 0, 1, 2, 3, or 4.

In another embodiment, the peptide linker of formula (a) above comprises a $—F-(L^1)_m-$ that comprises the structure:

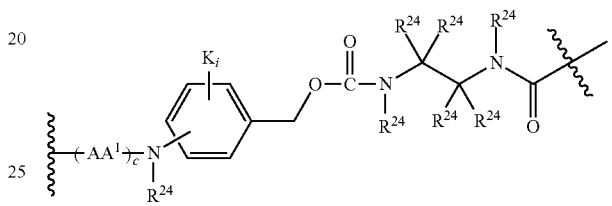

where each $R^{24}$ is a member independently selected from the group consisting of H, substituted alkyl, unsubstituted alkyl, substituted heteroalkyl, and unsubstituted heteroalkyl.

In some embodiments, the self-immolative spacer $L^1$ or $L^2$ includes

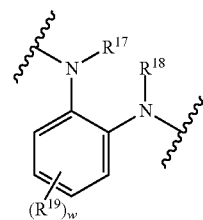

where each $R^{17}$, $R^{18}$, and $R^{19}$ is independently selected from H, substituted or unsubstituted alkyl, substituted or unsubstituted heteroalkyl and substituted or unsubstituted aryl, and w is an integer from 0 to 4. In some embodiments, $R^{17}$ and $R^{18}$ are independently H or alkyl (preferably, unsubstituted $C_{1-4}$ alkyl). Preferably, $R^{17}$ and $R^{18}$ are C1-4 alkyl, such as methyl or ethyl. In some embodiments, w is 0. While not wishing to be bound to any particular theory, it has been found experimentally that this particular self-immolative spacer cyclizes relatively quickly.

In some embodiments, $L^1$ or $L^2$ includes

The Spacer Group L³

The spacer group L³ is characterized in that it comprises a primary or secondary amine or a carboxyl functional group, and either the amine of the L³ group forms an amide bond with a pendant carboxyl functional group of D or the carboxyl of L³ forms an amide bond with a pendant amine functional group of D. L³ can be selected from the group consisting of substituted or unsubstituted alkyl, substituted or unsubstituted heteroalkyl, substituted or unsubstituted aryl, substituted or unsubstituted hteroaryl, or substituted or unsubstituted heterocycloalkyl. In a preferred embodiment, L³ comprises an aromatic group. More preferably, L³ comprises a benzoic acid group, an aniline group or indole group. Non-limiting examples of structures that can serve as an -L³-NH— spacer include the following structures:

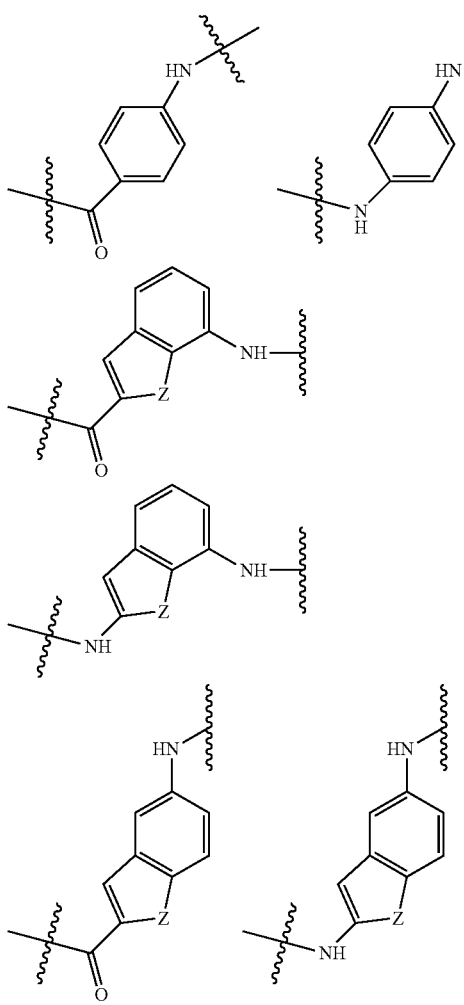

where Z is a member selected from O, S and NR²³, and where R²³ is a member selected from H, substituted or unsubstituted alkyl, substituted or unsubstituted heteroalkyl, and acyl.

Upon cleavage of the linker of the invention containing L³, the L³ moiety remains attached to the drug, D. Accordingly, the L³ moiety is chosen such that its presence attached to D does not significantly alter the activity of D. In another embodiment, a portion of the drug D itself functions as the L³ spacer. For example, in one embodiment, the drug, D, is a duocarmycin derivative in which a portion of the drug functions as the L³ spacer. Non-limiting examples of such embodiments include those in which NH₂-(L³)-D has a structure selected from the group consisting of:

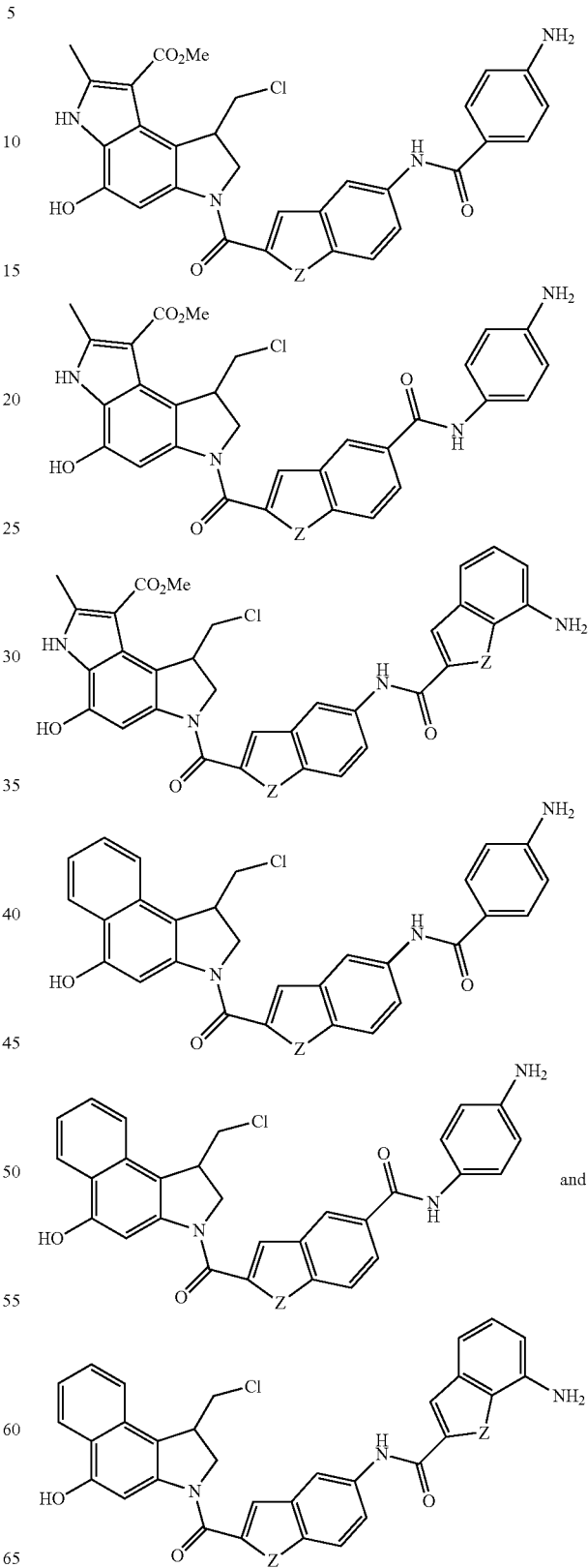

and where Z is a member selected from O, S and $NR^{23}$, where $R^{23}$ is a member selected from H, substituted or unsubstituted alkyl, substituted or unsubstituted heteroalkyl, and acyl; and where the $NH_2$ group on each structure reacts with $(AA^1)_c$ to form $-(AA^1)_cNH-$.

The Peptide Sequence $AA^1$

The group $AA^1$ represents a single amino acid or a plurality of amino acids that are joined together by amide bonds. The amino acids may be natural amino acids and/or unnatural α-amino acids.

The peptide sequence $(AA^1)_c$ is functionally the amidification residue of a single amino acid (when c=1) or a plurality of amino acids joined together by amide bonds. The peptide of the current invention is selected for directing enzyme-catalyzed cleavage of the peptide by an enzyme in a location of interest in a biological system. For example, for conjugates that are targeted to a cell using a targeting agent, but not internalized by that cell, a peptide is chosen that is cleaved by one or more proteases that may exist in in the extracellular matrix, e.g., due to release of the cellular contents of nearby dying cells, such that the peptide is cleaved extracellularly. The number of amino acids within the peptide can range from 1 to 20; but more preferably there will be 1-8 amino acids, 1-6 amino acids or 1, 2, 3 or 4 amino acids comprising $(AA^1)_c$. Peptide sequences that are susceptible to cleavage by specific enzymes or classes of enzymes are well known in the art.

Many peptide sequences that are cleaved by enzymes in the serum, liver, gut, etc. are known in the art. An exemplary peptide sequence of the invention includes a peptide sequence that is cleaved by a protease. The focus of the discussion that follows on the use of a protease-sensitive sequence is for clarity of illustration and does not serve to limit the scope of the present invention.

When the enzyme that cleaves the peptide is a protease, the linker generally includes a peptide containing a cleavage recognition sequence for the protease. A cleavage recognition sequence for a protease is a specific amino acid sequence recognized by the protease during proteolytic cleavage. Many protease cleavage sites are known in the art, and these and other cleavage sites can be included in the linker moiety. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); Bouvier et al. *Meth. Enzymol.* 248: 614 (1995), Hardy et al., in Amyloid Protein Precursor in Development, Aging, and Alzheimer's Disease, ed. Masters et al. pp. 190-198 (1994).

The amino acids of the peptide sequence $(AA^1)_c$ are chosen based on their suitability for selective enzymatic cleavage by particular molecules such as tumor-associated protease. The amino acids used may be natural or unnatural amino acids. They may be in the L or the D configuration. In one embodiment, at least three different amino acids are used. In another embodiment, only two amino acids are used.

In a preferred embodiment, the peptide sequence $(AA^1)_c$ is chosen based on its ability to be cleaved by a lysosomal proteases, non-limiting examples of which include cathepsins B, C, D, H, L and S. Preferably, the peptide sequence $(AA^1)_c$ is capable of being cleaved by cathepsin B in vitro, which can be tested using in vitro protease cleavage assays known in the art.

In another embodiment, the peptide sequence $(AA^1)_c$ is chosen based on its ability to be cleaved by a tumor-associated protease, such as a protease that is found extracellularly in the vicinity of tumor cells, non-limiting examples of which include thimet oligopeptidase (TOP) and CD10. The ability of a peptide to be cleaved by TOP or CD10 can be tested using in vitro protease cleavage assays known in the art.

Suitable, but non-limiting, examples of peptide sequences suitable for use in the conjugates of the invention include Val-Cit, Cit-Cit, Val-Lys, Phe-Lys, Lys-Lys, Ala-Lys, Phe-Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ. ID NO: 94), β-Ala-Leu-Ala-Leu (SEQ. ID NO: 95) and Gly-Phe-Leu-Gly (SEQ. ID NO: 96), Val-Ala, Leu-Leu-Gly-Leu (SEQ. ID NO: 97), Leu-Asn-Ala, and Lys-Leu-Val. Preferred peptides sequences are Val-Cit and Val-Lys.

In another embodiment, the amino acid located the closest to the drug moiety is selected from the group consisting of: Ala, Asn, Asp, Cit, Cys, Gln, Glu, Gly, Ile, Leu, Lys, Met, Phe, Pro, Ser, Thr, Trp, Tyr, and Val. In yet another embodiment, the amino acid located the closest to the drug moiety is selected from the group consisting of: Ala, Asn, Asp, Cys, Gln, Glu, Gly, Ile, Leu, Met, Phe, Pro, Ser, Thr, Trp, Tyr, and Val.

Proteases have been implicated in cancer metastasis. Increased synthesis of the protease urokinase was correlated with an increased ability to metastasize in many cancers. Urokinase activates plasmin from plasminogen, which is ubiquitously located in the extracellular space and its activation can cause the degradation of the proteins in the extracellular matrix through which the metastasizing tumor cells invade. Plasmin can also activate the collagenases thus promoting the degradation of the collagen in the basement membrane surrounding the capillaries and lymph system thereby allowing tumor cells to invade into the target tissues (Dano, et al. *Adv. Cancer. Res.*, 44:139 (1985)). Thus, it is within the scope of the present invention to utilize as a linker a peptide sequence that is cleaved by urokinase.

The invention also provides the use of peptide sequences that are sensitive to cleavage by tryptases. Human mast cells express at least four distinct tryptases, designated αβI, βII, and βIII. These enzymes are not controlled by blood plasma proteinase inhibitors and only cleave a few physiological substrates in vitro. The tryptase family of serine proteases has been implicated in a variety of allergic and inflammatory diseases involving mast cells because of elevated tryptase levels found in biological fluids from patients with these disorders. However, the exact role of tryptase in the pathophysiology of disease remains to be delineated. The scope of biological functions and corresponding physiological consequences of tryptase are substantially defined by their substrate specificity.

Tryptase is a potent activator of pro-urokinase plasminogen activator (uPA), the zymogen form of a protease associated with tumor metastasis and invasion. Activation of the plasminogen cascade, resulting in the destruction of extracellular matrix for cellular extravasation and migration, may be a function of tryptase activation of pro-urokinase plasminogen activator at the P4-P1 sequence of Pro-Arg-Phe-Lys (SEQ. ID NO: 98) (Stack, et al., *Journal of Biological Chemistry* 269 (13): 9416-9419 (1994)). Vasoactive intestinal peptide, a neuropeptide that is implicated in the regulation of vascular permeability, is also cleaved by tryptase, primarily at the Thr-Arg-Leu-Arg (SEQ. ID NO: 99) sequence (Tam, et al., *Am. J. Respir. Cell Mol. Biol.* 3: 27-32 (1990)). The G-protein coupled receptor PAR-2 can be cleaved and activated by tryptase at the Ser-Lys-Gly-Arg (SEQ. ID NO: 100) sequence to drive fibroblast proliferation, whereas the thrombin activated receptor PAR-1 is inactivated by tryptase at the Pro-Asn-Asp-Lys (SEQ. ID NO: 101) sequence (Molino et al., *Journal of Biological Chemistry* 272(7): 4043-4049 (1997)). Taken together, this evidence suggests a central role for tryptase in tissue remodeling as a consequence of disease. This is consistent with the profound changes observed in several mast cell-mediated disorders. One hallmark of chronic asthma and other long-term respiratory diseases is fibrosis and thickening of the underlying tissues that could be the result of tryptase activation of its physiological targets. Similarly, a series of reports have shown angiogenesis to be associated with mast cell density, tryptase activity and poor prognosis in a variety of cancers (Coussens et al., *Genes and Development* 13(11): 1382-97 (1999)); Takanami et al., *Cancer* 88(12): 2686-92 (2000); Toth-Jakatics et al., *Human Pathology* 31(8): 955-960 (2000); Ribatti et al., *International Journal of Cancer* 85(2): 171-5 (2000)).

Methods are known in the art for evaluating whether a particular protease cleaves a selected peptide sequence. For example, the use of 7-amino-4-methyl coumarin (AMC) fluorogenic peptide substrates is a well-established method for the determination of protease specificity (Zimmerman, M., et al., (1977) *Analytical Biochemistry* 78:47-51). Specific cleavage of the anilide bond liberates the fluorogenic AMC leaving group allowing for the simple determination of cleavage rates for individual substrates. More recently, arrays (Lee, D., et al., (1999) *Bioorganic and Medicinal Chemistry Letters* 9:1667-72) and positional-scanning libraries (Rano, T. A., et al., (1997) *Chemistry and Biology* 4:149-55) of AMC peptide substrate libraries have been employed to rapidly profile the N-terminal specificity of proteases by sampling a wide range of substrates in a single experiment. Thus, one of skill in the art may readily evaluate an array of peptide sequences to determine their utility in the present invention without resort to undue experimentation.

The antibody-partner conjugate of the current invention may optionally contain two or more linkers. These linkers may be the same or different. For example, a peptidyl linker may be used to connect the drug to the ligand and a second peptidyl linker may attach a diagnostic agent to the complex. Other uses for additional linkers include linking analytical agents, biomolecules, targeting agents, and detectable labels to the antibody-partner complex.

Also within the scope of the present invention are compounds of the invention that are poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, is attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Moreover, the present invention includes compounds that are functionalized to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to, for example, replace a hydroxyl group with a diol, or an amine with a quaternary amine, hydroxy amine or similar more water-soluble moiety. In a preferred embodiment, additional water solubility is imparted by substitution at a site not essential for the activity towards the ion channel of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

Hydrazine Linkers (H)

In a second embodiment, the conjugate of the invention comprises a hydrazine self-immolative linker, wherein the conjugate has the structure:

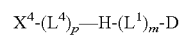

wherein D, $L^1$, $L^4$, and $X^4$ are as defined above and described further herein, and H is a linker comprising the structure:

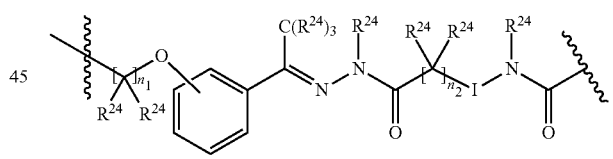

wherein $n_1$ is an integer from 1-10; $n_2$ is 0, 1, or 2; each $R^{24}$ is a member independently selected from the group consisting of H, substituted alkyl, unsubstituted alkyl, substituted heteroalkyl, and unsubstituted heteroalkyl; and I is either a bond (i.e., the bond between the carbon of the backbone and the adjacent nitrogen) or:

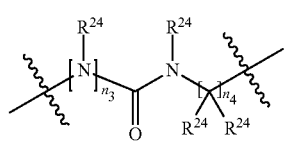

wherein $n_3$ is 0 or 1, with the proviso that when $n_3$ is 0, $n_2$ is not 0; and $n_4$ is 1, 2, or 3, wherein when I is a bond, $n_1$ is 3 and $n_2$ is 1, D can not be

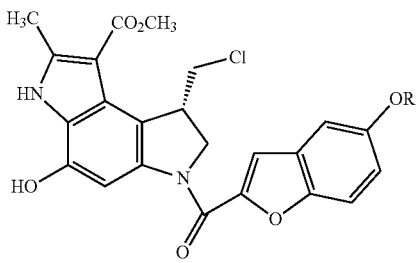

where R is Me or $CH_2$—$CH_2$—$NMe_2$.

In one embodiment, the substitution on the phenyl ring is a para substitution. In preferred embodiments, $n_1$ is 2, 3, or 4 or $n_1$ is 3. In preferred embodiments, $n_2$ is 1. In preferred embodiments, I is a bond (i.e., the bond between the carbon of the backbone and the adjacent nitrogen). In one aspect, the hydrazine linker, H, can form a 6-membered self immolative linker upon cleavage, for example, when $n_3$ is 0 and $n_4$ is 2. In another aspect, the hydrazine linker, H, can form two 5-membered self immolative linkers upon cleavage. In yet other aspects, H forms a 5-membered self immolative linker, H forms a 7-membered self immolative linker, or H forms a 5-membered self immolative linker and a 6-membered self immolative linker, upon cleavage. The rate of cleavage is affected by the size of the ring formed upon cleavage. Thus, depending upon the rate of cleavage desired, an appropriate size ring to be formed upon cleavage can be selected.

Five Membered Hydrazine Linkers

In one embodiment, the hydrazine linker comprises a 5-membered hydrazine linker, wherein H comprises the structure:

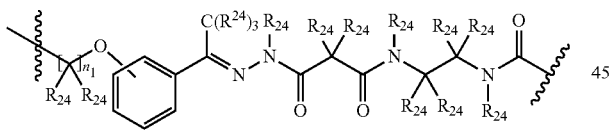

In a preferred embodiment, $n_1$ is 2, 3, or 4. In another preferred embodiment, $n_1$ is 3.

In the above structure, each $R^{24}$ is a member independently selected from the group consisting of H, substituted alkyl, unsubstituted alkyl, substituted heteroalkyl, and unsubstituted heteroalkyl. In one embodiment, each $R^{24}$ is independently H or a $C_1$-$C_6$ alkyl. In another embodiment, each $R^{24}$ is independently H or a $C_1$-$C_3$ alkyl, more preferably H or $CH_3$. In another embodiment, at least one $R^{24}$ is a methyl group. In another embodiment, each $R_{24}$ is H. Each $R^{24}$ is selected to tailor the compounds steric effects and for altering solubility.

The 5-membered hydrazine linkers can undergo one or more cyclization reactions that separate the drug from the linker, and can be described, for example, by:

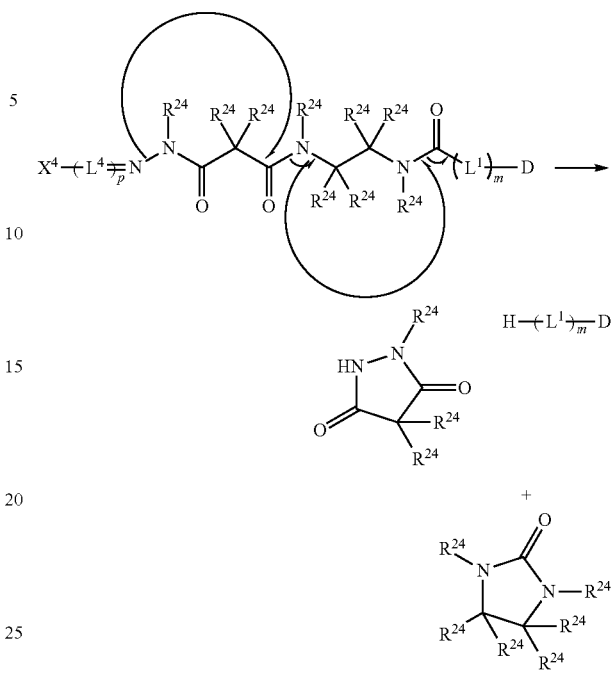

An exemplary synthetic route for preparing a five membered linker of the invention is:

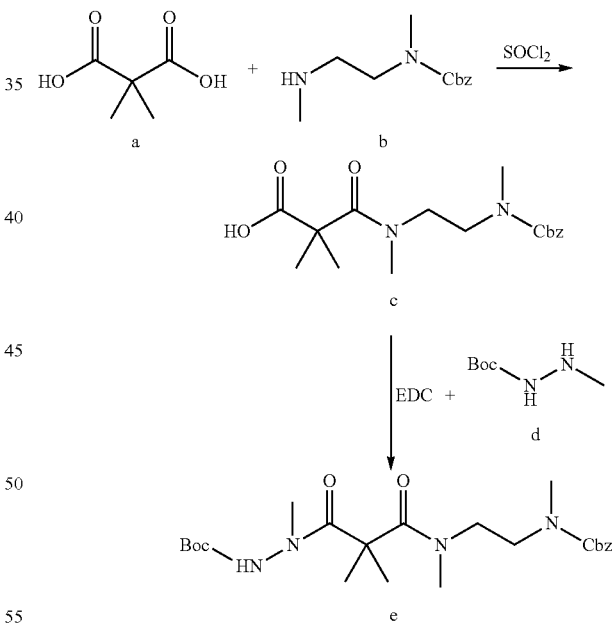

The Cbz-protected DMDA b is reacted with 2,2-Dimethylmalonic acid a in solution with thionyl chloride to form a Cbz-DMDA-2,2-dimethylmalonic acid c. Compound c is reacted with Boc-N-methyl hydrazine d in the presence of EDC to form DMDA-2,2-dimethylmalonic-Boc-N-methylhydrazine e.

Six Membered Hydrazine Linkers

In another embodiment, the hydrazine linker comprises a 6-membered hydrazine linker, wherein H comprises the structure:

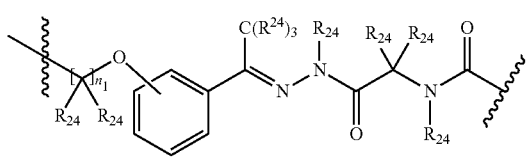

In a preferred embodiment, $n_1$ is 3. In the above structure, each $R^{24}$ is a member independently selected from the group consisting of H, substituted alkyl, unsubstituted alkyl, substituted heteroalkyl, and unsubstituted heteroalkyl. In one embodiment, each $R^{24}$ is independently H or a $C_1$-$C_6$ alkyl. In another embodiment, each $R^{24}$ is independently H or a $C_1$-$C_3$ alkyl, more preferably H or $CH_3$. In another embodiment, at least one $R^{24}$ is a methyl group. In another embodiment, each $R_{24}$ is H. Each $R^{24}$ is selected to tailor the compounds steric effects and for altering solubility. In a preferred embodiment, H comprises the structure:

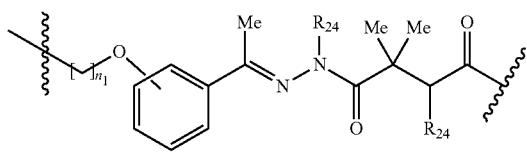

In one embodiment, H comprises a geminal dimethyl substitution. In one embodiment of the above structure, each $R^{24}$ is independently an H or a substituted or unsubstituted alkyl.

The 6-membered hydrazine linkers will undergo a cyclization reaction that separates the drug from the linker, and can be described as:

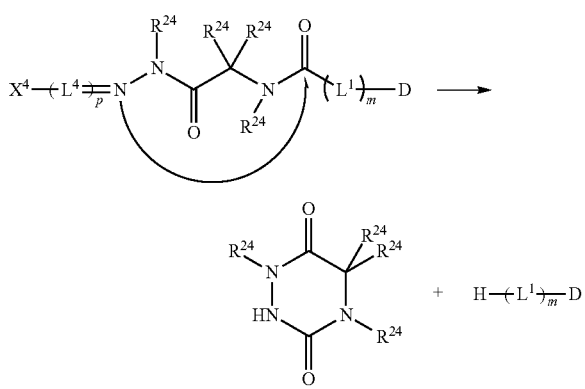

An exemplary synthetic route for preparing a six membered linker of the invention is:

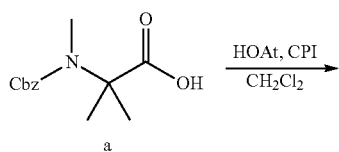

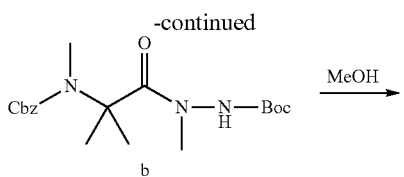

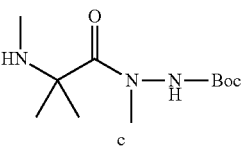

The Cbz-protected dimethyl alanine a in solution with dichlormethane, was reacted with HOAt, and CPI to form a Cbz-protected dimethylalanine hydrazine b. The hydrazine b is deprotected by the action of methanol, forming compound c.

Other Hydrazine Linkers

It is contemplated that the invention comprises a linker having seven members. This linker would likely not cyclize as quickly as the five or six membered linkers, but this may be preferred for some antibody-partner conjugates. Similarly, the hydrazine linker may comprise two six membered rings or a hydrazine linker having one six and one five membered cyclization products. A five and seven membered linker as well as a six and seven membered linker are also contemplated.

Another hydrazine structure, H, has the formula:

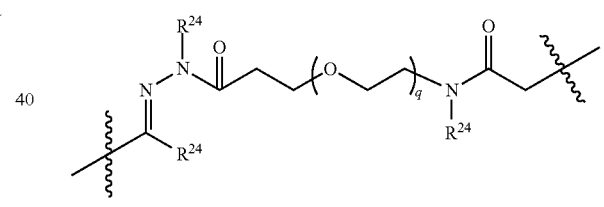

where q is 0, 1, 2, 3, 4, 5, or 6; and each $R^{24}$ is a member independently selected from the group consisting of H, substituted alkyl, unsubstituted alkyl, substituted heteroalkyl, and unsubstituted heteroalkyl. This hydrazine structure can also form five-, six-, or seven-membered rings and additional components can be added to form multiple rings.

Disulfide Linkers (J)

In yet another embodiment, the linker comprises an enzymatically cleavable disulfide group. In one embodiment, the invention provides a cytotoxic antibody-partner compound having a structure according to Formula (d):

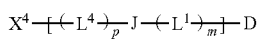

wherein D, $L^1$, $L^4$, and $X^4$ are as defined above and described further herein, and J is a disulfide linker comprising a group having the structure:

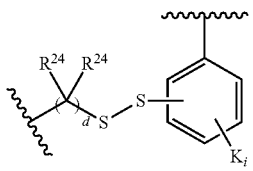

wherein each $R^{24}$ is a member independently selected from the group consisting of H, substituted alkyl, unsubstituted alkyl, substituted heteroalkyl, and unsubstituted heteroalkyl; each K is a member independently selected from the group consisting of substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, halogen, $NO_2$, $NR^{21}R^{22}$, $NR^{21}COR^{22}$, $OCONR^{21}R^{22}$, $OCOR^{21}$, and $OR^{21}$ wherein $R^{21}$ and $R^{22}$ are independently selected from the group consisting of H, substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl and unsubstituted heterocycloalkyl; i is an integer of 0, 1, 2, 3, or 4; and d is an integer of 0, 1, 2, 3, 4, 5, or 6.

The aromatic ring of the disulfides linker may be substituted with one or more "K" groups. A "K" group is a substituent on the aromatic ring that replaces a hydrogen otherwise attached to one of the four non-substituted carbons that are part of the ring structure. The "K" group may be a single atom, such as a halogen, or may be a multi-atom group, such as alkyl, heteroalkyl, amino, nitro, hydroxy, alkoxy, haloalkyl, and cyano. Exemplary K substituents independently include, but are not limited to, F, Cl, Br, I, $NO_2$, OH, $OCH_3$, $NHCOCH_3$, $N(CH_3)_2$, $NHCOCF_3$ and methyl. For "$K_i$", i is an integer of 0, 1, 2, 3, or 4. In a specific embodiment, i is 0.

In a preferred embodiment, the linker comprises an enzymatically cleavable disulfide group of the following formula:

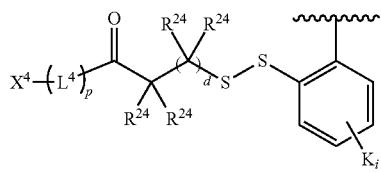

In this embodiment, the identities of $L^4$, $X^4$, p, and $R^{24}$ are as described above, and d is 0, 1, 2, 3, 4, 5, or 6. In a particular embodiment, d is 1 or 2.

A more specific disulfide linker is shown in the formula below:

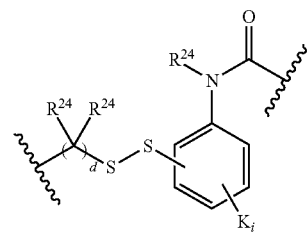

A specific example of this embodiment is as follows:

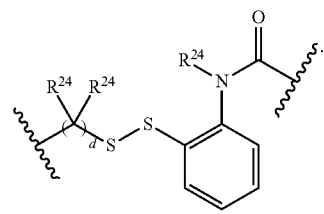

Preferably, d is 1 or 2.

Another disulfide linker is shown in the formula below:

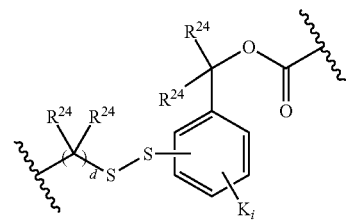

A specific example of this embodiment is as follows:

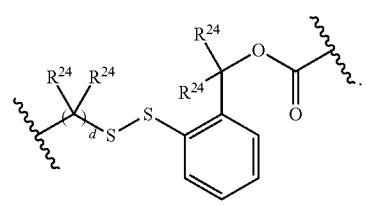

Preferably, d is 1 or 2.

In various embodiments, the disulfides are ortho to the amine 1n another specific embodiment, a is 0. In preferred embodiments, $R^{24}$ is independently selected from H and $CH_3$.

An exemplary synthetic route for preparing a disulfide linker of the invention is as follows:

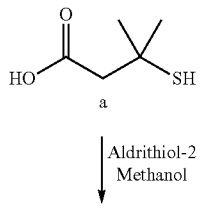

Aldrithiol-2
Methanol

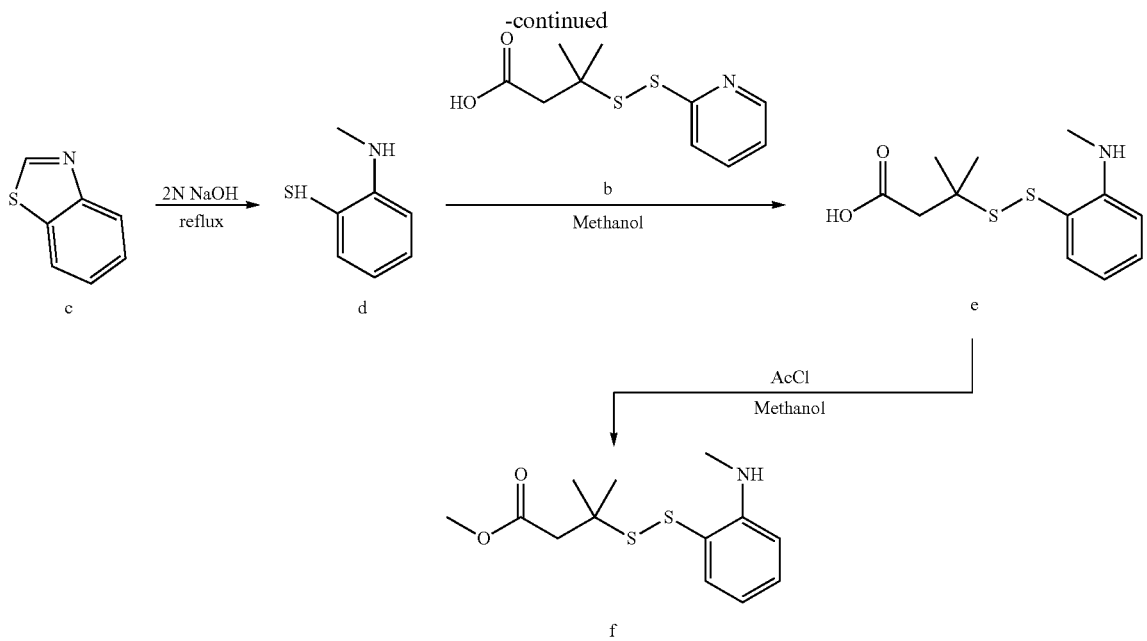

A solution of 3-mercaptopropionic acid a is reacted with aldrithiol-2 to form 3-methyl benzothiazolium iodide b. 3-methylbenzothiazolium iodide c is reacted with sodium hydroxide to form compound d. A solution of compound d with methanol is further reacted with compound b to form compound e. Compound e deprotected by the action of acetyl chloride and methanol forming compound f.

For further discussion of types of cytotoxins, linkers and other methods for conjugating therapeutic agents to antibodies, see also PCT Publication WO 2007/059404 to Gangwar et al. and entitled "Cytotoxic Compounds And Conjugates," Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264, each of which are hereby incorporated by reference in their entirety.

Partner Molecules

In one aspect, the present invention features an antibody conjugated to a partner molecule, such as a cytotoxin, a drug (e.g., an immunosuppressant) or a radiotoxin. Such conjugates are also referred to herein as "immunoconjugates" Immunoconjugates that include one or more cytotoxins are referred to as "immunotoxins." A cytotoxin or cytotoxic agent includes any agent that is detrimental to (e.g., kills) cells.

Examples of partner molecules of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Examples of partner molecules also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of partner molecules that can be conjugated to an antibody of the invention include duocarmycins, calicheamicins, maytansines and auristatins, and derivatives thereof. An example of a calicheamicin antibody conjugate is commercially available (Mylotarg®; American Home Products).

Preferred examples of partner molecule are CC-1065 and the duocarmycins. CC-1065 was first isolated from *Streptomyces zelensis* in 1981 by the Upjohn Company (Hanka et al., J. Antibiot. 31: 1211 (1978); Martin et al., J. Antibiot. 33: 902 (1980); Martin et al., J. Antibiot. 34: 1119 (1981)) and was found to have potent antitumor and antimicrobial activity both in vitro and in experimental animals ($L^1$ et al., Cancer Res. 42: 999 (1982)). CC-1065 binds to double-stranded B-DNA within the minor groove (Swenson et al., Cancer Res. 42: 2821 (1982)) with the sequence preference of 5'-d(A/GNTTA)-3' and 5'-d(AAAAA)-3' and alkylates the N3 position of the 3'-adenine by its CPI left-hand unit present in the molecule (Hurley et al., Science 226: 843 (1984)). Despite its potent and broad antitumor activity, CC-1065 cannot be used in humans because it causes delayed death in experimental animals.

Many analogues and derivatives of CC-1065 and the duocarmycins are known in the art. The research into the structure, synthesis and properties of many of the compounds has been reviewed. See, for example, Boger et al., Angew. Chem. Int. Ed. Engl. 35: 1438 (1996); and Boger et al., Chem. Rev. 97: 787 (1997).

A group at Kyowa Hakko Kogya Co., Ltd. has prepared a number of CC-1065 derivatives. See, for example, U.S. Pat. Nos. 5,101,038; 5,641,780; 5,187,186; 5,070,092; 5,703,080; 5,070,092; 5,641,780; 5,101,038; and 5,084,468;

and published PCT application, WO 96/10405 and published European application 0 537 575 A1.

The Upjohn Company (Pharmacia Upjohn) has also been active in preparing derivatives of CC-1065. See, for example, U.S. Pat. Nos. 5,739,350; 4,978,757; 5,332, 837 and 4,912,227.

A particularly preferred aspect of the current invention provides a cytotoxic compound having a structure according to the following formula (e):

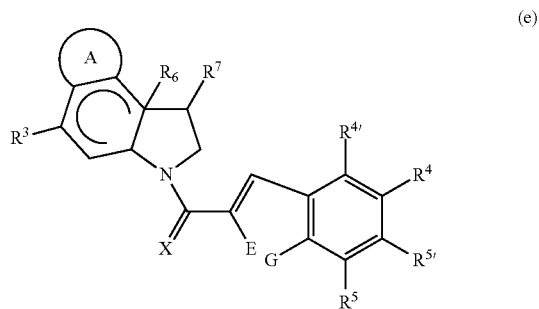

(e)

in which ring system A is a member selected from substituted or unsubstituted aryl substituted or unsubstituted heteroaryl and substituted or unsubstituted heterocycloalkyl groups. Exemplary ring systems include phenyl and pyrrole.

The symbols E and G are independently selected from H, substituted or unsubstituted alkyl, substituted or unsubstituted heteroalkyl, a heteroatom, a single bond or E and G are optionally joined to form a ring system selected from substituted or unsubstituted aryl, substituted or unsubstituted heteroaryl and substituted or unsubstituted heterocycloalkyl.

The symbol X represents a member selected from O, S and $NR^{23}$. $R^{23}$ is a member selected from H, substituted or unsubstituted alkyl, substituted or unsubstituted heteroalkyl, and acyl.

The symbol $R^3$ represents a member selected from (=O), $SR^{11}$, $NHR^{11}$ and $OR^{11}$, in which $R^{11}$ is H, substituted or unsubstituted alkyl, substituted or unsubstituted heteroalkyl, monophosphates, diphosphates, triphosphates, sulfonates, acyl, $C(O)R^{12}R^{13}$, $C(O)OR^{12}$, $C(O)NR^{12}R^{13}$, $P(O)(OR^{12})_2$, $C(O)CHR^{12}R^{13}$, $SiR^{12}$ or $SiR^{12}R^{13}R^{14}$. The symbols $R^{12}$, $R^{13}$, and $R^{14}$ independently represent H, substituted or unsubstituted alkyl, substituted or unsubstituted heteroalkyl and substituted or unsubstituted aryl, where $R^{12}$ and $R^{13}$ together with the nitrogen or carbon atom to which they are attached are optionally joined to form a substituted or unsubstituted heterocycloalkyl ring system having from 4 to 6 members, optionally containing two or more heteroatoms. One or more of $R^{12}$, $R^{13}$, or $R^{14}$ can include a cleavable group within its structure.

$R^4$, $R^{4'}$, $R^4$ and $R^{5'}$ are members independently selected from H, substituted or unsubstituted alkyl, substituted or unsubstituted aryl, substituted or unsubstituted heteroaryl, substituted or unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $SR^{15}$, $OR^{15}$, $CR^{15}=NR^{16}$, and $O(CH_2)_nN(CH_3)_2$, where n is an integer from 1 to 20, or any adjacent pair of $R^4$, $R^{4'}$, $R^5$ and $R^{5'}$, together with the carbon atoms to which they are attached, are joined to form a substituted or unsubstituted cycloalkyl or heterocycloalkyl ring system having from 4 to 6 members. $R^{15}$ and $R^{16}$ independently represent H, substituted or unsubstituted alkyl, substituted or unsubstituted heteroalkyl, substituted or unsubstituted aryl, substituted or unsubstituted heteroaryl, substituted or unsubstituted heterocycloalkyl and substituted or unsubstituted peptidyl, where $R^{15}$ and $R^{16}$ together with the nitrogen atom to which they are attached are optionally joined to form a substituted or unsubstituted heterocycloalkyl ring system having from 4 to 6 members, optionally containing two or more heteroatoms. One exemplary structure is aniline.

$R^4$, $R^{4'}$, $R^5$, $R^{5'}$, $R^{11}$, $R^{12}$, $R^{13}$, $R^{15}$ and $R^{16}$ optionally contain one or more cleavable groups within their structure, such as a cleavable linker or cleavable substrate. Exemplary cleavable groups include, but are not limited to peptides, amino acids, hydrazines, disulfides, and cephalosporin derivatives.

In some embodiments, at least one of $R^4$, $R^{4'}$, $R^5$, $R^{5'}$, $R^{11}$, $R^{12}$, $R^{13}$, $R^{15}$ and $R^{16}$ is used to join the drug to a linker or enzyme cleavable substrate of the present invention, as described herein, for example to $L^1$, if present or to F, H, J, or $X^2$, or J.

In a still further exemplary embodiment, at least one of $R^4$, $R^{4'}$, $R^5$, $R^{5'}$, $R^{11}$, $R^{12}$, $R^{13}$, $R^{15}$ and $R^{16}$ bears a reactive group appropriate for conjugating the compound. In a further exemplary embodiment, $R^4$, $R^{4'}$, $R^5$, $R^{5'}$, $R^{11}$, $R^{12}$, $R^{13}$, $R^{15}$ and $R^{16}$ are independently selected from H, substituted alkyl and substituted heteroalkyl and have a reactive functional group at the free terminus of the alkyl or heteroalkyl moiety. One or more of $R^4$, $R^{4'}$, $R^5$, $R^{5'}$, $R^{11}$, $R^{12}$, $R^{13}$, $R^{15}$ and $R^{16}$ may be conjugated to another species, e.g, targeting agent, detectable label, solid support, etc.

$R^6$ is a single bond which is either present or absent. When $R^6$ is present, $R^6$ and $R^7$ are joined to form a cyclopropyl ring. $R^7$ is $CH_2$—$X^1$ or —$CH_2$—. When $R^7$ is —$CH_2$— it is a component of the cyclopropane ring. The symbol $X^1$ represents a leaving group such as a halogen, for example Cl, Br or F. The combinations of $R^6$ and $R^7$ are interpreted in a manner that does not violate the principles of chemical valence.

$X^1$ may be any leaving group. Useful leaving groups include, but are not limited to, halogens, azides, sulfonic esters (e.g., alkylsulfonyl, arylsulfonyl), oxonium ions, alkyl perchlorates, ammonioalkanesulfonate esters, alkylfluorosulfonates and fluorinated compounds (e.g., triflates, nonaflates, tresylates) and the like. Particular halogens useful as leaving groups are F, Cl and Br. The choice of these and other leaving groups appropriate for a particular set of reaction conditions is within the abilities of those of skill in the art (see, for example, March J, Advanced Organic Chemistry, 2nd Edition, John Wiley and Sons, 1992; Sandler S R, Karo W, Organic Functional Group Preparations, 2nd Edition, Academic Press, Inc., 1983; and Wade L G, Compendium of Organic Synthetic Methods, John Wiley and Sons, 1980).

The curved line within the six-membered ring indicates that the ring may have one or more degrees of unsaturation, and it may be aromatic. Thus, ring structures such as those set forth below, and related structures, are within the scope of Formula (f):

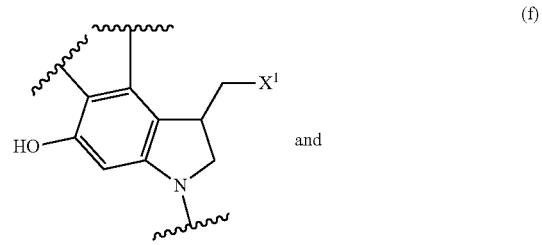

(f)

and

-continued

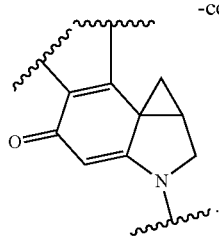

In some embodiments, at least one of $R^4$, $R^{4'}$, $R^5$, and $R^{5'}$ links said drug to $L^1$, if present, or to F, H, J, or $X^2$, and includes

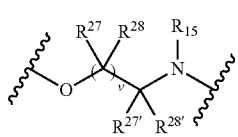

where v is an integer from 1 to 6; and each $R^{27}$, $R^{27'}$, $R^{28}$, and $R^{28'}$ is independently selected from H, substituted or unsubstituted alkyl, substituted or unsubstituted heteroalkyl, substituted or unsubstituted aryl, substituted or unsubstituted heteroaryl, and substituted or unsubstituted heterocycloalkyl. In some embodiments, $R^{27}$, $R^{27'}$, $R^{28}$, and $R^{28'}$ are all H. In some embodiments, v is an integer from 1 to 3 (preferably, 1). This unit can be used to separate aryl substituents from the drug and thereby resist or avoid generating compounds that are substrates for multi-drug resistance.

In one embodiment, $R^{11}$ includes a moiety, $X^5$, that does not self-cyclize and links the drug to $L^1$, if present, or to F, H, J, or $X^2$. The moiety, $X^5$, is preferably cleavable using an enzyme and, when cleaved, provides the active drug. As an example, $R^{11}$ can have the following structure (with the right side coupling to the remainder of the drug):

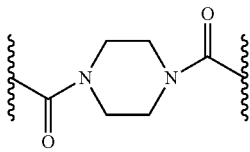 [SMILES: *C(=O)N1CCN(C(*)=O)CC1]

In an exemplary embodiment, ring system A of formula (e) is a substituted or unsubstituted phenyl ring. Ring system A may be substituted with one or more aryl group substituents as set forth in the definitions section herein. In some embodiments, the phenyl ring is substituted with a CN or methoxy moiety.

In some embodiments, at least one of $R^4$, $R^{4'}$, $R^5$, and $R^{5'}$ links said drug to $L^1$, if present, or to F, H, J, or $X^2$, and $R^3$ is selected from $SR^{11}$, $NHR^{11}$ and $OR^{11}$. $R^{11}$ is selected from —SO(OH)$_2$, —PO(OH)$_2$, -AA$_n$, —Si(CH$_3$)$_2$C(CH$_3$)$_3$, —C(O)OPhNH(AA)$_m$,

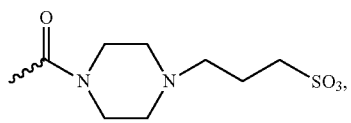

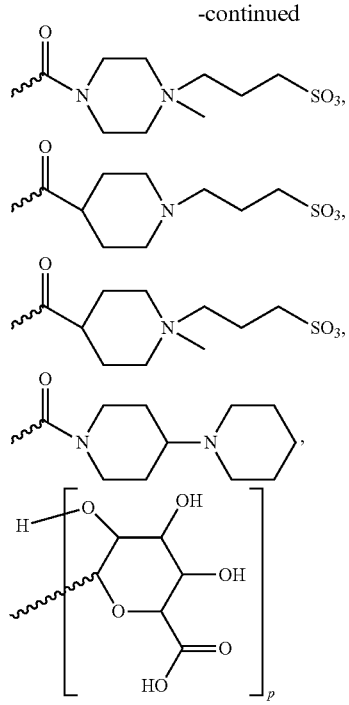

or any other sugar or combination of sugars,

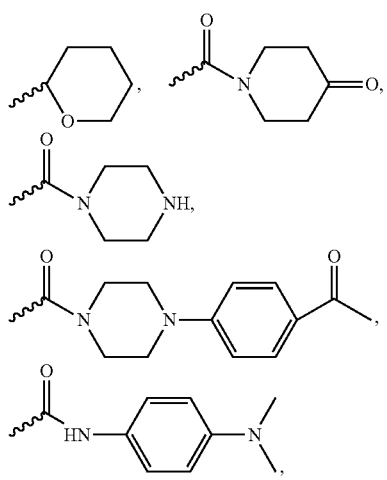

and pharmaceutically acceptable salts thereof, where n is any integer in the range of 1 to 10, m is any integer in the range of 1 to 4, p is any integer in the range of 1 to 6, and AA is any natural or non-natural amino acid. In some embodiments, AA$_n$ or AA$_m$ is selected from the same amino acid sequences described above for the peptide linkers (F) and optionally is the same as the amino acid sequence used in the linker portion of $R^4$, $R^{4'}$, $R^5$, or $R^{5'}$. In at least some embodiments, $R^3$ is cleavable in vivo to provide an active drug compound. In at least some embodiments, $R^3$ increases in vivo solublility of the compound. In some embodiments, the rate of decrease of the concentration of the active drug in the blood is substantially faster than the rate of cleavage of $R^3$ to provide the active drug. This may be particularly useful where the toxicity of the active drug is substantially higher than that of the prodrug form. In other embodiments, the rate of cleavage of $R^3$ to provide the active drug is faster than the rate of decrease of concentration of the active drug in the blood.

In another exemplary embodiment, the invention provides a compound having a structure according to Formula (g):

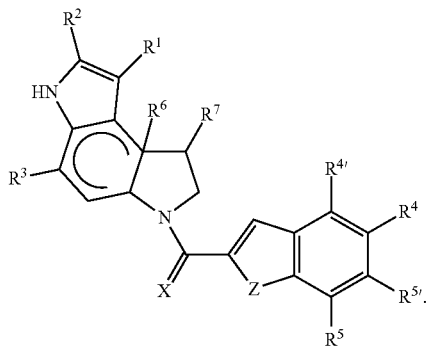

(g)

In this embodiment, the identities of the substituents $R^3$, $R^4$, $R^{4'}$, $R^5$, $R^{5'}$, $R^6$, $R^7$ and X are substantially as described above for Formula (a), as well as preferences for particular embodiments. The symbol Z is a member independently selected from O, S and $NR^{23}$. The symbol $R^{23}$ represents a member selected from H, substituted or unsubstituted alkyl, substituted or unsubstituted heteroalkyl, and acyl. Each $R^{23}$ is independently selected. The symbol $R^1$ represents H, substituted or unsubstituted lower alkyl, or $C(O)R^8$ or $CO_2R^8$. $R^8$ is a member selected from substituted alkyl, unsubstituted alkyl, $NR^9R^{10}$, $NR^9NHR^{10}$ and $OR^9$. $R^9$ and $R^{10}$ are independently selected from H, substituted or unsubstituted alkyl and substituted or unsubstituted heteroalkyl. $R^2$ is H, or substituted or unsubstituted lower alkyl. It is generally preferred that when $R^2$ is substituted alkyl, it is other than a perfluoroalkyl, e.g., $CF_3$. In one embodiment, $R^2$ is a substituted alkyl wherein the substitution is not a halogen. In another embodiment, $R^2$ is an unsubstituted alkyl.

In some embodiments $R^1$ is an ester moiety, such as $CO_2CH_3$. In some embodiments, $R^2$ is a lower alkyl group, which may be substituted or unsubstituted. A presently preferred lower alkyl group is $CH_3$. In some preferred embodiments, $R^1$ is $CO_2CH_3$ and $R^2$ is $CH_3$.

In some embodiments, $R^4$, $R^{4'}$, $R^5$, and $R^{5'}$ are members independently selected from H, halogen, $NH_2$, OMe, $O(CH_2)_2N(R^{29})_2$ and $NO_2$. Each $R^{29}$ is independently H or lower alkyl (e.g., methyl).

In some embodiments, the drug is selected such that the leaving group $X^1$ is a member selected from the group consisting of halogen, alkylsulfonyl, arylsulfonyl, and azide. In some embodiments, $X^1$ is F, Cl, or Br.

In some embodiments, Z is O or NH. In some embodiments, X is O.

In yet another exemplary embodiment, the invention provides compounds having a structure according to Formula (h) or (i):

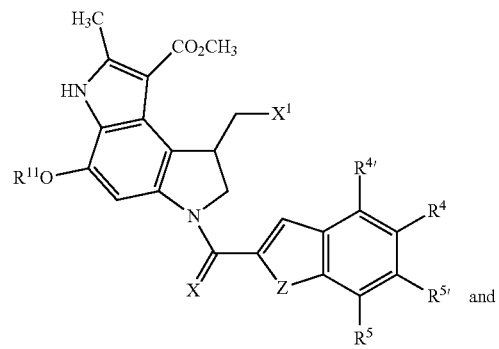

(h)

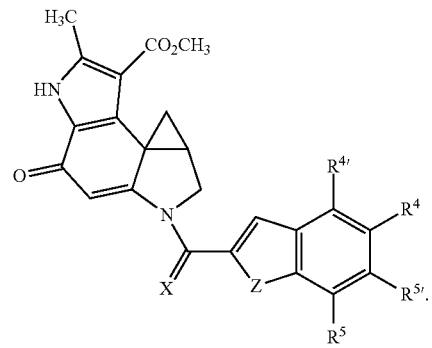

(i)

Another preferred structure of the duocarmycin analog of Formula (e) is a structure in which the ring system A is an unsubstituted or substituted phenyl ring. The preferred substituents on the drug molecule described hereinabove for the structure of Formula 7 when the ring system A is a pyrrole are also preferred substituents when the ring system A is an unsubstituted or substituted phenyl ring.

For example, in a preferred embodiment, the drug (D) comprises a structure (j):

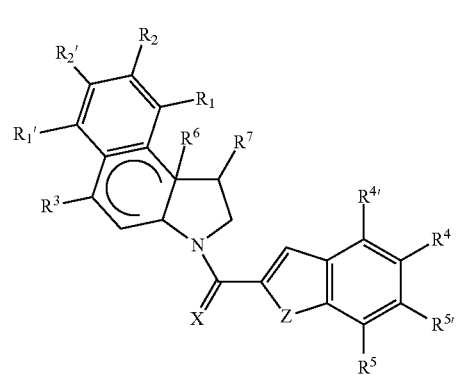

(j)

In this structure, $R^3$, $R^6$, $R^2$, X are as described above for Formula (e). Furthermore, Z is a member selected from O, S and $NR^{23}$, wherein $R^{23}$ is a member selected from H, substituted or unsubstituted alkyl, substituted or unsubstituted heteroalkyl, and acyl;

$R^1$ is H, substituted or unsubstituted lower alkyl, $C(O)R^8$, or $CO_2R^8$, wherein $R^8$ is a member selected from $NR^9R^{10}$ and $OR^9$, in which $R^9$ and $R^{10}$ are members independently selected from H, substituted or unsubstituted alkyl and substituted or unsubstituted heteroalkyl;

$R^{1'}$ is H, substituted or unsubstituted lower alkyl, or $C(O)R^8$, wherein $R^8$ is a member selected from $NR^9R^{10}$ and $OR^9$, in which $R^9$ and $R^{10}$ are members independently selected from H, substituted or unsubstituted alkyl and substituted or unsubstituted heteroalkyl;

$R^2$ is H, or substituted or unsubstituted lower alkyl or unsubstituted heteroalkyl or cyano or alkoxy; and $R^{2'}$ is H, or substituted or unsubstituted lower alkyl or unsubstituted heteroalkyl.

At least one of $R^4$, $R^{4'}$, $R^5$, $R^{5'}$, $R^{11}$, $R^{12}$, $R^{13}$, $R^{15}$ and $R^{16}$ links the drug to $L^1$, if present, or to F, H, J, or $X^2$.

Another embodiment of the drug (D) comprises a structure (k) where $R^4$ and $R^{4'}$ have been joined to from a heterocycloalkyl:

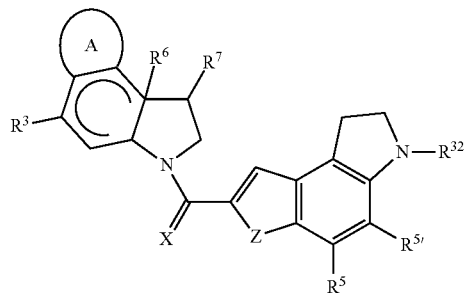

(k)

In this structure, $R^3$, $R^5$, $R^{5'}$, $R^6$, $R^7$, X are as described above for Formula (e). Furthermore, Z is a member selected from O, S and $NR^{23}$, wherein $R^{23}$ is a member selected from H, substituted or unsubstituted alkyl, substituted or unsubstituted heteroalkyl, and acyl;

$R^{32}$ is selected from H, substituted or unsubstituted alkyl, substituted or unsubstituted aryl, substituted or unsubstituted heteroaryl, substituted or unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $SR^{15}$, $OR^{15}$, $CR^{15}{=}NR^{16}$, and $O(CH_2)_nN(CH_3)_2$, where n is an integer from 1 to 20. $R^{15}$ and $R^{16}$ independently represent H, substituted or unsubstituted alkyl, substituted or unsubstituted heteroalkyl, substituted or unsubstituted aryl, substituted or unsubstituted heteroaryl, substituted or unsubstituted heterocycloalkyl and substituted or unsubstituted peptidyl, where $R^{15}$ and $R^{16}$ together with the nitrogen atom to which they are attached are optionally joined to form a substituted or unsubstituted heterocycloalkyl ring system having from 4 to 6 members, optionally containing two or more heteroatoms. $R^{32}$ optionally contains one or more cleavable groups within its structure, such as a cleavable linker or cleavable substrate. Exemplary cleavable groups include, but are not limited to, peptides, amino acids, hydrazines, disulfides, and cephalosporin derivatives. Moreover, any selection of substituents described herein for $R^4$, $R^{4'}$, $R^5$, $R^{5'}$, $R^{15}$ and $R^{16}$ is also applicable to $R^{32}$.

At least one of $R^5$, $R^{5'}$, $R^{11}$, $R^{12}$, $R^{13}$, $R^{15}$ and $R^{16}$ or $R^{32}$ links the drug to $L^1$, if present, or to F, H, J, or $X^2$. In at least some embodiments, $R^{32}$ links the drug to $L^1$, if present, or to F, H, J, or $X^2$.

One preferred embodiment of this compound is:

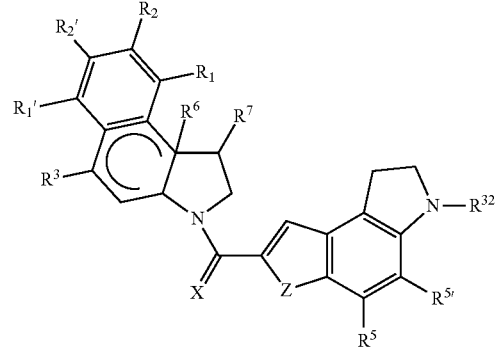

$R^1$ is H, substituted or unsubstituted lower alkyl, $C(O)R^8$, or $CO_2R^8$, wherein $R^8$ is a member selected from $NR^9R^{10}$ and $OR^9$, in which $R^9$ and $R^{10}$ are members independently selected from H, substituted or unsubstituted alkyl and substituted or unsubstituted heteroalkyl;

$R^{1'}$ is H, substituted or unsubstituted lower alkyl, or $C(O)R^8$, wherein $R^8$ is a member selected from $NR^9R^{10}$ and $OR^9$, in which $R^9$ and $R^{10}$ are members independently selected from H, substituted or unsubstituted alkyl and substituted or unsubstituted heteroalkyl;

$R^2$ is H, or substituted or unsubstituted lower alkyl or unsubstituted heteroalkyl or cyano or alkoxy; and $R^{2'}$ is H, or substituted or unsubstituted lower alkyl or unsubstituted heteroalkyl.

A further embodiment has the formula:

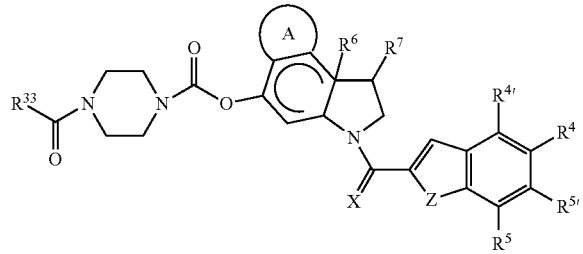

In this structure, A, $R^6$, $R^7$, X, $R^4$, $R^{4'}$, $R^5$, and $R^{5'}$ are as described above for Formula (e). Furthermore, Z is a member selected from O, S and $NR^{23}$, where $R^{23}$ is a member selected from H, substituted or unsubstituted alkyl, substituted or unsubstituted heteroalkyl, and acyl;

$R^{33}$ is selected from H, substituted or unsubstituted alkyl, substituted or unsubstituted aryl, substituted or unsubstituted heteroaryl, substituted or unsubstituted heterocycloalkyl, halogen, $NO_2$, $NR^{15}R^{16}NC(O)R^{15}$, $OC(O)NR^{15}R^{16}$, $OC(O)OR^{15}$, $C(O)R^{15}$, $SR^{15}$, $OR^{15}$, $CR^{15}{=}NR^{16}$, and $O(CH_2)_nN(CH_3)_2$, where n is an integer from 1 to 20. $R^{15}$ and $R^{16}$ independently represent H, substituted or unsubstituted alkyl, substituted or unsubstituted heteroalkyl, substituted or unsubstituted aryl, substituted or unsubstituted heteroaryl, substituted or unsubstituted heterocycloalkyl and substituted or unsubstituted peptidyl, where $R^{15}$ and $R^{16}$ together with the nitrogen atom to which they are attached are optionally joined to form a substituted or unsubstituted heterocycloalkyl ring system having from 4 to 6 members, optionally containing two or more heteroatoms. $R^{33}$ links the drug to $L^1$, if present, or to F, H, J, or $X^2$.

Preferably, A is substituted or unsubstituted phenyl or substituted or unsubstituted pyrrole. Moreover, any selection of substituents described herein for $R^{11}$ is also applicable to $R^{33}$.

Ligands $X^4$ represents a ligand selected from the group consisting of protected reactive functional groups, unprotected reactive functional groups, detectable labels, and targeting agents. Preferred ligands are targeting agents, such as antibodies and fragments thereof.

In some embodiments, the group $X^4$ can be described as a member selected from $R^{29}$, $COOR^{29}$, $C(O)NR^{29}$, and $C(O)NNR^{29}$ wherein $R^{29}$ is a member selected from substituted or unsubstituted alkyl, substituted or unsubstituted heteroalkyl and substituted or unsubstituted heteroaryl. In yet another exemplary embodiment, $R^{29}$ is a thiol reactive member. In a further exemplary embodiment, $R^{29}$ is a thiol reactive member selected from haloacetyl and alkyl halide derivatives, maleimides, aziridines, and acryloyl derivatives. The above thiol reactive members can act as reactive protective groups that can be reacted with, for example, a side chain of an amino acid of a targeting agent, such as an antibody, to thereby link the targeting agent to the linker-drug moiety.

Detectable Labels

The particular label or detectable group used in conjunction with the compounds and methods of the invention is generally not a critical aspect of the invention, as long as it does not significantly interfere with the activity or utility of the compound of the invention. The detectable group can be any material having a detectable physical or chemical property. Such detectable labels have been well developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™) fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to a compound of the invention according to methods well known in the art. As indicated above, a wide variety of labels may be used, with the choice of label depending on sensitivity required, ease of conjugation with the compound, stability requirements, available instrumentation, and disposal provisions.

When the compound of the invention is conjugated to a detectable label, the label is preferably a member selected from the group consisting of radioactive isotopes, fluorescent agents, fluorescent agent precursors, chromophores, enzymes and combinations thereof. Methods for conjugating various groups to antibodies are well known in the art. For example, a detectable label that is frequently conjugated to an antibody is an enzyme, such as horseradish peroxidase, alkaline phosphatase, β-galactosidase, and glucose oxidase.

Non-radioactive labels are often attached by indirect means. Generally, a ligand molecule (e.g., biotin) is covalently bound to a component of the conjugate. The ligand then binds to another molecules (e.g., streptavidin) molecule, which is either inherently detectable or covalently bound to a signal system, such as a detectable enzyme, a fluorescent compound, or a chemiluminescent compound.

Components of the conjugates of the invention can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Fluorescent labels are presently preferred as they have the advantage of requiring few precautions in handling, and being amenable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Many fluorescent labels are commercially available from the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label.

In addition to small molecule fluorophores, naturally occurring fluorescent proteins and engineered analogues of such proteins are useful in the present invention. Such proteins include, for example, green fluorescent proteins of cnidarians (Ward et al., *Photochem. Photobiol.* 35:803-808 (1982); Levine et al., *Comp. Biochem. Physiol.*, 72B:77-85 (1982)), yellow fluorescent protein from *Vibrio fischeri* strain (Baldwin et al., *Biochemistry* 29:5509-15 (1990)), Peridinin-chlorophyll from the dinoflagellate *Symbiodinium* sp. (Morris et al., *Plant Molecular Biology* 24:673:77 (1994)), phycobiliproteins from marine cyanobacteria, such as Synechococcus, e.g., phycoerythrin and phycocyanin (Wilbanks et al., *J. Biol. Chem.* 268:1226-35 (1993)), and the like.

Generally, prior to forming the linkage between the cyto-Cytotoxin And the targeting (or other) agent, and optionally, the spacer group, at least one of the chemical functionalities will be activated. One skilled in the art will appreciate that a variety of chemical functionalities, including hydroxy, amino, and carboxy groups, can be activated using a variety of standard methods and conditions. For example, a hydroxyl group of the cytotoxin or targeting agent can be activated through treatment with phosgene to form the corresponding chloroformate, or p-nitrophenylchloroformate to form the corresponding carbonate.

In an exemplary embodiment, the invention makes use of a targeting agent that includes a carboxyl functionality. Carboxyl groups may be activated by, for example, conversion to the corresponding acyl halide or active ester. This reaction may be performed under a variety of conditions as illustrated in March, supra pp. 388-89. In an exemplary embodiment, the acyl halide is prepared through the reaction of the carboxyl-containing group with oxalyl chloride. The activated agent is reacted with a cytotoxin or cytotoxin-linker arm combination to form a conjugate of the invention. Those of skill in the art will appreciate that the use of carboxyl-containing targeting agents is merely illustrative, and that agents having many other functional groups can be conjugated to the linkers of the invention.

Reactive Functional Groups

For clarity of illustration the succeeding discussion focuses on the conjugation of a cytotoxin of the invention to a targeting agent. The focus exemplifies one embodiment of the invention from which, others are readily inferred by one of skill in the art. No limitation of the invention is implied, by focusing the discussion on a single embodiment.

Exemplary compounds of the invention bear a reactive functional group, which is generally located on a substituted or unsubstituted alkyl or heteroalkyl chain, allowing their facile attachment to another species. A convenient location for the reactive group is the terminal position of the chain.

Reactive groups and classes of reactions useful in practicing the present invention are generally those that are well known in the art of bioconjugate chemistry. The reactive functional group may be protected or unprotected, and the protected nature of the group may be changed by methods known in the art of organic synthesis. Preferred classes of reactions available with reactive cytoCytotoxin Analogues are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, Advanced Organic Chemistry, 3rd Ed., John Wiley & Sons, New York, 1985; Hermanson, Bioconjugate Techniques, Academic Press, San Diego, 1996; and Feeney et al., Modification of Proteins; Advances in Chemistry Series, Vol. 198, American Chemical Society, Washington, D.C., 1982.

Exemplary reaction types include the reaction of carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters. Hydroxyl groups can be converted to esters, ethers, aldehydes, etc. Haloalkyl groups are converted to new species by reaction with, for example, an amine, a carboxylate anion, thiol anion, carbanion, or an alkoxide ion. Dienophile (e.g., maleimide) groups participate in Diels-Alder. Aldehyde or ketone groups can be converted to imines, hydrazones, semicarbazones or oximes, or via such mechanisms as Grignard addition or alkyllithium addition. Sulfonyl halides react readily with amines, for example, to form sulfonamides Amine or sulfhydryl groups are, for example, acylated, alkylated or oxidized. Alkenes, can be converted to an array of new species using cycloadditions, acylation, Michael addition, etc. Epoxides react readily with amines and hydroxyl compounds.

One skilled in the art will readily appreciate that many of these linkages may be produced in a variety of ways and using a variety of conditions. For the preparation of esters, see, e.g., March supra at 1157; for thioesters, see, March, supra at 362-363, 491, 720-722, 829, 941, and 1172; for carbonates, see, March, supra at 346-347; for carbamates, see, March, supra at 1156-57; for amides, see, March supra at 1152; for ureas and thioureas, see, March supra at 1174; for acetals and ketals, see, Greene et al. supra 178-210 and March supra at 1146; for acyloxyalkyl derivatives, see, Prodrugs: Topical and Ocular Drug Delivery, K. B. Sloan, ed., Marcel Dekker, Inc., New York, 1992; for enol esters, see, March supra at 1160; for N-sulfonylimidates, see, Bundgaard et al., J. Med. Chem., 31:2066 (1988); for anhydrides, see, March supra at 355-56, 636-37, 990-91, and 1154; for N-acylamides, see, March supra at 379; for N-Mannich bases, see, March supra at 800-02, and 828; for hydroxymethyl ketone esters, see, Petracek et al. *Annals NY Acad. Sci.*, 507:353-54 (1987); for disulfides, see, March supra at 1160; and for phosphonate esters and phosphonamidates.

The reactive functional groups can be unprotected and chosen such that they do not participate in, or interfere with, the reactions. Alternatively, a reactive functional group can be protected from participating in the reaction by the presence of a protecting group. Those of skill in the art will understand how to protect a particular functional group from interfering with a chosen set of reaction conditions. For examples of useful protecting groups, See Greene et al., Protective Groups in Organic Synthesis, John Wiley & Sons, New York, 1991.

Typically, the targeting agent is linked covalently to a cytotoxin using standard chemical techniques through their respective chemical functionalities. Optionally, the linker or agent is coupled to the agent through one or more spacer groups. The spacer groups can be equivalent or different when used in combination.

Generally, prior to forming the linkage between the cyto-Cytotoxin And the reactive functional group, and optionally, the spacer group, at least one of the chemical functionalities will be activated. One skilled in the art will appreciate that a variety of chemical functionalities, including hydroxy, amino, and carboxy groups, can be activated using a variety of standard methods and conditions. In an exemplary embodiment, the invention comprises a carboxyl functionality as a reactive functional group. Carboxyl groups may be activated as described hereinabove.

Cleavable Substrate

The cleavable substrates of the current invention are depicted as "$X^2$". Preferably, the cleavable substrate is a cleavable enzyme substrate that can be cleaved by an enzyme. Preferably, the enzyme is preferentially associated, directly or indirectly, with the tumor or other target cells to be treated. The enzyme may be generated by the tumor or other target cells to be treated. For example, the cleavable substrate can be a peptide that is preferentially cleavable by an enzyme found around or in a tumor or other target cell. Additionally or alternatively, the enzyme can be attached to a targeting agent that binds specifically to tumor cells, such as an antibody specific for a tumor antigen.

As examples of enzyme cleavable substrates suitable for coupling to the drugs described above, PCT Patent Applications Publication Nos. WO 00/33888, WO 01/95943, WO 01/95945, WO 02/00263, and WO 02/100353, all of which are incorporated herein by reference, disclose attachment of a cleavable peptide to a drug. The peptide is cleavable by an enzyme, such as a trouase (such as thimet oligopeptidase), CD10 (neprilysin), a matrix metalloprotease (such as MMP2 or MMP9), a type II transmembrane serine protease (such as Hepsin, testisin, TMPRSS4, or matriptase/MT-SP1), or a cathepsin, associated with a tumor. In this embodiment, a prodrug includes the drug as described above, a peptide, a stabilizing group, and optionally a linking group between the drug and the peptide. The stabilizing group is attached to the end of the peptide to protect the prodrug from degradation before arriving at the tumor or other target cell. Examples of suitable stabilizing groups include non-amino acids, such as succinic acid, diglycolic acid, maleic acid, polyethylene glycol, pyroglutamic acid, acetic acid, naphthylcarboxylic acid, terephthalic acid, and glutaric acid derivatives; as well as non-genetically-coded amino acids or aspartic acid or glutamic acid attached to the N-terminus of the peptide at the β-carboxy group of aspartic acid or the γ-carboxyl group of glutamic acid.

The peptide typically includes 3-12 (or more) amino acids. The selection of particular amino acids will depend, at least in part, on the enzyme to be used for cleaving the peptide, as well as, the stability of the peptide in vivo. One example of a suitable cleavable peptide is β-AlaLeuAlaLeu. This can be combined with a stabilizing group to form succinyl-β-AlaLeuAlaLeu. Other examples of suitable cleavable peptides are provided in the references cited above.

As one illustrative example, CD10, also known as neprilysin, neutral endopeptidase (NEP), and common acute lymphoblastic leukemia antigen (CALLA), is a type II cell-surface zinc-dependent metalloprotease. Cleavable substrates suitable for use with CD10 include LeuAlaLeu and IleAlaLeu. Other known substrates for CD10 include peptides of up to 50 amino acids in length, although catalytic efficiency often declines as the substrate gets larger.

Another illustrative example is based on matrix metalloproteases (MMP). Probably the best characterized proteolytic enzymes associated with tumors, there is a clear correlation of activation of MMPs within tumor microenvironments. In particular, the soluble matrix enzymes MMP2 (gelatinase A) and MMP9 (gelatinase B), have been intensively studied, and shown to be selectively activated during tissue remodeling including tumor growth. Peptide sequences designed to be cleaved by MMP2 and MMP9 have been designed and tested for conjugates of dextran and methotrexate (Chau et al., *Bioconjugate Chem.* 15:931-941 (2004)); PEG (polyethylene glycol) and doxorubicin (Bae et al., *Drugs Exp. Clin. Res.* 29:15-23 (2004)); and albumin and doxorubicin (Kratz et al., *Bioorg. Med. Chem. Lett.* 11:2001-2006 (2001)). Examples of suitable sequences for use with MMPs include, but are not limited to, ProValGlyLeuIleGly (SEQ. ID NO. 102), GlyProLeuGlyVal (SEQ. ID NO. 103), GlyProLeuGlyIleAlaGlyGln (SEQ. ID NO. 104), ProLeuGlyLeu (SEQ. ID NO. 105), GlyProLeuGlyMetLeuSerGln (SEQ. ID NO. 106), and GlyProLeuGlyLeuTrpAlaGln (SEQ. ID NO. 107). (See, e.g., the previously cited references as well as Kline et al., *Mol. Pharmaceut.* 1:9-22 (2004) and Liu et al., *Cancer Res.* 60:6061-6067 (2000).) Other cleavable substrates can also be used.

Yet another example is type II transmembrane serine proteases. This group of enzymes includes, for example, hepsin, testisin, and TMPRSS4. GlnAlaArg is one substrate sequence that is useful with matriptase/MT-SP1 (which is over-expressed in breast and ovarian cancers) and LeuSerArg is useful with hepsin (over-expressed in prostate and some other tumor types). (See, e.g., Lee et. al., *J. Biol. Chem.* 275:36720-36725 and Kurachi and Yamamoto, Handbook of Proeolytic Enzymes Vol. 2, $2^{nd}$ edition (Barrett A J, Rawlings N D & Woessner J F, eds) pp. 1699-1702 (2004).) Other cleavable substrates can also be used.

Another type of cleavable substrate arrangement includes preparing a separate enzyme capable of cleaving the cleavable substrate that becomes associated with the tumor or cells. For example, an enzyme can be coupled to a tumor-specific antibody (or other entity that is preferentially attracted to the tumor or other target cell such as a receptor ligand) and then the enzyme-antibody conjugate can be provided to the patient. The enzyme-antibody conjugate is directed to, and binds to, antigen associated with the tumor. Subsequently, the drug-cleavable substrate conjugate is provided to the patient as a prodrug. The drug is only released in the vicinity of the tumor when the drug-cleavable substrate conjugate interacts with the enzyme that has become associated with the tumor so that the cleavable substrate is cleaved and the drug is freed. For example, U.S. Pat. Nos. 4,975,278; 5,587,161; 5,660,829; 5,773,435; and 6,132,722, all of which are incorporated herein by reference, disclose such an arrangement. Examples of suitable enzymes and substrates include, but are not limited to, β-lactamase and cephalosporin derivatives, carboxypeptidase G2 and glutamic and aspartic folate derivatives.

In one embodiment, the enzyme-antibody conjugate includes an antibody, or antibody fragment, that is selected based on its specificity for an antigen expressed on a target cell, or at a target site, of interest. A discussion of antibodies is provided hereinabove. One example of a suitable cephalosporin-cleavable substrate is

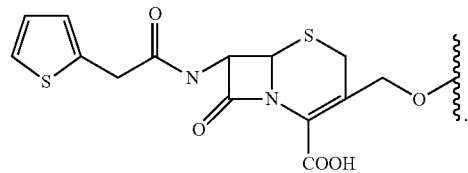 [SMILES: *OCC1=C(C(=O)O)N2C(=O)C(NC(=O)Cc3cccs3)C2SC1]

Examples of Conjugates

The linkers and cleavable substrates of the invention can be used in conjugates containing a variety of partner molecules. Examples of conjugates of the invention are described in further detail below. Unless otherwise indicated, substituents are defined as set forth above in the sections regarding cytotoxins, linkers, and cleavable substrates.

A. Linker Conjugates

One example of a suitable conjugate is a compound of the formula:

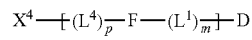

wherein $L^1$ is a self-immolative linker; m is an integer 0, 1, 2, 3, 4, 5, or 6; F is a linker comprising the structure:

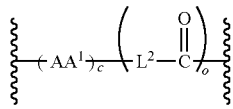

wherein $AA^1$ is one or more members independently selected from the group consisting of natural amino acids and unnatural α-amino acids; c is an integer from 1 to 20; $L^2$ is a self-immolative linker and comprises

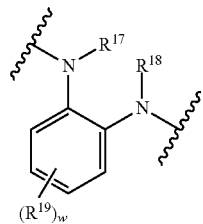

wherein each $R^{17}$, $R^{18}$, and $R^{19}$ is independently selected from H, substituted or unsubstituted alkyl, substituted or unsubstituted heteroalkyl and substituted or unsubstituted aryl, and w is an integer from 0 to 4; o is 1; $L^4$ is a linker member; p is 0 or 1; $X^4$ is a member selected from the group consisting of protected reactive functional groups, unprotected reactive functional groups, detectable labels, and targeting agents; and D comprises a structure:

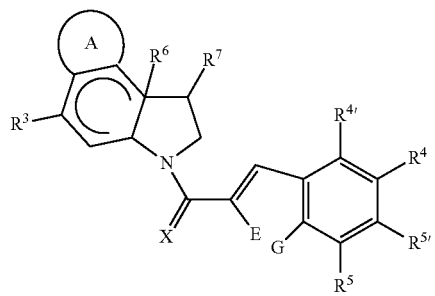

wherein the ring system A is a member selected from substituted or unsubstituted aryl, substituted or unsubstituted heteroaryl and substituted or unsubstituted heterocycloalkyl groups; E and G are members independently selected from H, substituted or unsubstituted alkyl, substituted or unsubstituted heteroalkyl, a heteroatom, a single bond, or E and G are joined to form a ring system selected from substituted or unsubstituted aryl, substituted or unsubstituted heteroaryl and substituted or unsubstituted heterocycloalkyl; X is a member selected from O, S and $NR^{23}$; $R^{23}$ is a member selected from H, substituted or unsubstituted alkyl, substituted or unsubstituted heteroalkyl, and acyl; $R^3$ is $OR^{11}$, wherein $R^{11}$ is a member selected from the group consisting of H, substituted alkyl, unsubstituted alkyl, substituted heteroalkyl, unsubstituted heteroalkyl, monophosphates, diphosphates, triphosphates, sulfonates, acyl, $C(O)R^{12}R^{13}$, $C(O)OR^{12}$, $C(O)NR^{12}R^{13}$, $P(O)(OR^{12})_2$, $C(O)CHR^{12}R^{13}$, $SR^{12}$ and $SiR^{12}R^{13}R^{14}$, $R^4$, $R^{4'}$, $R^5$ and $R^{5'}$ are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $SR^{15}$, $OR^{15}$, $CR^{15}=NR^{16}$, and $O(CH_2)_nN(CH_3)_2$, or any adjacent pair of $R^4$, $R^{4'}$, $R^5$ and $R^{5'}$, together with the carbon atoms to which they are attached, are joined to form a substituted or unsubstituted cycloalkyl or heterocycloalkyl ring system having from 4 to 6 members; wherein n is an integer from 1 to 20; $R^{15}$ and $R^{16}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and substituted or unsubstituted peptidyl, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms; $R^6$ is a single bond which is either present or absent and when present $R^6$ and $R^7$ are joined to form a cyclopropyl ring; and $R^7$ is $CH_2$—$X^1$ or —$CH_2$— joined in said cyclopropyl ring with $R^6$, wherein $X^1$ is a leaving group, wherein $R^{11}$ links said drug to $L^1$, if present, or to F.

In some embodiments, the drug has structure (c) or (f) above. One specific example of a compound suitable for use as a conjugate is

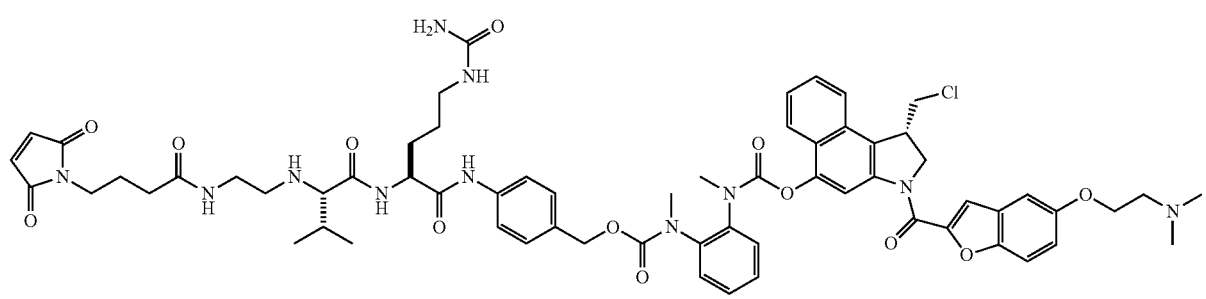 [SMILES: CC(C)[C@H](NCCNC(=O)CCCN1C(=O)C=CC1=O)C(=O)N[C@@H](CCCNC(N)=O)C(=O)Nc1ccc(COC(=O)N(C)c2ccccc2N(C)C(=O)Oc2cc3c(c4ccccc24)[C@H](CCl)CN3C(=O)c2cc3cc(OCCN(C)C)ccc3o2)cc1]

Another example of a type of conjugate is a compound of the formula

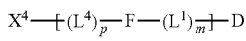

wherein $L^1$ is a self-immolative linker; m is an integer 0, 1, 2, 3, 4, 5, or 6; F is a linker comprising the structure:

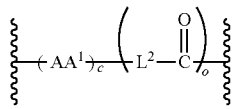

wherein $AA^1$ is one or more members independently selected from the group consisting of natural amino acids and unnatural α-amino acids; c is an integer from 1 to 20; $L^2$ is a self-immolative linker; o is 0 or 1; $L^4$ is a linker member; p is 0 or 1; $X^4$ is a member selected from the group consisting of protected reactive functional groups, unprotected reactive functional groups, detectable labels, and targeting agents; and D comprises a structure:

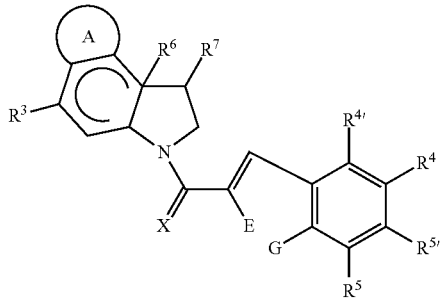

wherein the ring system A is a member selected from substituted or unsubstituted aryl, substituted or unsubstituted heteroaryl and substituted or unsubstituted heterocycloalkyl groups; E and G are members independently selected from H, substituted or unsubstituted alkyl, substituted or unsubstituted heteroalkyl, a heteroatom, a single bond, or E and G are joined to form a ring system selected from substituted or unsubstituted aryl, substituted or unsubstituted heteroaryl and substituted or unsubstituted heterocycloalkyl; X is a member selected from O, S and $NR^{23}$; $R^{23}$ is a member selected from H, substituted or unsubstituted alkyl, substituted or unsubstituted heteroalkyl, and acyl; $R^3$ is a member selected from the group consisting of (=O), $SR^{11}$, $NHR^{11}$ and $OR^{11}$, wherein $R^{11}$ is a member selected from the group consisting of H, substituted alkyl, unsubstituted alkyl, substituted heteroalkyl, unsubstituted heteroalkyl, monophosphates, diphosphates, triphosphates, sulfonates, acyl, C(O)$R^{12}R^{13}$, C(O)O$R^{12}$, C(O)N$R^{12}R^{13}$, P(O)(O$R^{12}$)$_2$, C(O)CH$R^{12}R^{13}$, S$R^{12}$ and SiR$^{12}$R$^{13}$R$^{14}$, in which $R^{12}$, $R^{13}$, and $R^{14}$ are members independently selected from H, substituted or unsubstituted alkyl, substituted or unsubstituted heteroalkyl and substituted or unsubstituted aryl, wherein $R^{12}$ and $R^{13}$ together with the nitrogen or carbon atom to which they are attached are optionally joined to form a substituted or unsubstituted heterocycloalkyl ring system having from 4 to 6 members, optionally containing two or more heteroatoms; $R^4$, $R^{4'}$, $R^5$ and $R^{5'}$ are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, NO$_2$, NR$^{15}$R$^{16}$, NC(O)R$^{15}$, OC(O)NR$^{15}$R$^{16}$, OC(O)OR$^{15}$, C(O)R$^{15}$, SR$^{15}$, OR$^{15}$, CR$^{15}$=NR$^{16}$, and O(CH$_2$)$_n$N(CH$_3$)$_2$, or any adjacent pair of $R^4$, $R^{4'}$, $R^5$ and $R^{5'}$, together with the carbon atoms to which they are attached, are joined to form a substituted or unsubstituted cycloalkyl or heterocycloalkyl ring system having from 4 to 6 members, wherein n is an integer from 1 to 20; $R^{15}$ and $R^{16}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and substituted or unsubstituted peptidyl, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms; wherein at least one of $R^4$, $R^{4'}$, $R^5$ and $R^{5'}$ links said drug to $L^1$, if present, or to F, and comprises

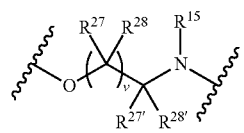

wherein v is an integer from 1 to 6; and each $R^{27}$, $R^{27'}$, $R^{28}$, and $R^{28'}$ is independently selected from H, substituted or unsubstituted alkyl, substituted or unsubstituted heteroalkyl, substituted or unsubstituted aryl, substituted or unsubstituted heteroaryl, and substituted or unsubstituted heterocycloalkyl; $R^6$ is a single bond which is either present or absent and when present $R^6$ and $R^7$ are joined to form a cyclopropyl ring; and $R^7$ is CH$_2$—X$^1$ or —CH$_2$— joined in said cyclopropyl ring with $R^6$, wherein $X^1$ is a leaving group.

In some embodiment, the drug has structure (c) or (f) above. One specific example of a compound suitable for use as a conjugate is

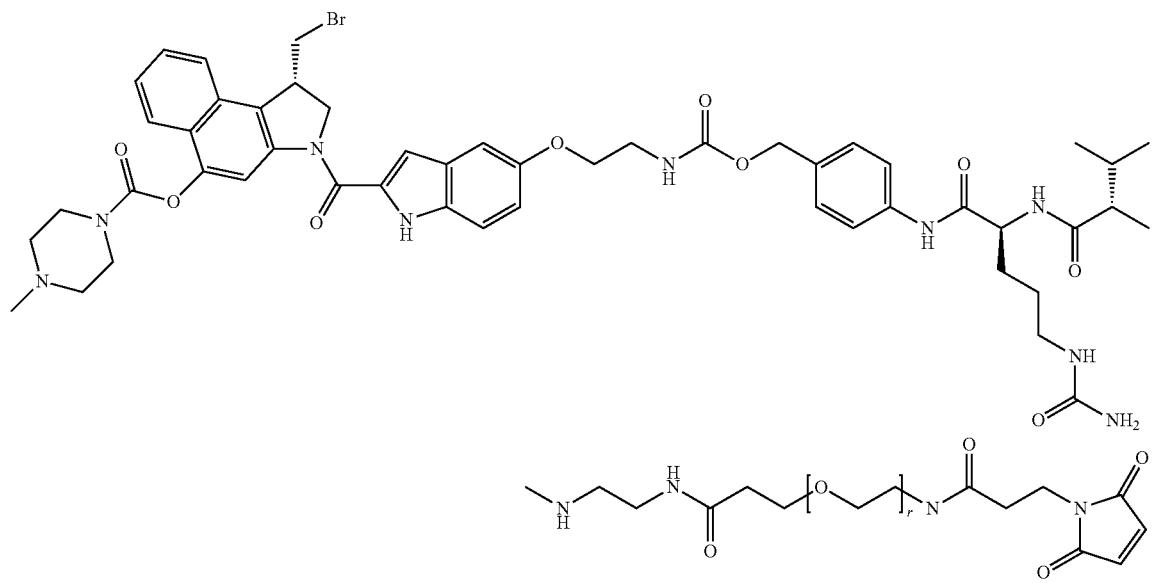

where r is an integer in the range from 0 to 24.

Another example of a suitable conjugate is a compound of the formula

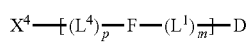

wherein $L^1$ is a self-immolative linker; m is an integer 0, 1, 2, 3, 4, 5, or 6; F is a linker comprising the structure:

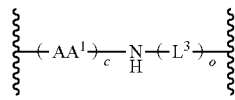

wherein $AA^1$ is one or more members independently selected from the group consisting of natural amino acids and unnatural α-amino acids; c is an integer from 1 to 20; $L^3$ is a spacer group comprising a primary or secondary amine or a carboxyl functional group; wherein if $L^3$ is present, m is 0 and either the amine of $L^3$ forms an amide bond with a pendant carboxyl functional group of D or the carboxyl of $L^3$ forms an amide bond with a pendant amine functional group of D; o is 0 or 1; $L^4$ is a linker member, wherein $L^4$ comprises

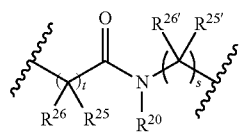

directly attached to the N-terminus of $(AA^1)_c$, wherein $R^{26}$ is a member selected from H, substituted or unsubstituted alkyl, substituted or unsubstituted heteroalkyl, and acyl; each $R^{25}$, $R^{25'}$, $R^{26}$, and $R^{26'}$ is independently selected from H, substituted or unsubstituted alkyl, substituted or unsubstituted heteroalkyl, substituted or unsubstituted aryl, substituted or unsubstituted heteroaryl, and substituted or unsubstituted heterocycloalkyl; and s and t are independently integers from 1 to 6; p is 1; $X^4$ is a member selected from the group consisting of protected reactive functional groups, unprotected reactive functional groups, detectable labels, and targeting agents; and D comprises a structure:

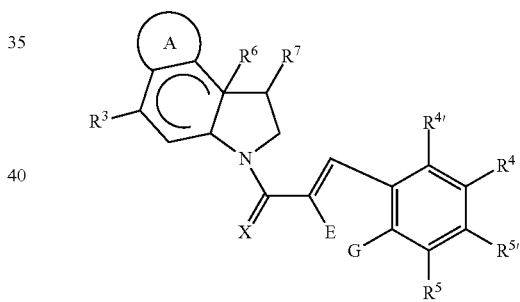

wherein the ring system A is a member selected from substituted or unsubstituted aryl, substituted or unsubstituted heteroaryl and substituted or unsubstituted heterocycloalkyl groups; E and G are members independently selected from H, substituted or unsubstituted alkyl, substituted or unsubstituted heteroalkyl, a heteroatom, a single bond, or E and G are joined to form a ring system selected from substituted or unsubstituted aryl, substituted or unsubstituted heteroaryl and substituted or unsubstituted heterocycloalkyl; X is a member selected from O, S and $NR^{23}$; $R^{23}$ is a member selected from H, substituted or unsubstituted alkyl, substituted or unsubstituted heteroalkyl, and acyl; $R^3$ is a member selected from the group consisting of (=O), $SR^{11}$, $NHR^{11}$ and $OR^{11}$, wherein $R^{11}$ is a member selected from the group consisting of H, substituted alkyl, unsubstituted alkyl, substituted heteroalkyl, unsubstituted heteroalkyl, monophosphates, diphosphates, triphosphates, sulfonates, acyl, C(O)$R^{12}R^{13}$, C(O)$OR^{12}$, C(O)$NR^{12}R^{13}$, P(O)$(OR^{12})_2$, C(O)CHR$^{12}R^{13}$, SR$^{12}$ and SiR$^{12}R^{13}R^{14}$, in which $R^{12}$, $R^{13}$, and $R^{14}$ are members independently selected from H, substituted or unsubstituted alkyl, substituted or unsubstituted heteroalkyl and substituted or unsubstituted aryl, wherein $R^{12}$ and $R^{13}$ together with the nitrogen or carbon atom to which they are attached are optionally joined to form a substituted or unsubstituted heterocycloalkyl ring system having from 4 to 6 members, optionally containing two or more heteroatoms; $R^4$, $R^{4'}$, $R^5$ and $R^{5'}$ are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $SR^{15}$, $OR^{15}$, $CR^{15}=NR^{16}$, and $O(CH_2)_nN(CH_3)_2$, or any adjacent pair of $R^4$, $R^{4'}$, $R^5$ and $R^{5'}$, together with the carbon atoms to which they are attached, are joined to form a substituted or unsubstituted cycloalkyl or heterocycloalkyl ring system having from 4 to 6 members, wherein n is an integer from 1 to 20; $R^{15}$ and $R^{16}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and substituted or unsubstituted peptidyl, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms; $R^6$ is a single bond which is either present or absent and when present $R^6$ and $R^7$ are joined to form a cyclopropyl ring; and $R^7$ is $CH_2$—$X^1$ or —$CH_2$— joined in said cyclopropyl ring with $R^6$, wherein $X^1$ is a leaving group, wherein at least one of $R^4$, $R^{4'}$, $R^5$, $R^{5'}$, $R^{15}$ or $R^{16}$ links said drug to $L^1$, if present, or to F.

In some embodiment, the drug has structure (c) or (f) above. One specific example of a compound suitable for use as conjugate is

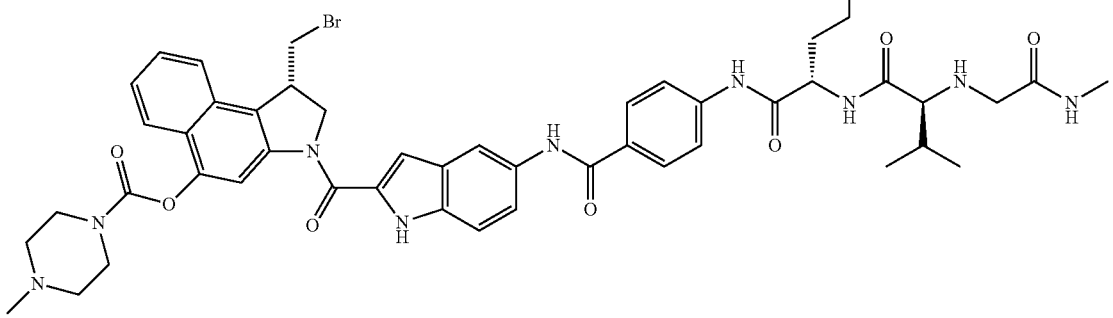

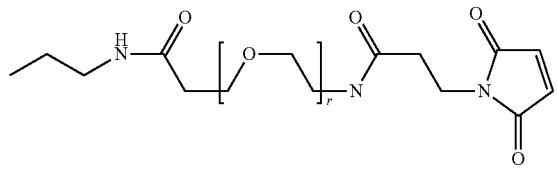

where r is an integer in the range from 0 to 24.

Other examples of suitable compounds for use as conjugates include:

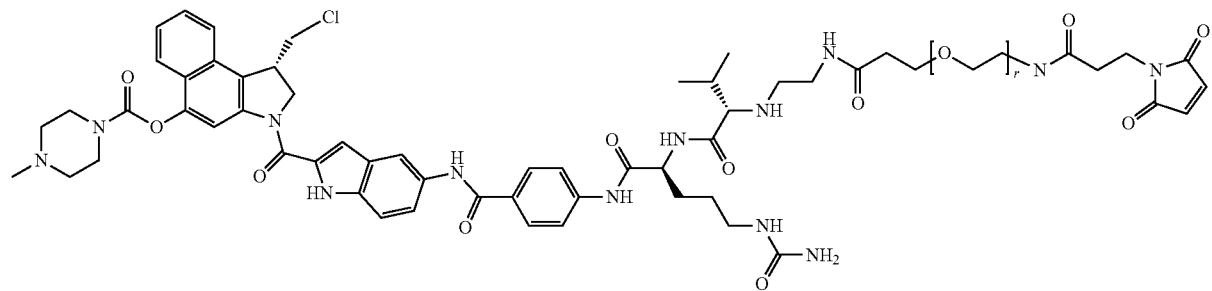

-continued
formula (m)
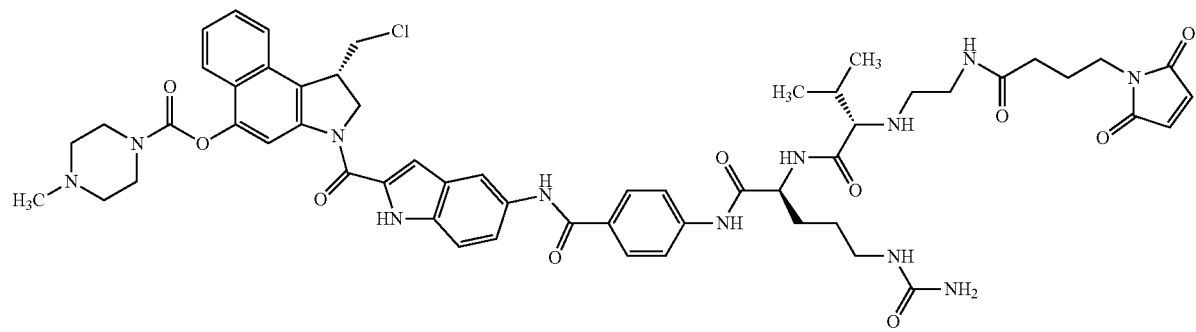
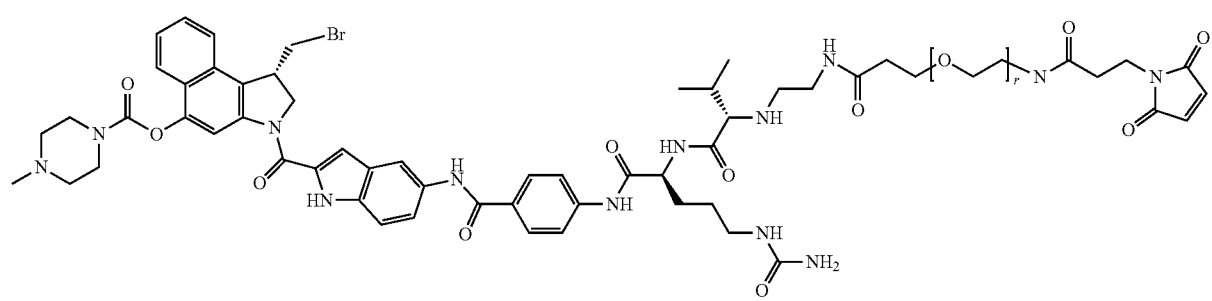
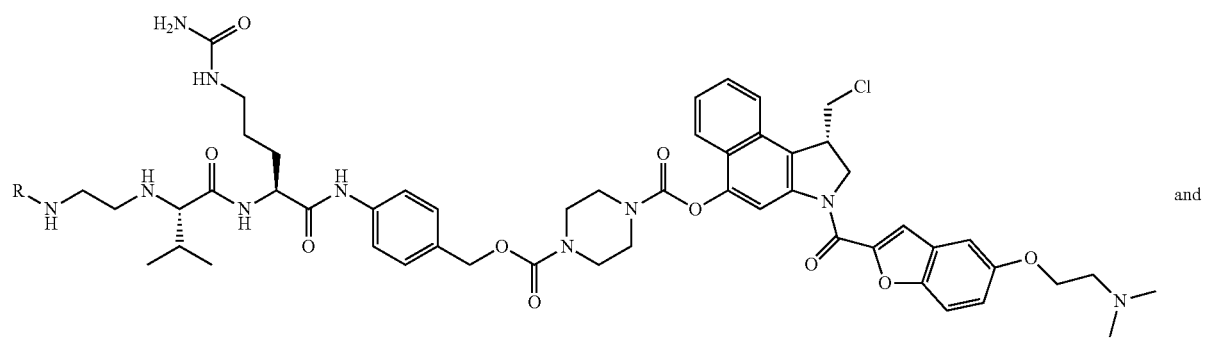
and
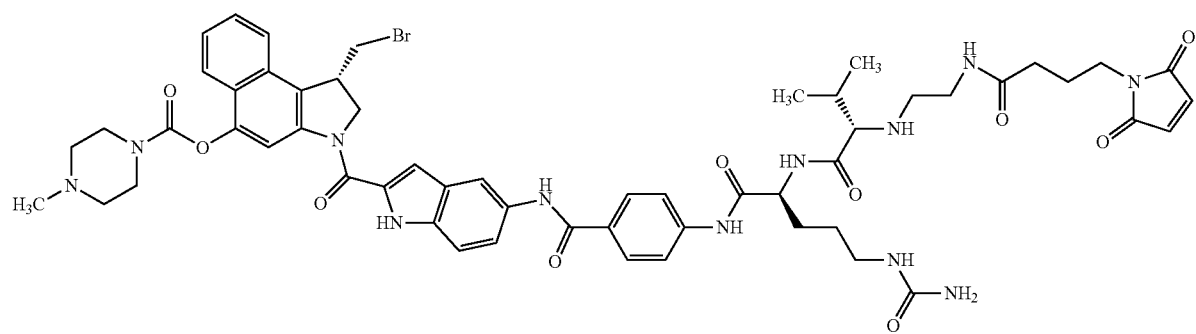

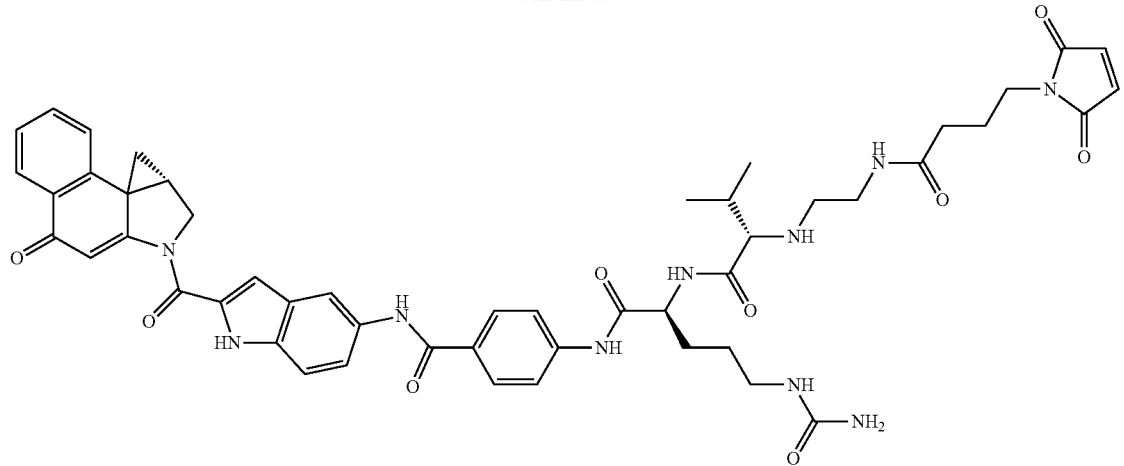
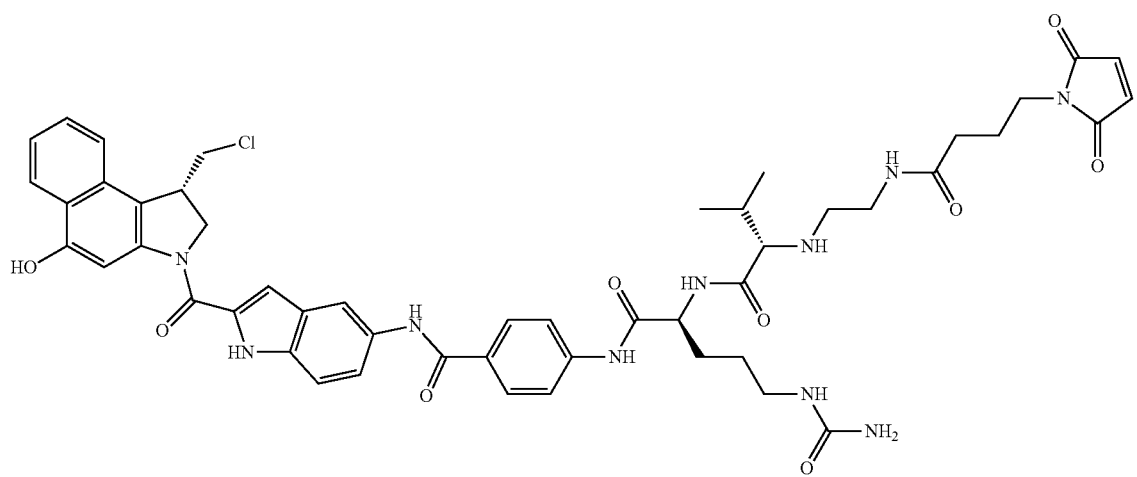
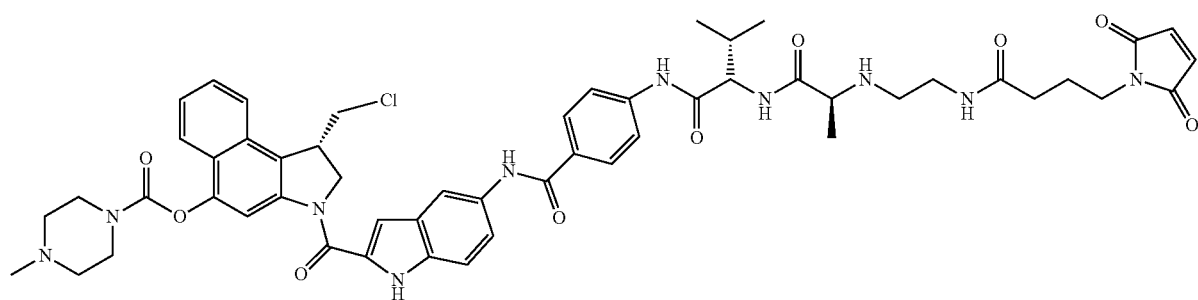
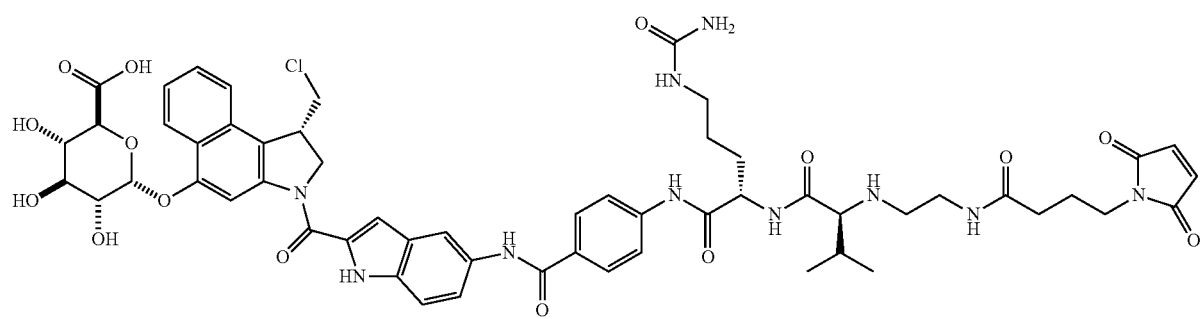

-continued
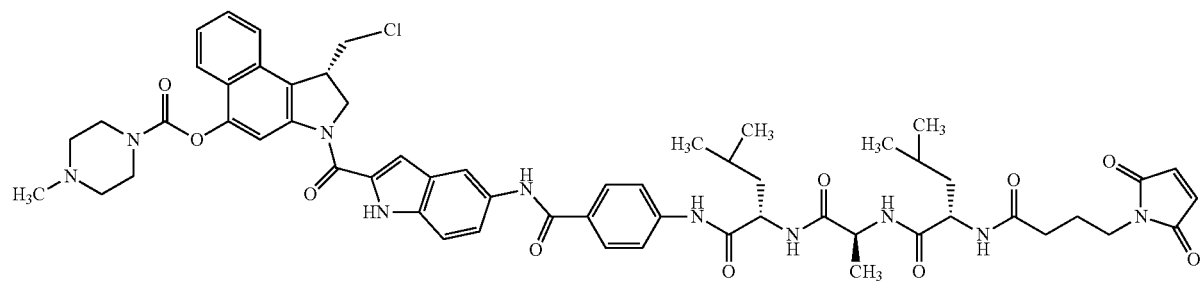
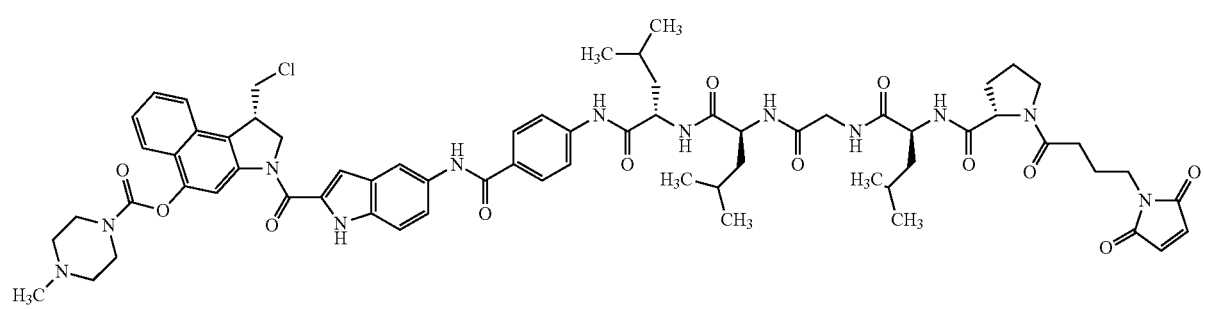
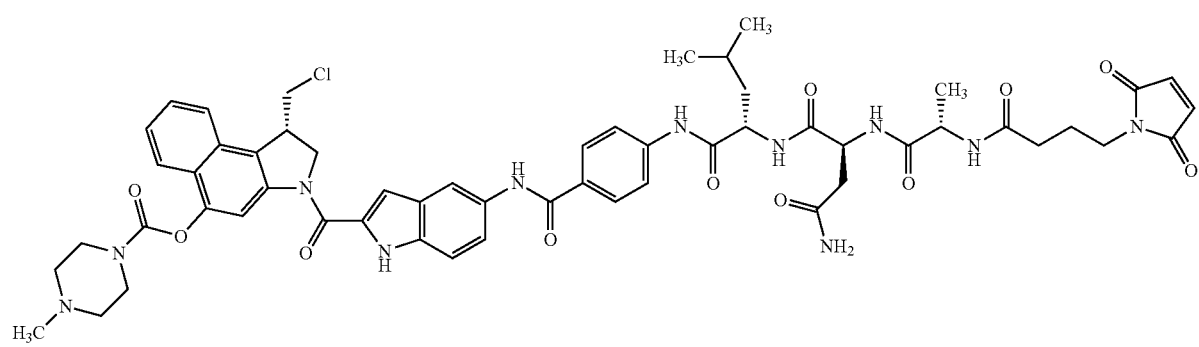
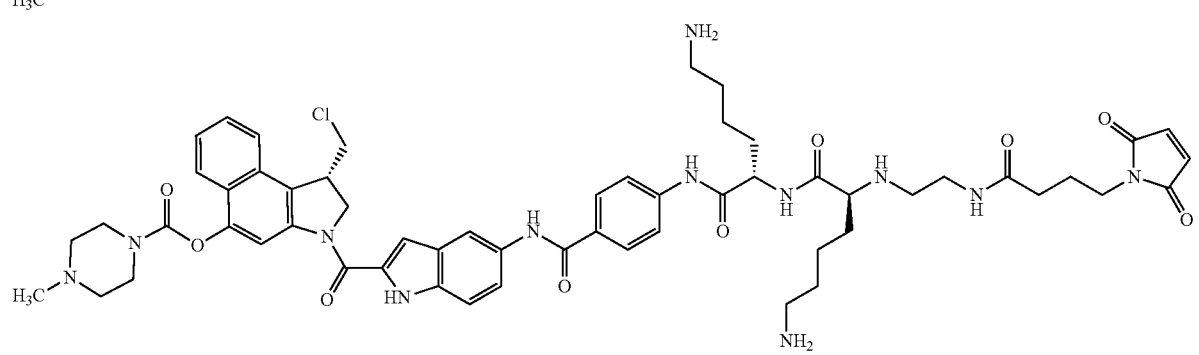
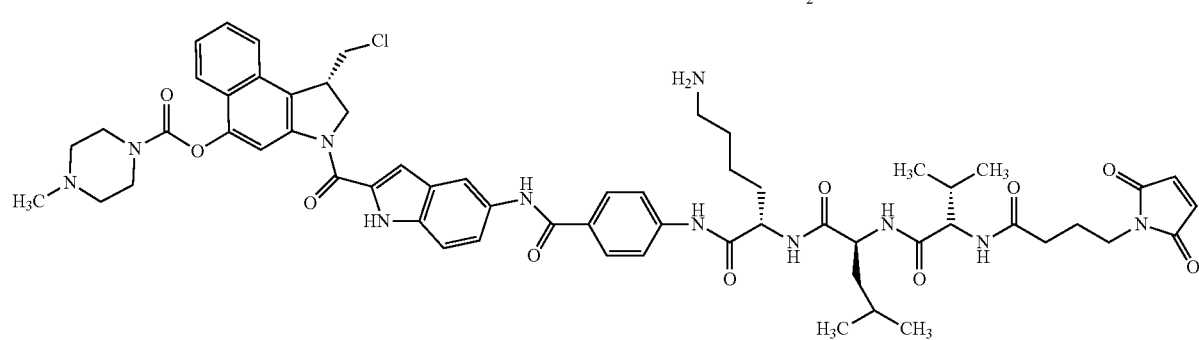

-continued
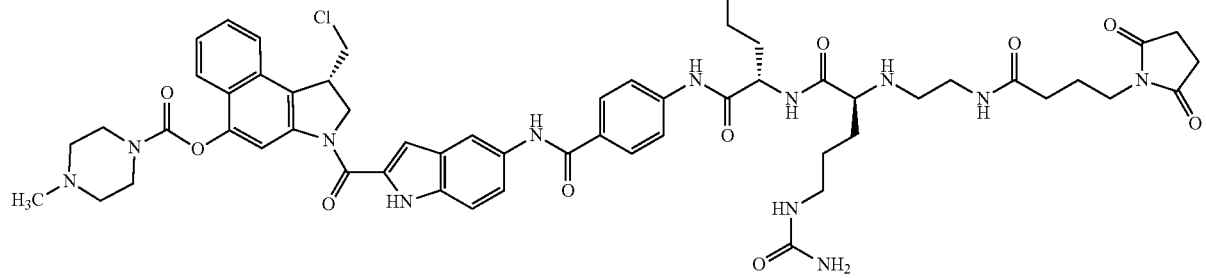
where R is
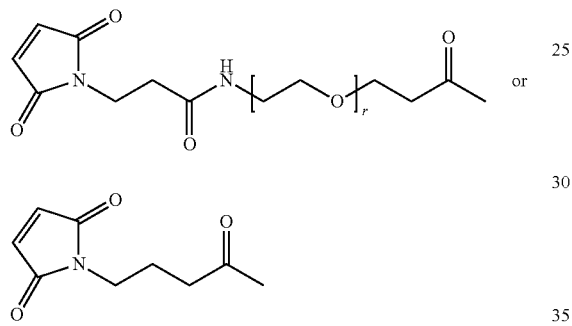
and r is an integer in the range from 0 to 24
Conjugates can also be formed using the drugs having structure (g), such as the following compounds:
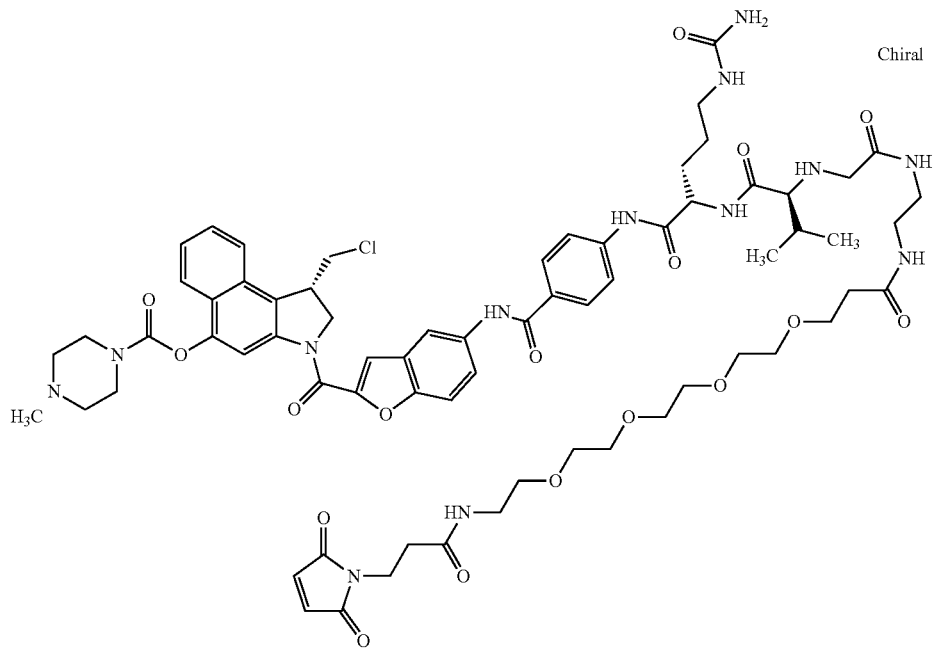

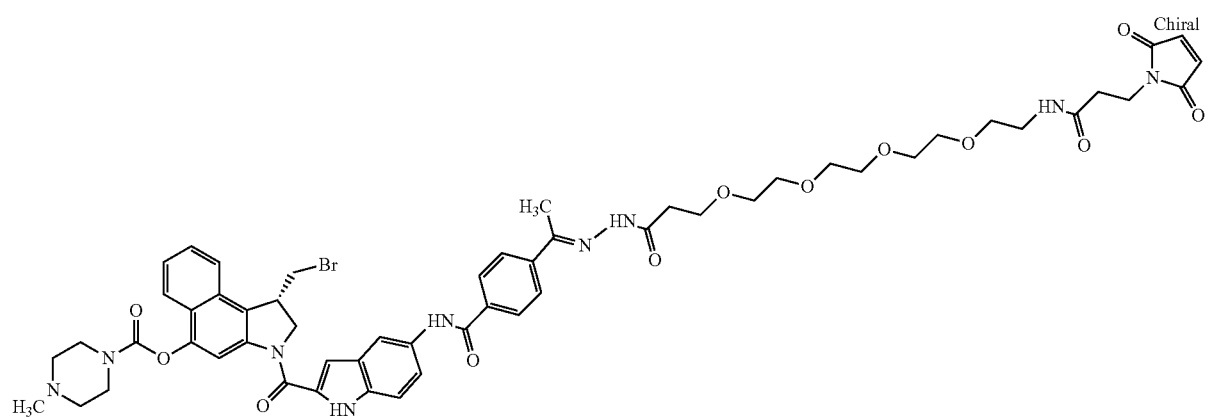
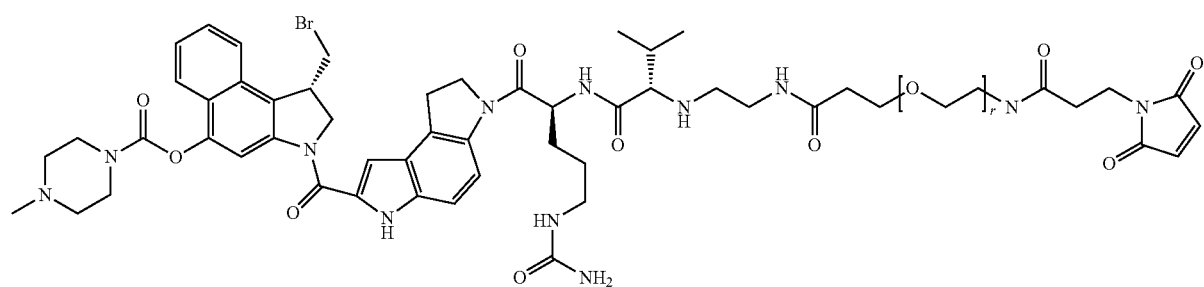
formula (n)
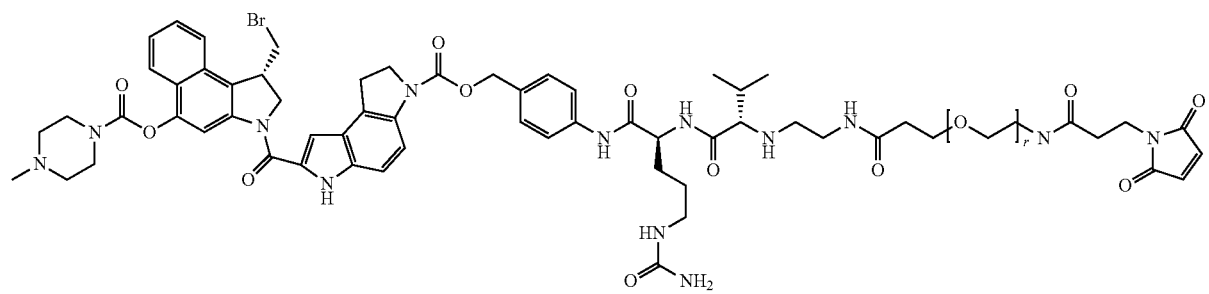
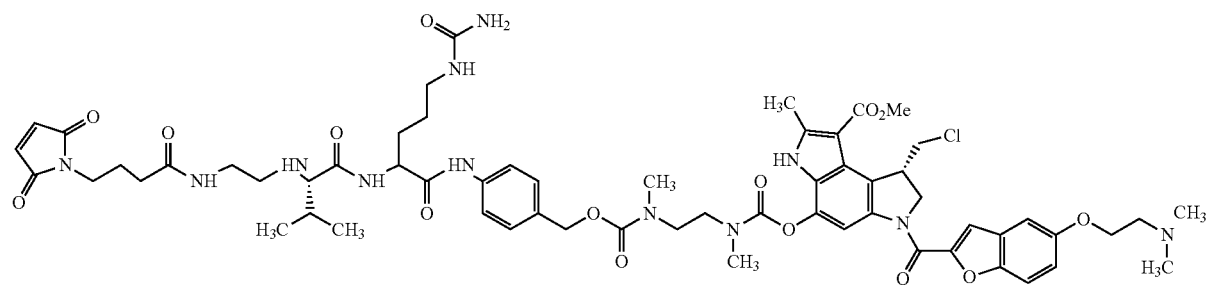

109 110
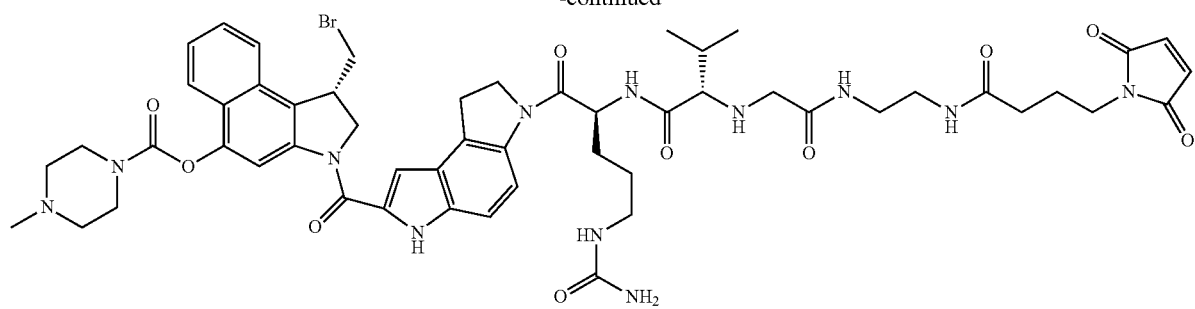
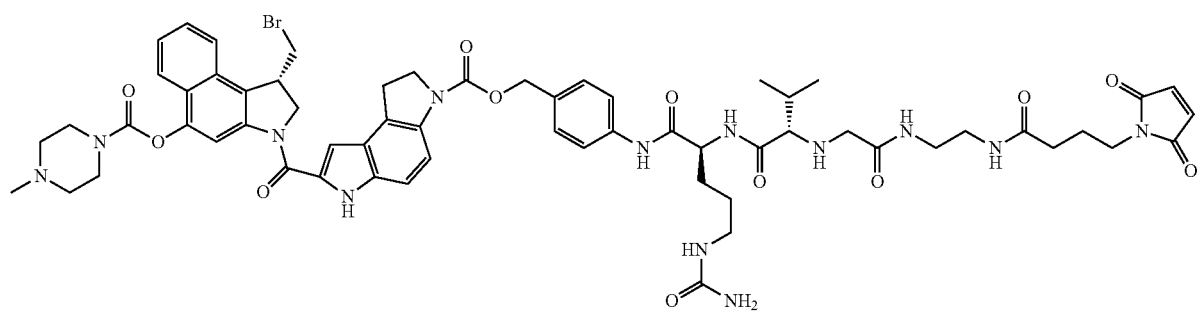
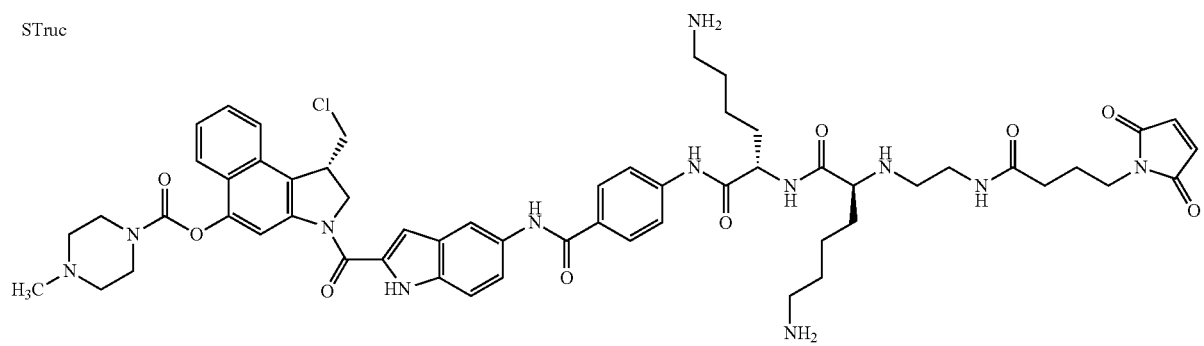
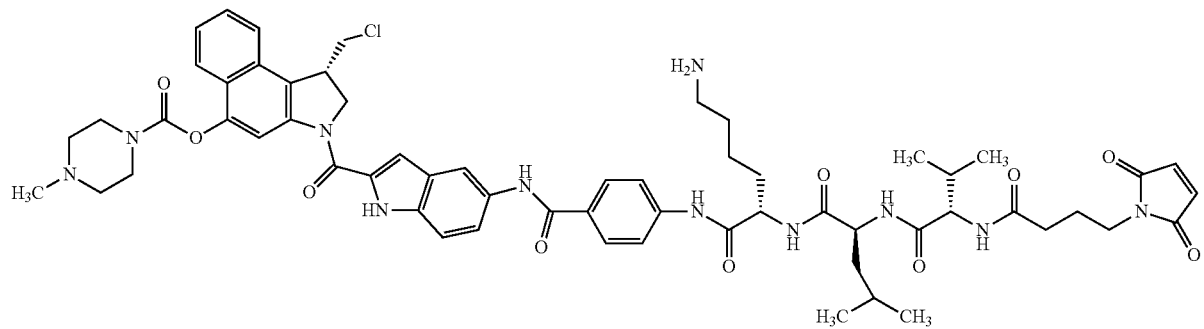

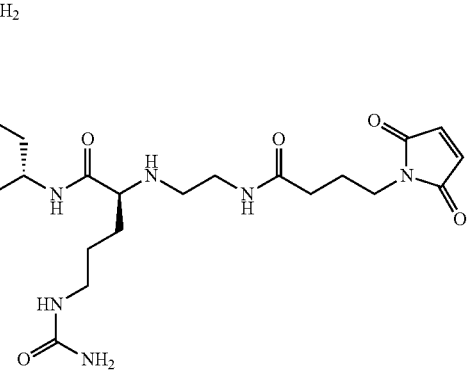
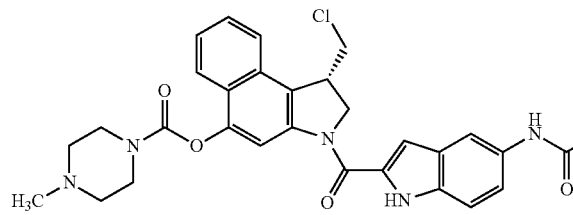
(where r is an integer in the range from 0 to 24.
Conjugates can also be formed using the drugs having the following structures:
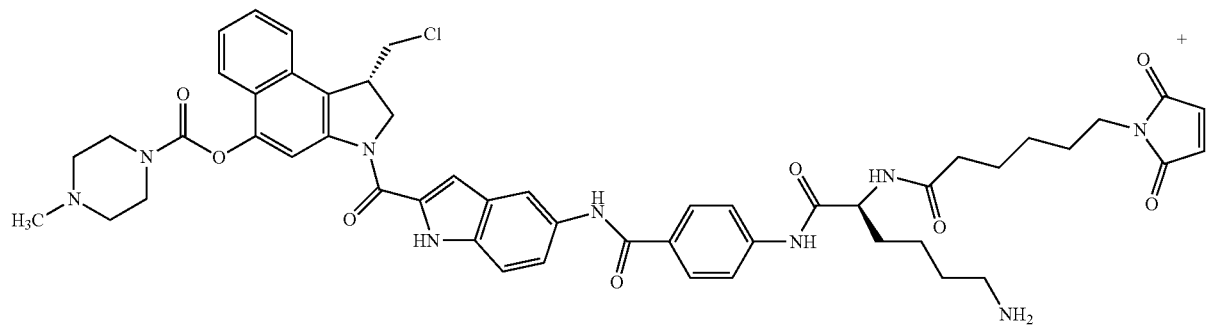
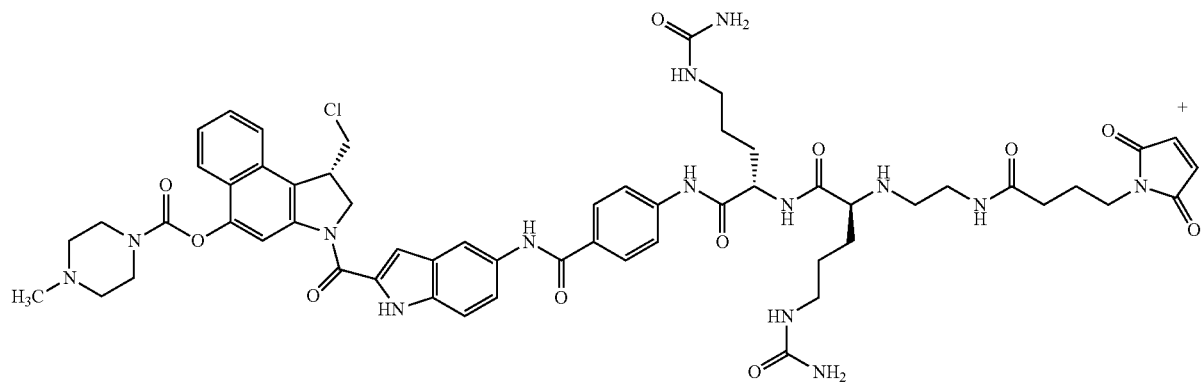

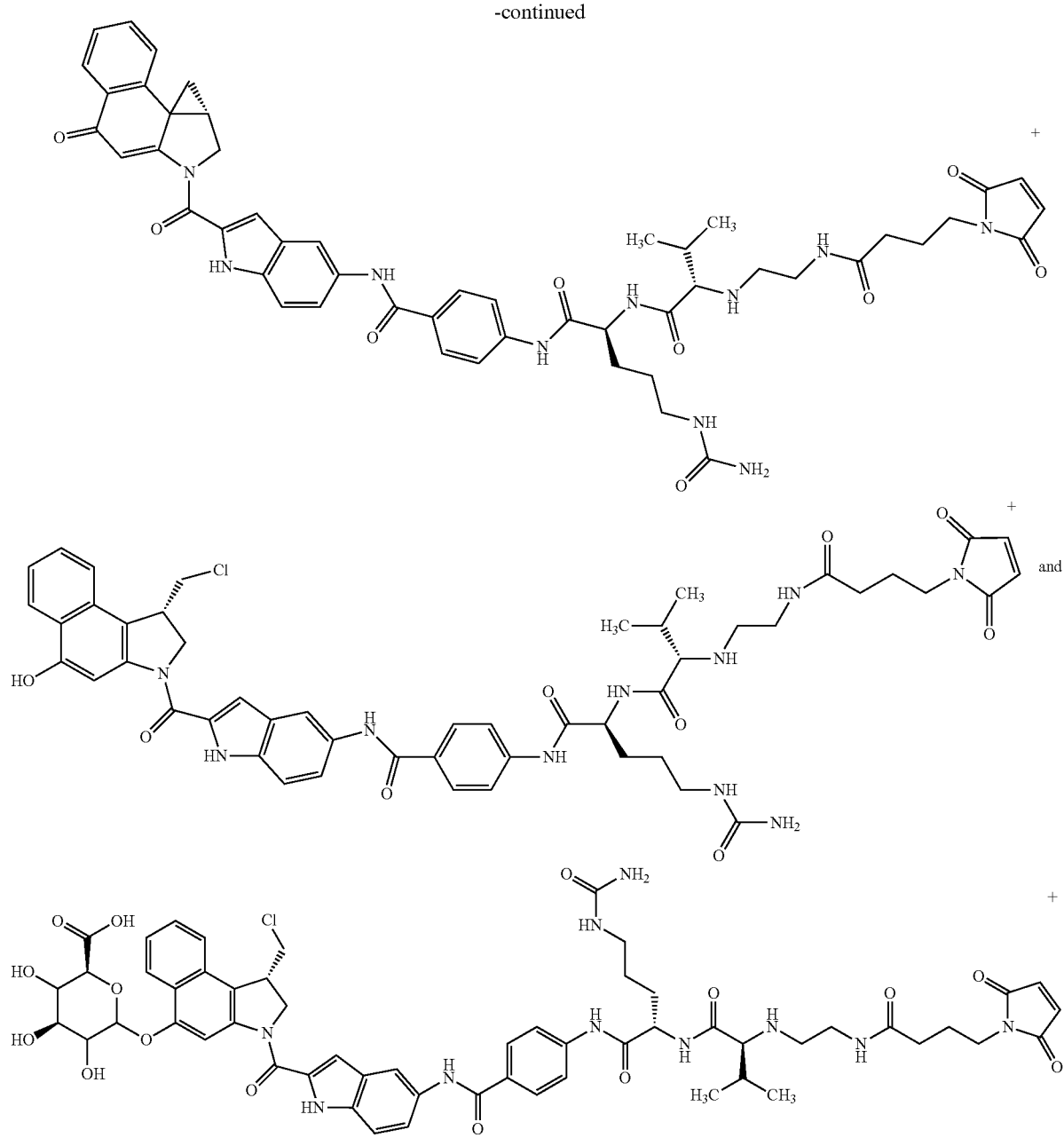

Synthesis of such toxins, as well as details regarding their linkage to antibodies is disclosed in U.S. patent application Ser. No. 60/991,300.

B. Cleavable Linker Conjugates

One example of a suitable conjugate is a compound having the following structure:

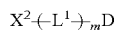

wherein $L^1$ is a self-immolative spacer; m is an integer of 0, 1, 2, 3, 4, 5, or 6; $X^2$ is a cleavable substrate; and D comprises a structure:

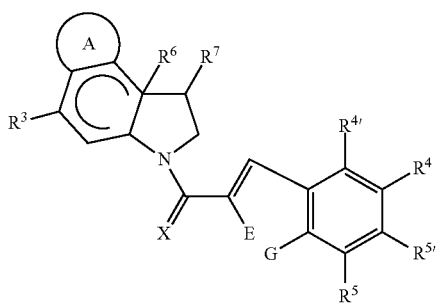

wherein the ring system A is a member selected from substituted or unsubstituted aryl, substituted or unsubstituted heteroaryl and substituted or unsubstituted heterocycloalkyl groups; E and G are members independently selected from H, substituted or unsubstituted alkyl, substituted or unsubstituted heteroalkyl, a heteroatom, a single bond, or E and G are joined to form a ring system selected from substituted or unsubstituted aryl, substituted or unsubstituted heteroaryl and substituted or unsubstituted heterocycloalkyl; X is a member selected from O, S and $NR^{23}$; $R^{23}$ is a member selected from H, substituted or unsubstituted alkyl, substituted or unsubstituted heteroalkyl, and acyl; $R^3$ is a member selected from the group consisting of (=O), $SR^{11}$, $NHR^{11}$ and $OR^{11}$, wherein $R^{11}$ is a member selected from the group consisting of H, substituted alkyl, unsubstituted alkyl, substituted heteroalkyl, unsubstituted heteroalkyl, monophosphates, diphosphates, triphosphates, sulfonates, acyl, C(O)$R^{12}R^{13}$, C(O)$OR^{12}$, C(O)$NR^{12}R^{13}$, P(O)$(OR^{12})_2$, C(O)CH$R^{12}R^{13}$, $SR^{12}$ and Si$R^{12}R^{13}R^{14}$, in which $R^{12}$, $R^{13}$, and $R^{14}$ are members independently selected from H, substituted or unsubstituted alkyl, substituted or unsubstituted heteroalkyl and substituted or unsubstituted aryl, wherein $R^{12}$ and $R^{13}$ together with the nitrogen or carbon atom to which they are attached are optionally joined to form a substituted or unsubstituted heterocycloalkyl ring system having from 4 to 6 members, optionally containing two or more heteroatoms; $R^6$ is a single bond which is either present or absent and when present $R^6$ and $R^7$ are joined to form a cyclopropyl ring; and $R^7$ is CH$_2$—$X^1$ or —CH$_2$— joined in said cyclopropyl ring with $R^6$, wherein $X^1$ is a leaving group, $R^4$, $R^{4'}$, $R^5$ and $R^{5'}$ are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, NO$_2$, $NR^{15}R^{16}$NC(O)$R^{15}$, OC(O)$NR^{15}R^{16}$, OC(O)$OR^{15}$, C(O)$R^{15}$, $SR^{15}$, $OR^{15}$, $CR^{15}$=$NR^{16}$, and O(CH$_2$)$_n$N(CH$_3$)$_2$, or any adjacent pair of $R^4$, $R^{4'}$, $R^5$ and $R^{5'}$, together with the carbon atoms to which they are attached, are joined to form a substituted or unsubstituted cycloalkyl or heterocycloalkyl ring system having from 4 to 6 members, wherein n is an integer from 1 to 20; $R^{15}$ and $R^{16}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and substituted or unsubstituted peptidyl, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms; wherein at least one of members $R^4$, $R^{4'}$, $R^5$ and $R^{5'}$ links said drug to $L^1$, if present, or to $X^2$, and is selected from the group consisting of

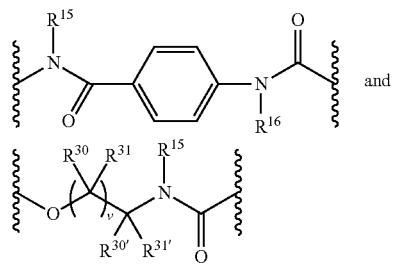

wherein $R^{30}$, $R^{30'}$, $R^{31}$, and $R^{31'}$ are independently selected from H, substituted or unsubstituted alkyl, substituted or unsubstituted heteroalkyl, substituted or unsubstituted aryl, substituted or unsubstituted heteroaryl, and substituted or unsubstituted heterocycloalkyl; and v is an integer from 1 to 6.

Examples of suitable cleavable linkers include β-Ala-LeuAlaLeu and

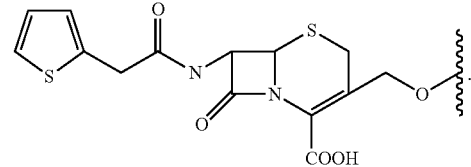 [SMILES: *OCC1=C(C(=O)O)N2C(=O)C(NC(=O)Cc3cccs3)C2SC1]

Pharmaceutical Compositions

In another aspect, the present disclosure provides a composition, e.g., a pharmaceutical composition, containing one or a combination of monoclonal antibodies, or antigen-binding portion(s) thereof, of the present disclosure, formulated together with a pharmaceutically acceptable carrier. Such compositions may include one or a combination of (e.g., two or more different) antibodies, or immunoconjugates or bispecific molecules of this disclosure. For example, a pharmaceutical composition of this disclosure can comprise a combination of antibodies (or immunoconjugates or bispecifics) that bind to different epitopes on the target antigen or that have complementary activities.

Pharmaceutical compositions of this disclosure also can be administered in combination therapy, i.e., combined with other agents. For example, the combination therapy can include an anti-CD22 antibody of the present disclosure combined with at least one other anti-cancer, anti-inflammatory or immunosuppressant agent. Examples of therapeutic agents that can be used in combination therapy are described in greater detail below in the section on uses of the antibodies of this disclosure.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds of this disclosure may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of this disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of this disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of this disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of this disclosure are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-CD22 antibody of this disclosure include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three monthgs or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

For use in the prophylaxis and/or treatment of diseases related to abnormal cellular proliferation, a circulating concentration of administered compound of about 0.001 µM to 20 µM is preferred, with about 0.01 µM to 5 µM being preferred.

Patient doses for oral administration of the compounds described herein, typically range from about 1 mg/day to about 10,000 mg/day, more typically from about 10 mg/day to about 1,000 mg/day, and most typically from about 50 mg/day to about 500 mg/day. Stated in terms of patient body weight, typical dosages range from about 0.01 to about 150 mg/kg/day, more typically from about 0.1 to about 15 mg/kg/day, and most typically from about 1 to about 10 mg/kg/day, for example 5 mg/kg/day or 3 mg/kg/day.

In at least some embodiments, patient doses that retard or inhibit tumor growth can be 1 µmol/kg/day or less. For example, the patient doses can be 0.9, 0.6, 0.5, 0.45, 0.3, 0.2, 0.15, or 0.1 µmol/kg/day or less (referring to moles of the drug). Preferably, the antibody-drug conjugate retards growth of the tumor when administered in the daily dosage amount over a period of at least five days. In at least some embodiments, the tumor is a human-type tumor in a SCID mouse. As an example, the SCID mouse can be a CB17.SCID mouse (available from Taconic, Germantown, N.Y.).

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-CD22 antibody of this disclosure preferably results in a decrease in severity of disease symptoms, an increase in frequency and duration of disease symptom-free periods, or a prevention of impairment or disability due to the disease affliction. For example, for the treatment of $CD22^+$ tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present disclosure can be administered via one or more routes of administration using one or more of a variety of methods known in the art. As will be appreciated by the skilled artisan, the route and/or mode of administration will vary depending upon the desired results. Preferred routes of administration for antibodies of this disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of this disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of this disclosure can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of this disclosure can be formulated to ensure proper distribution in vivo. For example, the blood-brain barrier (BBB) excludes many highly hydrophilic compounds. To ensure that the therapeutic compounds of this disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134); p 120 (Schreier et cd. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

Uses and Methods of the Invention

The antibodies, particularly the human antibodies, antibody compositions and methods of the present disclosure have numerous in vitro and in vivo diagnostic and therapeutic utilities involving the diagnosis and treatment of diseases and disorders involving CD22. For example, these molecules can be administered to cells in culture, in vitro or ex vivo, or to human subjects, e.g., in vivo, to treat, prevent and to diagnose a variety of disorders.

As used herein, the term "subject" is intended to include human and non-human animals. Non-human animals include all vertebrates, e.g., mammals and non-mammals, such as non-human primates, sheep, dogs, cats, cows, horses, chickens, amphibians, and reptiles. Preferred subjects include human patients having disorders mediated by or modulated by CD22 activity. When antibodies to CD22 are administered together with another agent, the two can be administered in either order or simultaneously.

Given the specific binding of the antibodies of this disclosure for CD22, the antibodies of this disclosure can be used to specifically detect CD22 expression on the surface of cells and, moreover, can be used to purify CD22 via immunoaffinity purification.

Suitable routes of administering the antibody compositions (e.g., human monoclonal antibodies, multispecific and bispecific molecules and immunoconjugates) of this disclosure in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-CD22 antibodies of this disclosure can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/kg dose once every four weeks and adriamycin is intravenously administered as a 60-75 mg/ml dose once every 21 days. Co-administration of human anti-CD22 antibodies, or antigen binding fragments thereof, of the present disclosure with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells that would render them unreactive with the antibody.

Target-specific effector cells, e.g., effector cells linked to compositions (e.g., human antibodies, multispecific and bispecific molecules) of this disclosure can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing CD22, and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of this disclosure and/or effector cells armed with these compositions can be used in conjunction with chemotherapy. Additionally, combination immunotherapy may be used to direct two distinct cytotoxic effector populations toward tumor cell rejection. For example, anti-CD22 antibodies linked to anti-Fc-gamma RI or anti-CD3 may be used in conjunction with IgG- or IgA-receptor specific binding agents.

Bispecific and multispecific molecules of this disclosure can also be used to modulate FcγR or FcγR levels on effector cells, such as by capping and elimination of receptors on the cell surface. Mixtures of anti-Fc receptors can also be used for this purpose.

The compositions (e.g., human, humanized, or chimeric antibodies, multispecific and bispecific molecules and immunoconjugates) of this disclosure which have complement binding sites, such as portions from IgG1, -2, or -3 or IgM which bind complement, can also be used in the presence of complement. In one embodiment, ex vivo treatment of a population of cells comprising target cells with a binding agent of this disclosure and appropriate effector cells can be supplemented by the addition of complement or serum containing complement. Phagocytosis of target cells coated with a binding agent of this disclosure can be improved by binding of complement proteins. In another embodiment target cells coated with the compositions (e.g., human antibodies, multispecific and bispecific molecules) of this disclosure can also be lysed by complement. In yet another embodiment, the compositions of this disclosure do not activate complement.

The compositions (e.g., human, humanized, or chimeric antibodies, multispecific and bispecific molecules and immunoconjugates) of this disclosure can also be administered together with complement. Accordingly, within the scope of this disclosure are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of this disclosure and the complement or serum can be administered separately.

The antibodies of this disclosure also can be used in combination with one or more additional therapeutic antibodies or other binding agents, such as Ig fusion proteins. Non-limiting examples of other antibodies or binding agents with which an anti-CD22 antibody of this disclosure can be administered in combination include antibodies or binding agents to CTLA-4, PSMA, CD30, IP-10, IFN-γ, CD70, PD-1, PD-L$^1$, TNF, TNF-R, VEGF, VEGF-R, CCR5, IL-1, IL-18, IL-18R, CD19, Campath-1, EGFR, CD33, CD20, Her-2, CD25, gpIIb/IIIa, IgE, CD11a, α4 integrin.

Also within the scope of the present disclosure are kits comprising antibody compositions of this disclosure (e.g., human antibodies, bispecific or multispecific molecules, or immunoconjugates) and instructions for use. The kit can further contain one ore more additional reagents, such as an immunosuppressive reagent, a cytotoxic agent or a radiotoxic agent, or one or more additional human antibodies of this disclosure (e.g., a human antibody having a complementary activity which binds to an epitope in the CD22 antigen distinct from the first human antibody).

Accordingly, patients treated with antibody compositions of this disclosure can be additionally administered (prior to, simultaneously with, or following administration of a human antibody of this disclosure) with another therapeutic agent, such as a cytotoxic or radiotoxic agent, which enhances or augments the therapeutic effect of the human antibodies.

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

The compositions (e.g., human antibodies, multispecific and bispecific molecules) of this disclosure can also be used to target cells expressing CD22, for example for labeling such cells. For such use, the binding agent can be linked to a molecule that can be detected. Thus, this disclosure provides methods for localizing ex vivo or in vitro cells expressing CD22. The detectable label can be, e.g., a radioisotope, a fluorescent compound, an enzyme, or an enzyme co-factor.

In a particular embodiment, this disclosure provides methods for detecting the presence of CD22 antigen in a sample, or measuring the amount of CD22 antigen, comprising contacting the sample, and a control sample, with a human monoclonal antibody, or an antigen binding portion thereof, which specifically binds to CD22, under conditions that allow for formation of a complex between the antibody or portion thereof and CD22. The formation of a complex is then detected, wherein a difference complex formation between the sample compared to the control sample is indicative the presence of CD22 antigen in the sample.

In yet another embodiment, immunoconjugates of the invention can be used to target compounds (e.g., therapeutic agents, labels, cytotoxins, radiotoxoins immunosuppressants, etc.) to cells which express CD22 by linking such compounds to the antibody. For example, an anti-CD22 antibody can be conjugated to any of the toxin compounds described in U.S. Pat. Nos. 6,281,354 and 6,548,530, U.S. patent publication Nos. 20030050331, 20030064984, 20030073852, and 20040087497, or published in WO 03/022806. Thus, the invention also provides methods for localizing ex vivo or in vivo cells expressing CD22 (e.g., with a detectable label, such as a radioisotope, a fluorescent compound, an enzyme, or an enzyme co-factor). Alternatively, the immunoconjugates can be used to kill cells which have CD22 cell surface receptors by targeting cytotoxins or radiotoxins to CD22.

CD22 is known to be expressed on a large percentage of B cell lymphomas and also is known to be involved in regulating B cell activity such that autoimmune disorders can be treated via targeting of CD22. Accordingly, the anti-CD22 antibodies (and immunoconjugates and bispecific molecules) of this disclosure can be used to modulate CD22 activity in each of these clinical situations.

Accordingly, in one aspect, the invention provides a method of inhibiting growth of a CD22-expressing tumor cell. The method comprises contacting the CD22-expressing tumor cell with the antibody, or antigen-binding portion thereof, of the invention such that growth of the CD22-expressing tumor cell is inhibited. Preferably, the CD22-expressing tumor cell is a B cell lymphoma, such as a non-Hodgkin's lymphoma. Other types of CD22-expressing tumor cells include Burkitt's lymphomas and B cell chronic lymphocytic leukemias.

In one embodiment of the method of inhibiting tumor cell growth, the antibody, or antigen-binding portion thereof, is conjugated to a partner molecule, such as a therapeutic agent, such as a cytotoxin, radioisotope or chemotherapeutic agent. In other embodiments, the antibody, or antigen-binding portion thereof, in administered in combination with one or more additional anti-tumor agents. The antibody can be used in combination other cancer treatments, such as surgery and/or radiation, and/or with other anti-neoplastic agents, such as the anti-neoplastic agents discussed and set forth above, including chemotherapeutic drugs and other anti-tumor antigen antibodies, including but not limited to an anti-CD20 antibody (e.g., Rituxan®).

In another aspect, the invention provides a method of treating an inflammatory or autoimmune disorder in a subject. The method comprises administering to the subject the antibody, or antigen-binding portion thereof, of the invention such that the inflammatory or autoimmune disorder in the subject is treated. Non-limiting examples of preferred autoimmune disorders include systemic lupus erythematosus and rheumatoid arthritis. Other examples of autoimmune disorders include inflammatory bowel disease (including ulcerative colitis and Crohn's disease), Type I diabetes, multiple sclerosis, Sjogren's syndrome, autoimmune thyroiditis (including Grave's disease and Hashimoto's thyroiditis), psoriasis and glomerulonephritis. The antibody can be used alone or in combination with other anti-inflammatory or immunsuppresant agents, such as non-steroidal anti-inflammatory drugs (NSAIDs), corticosteroids (e.g., prednisone, hydrocortisone), methotrexate, COX-2 inhibitors, TNF antagonists (e.g., etanercept, infliximab, adalimumab) and immunosuppressants (such as 6-mercaptopurine, azathioprine and cyclosporine A).

The present disclosure is further illustrated by the following examples, which should not be construed as further limiting. The contents of all figures and all references, patents and published patent applications cited throughout this application are expressly incorporated herein by reference.

Example 1

Generation of Human Monoclonal Antibodies Against CD22

Anti-CD22 human monoclonal antibodies were generated using transgenic mice that express human antibody genes, as follows.

Antigen

The antigens used to raise anti-CD22 antibodies were the extracellular domain of human CD22 and the full-length CD22 protein expressed on CHO cells. To obtain the extracellular domain, a cDNA encoding human CD22 (commercially available from Open Biosystems, Inc.) was used to construct an expression vector encoding the entire CD22β extracellular domain (CD22 ECD) fused to a C-terminal hexahistidine tag. After transfection of CHO cells and selection of stable transfectants by standard techniques, CD22 ECD was purified from the cell culture medium using metal chelate chromatography. In addition, recombinant CHO cells were created that expressed full-length CD22 on the cell surface by transfecting the cells with an expression vector that contained the full-length CD22 cDNA. After selection of the transfected cells, those cells expressing high levels of CD22 on the cell surface were isolated by fluorescent-activated cell sorting, based on reactivity with a fluorescein-labeled anti-CD22 (commercially available from Becton-Dickinson-Pharmingen).

Mouse Strains

Fully human monoclonal antibodies to CD22 were prepared using HCo7/HCo12 and HCo12/Balbc strains of the transgenic HuMAb Mouse®, and the KM and KM-XHAC strains of transgenic transchromosomic mice, all of which express human antibody genes.

In each of these mouse strains, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187. Each of these strains carries a human kappa light chain transgene, KCoS (as described in Fishwild et al. (1996) *Nature Biotechnology* 14:845-851) and also contains the SC20 transchromosome, which carries the human Ig heavy chain locus, as described in PCT Publication WO 02/43478.

The HCo7 strain carries the HCo7 human heavy chain transgene as described in U.S. Pat. Nos. 5,545,806; 5,625,825; and 5,545,807. The HCo12 strain carries the HCo12 human heavy chain transgene as described in Example 2 of PCT Publication WO 01/09187.

The KM Mouse® strain is described in detail in U.S. Application No. 20020199213.

The KM-λHAC strain is very similar to the KM strain in that the endogenous mouse heavy chain and kappa light chain loci have been disrupted and the SC20 transchromosome and KCoS transgene have bee inserted, but the KM-λHAC strain also carries a human artificial chromosome derived from human chromosome 22 that carries the human lambda light chain locus. Thus, the KM-λHAC strain can express human antibodies that utilize either a lambda light chain or a kappa light chain. The KM-λHAC mice are also described in detail in U.S. Application No. 20060015958.

Immunization

To raise fully human monoclonal antibodies to CD22, animals of the strains described above were immunized with recombinant human CD22 ECD and CD22-expressing CHO cells (prepeared as described above for the antigen). General immunization schemes for the raising human antibodies in mice strains carrying human antibody genes are described in, for example, Lonberg, N. et al (1994) *Nature* 368(6474): 856-859; Fishwild, D. et al. (1996) *Nature Biotechnology* 14: 845-851 and PCT Publication WO 98/24884. Mice were 10-12 weeks of age when the immunizations were initiated. Mice were immunized weekly intraperitoneally and subcutaneously with 20 µg of CD22 ECD or $10^7$ transfected CHO cells with RIBI as adjuvant. The first two immunizations were performed with CD22 ECD in RIBI adjuvant followed by six additional weekly immunizations alternately using CD22 ECD or transfected cells (up to a total of 8 immunizations). The immune response was monitored in blood harvested by retroorbital bleeds. The serum was screened by ELISA and FACS. Mice with adequate titer of anti-CD22 human IgG immunoglobulin were used for fusions. Mice were boosted once with CD22 ECD and once with CD22 expressing CHO cells both intravenously and intraperitoneally on days-4 and -3, respectively, before sacrifice and removal of the spleen.

Antibody Selection

To identify mice producing antibodies that bound CD22, sera from immunized mice were screened by flow cytometry for binding to CHO cells expressing human CD22 as well as to parental CHO cells. The sera were also screened by flow cytometry (FACS) on human Daudi B cells, which express CD22. Sera from all immunized mice were tested at a dilution of 1:50 in the FACS experiment. After addition of diluted serum to the cells and incubation for 30 minutes at 37° C., cells were washed and binding was detected with a PE-labeled anti-human IgG Ab. Flow cytometric analyses were performed using a FACSCalibur flow cytometry (Becton Dickinson, San Jose, Calif.). A murine anti-CD22 monoclonal antibody (M anti-CD22) was used as positive control in the experiment. All three mice tested exhibited titer to CHO-CD22 and CHO parental cells (CHO-S). Binding to CHO-S cells reflect the presence of antibodies binding to molecules other than CD22 on the surface of CHO cells. This result was expected since mice were immunized with CHO transfected cells. Titer to human Daudi cells was also detected in the three mice indicating the potential presence of antibodies specific to CD22 that could bind CD22 from a non-recombinant source.

Sera were further tested for binding to human CD22 ECD by ELISA. Briefly, microtiter plates were coated with purified CD22 ECD protein produced in CHO cells at 1-2.5 µg/ml in PBS (50 µl/well) for 2 hrs at room temperature. The plate was then blocked with 300 µl/well of 1% BSA in PBS. Dilutions of sera (100 to 20000) from CD22-immunized mice were added to each well and incubated for 1-2 hours at ambient temperature. The plates were washed with PBS/Tween and incubated with a goat-anti-human IgG polyclonal antibody conjugated with horseradish peroxidase (HRP) for 1 hour at room temperature. After washing, the plates were developed with ABTS substrate (Sigma #A9941) in phosphate citrate buffer with perborate (Sigma#P4922) or Moss ABTS-1000 and analyzed by spectrophotometry at OD 415-495 nm. The three mice tested had good titer of anti-CD22 antibodies and were therefore used for fusions.

Splenocyte Fusions

Mouse splenocytes were fused to a mouse myeloma cell line using electric field based electrofusion using a Cyto Pulse large chamber cell fusion electroporator (Cyto Pulse Sciences, Inc., Glen Burnie, Md.). Single cell suspensions of splenocytes from immunized mice were fused to Ag8.653 mouse myeloma cells (ATCC, CRL 1581) at a ratio of 1:1. Cells were plated at approximately $2 \times 10^4$/well in flat bottom microtiter plates. Plates were incubated for one week in DMEM high glucose medium with L-glutamine, sodium pyruvate (Mediatech, Inc., Herndon, Va.), 10% fetal Bovine Serum (Hyclone, Logan, Utah), 18% P388DI conditional media, 5% Origen Hybridoma cloning factor (BioVeris, Gaithersburg, Va.), 4 mM L-glutamine, 5 mM HEPES, 0.055 mM β-mercaptoethanol, 50 units/ml penicillin, 50 mg/ml streptomycin and 1× Hypoxanthine-aminopterin-thymidine (HAT). After one week (day 7), HAT growth media was replaced with medium containing HT. When extensive hybridoma growth occurred (day 10-11), hybridoma supernatants were tested for the presence of human IgG antibodies in an HTRF homogeneous assay. Fusions from KM-XHAC mice were screened for presence of human IgG bearing either a human kappa or a human lambda light chain. Positive hybridomas were then screened by FACS on Daudi cells and by ELISA for the presence of CD22 specific human IgG antibodies. ELISA and FACS experiments were performed as described above except that hybridoma supernatanst (50-100 µl/well) were used instead of serum dilutions. The antigen specific parental hybridoma lines were transferred to 24 well plates, screened again and, if still positive for human IgG, subcloned once by limiting dilution. The stable subclones were then scaled up in vitro and antibodies were purified for further characterization.

Eighteen subclones were chosen for expansion for antibody purification. The isotypes of the expanded subclones included the following isotypes: IgG1; IgG4; IgG4/IgM; IgG1/IgM; IgG1/IgG2/λ; and IgG4/λ. Thirteen of the purified antibodies were titrated by ELISA and FACS and each exhibited specific binding to human CD22 in both assays. Four subclones, 12C5, 19A3, 16F7, 23C6, were selected for further structural analysis and sequencing.

Production of Recombinant Antibodies CD22.1 and CD22.2

The anti-CD22 antibody 19A3 was expressed in CHO cells as a human IgG1 (f allotype) and the recombinant antibody was designated CD22.1. In addition, a variant of 19A3 designated CD22.2 was made in which the mutation N57Q was made to remove the N-glycosylation site in the CDR2 region of the $V_H$ chain.

The $V_K$ and $V_H$ regions of 19A3 were amplified by PCR from cDNA clones and cloned into pCR4Blunt-TOPO (Invitrogen) to introduce restriction sites for cloning. Site directed mutagenesis was then performed to introduce an N57Q mutation into the heavy chain sequence to remove the N-glycosylation site in CDR2. The 19A3 $V_K$ was subcloned into the pICOFSneoK2.hCMV2.1 kb vector to produce vector pICOFSneoK2.hCMV2.1 kb(CD22.19A3), and the $V_H$ (both wild type and N57Q mutation) regions were subcloned into the pICOFSpurG vector to produce vectors pICOFSpurG(CD22.19A3) and pICOFSpurG (CD22.19A3.VH.N57Q). These constructs for expression of light and heavy chain were linearized and co-transfected into CHO-S cells using DMRIE-C (Invitrogen) and stable clones selected using standard techniques.

CHO-S clone 8G9 was chosen for CD22.1 expression. An overgrown culture of this clone produced approximately 75 mg/liter of antibody. CHO-S clone 17E11 was chosen for CD22.2 expression and yielded approximately 413 mg/liter in overgrown culture. The structure and function of the recombinant antibodies CD22.1 and CD22.2 were then determined (see Example 3 and Example 10, below).

Example 2

Structural Characterization of Human Anti-CD22 Monoclonal Antibodies

The cDNA sequences encoding the heavy and light chain variable regions of the mAbs expressed by the 12C5, 19A3, 16F7, 23C6, CD22.1, CD22.2, 4G6 and 21F6 clones described in Example 1 were sequenced using standard DNA sequencing techniques and the expressed proteins were characterized by standard protein chemistry analysis.

Characterization of 12C5, 19A3, CD22.1, CD22.2, 16F7 and 23C6

The 12C5 clone was found to express an antibody comprising an IgG1 heavy chain and a lambda light chain. The 19A3 clone was found to express an antibody comprising an IgG1 heavy chain and a kappa light chain. The heavy and light chains of the recombinant mAb expressed by the 8G9 clone were identical to those expressed by the 19A3 clone. The heavy chain of the recombinant mAb expressed by the 17E11 was identical to that of the 19A3 with the exception of the introduced N57Q mutation. The light chain of the recombinant mAb expressed by thte 17E11 clone was identical to that expressed by the 19A3 clone. The 16F7 clone was found to express antibodies comprising an IgG1 heavy chain and one of two different kappa light chains (referred to herein as $V_K.1$ and $V_K.2$, wherein 43% of antibody protein comprised $V_K.1$ and 57% of antibody protein comprised $V_K.2$). The 23C6 clone also was found to express antibodies comprising an IgG1 heavy chain and one of two different kappa light chains ($V_K.1$ and $V_K.2$, wherein 40% of antibody protein comprised $V_K.1$ and 60% of antibody protein comprised $V_K.2$). The 4G6 clone was found to express antibodies comprising an IgG1 heavy chain and one of two different kappa light chains (referred to herein as $V_K.1$ and $V_K.2$). The 21F6 clone was found to express antibodies comprising one of two different IgG1 heavy chains (referred to herein as $V_H1$ and $V_H2$) and a kappa light chain.

The nucleotide and amino acid sequences of the heavy chain variable region of 12C5 are shown in FIG. 1A and in SEQ ID NO:41 and 31, respectively.

The nucleotide and amino acid sequences of the lambda light chain variable region of 12C5 are shown in FIG. 1B and in SEQ ID NO:45 and 35, respectively.

Comparison of the 12C5 heavy chain immunoglobulin sequence to the known human germline immunoglobulin heavy chain sequences demonstrated that the 12C5 heavy chain utilizes a $V_H$ segment from human germline $V_H$ 7-4.1, a D segment from the human germline 3-3, and a JH segment from human germline JH 6B. Further analysis of the 12C5 $V_H$ sequence using the Kabat system of CDR region determination led to the delineation of the heavy chain CDR1, CDR2 and CDR3 regions as shown in FIG. 1A and in SEQ ID NOs: 1, 5 and 9, respectively.

Comparison of the 12C5 light chain immunoglobulin sequence to the known human germline immunoglobulin light chain sequences demonstrated that the 12C5 lambda light chain utilizes a $V_\lambda$ segment from human germline $V_\lambda$ 2b2 and a $J\lambda$, segment from human germline JL 2. Further analysis of the 12C5 $V_\lambda$ sequence using the Kabat system of CDR region determination led to the delineation of the light chain CDR1, CDR2 and CDR3 regions as shown in FIG. 1B and in SEQ ID NOs: 13, 19 and 25, respectively.

The nucleotide and amino acid sequences of the heavy chain variable region of 19A3 are shown in FIG. 2A and in SEQ ID NOs:42 and 32, respectively. The nucleotide and amino acid sequences of the heavy chain variable region of CD22.1 are identical to those of 19A3, and correspond to the nucleotide and amino acid sequences shown in FIG. 2A and SEQ ID NOs:42 and 32, respectively.

The nucleotide and amino acid sequences of the heavy chain variable region of CD22.2 are shown in FIG. 2C and in SEQ ID NOs:61 and 60, respectively.

The nucleotide and amino acid sequences of the light chain variable region of 19A3 are shown in FIG. 2B and in SEQ ID NO:46 and 36, respectively. The nucleotide and amino acid sequences of the light chain variable regions of both CD22.1 and CD22.2 are identical to those of 19A3, and correspond to the nucleotide and amino acid sequences shown in FIG. 2A and SEQ ID NOs:46 and 36, respectively.

Comparison of the 19A3/CD22.1 heavy chain immunoglobulin sequence to the known human germline immunoglobulin heavy chain sequences demonstrated that the 19A3 heavy chain utilizes a $V_H$ segment from human germline $V_H$ 4-34, a D segment from the human germline 3-9, and a JH segment from human germline JH 4B. Further analysis of the 19A3/CD22.1 $V_H$ sequence using the Kabat system of CDR region determination led to the delineation of the heavy chain CDR1, CDR2 and CDR3 regions as shown in FIG. 2A and in SEQ ID NOs: 2, 6 and 10, respectively Comparison of the CD22.2 heavy chain immunoglobulin sequence to the known human germline immunoglobulin heavy chain sequences demonstrated that the CD22.2 heavy chain utilizes a $V_H$ segment from human germline $V_H$ 4-34, a D segment from the human germline 3-9, and a JH segment from human germline JH 4B. Further analysis of the CD22.2 $V_H$ sequence using the Kabat system of CDR region determination led to the delineation of the heavy chain CDR1, CDR2 and CDR3 regions as shown in FIG. 2C and in SEQ ID NOs: 2, 60 and 10, respectively.

Comparison of the 19A3/CD22.1/CD22.2 light chain immunoglobulin sequence to the known human germline immunoglobulin light chain sequences demonstrated that the 19A3/CD22.1/CD22.2 kappa light chain utilizes a $V_K$ segment from human germline $V_K L^6$ and a JK segment from human germline JK 1. Further analysis of the 19A3/CD22.1/CD22.2 $V_K$ sequence using the Kabat system of CDR region determination led to the delineation of the light chain CDR1, CDR2 and CDR3 regions as shown in FIG. 2B and in SEQ ID NOs: 14, 20 and 26, respectively.

The nucleotide and amino acid sequences of the heavy chain variable region of 16F7 are shown in FIG. 3A and in SEQ ID NO:43 and 33, respectively.

The nucleotide and amino acid sequences of the $V_K.1$ kappa light chain variable region of 16F7 are shown in FIG. 3B and in SEQ ID NO:47 and 37, respectively.

The nucleotide and amino acid sequences of the $V_K.2$ kappa light chain variable region of 16F7 are shown in FIG. 3C and in SEQ ID NO:48 and 38, respectively.

Comparison of the 16F7 heavy chain immunoglobulin sequence to the known human germline immunoglobulin heavy chain sequences demonstrated that the 16F7 heavy chain utilizes a $V_H$ segment from human germline $V_H$ 5-51, a D segment from the human germline 3-10, and a JH segment from human germline JH 3B. Further analysis of the 16F7 $V_H$ sequence using the Kabat system of CDR region determination led to the delineation of the heavy chain CDR1, CDR2 and CDR3 regions as shown in FIG. 3A and in SEQ ID NOs: 3, 7 and 11, respectively.

Comparison of the 16F7 $V_K.1$ kappa light chain immunoglobulin sequence to the known human germline immunoglobulin kappa light chain sequences demonstrated that the 16F7 $V_K.1$ kappa light chain utilizes a $V_K$ segment from human germline $V_K$ A27 and a JK segment from human germline JK 1. Further analysis of the 16F7 $V_K$ sequence using the Kabat system of CDR region determination led to the delineation of the light chain CDR1, CDR2 and CDR3 regions as shown in FIG. 3B and in SEQ ID NOs: 15, 21 and 27, respectively.

Comparison of the 16F7 $V_K.2$ kappa light chain immunoglobulin sequence to the known human germline immunoglobulin kappa light chain sequences demonstrated that the 16F7 $V_K.2$ kappa light chain utilizes a $V_K$ segment from human germline $V_K$ A10 and a JK segment from human germline JK 2. Further analysis of the 16F7 $V_K$ sequence using the Kabat system of CDR region determination led to the delineation of the light chain CDR1, CDR2 and CDR3 regions as shown in FIG. 3C and in SEQ ID NOs: 16, 22 and 28, respectively.

The nucleotide and amino acid sequences of the heavy chain variable region of 23C6 are shown in FIG. 4A and in SEQ ID NO:44 and 34, respectively.

The nucleotide and amino acid sequences of the $V_K.1$ kappa light chain variable region of 23C6 are shown in FIG. 4B and in SEQ ID NO:49 and 39, respectively.

The nucleotide and amino acid sequences of the $V_K.2$ kappa light chain variable region of 23C6 are shown in FIG. 4C and in SEQ ID NO:50 and 40, respectively.

Comparison of the 23C6 heavy chain immunoglobulin sequence to the known human germline immunoglobulin heavy chain sequences demonstrated that the 23C6 heavy chain utilizes a $V_H$ segment from human germline $V_H$ 1-69, a D segment from the human germline 2-15, and a JH segment from human germline JH 6B. Further analysis of the 23C6 $V_H$ sequence using the Kabat system of CDR region determination led to the delineation of the heavy chain CDR1, CDR2 and CDR3 regions as shown in FIG. 4A and in SEQ ID NOs:4, 8 and 12, respectively.

Comparison of the 23C6 $V_K.1$ kappa light chain immunoglobulin sequence to the known human germline immunoglobulin kappa light chain sequences demonstrated that the $V_K.1$ kappa light chain utilizes a $V_K$ segment from human germline $V_K$ $L^6$ and a JK segment from human germline JK 1. Further analysis of the 23 C6 $V_K.1$ sequence using the Kabat system of CDR region determination led to the delineation of the light chain CDR1, CDR2 and CDR3 regions as shown in FIG. 4B and in SEQ ID NOs:17, 23 and 29, respectively.

Comparison of the 23C6 $V_K.2$ kappa light chain immunoglobulin sequence to the known human germline immunoglobulin kappa light chain sequences demonstrated that the $V_K.2$ kappa light chain utilizes a $V_K$ segment from human germline $V_K$ $L^6$ and a JK segment from human germline JK 1. Further analysis of the 23C6 $V_K.2$ sequence using the Kabat system of CDR region determination led to the delineation of the light chain CDR1, CDR2 and CDR3 regions as shown in FIG. 4B and in SEQ ID NOs:18, 24 and 30, respectively.

Figure 5B:
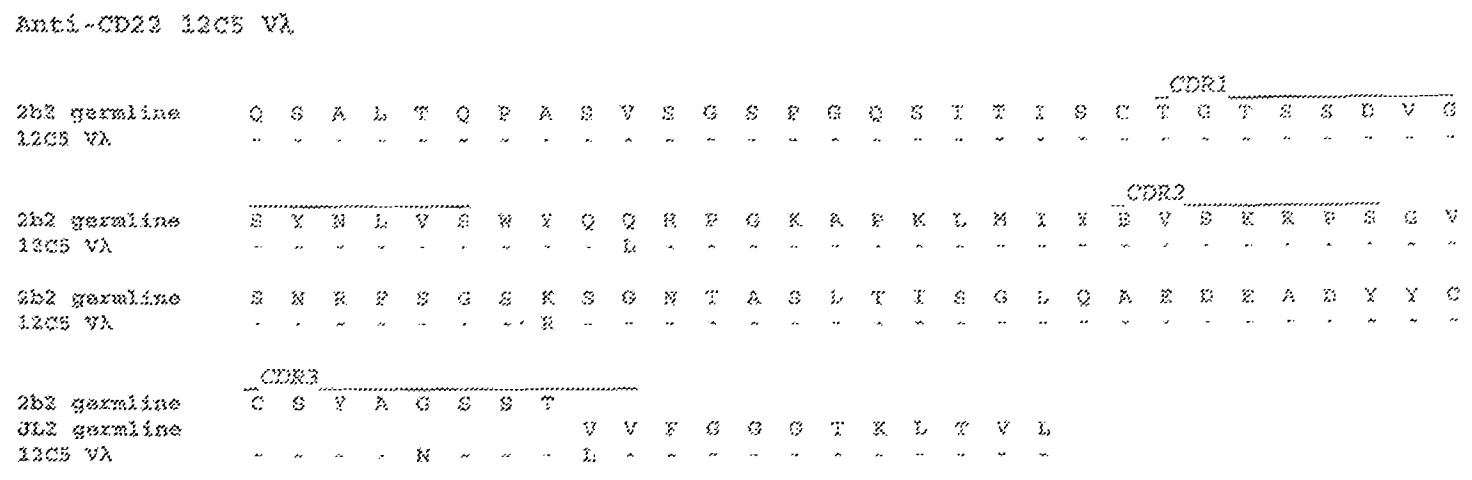

FIG. 5A shows the alignment of the 12C5 heavy chain variable amino acid sequencfe (SEQ ID NO:31) with the germline $V_H$ 7-4.1 encoded amino acid sequence (SEQ ID NO:51). The CDR1, CDR2 and CDR3 regions are delineated.

FIG. 5B shows the alignment of the 12C5 lambda light chain variable amino acid sequence (SEQ ID NO:35) with the germline V), 2b2 encoded amino acid sequence (SEQ ID NO:55). The CDR1, CDR2 and CDR3 regions are delineated.

FIG. 6A shows the alignment of the 19A3 heavy chain variable amino acid sequence and the CD22.1 heavy chain variable amino acid sequence (SEQ ID NO:32) with the germline $V_H$ 4-34 encoded amino acid sequence (SEQ ID NO:52). The CDR1, CDR2 and CDR3 regions are delineated.

FIG. 6B shows the alignment of the 19A3, CD22.1 and CD22.2 kappa light chain variable amino acid sequences (all of which are identical to SEQ ID NO:36) with the germline $V_K$ $L^6$ encoded amino acid sequence (SEQ ID NO:56). The CDR1, CDR2 and CDR3 regions are delineated.

FIG. 6C shows the alignment of the CD22.2 heavy chain variable amino acid sequence (SEQ ID NO:32) with the germline $V_H$ 4-34 encoded amino acid sequence (SEQ ID NO:52). The CDR1, CDR2 and regions are delineated.

FIG. 7A shows the alignment of the 16F7 heavy chain variable amino acid sequence (SEQ ID NO:33) with the germline $V_H$ 5-51 encoded amino acid sequence (SEQ ID NO:53). The CDR1, CDR2 and CDR3 regions are delineated.

FIG. 7B shows the alignment of the 16F7 $V_K.1$ kappa light chain variable amino acid sequence (SEQ ID NO:37) with the germline $V_K$ A27 encoded amino acid sequence (SEQ ID NO:57). The CDR1, CDR2 and CDR3 regions are delineated.

FIG. 7C shows the alignment of the 16F7 $V_K.2$ kappa light chain variable amino acid sequence (SEQ ID NO:38) with the germline $V_K$ A10 encoded amino acid sequence (SEQ ID NO:58). The CDR1, CDR2 and CDR3 regions are delineated.

FIG. 8A shows the alignment of the 23C6 heavy chain variable amino acid sequence (SEQ ID NO:34) with the germline $V_H$ 1-69 encoded amino acid sequence (SEQ ID NO:54). The CDR1, CDR2 and CDR3 regions are delineated.

FIG. 8B shows the alignment of the 23C6 $V_K.1$ kappa light chain variable amino acid sequence (SEQ ID NO:39) and the $V_K.2$ kappa light chain variable amino acid sequence (SEQ ID NO:40) with the germline $V_K$ $L^6$ encoded amino acid sequence (SEQ ID NO:56). The CDR1, CDR2 and CDR3 regions are delineated.

Characterization of 4G6 and 21F6

The nucleotide and amino acid sequences of the heavy chain variable region of 4G6 are shown in FIG. 17A and in SEQ ID NO:87 and 81, respectively.

The nucleotide and amino acid sequences of the $V_K.1$ kappa light chain variable region of 4G6 are shown in FIG. 17B and in SEQ ID NO:90 and 84, respectively.

The nucleotide and amino acid sequences of the $V_K.2$ kappa light chain variable region of 4G6 are shown in FIG. 17C and in SEQ ID NO:91 and 85, respectively.

Comparison of the 4G6 heavy chain immunoglobulin sequence to the known human germline immunoglobulin heavy chain sequences demonstrated that the 4G6 heavy chain utilizes a $V_H$ segment from human germline $V_H$ 1-69, a D segment from the human germline 7-27, and a JH segment from human germline JH 4B. Further analysis of the 4G6 $V_H$ sequence using the Kabat system of CDR region determination led to the delineation of the heavy chain CDR1, CDR2 and CDR3 regions as shown in FIG. 17A and in SEQ ID NOs: 63, 66 and 69, respectively.

Comparison of the 4G6 $V_K.1$ kappa light chain immunoglobulin sequence to the known human germline immunoglobulin kappa light chain sequences demonstrated that the 16F7 $V_K.1$ kappa light chain utilizes a $V_K$ segment from human germline $V_K$ $L^{18}$ and a JK segment from human germline JK 2. Further analysis of the 4G6 $V_K$ sequence using the Kabat system of CDR region determination led to the delineation of the light chain CDR1, CDR2 and CDR3 regions as shown in FIG. 3B and in SEQ ID NOs: 72, 75 and 78, respectively.

Comparison of the 4G6 $V_K.2$ kappa light chain immunoglobulin sequence to the known human germline immunoglobulin kappa light chain sequences demonstrated that the 4G5 $V_K.2$ kappa light chain utilizes a $V_K$ segment from human germline $V_K$ A27 and a JK segment from human germline JK 4. Further analysis of the 4G6 $V_K$ sequence using the Kabat system of CDR region determination led to the delineation of the light chain CDR1, CDR2 and CDR3 regions as shown in FIG. 17C and in SEQ ID NOs: 73, 76 and 79, respectively.

The nucleotide and amino acid sequences of the $V_H.1$ heavy chain variable region of 21F6 are shown in FIG. 18A and in SEQ ID NO:88 and 82, respectively.

The nucleotide and amino acid sequences of the $V_H.2$ heavy chain variable region of 21F6 are shown in FIG. 18B and in SEQ ID NO:89 and 83, respectively.

The nucleotide and amino acid sequences of the kappa light chain variable region of 21F6 are shown in FIG. 18C and in SEQ ID NO:92 and 86, respectively.

Comparison of the 21F6 $V_H.1$ heavy chain immunoglobulin sequence to the known human germline immunoglobulin heavy chain sequences demonstrated that the 21F6 heavy chain utilizes a $V_H$ segment from human germline $V_H$ 4-34, a D segment from the human germline 3-9, and a JH segment from human germline JH 4B. Further analysis of the 21F6 $V_H$ sequence using the Kabat system of CDR region determination led to the delineation of the heavy chain CDR1, CDR2 and CDR3 regions as shown in FIG. 3A and in SEQ ID NOs: 64, 67 and 70, respectively.

Comparison of the 21F6 $V_H.2$ kappa light chain immunoglobulin sequence to the known human germline immunoglobulin kappa light chain sequences demonstrated that the 21F6 $V_H.2$ heavy chain utilizes a $V_H$ segment from human germline $V_H$ 4-34, a D segment from the human germline 3-9, and a JH segment from human germline JH 4B. Further analysis of the 21F6 $V_H$ sequence using the Kabat system of CDR region determination led to the delineation of the light chain CDR1, CDR2 and CDR3 regions as shown in FIG. 18B and in SEQ ID NOs: 65, 68 and 71, respectively.

Comparison of the 21F6 kappa light chain immunoglobulin sequence to the known human germline immunoglobulin kappa light chain sequences demonstrated that the 21F6 kappa light chain utilizes a $V_K$ segment from human germline $V_K$ $L^6$ and a JK segment from human germline JK 4. Further analysis of the 21F6 $V_H$ sequence using the Kabat system of CDR region determination led to the delineation of the light chain CDR1, CDR2 and CDR3 regions as shown in FIG. 18C and in SEQ ID NOs: 74, 77 and 80, respectively.

FIG. 19A shows the alignment of the 4G6 heavy chain variable amino acid sequence (SEQ ID NO:81) with the germline $V_H$ 1-69 encoded amino acid sequence (SEQ ID NO:54). The CDR1, CDR2 and CDR3 regions are delineated.

FIG. 19B shows the alignment of the 4G6 $V_K.1$ kappa light chain variable amino acid sequence (SEQ ID NO:84)

with the germline $V_{K1}$ $L^{18}$ encoded amino acid sequence (SEQ ID NO:93). The CDR1, CDR2 and CDR3 regions are delineated.

FIG. 18C shows the alignment of the 4G6 $V_K$-2 kappa light chain variable amino acid sequence (SEQ ID NO:85) with the germline $V_K$ A27 encoded amino acid sequence (SEQ ID NO:57). The CDR1, CDR2 and CDR3 regions are delineated.

FIG. 20A shows the alignment of the 21F6 $V_H$-1 heavy chain variable amino acid sequence (SEQ ID NO:82) with the germline $V_H$ 4-34 encoded amino acid sequence (SEQ ID NO:52). The CDR1, CDR2 and CDR3 regions are delineated.

FIG. 20B shows the alignment of the 21F6 $V_H$-2 kappa light chain variable amino acid sequence (SEQ ID NO:83) with the germline $V_H$ 4-34 encoded amino acid sequence (SEQ ID NO:52). The CDR1, CDR2 and CDR3 regions are delineated.

FIG. 20C shows the alignment of the 21F6 kappa light chain variable amino acid sequence (SEQ ID NO:86) with the germline $V_K$ $L^6$ encoded amino acid sequence (SEQ ID NO:56). The CDR1, CDR2 and CDR3 regions are delineated.

Recombinant Isotype Conversion

The 12C5, 19A3, 16F7, 23C6, CD22.1, CD22.2, 4G6 and 21F6 variable regions can be converted to full-length antibodies of any desired isotype using standard recombinant DNA techniques. For example, DNA encoding the $V_H$ and $V_L$ regions can be cloned into an expression vector that carries the heavy and light chain constant regions such that the variable regions are operatively linked to the constant regions. Alternatively, separate vectors can be used for expression of the full-length heavy chain and the full-length light chain. Non-limiting examples of expression vectors suitable for use in creating full-length antibodies include the pIE vectors described in U.S. Patent Application No. 20050153394 by Black.

Example 3

Binding Characteristics of Anti-CD22 Human Monoclonal Antibodies

In this example, binding affinities of the anti-CD22 antibodies 12C5, 19A3, 16F7, 23C6 and 4G6 were examined by BIAcore analysis. Retention of CD22 binding affinity by the 19A32 recombinant derivative antibodies CD22.1 and CD22.2 was confirmed by means of ELISA analysis and FACS flow cytometry.

Epitope grouping of the 12C5, 19A3, 16F7, and 23C6 antibodies was performed by BIAcore analysis.

Finally, the CD22 domains to which the anti-CD22 antibodies of the present invention specifically bind were mapped using CHO cells that expressed a fusion protein containing only the amino terminal domains 1 and 2 of CD22.

Binding Affinity and Kinetics

For determination of antibody affinity ($K_D$), experiments were performed in which the CD22 antigen was captured on a BIAcore chip using an antibody to the His tag present on the antigen. Anti-His monoclonal antibody ab15149 (Abcam, Stock conc.0.5 mg/mL) was coated on a CMS chip at high density (3500RUs), as recommended by the manufacturer. CD22 ECD (6.6 µg/mL) was captured on this surface for 60 sec at a flow-rate of 6 µL/min. A single concentration (20 µg/mL) of anti-CD22 purified mAbs was injected over the captured antigen with an association time of 5 minutes and a dissociation time of 8 minutes, at a flow rate of 25 µg/mL. The chip surface was regenerated after each cycle with —10µL of 25 mM NaOH. Isotype controls were run on the chip and the data used to subtract non-specific binding. All experiments were carried out on a BIAcore 3000 surface plasmon resonance instrument, using BIAcore Control software v 3.2. Data analysis was carried out using BiaEvaluation v. 3.2 software.

Fourteen of the selected anti-CD22 antibodies were tested in the affinity experiment. The range of obtained affinity values for the twelve antibodies was $0.07-9.95 \times 10^{-9}$ M. The results for the four antibodies structurally characterized in Example 2 are summarized below in Table 1:

TABLE 1

| BIAcore Binding Data for Anti-CD22 HuMAbs. | |
|---|---|
| Anti-CD22 antibody | BIAcore Affinity ($K_D$) $10^{-9}$ M |
| Positive control | 1.48 |
| 12C5 | 0.23 |
| 19A3 | 0.15 |
| 16F7 | 1.03 |
| 23C6 | 0.87 |
| 4G6 | 0.07 |

Retention of CD22 Binding Affinity by Recombinant Derivative Antibodies CD22.1 and CD22.2

To determine whether CD22.1 and CD22.2 retained CD22 binding affinity, ELISA analysis was performed in which binding to CD22 ECD by CD22.1 and CD22.2 were compared to binding by the hybridoma-derived parental antibody 19A3.

Figure 12:
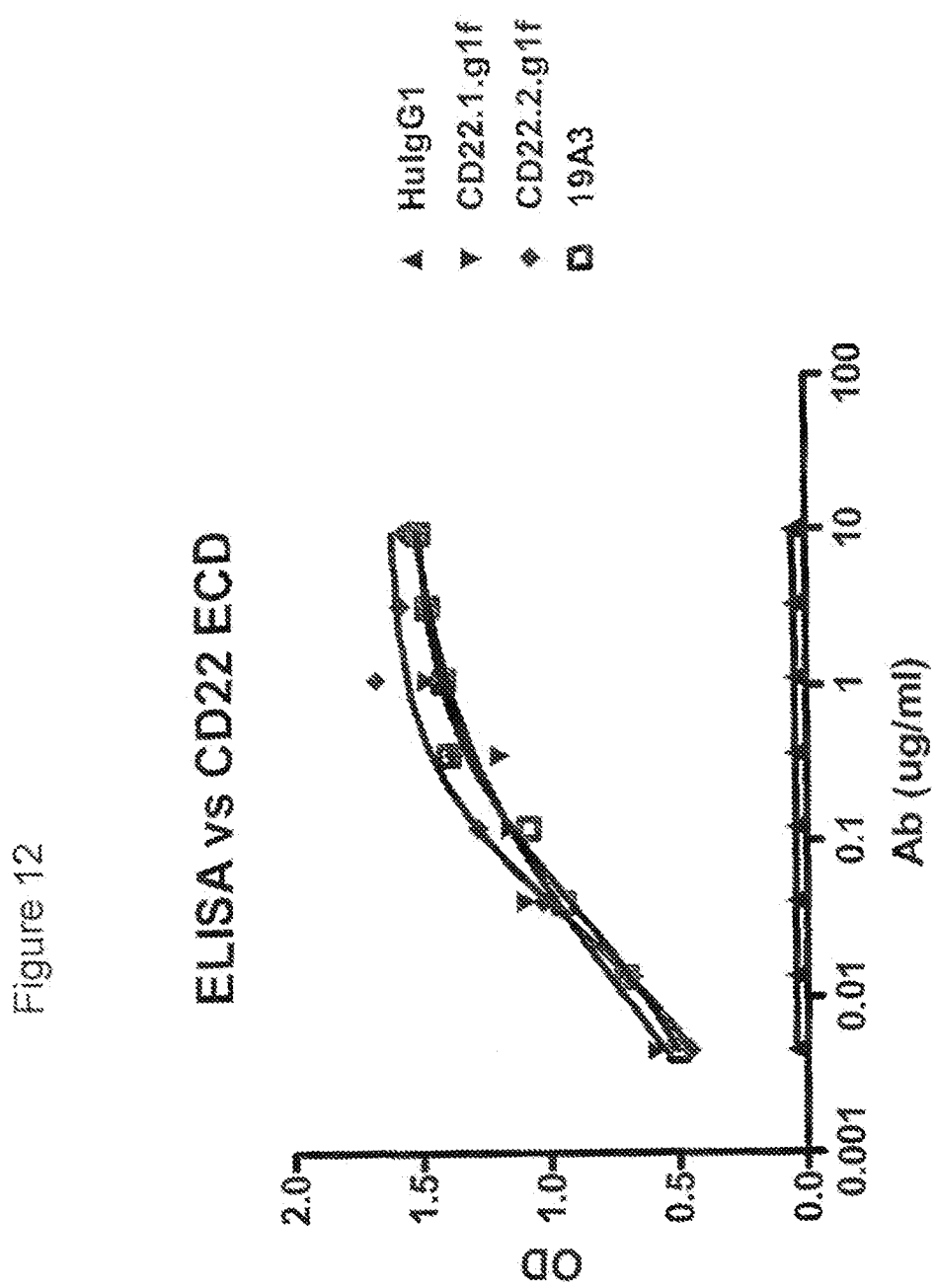
FIG. 12 is a graph showing CD22 ECD binding by anti-CD22 recombinant human antibodies CD22.1 and CD22.2 as compared to that of the 19A3 parent human antibody.

Recombinant CD22 extracellular domain (CD22 ECD) was coated on 96-well ELISA plates at 2 µg/ml, and after washing, blocking with 5% bovine serum albumin and washing again, the test antibodies were titrated from 10 µg/ml downwards in 1:3 dilutions. After incubating for an hour, plates were washed, and goat anti-human IgG HRP conjugate was added to each well. After a further one hour incubation plates were washed again and bound HRP conjugate detected through addition of TMB substrate, incubating until color developed and stopping with 1M hydrochloric acid. Absorbance was then read in a plate reader at 450 nm. Results (FIG. 12) clearly showed that the ability of CD22.1 and CD22.2 to bind to CD22 ECD was equivalent to the parental antibody 19A3. This revealed that expression of the antibody in CHO cells was successful, and that the mutation to remove the N-glycosylation site did not affect antigen binding.

The ability of the 4G6 and 21F6 anti-CD22 monoclonal antibodies to bind CD22 ECD was also investigated, and found to bind specifically to CD22 ECD.

FACS Analysis of CD22 Expressed on Cell Surfaces

Figure 13:
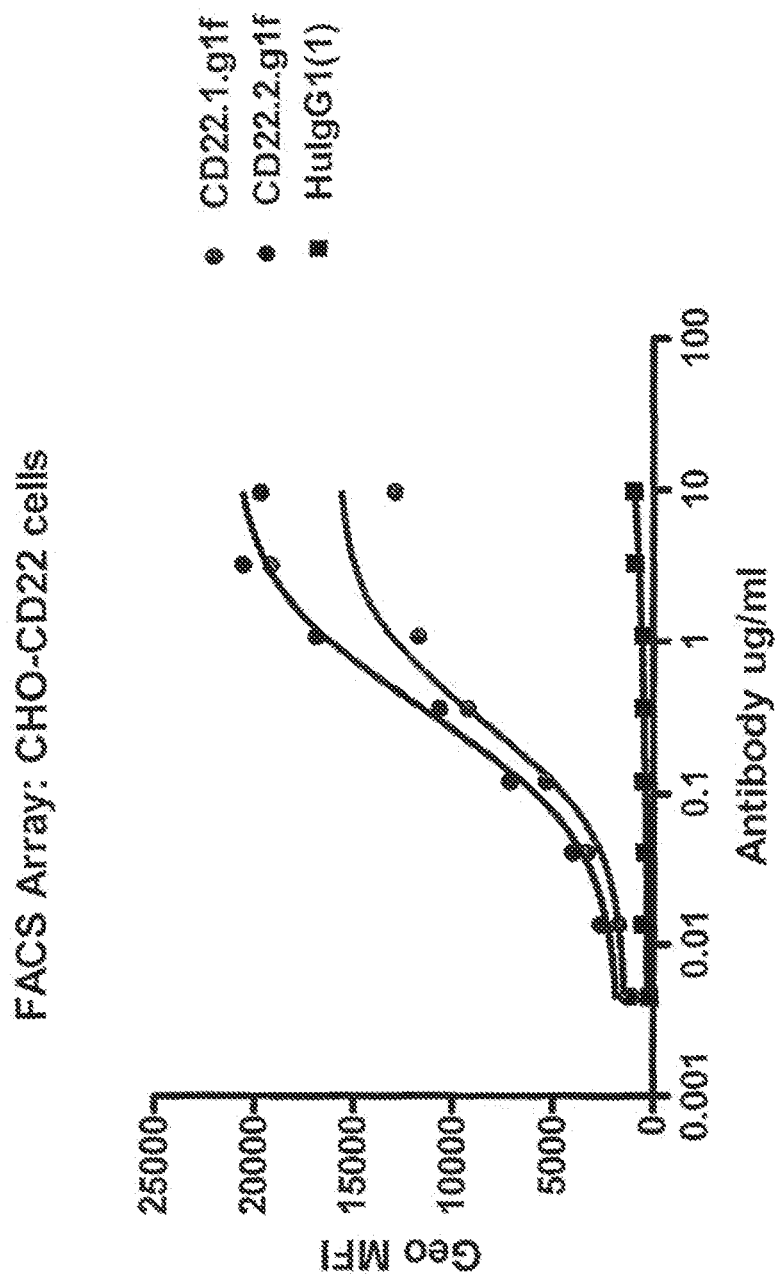
FIG. 13 is a graph showing binding of CD22 expressed on the surface of CHO cells by the by anti-CD22 recombinant human antibodies CD22.1 and CD22.2.

The ability of CD22.1 and CD22.2 to bind CD22 was also confirmed by flow cytometry. Either CHO cells transfected with full-length CD22 (CHO-CD22) or Raji cells were resuspended in FACS buffer at $2 \times 10^5$ cells/well, and after pelleting the cells, antibody was titrated into the wells starting at 10 µg/ml and serially diluting 1:3. After mixing and incubating on ice for 45 minutes, FACS buffer was added and the cells washed 4 times. After washing, goat anti-human IgG PE conjugate was added, and following a further 30 minute incubation on ice, cells were again washed 4 times before resuspending in FACS buffer and reading PE fluorescence on a FACS array machine. Results (FIGS. 13 and 14) showed that CD22.1 and CD22.2 bound strongly and equivalently to both the CHO-CD22 transfectants and Raji cells.

Figure 22:
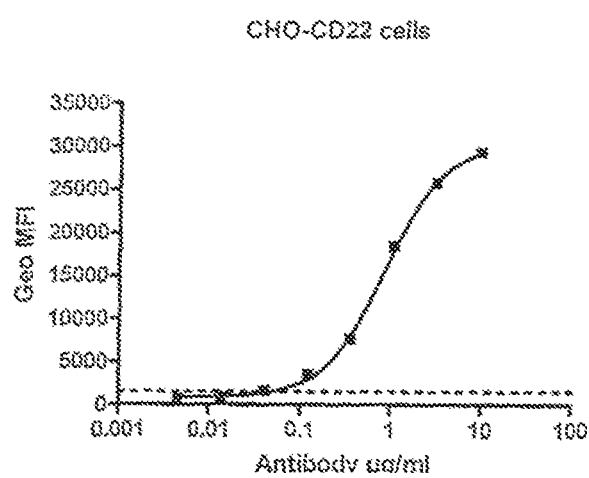
FIG. 22 is a graph showing binding of CD22 expressed on the surface of CHO cells by anti-CD22 human antibody 21F6.
Figure 23:
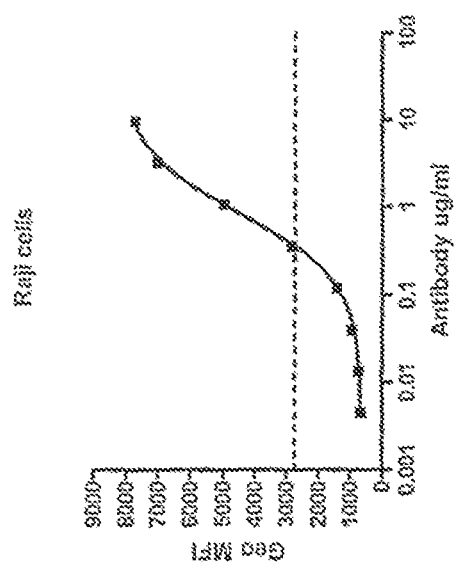
FIG. 23 is a graph showing binding of CD22 expressed on the surface of Raji cells by anti-CD22 human antibody 21F6.

Binding of 4G6 and 21F6 to CD22 expressed on the surfaces of Raji cells and CHO cells transformed with CD22 was also analyzed by FACS analysis. The results demonstrated that a high level of cell binding was obtained. See FIGS. 21, 22A and 22B. Neither antibody was able to bind to CHO cells absent transfection with CD22.

Epitope Grouping

Epitope binning was carried out by immobilizing selected antibodies on the CMS chip, based on standard immobilization protocols and flowing antibody-antigen complexes over the surface. Antibodies that had overlapping epitopes were competed out while those having non-overlapping epitopes gave rise to simultaneous binding to the antigen. An increasing signal denotes an epitope different from the antibody coated on the chip, and the opposite is true if signal decreases. Antibodies that exhibited faster off-rate constants were chosen to be coated on the Biacore CMS chip as they would facilitate easier regeneration for repeated use of the chip. Purified anti-CD22 antibodies were coated at high densities on different surfaces of different CMS chips. Several rounds of iterative binning were carried out until the distinct epitope groups were identified. The concentrations of antibodies varied between 50-200 µg/mL, which were incubated with 4 nM-50 nM CD22 ECD for 2 hrs at RT. The incubated complexes were passed over the antibody coated surfaces on each chip for 2-6 min at 5-10 µL/min. Each cycle was regenerated by 15-30 mM NaOH. The signal obtained after 2-5 minutes of injection was plotted against antibody concentration to determine the epitope groups. Antibodies were grouped into various epitopes based on the above interpretation of the experimental observation.

The results of the epitope grouping experiment were that four distinct epitope groups could be identified. Of fourteen anti-CD22 antibodies examined, five were found to be in Epitope Group 1, three were found to be in Epitope Group 2, four were found to be in Epitope Group 3, one was found to be in Epitope Group 4 and one was found to be in Epitope Groups 3 & 4, indicating that there is some overlap between Epitope Groups 3 and 4. The results for the four antibodies structurally characterized in Example 2 are summarized below in Table 2:

TABLE 2

CD22 Epitope Groups Mapped by BIAcore

| Anti-CD22 antibody | Epitope Group |
|---|---|
| Positive control | 1 |
| 12C5 | 4 |
| 19A3 | 1 |
| 16F7 | 3 |
| 23C6 | 2 |

Recognition of CD22 Amino Terminal Domains

The extracellular region of CD22 contains 7 immunoglobulin-type domains, of which the amino terminal 2 Ig-type domains may be particularly important for CD22 ligand binding. In order to map which domains the human antibodies bound to, a recombinant construct was made in which only amino terminal domains 1 and 2 of the ECD were fused to the hinge and Fc regions of a mouse IgG heavy chain. The resultant fusion protein, designated CD22 d1d2-mFc, was expressed in CHO cells and purified for use in binding assays. Human antibodies, previously shown to bind to the entire ECD of CD22, were then tested for their ability to bind to CD22 d1d2-mFc.

Goat anti-mouse IgG was coated on 96-well ELISA plates at 5 µg/ml. After incubating overnight at 4° C., plates were washed and CD22 d1d2-mFc was added to each well at 2 µg/ml followed by incubation for 1 hour at room temperature. After plate washing, blocking with 5% bovine serum albumin and washing again, the test antibodies were added at 10 µg/ml. After incubating for an hour, plates were washed, and goat anti-human IgG HRP conjugate was added to each well. After a further one hour incubation plates were washed again and bound HRP conjugate detected through addition of TMB substrate, incubating until color developed and stopping with 1M hydrochloric acid. Absorbance was then read in a plate reader at 450 nm.

Figure 15:
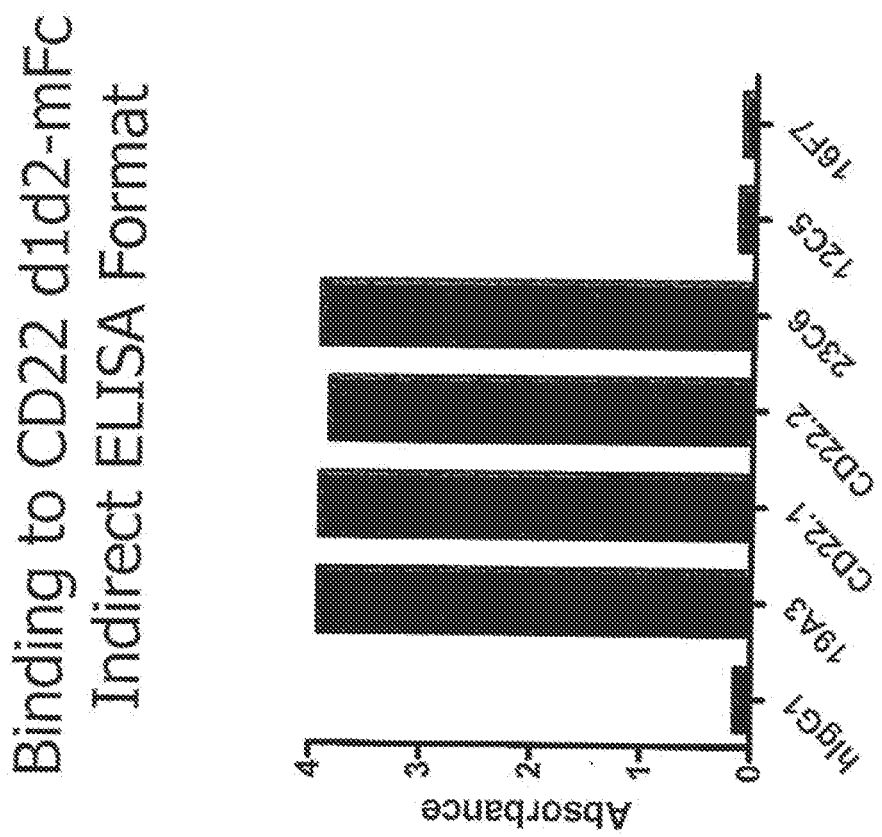
FIG. 15 is a bar graph showing binding of the CD22 ECD amino-terminal domains 1 and 2 by anti-CD22 antibodies 12C5, 19A3, 16F7 and 23C6, and by recombinant human antibodies CD22.1 and CD22.2.

Results (FIG. 15) showed that antibodies fell into two groups. Group 1 represented by 23C6, 19A3, and the recombinant derivatives of 19A3, CD22.1 and CD22.2 bound to CD22 d1d2-mFc whereas group 2 represented by 12C5 and 16F7 did not. This suggests that 12C5 and 16F7 recognize epitopes on the CD22 ECD outside of the amino-terminal domains.

FACS Analysis of CD22 Expressed on Cell Surfaces

Figure 14:
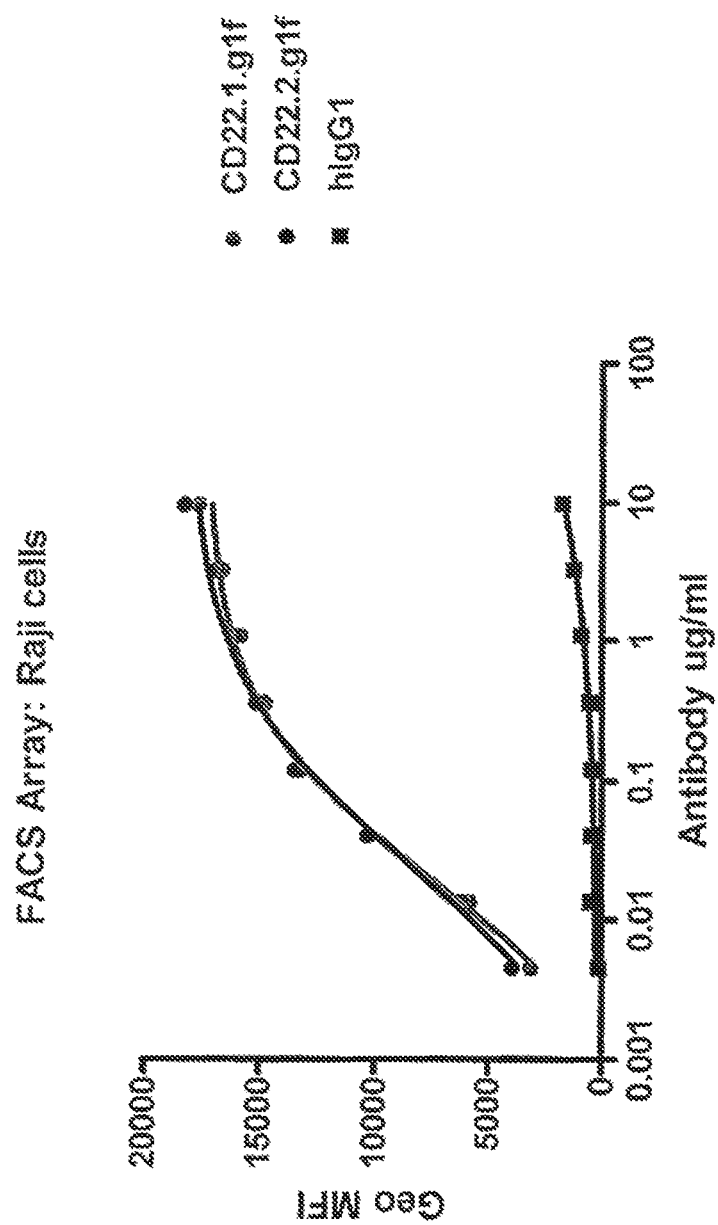
FIG. 14 is a graph showing binding of CD22 expressed on the surface of Raji cells by the by anti-CD22 recombinant human antibodies CD22.1 and CD22.2.

Binding of CD22.1 and CD22.2 to CD22 was also confirmed by flow cytometry. Either CHO cells transfected with full-length CD22 (CHO-CD22) or Raji cells were resuspended in FACS buffer at $2 \times 10^5$ cells/well, and after pelleting the cells, antibody was titrated into the wells starting at 10 µg/ml and serially diluting 1:3. After mixing and incubating on ice for 45 minutes, FACS buffer was added and the cells washed 4 times. After washing, goat anti-human IgG PE conjugate was added, and following a further 30 minute incubation on ice, cells were again washed 4 times before resuspending in FACS buffer and reading PE fluorescence on a FACS array machine. Results (FIGS. 13 and 14) showed that CD22.1 and CD22.2 bound strongly and equivalently to both the CHO-CD22 transfectants and Raji cells.

Binding of 4G6 and 21F6 to CD22 expressed on the surfaces of Raji cells and CHO cells transformed with CD22 was analyzed by FACS analysis. The results demonstrated that a high level of cell binding was obtained. See FIGS. 21, 22A and 22B. Neither antibody was able to bind to CHO cells absent transfection with CD22.

Example 4

Internalization of Anti-CD22 Antibodies

To determine the ability of the anti-CD22 human antibodies to internalize into CD22-expressing cells, a Hum-ZAP internalization assay was used with the Burkitt's lymphoma cell line Raji, which expresses CD22. The Hum-ZAP assay tests for internalization of a primary antibody through binding of a secondary antibody with affinity for human IgG conjugated to the toxin saporin.

The CD22-expressing Raji cells were seeded at $2.0 \times 10^4$ cells/well (35 µl/well). The anti-CD22 antibodies were added to the wells at 1.5 µg/ml (35 µl/well). Media alone was used as negative control. The Hum-ZAP reagent (Advanced Targeting Systems, San Diego, Calif., IT-22-25) was then added at a concentration of 3.0 µg/mL (35 µl/well) to half of the wells while the other half of the wells received media only. The plates were incubated for 72 hours at 37° C. The cell viability was determined using CellTiter-Glo Luminescent Cell Viability Assay (Promega, Madison, Wis.,

G7571). CellTiter-Glo buffer was mixed with CellTiter-Glo substrate and 100 µL of the mixture was added to each well. Luminescence was detected using Veritas Microplate Luminometer and Veritas software (Turner BioSystems, Sunnyvale, Calif.) per manufacturer directions.

Twelve different anti-CD22 antibodies were tested and all exhibited the ability to internalize. The results for the four antibodies that were structurally characterized in Example 2 are shown in the bar graph of FIG. 9. As illustrated in FIG. 9, a marked decrease in Raji cell viability was observed in all wells containing anti-CD22 antibodies and HumZAP reagent, including wells with positive control, while cell viability was not affected in wells containing only the anti-CD22 antibodies with no HumZAP reagent, demonstrating that the anti-CD22 antibodies do not trigger cell killing on their own. As expected, in absence of anti-CD22 antibodies, the negative control (referred to as media) did not show any cell killing in presence or absence of HumZAP reagent. These data demonstrate that the anti-CD22 antibodies internalize efficiently and release of saporin inside the cells is responsible for the killing of CD22-expressing Raji cells in presence of HumZAP reagent.

Example 5

Assessment of ADCC Activity of Anti-CD22 Antibodies

To determine the ability of the anti-CD22 human antibodies kill CD22+ cell lines in the presence of effector cells via antibody dependent cellular cyotoxicity (ADCC), a fluorescence cytotoxicity assay was used.

Human effector cells were prepared from whole blood as follows. Human peripheral blood mononuclear cells were purified from heparinized whole blood by standard Ficoll-paque separation. The cells were resuspended in RPMI1640 media containing 10% FBS (heat-inactivated) and 200 U/ml of human IL-2 and incubated overnight at 37° C. The following day, the cells were collected and washed four times in culture media and resuspended at $1\times10^7$ cells/ml. Target CD22+ cells were incubated with BATDA reagent (Perkin Elmer, Wellesley, Mass.) at 2.5 µl BATDA per $1\times10^6$ target cells/mL for 20 minutes at 37° C. The target cells were washed four times, spun down and brought to a final volume of $1\times10^5$ cells/ml.

The CD22+ cell lines Raji (human B lymphocyte Burkitt's lymphoma; ATCC Accession No. CCL-86) and Daudi (human B lymphocyte Burkitt's lymphoma; ATCC Accession No. CCL-213) were tested for antibody specific ADCC to the human anti-CD22 monoclonal antibodies using the Delfia fluorescence emission analysis as follows. Each target cell line (100 µl of labeled target cells, $10^4$ cells/well) was incubated with 50 µl of effector cells ($10^6$ cells/well) and 50 µl of antibody (10 ug/ml final concentration). A target to effector ratio of 1:50 was used throughout the experiments. In all studies, a human IgG1 isotype control was used as a negative control. Cells were spun down at 2000 rpm and incubated for one hour incubation at 37° C. The supernatants were then collected, submitted to centrifugation and 20 µl of supernatant was transferred to a flat bottom plate, to which 180 µl of Eu solution (Perkin Elmer, Wellesley, Mass.) was added and read in a RubyStar reader (BMG Labtech). The % lysis was calculated as follows: (sample release−spontaneous release*100)/(maximum release−spontaneous release), where the spontaneous release is the fluorescence from wells which contain target cells plus effector cells and maximum release is the fluorescence from wells containing target cells and have been treated with 2% Triton-X.

Figure 10A:
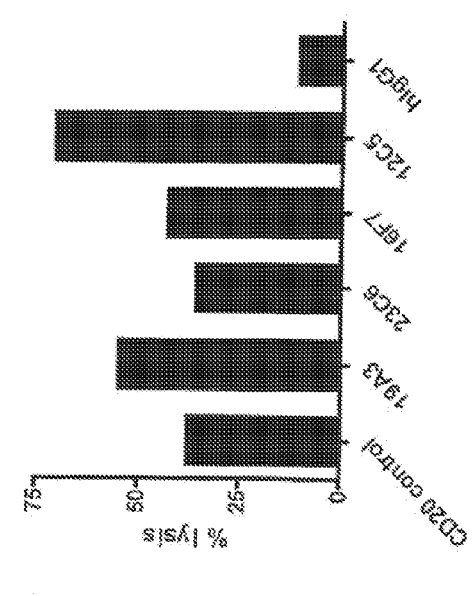
FIG. 10A is a graph showing ADCC activity (as measured by % lysis) of anti-CD22 human antibodies 12C5, 19A3, 16F7 and 23C6 against Daudi cells.
Figure 10B:
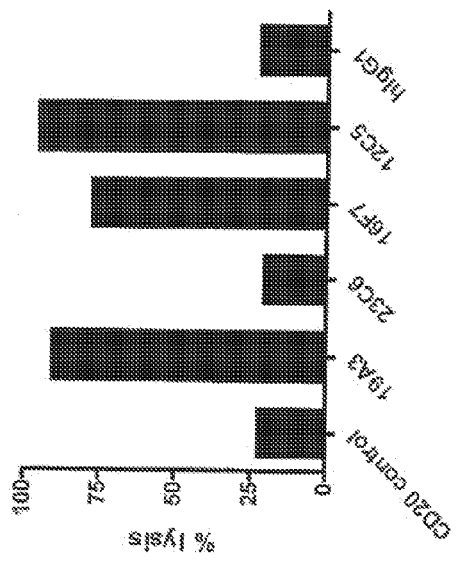
FIG. 10B is a graph showing ADCC activity (as measured by % lysis) of anti-CD22 human antibodies 12C5, 19A3, 16F7 and 23C6 against Raji cells.

For the Raji and Daudi cell ADCC assays, thirteen different anti-CD33 antibodies were tested along with negative and positive control antibodies (hIgG1 and $CD_2O$, respectively). In each assay, ten of the thirteen anti-CD22 antibodies exhibited levels of ADCC activity equal to or greater than the positive control antibody. The results for the four antibodies that were structurally characterized in Example 2 are shown in the graphs of FIG. 10A (Daudi cells) and 10B (Raji cells), which show % cell lysis. The data demonstrate that human anti-CD22 antibodies that exhibit ADCC activity can be selected, although the degree of cytotoxicity of each antibody against CD22+ cells may differ depending on which cell line is used as the target cell.

Example 6

Stimulation of Calcium Flux by Anti-CD22 Antibodies

To assess the ability of the anti-CD22 human antibodies to stimulate calcium flux in CD22+ cells, the following calcium flux assay was used. Viable Ramos cells (ATCC Accession No. CRL-1596) were counted by trypan blue exclusion microscopy and diluted to $2\times10^6$ cells/ml in RPMI+10% FBS culture media. From this cell suspension, $2\times10^5$ cells (100 µl/well) was dispensed into to all the wells of a Poly D-Lysine surface black with clear bottom 96 well plate (Corning #3667). Loading dye (Molecular Devices catalog #R7181) was added to the cell suspension, 100 µl/well. The plate was centrifuges at 1100 rpm for 4 minutes and then incubated at 37° C. for 30 minutes. Five-fold dilution series of anti-CD22 antibodies and human IgG1 isotype control, from 50 µg/ml to 40 ng/ml, were prepared in Component B (Molecular Devices # R7181)+0.1% BSA buffer. Antibodies were dispensed in triplicate into rows A-F of the previously prepared 96-well plate. Component B+0.1% BSA was dispensed into all the wells of rows G&H on the assay plate. Calcium flux was assayed using a Flex Station (Molecular Devices), adding 22 µl reagent per well to the assay plate at 17 seconds. Data was analyzed as FI Max-Min and plotted vs. antibody concentration using GraphPad™ PRISM, non-linear regression, sigmoidal dose response, variable slope.

Seventeen different anti-CD22 human antibodies were evaluated in the assay. The results showed that none of the seventeen anti-CD22 antibodies tested stimulated significant calcium flux, as compared to a human IgG1 isotype control or buffer alone. Ramos cells were previously demonstrated to flux calcium in response to BCR stimulation with goat anti-human IgM F(ab')$_2$.

Example 7

Modulation of BCR Stimulation-Induced Effects by Anti-CD22 Antibodies

In this example, the ability of immobilized anti-CD22 antibody to modulate B Cell Receptor (BCR) stimulation-induced effects was examined. In the assay, anti-CD22 human antibodies and human IgG1 isotype control were diluted to 5 µg/ml in RPMI+10% FBS and dispensed 100 µl/well in triplicate into Microlite 1 Flat Bottom plates (Corning #7416). Following overnight incubation at 4° C., the plates were washed once with cold PBS, then once with RPMI 1640 (Mediatech)+10% FBS (GIBCO). Viable Ramos cells (ATCC Accession No. CRL-1596) were counted by trypan blue exclusion microscopy and diluted to $2 \times 10^5$ cells/ml in RPMI+10% FBS. 20,000 cells (50 µl/well) were dispensed into the antibody coated 96-well plates. Anti-human IgM F(ab')$_2$ (Jackson catalog #109-006-129) was diluted to 5 µg/ml in RPMI+10% FBS and 100 µl/well was dispensed for a final concentration of 2.5 µg/ml. The assay plates were incubated 72 hours. Cell viability was assayed with the addition of CellTiter-Glo reagent (Promega G7571), 100 µl/well, for 10 minutes. Luminescence was measured using Luminescence Test 1 plate Nunc96 on Pherastar GMB Labtech. Data was analyzed as % cell death relative to the human IgG1 isotype control, which represented 100% cell viability.

Figure 11:
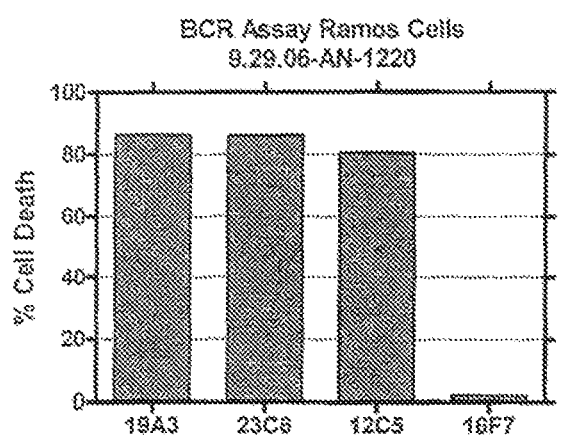
FIG. 11 is a bar graph showing the effect of immobilized anti-CD22 human antibodies 12C5, 19A3, 16F7 and 23C6 on BCR-stimulated Ramos cells, as measured by % cell death.

Seventeen different anti-CD22 antibodies were tested in the assay and this panel exhibited a broad range of activity, ranging from an observed % cell death value of approximately 80% to an observed % cell death value approximately equal to the isotype control, depending on the particualr antibody. The results for the four antibodies that were structurally characterized in Example 2 are shown in the bar graph of FIG. 11, which shows that immobilized 19A3, 23C6 and 12C5 each potently enhanced the anti-proliferative effects of BCR stimulation cell death whereas 16F7 did not differ significantly from the isotype control Example 8

Effects of Anti-CD22 Antibodies on Cell Proliferation

In this example, the direct effects of soluble anti-CD22 antibodies on cell proliferation, with or without antibody cross-linking, was examined. In the assay used, viable Ramos cells (ATCC Accession No. CRL-1596) were counted by trypan blue exclusion microscopy and diluted to $2 \times 10^5$ cells/ml in RPMI+10% FBS. 20,000 cells (50 µl/well) were dispensed into 96-well culture treated plates. Cross-linking antibody goat anti-human IgG Fc (Rockland catalog #709-1117) was diluted to 80 µg/ml in RPMI+10% FBS and 25 µl/well was dispensed into half of the Ramos cell assay plate. Diluent alone was dispensed (25 µl/well) into the remainder of the plate. Anti-CD22 human antibodies and human IgG1 isotype control were diluted to 20 µg/ml in RPMI+10% FBS and 25 µl/well was dispensed in triplicate to both Ramos plus cross-linker and Ramos plus diluent containing wells such that the final antibody concentrations were 5 µg/ml anti-CD22+/−20 µg/ml cross-linking antibody. Assay plates were incubated at 37° C. for 72 hours. Cell viability was assayed with the addition of CellTiter-Glo reagent (Promega G7571), 100 µl/well, for 10 minutes Luminescence was measured using Luminescence Test 1 plate Nunc96 on Pherastar GMB Labtech. Data was analyzed as % growth inhibition relative to the human IgG1 isotype control, which represented 0% inhibition.

Seventeen different anti-CD22 human antibodies were evaluated in the assay. The results showed that none of the seventeen anti-CD22 antibodies tested significantly altered the rate of Ramos cell proliferation, either when the antibodies were not cross-linked or when they were cross-linked. These results indicate that none of the anti-CD22 antibodies have a direct anti-proliferative effect on Ramos cells, even if the antibody is cross-linked.

Example 9

Assessment of CDC Activity of Anti-CD22 Antibodies

In this example, the ability of soluble anti-CD22 human antibodies to mediate complement dependent cytotoxicity (CDC) was examined. In the assay used, viable Ramos cells (ATCC Accession No. CRL-1596) were counted by trypan blue exclusion microscopy and diluted to $1 \times 10^6$ cells/ml in CDC buffer (RPMI 1640+0.1% BSA+20 mM HEPES+1% Pen/strep). The cell suspension was dispensed as 50,000 cells (50 µl/well) in a 96-well flat-bottomed tissue culture treated plate. Human complement (Quidel catalog #A113) was heat-inactivated by incubating 1 hr at 56° C. Active and heat-inactivated complement were each diluted 1:3 in CDC buffer and were dispensed 50 µl/well into the Ramos assay plates. Anti-CD22 human antibodies, human IgG1 isotype control and an anti-CD20 positive control antibody were each diluted to 40 µg/ml in CDC buffer. Diluted antibodies were dispensed 50 µl/well in duplicate into the Ramos assay plates with both active and heat-inactivated complement such that the final concentration of antibody was 10 µg/ml. The assay plates were were incubated 2 hrs at 37° C. To analyze cell viability, alamar blue reagent (BioSource catalog #DAL$^{1100}$) was added 50 µl/well and the plates were incubated a further 21 hrs at 37° C. Cell viability was assayed as being proportional to fluorescence measure using the SPECTROMAX GEMINI fluorescence plate reader (Molecular Devices S/N G 02243).

Eighteen different anti-CD22 antibodies were tested, along with, as a positive control, an anti-CD20 antibody known to exhibit robust cytotoxicity in the presence of active but not heat inactivated complement. The results showed that none of the anti-CD22 antibodies tested exhibited significant CDC activity as compared to the human IgG1 isotype control.

Example 10

Inhibition of Solid Tumor Cell Proliferation In Vivo by Anti-CD22 Antibody-Drug Conjugates To determine whether drug conjugates of CD22.1 and CD22.2 could be made which could effectively inhibit proliferation of an established solid tumor in vivo, the anti-CD22 recombinant antibodies CD22.1 and CD22.2 were conjugated to the cytotoxic drug Cytotoxin A and the efficacy of the resulting ADC compounds were examined using a Ramos subcutaneous tumor cell model.

Conjugation of CD22.1 and CD22.2 to Cytotoxic Compound Cytotoxin A

CD22.1 and CD22.2 were concentrated to approximately 5 mg/ml, buffer exchanged into 20 mM phosphate buffer, 50 mM NaCl, 2 mM DTPA, 3% Glycerol, pH 7.5 and thiolated with a 14-fold molar excess of 2-Imminothiolane for 60 minutes at room temperature. Following thiolation, the antibody was buffer exchanged into 50 mM HEPES buffer, containing 5 mM glycine, 2 mM DTPA, and 0.5% Povidone (10 K) pH 5.5. Thiolation was quantified with 4,4"-dithiodipyridine by measuring thiopyridine release at 324 nM. Conjugation was achieved by addition of Cytotoxin A at a 3:1 molar ratio of Cytotoxin A to thiols. Incubation was at room temperature for 60 minutes followed by blocking of any residual thiols by the addition of a 10:1 molar ratio of N-ethylmaleimide to thiols to the reaction mix.

The resulting conjugates were purified by ion-exchange chromatography. Each reaction mix was filtered and loaded onto an SP-Sepharose High Performance column equilibrated with Buffer A (50 mM HEPES, 5 mM Glycine, 0.5% Povidone (10K), pH 5.5). Antibody conjugates were eluted with 24% Buffer B (50 mM HEPES, 5 mM Glycine, 1M NaCl, 0.5% Povidone (10K), pH 5.5). Fractions containing monomeric antibody-Cytotoxin A conjugate were pooled and dialyzed against 50 mM HEPES, 5 mM glycine, 100 mM NaCl, 0.5% Povidone (10K), pH 6.0. Substitution ratios were determined by measuring absorbance at 280 and 340 nm, and the conjugates analyzed by SEC-HPLC.

CD22.1-Cytotoxin A conjugate was made with a substitution ratio of 1.7, and CD22.2 conjugate was made with a substitution ratio of 1.6.

Figure 16:
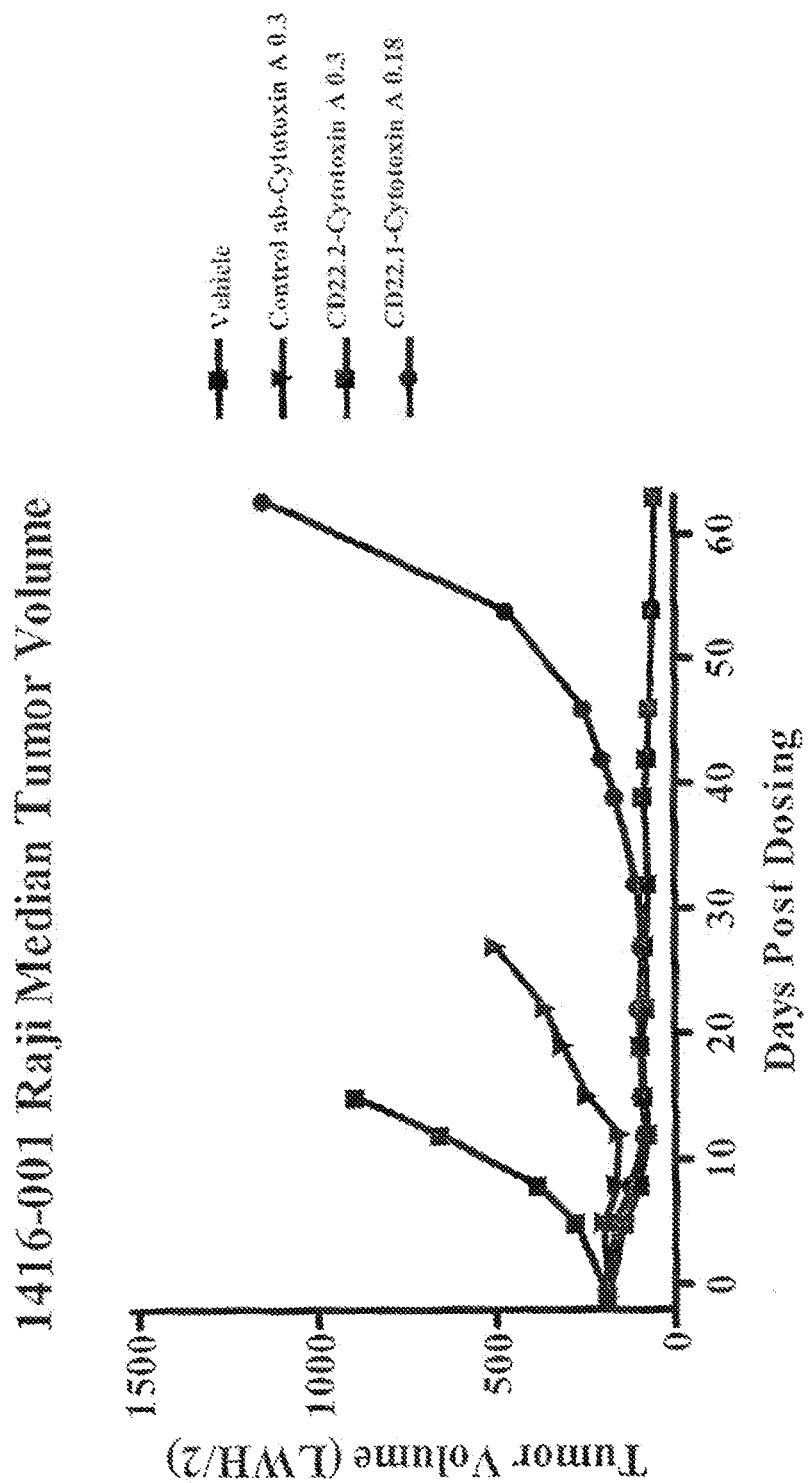
FIG. 16 shows the in-vivo effect of antibody-drug conjugates CD22.1-Cytotoxin A and CD22.2-Cytotoxin A on Raji-cell tumor size in SCID mice.

In Vivo Efficacy of Anti-CD22 Antibody-Drug Conjugates CD22.1-Cytotoxin A and CD22.2-Cytotoxin A SCID mice were implanted subcutaneously with Raji cells at 10 million cells per mouse in matrigel, and tumors allowed to grow until well established with a median size of approx. 190 mm³ Groups of 8 mice were then treated with a single dose of either CD22.1-Cytotoxin A antibody conjugate, CD22.2-Cytotoxin A conjugate, a control human IgG1-Cytotoxin A conjugate which did not bind to Raji cells, or with vehicle alone. Tumor size was monitored for 63 days post dosing, or until animals were euthanized due to tumor growth beyond 1500 mm³ CD22.1-Cytotoxin A was administered at 0.18 µmol/kg drug equivalent, and CD22.2-Cytotoxin A and control ab-Cytotoxin A were administered at 0.3 µmol/kg drug equivalent. Results demonstrated good anti-tumor efficacy for both CD22.1 and CD22.2 conjugates (FIG. 16).

| SUMMARY OF SEQUENCE LISTING | |
|---|---|
| SEQ ID NO: | SEQUENCE |
| 1 | $V_H$ CDR1 a.a. 12C5 |
| 2 | $V_H$ CDR1 a.a. 19A3 |
| 3 | $V_H$ CDR1 a.a. 16F7 |
| 4 | $V_H$ CDR1 a.a. 23C6 |
| 5 | $V_H$ CDR2 a.a. 12C5 |
| 6 | $V_H$ CDR2 a.a. 19A3 |
| 7 | $V_H$ CDR2 a.a. 16F7 |
| 8 | $V_H$ CDR2 a.a. 23C6 |
| 9 | $V_H$ CDR3 a.a. 12C5 |
| 10 | $V_H$ CDR3 a.a. 19A3 |
| 11 | $V_H$ CDR3 a.a. 16F7 |
| 12 | $V_H$ CDR3 a.a. 23C6 |
| 13 | $V_K$ CDR1 a.a. 12C5 |
| 14 | $V_K$ CDR1 a.a. 19A3 |
| 15 | $V_K.1$ CDR1 a.a. 16F7 |
| 16 | $V_K.2$ CDR1 a.a. 16F7 |
| 17 | $V_K.1$ CDR1 a.a. 23C6 |
| 18 | $V_K.2$ CDR1 a.a. 23C6 |
| 19 | $V_K$ CDR2 a.a. 12C5 |
| 20 | $V_K$ CDR2 a.a. 19A3 |
| 21 | $V_K.1$ CDR2 a.a. 16F7 |
| 22 | $V_K.2$ CDR2 a.a. 16F7 |
| 23 | $V_K.1$ CDR2 a.a. 23C6 |
| 24 | $V_K.2$ CDR2 a.a. 23C6 |
| 25 | $V_K$ CDR3 a.a. 12C5 |
| 26 | $V_K$ CDR3 a.a. 19A3 |
| 27 | $V_K.1$ CDR3 a.a. 16F7 |
| 28 | $V_K.2$ CDR3 a.a. 16F7 |
| 29 | $V_K.1$ CDR3 a.a. 23C6 |
| 30 | $V_K.2$ CDR3 a.a. 23C6 |
| 31 | $V_H$ a.a. 12C5 |
| 32 | $V_H$ a.a. 19A3 |
| 33 | $V_H$ a.a. 16F7 |
| 34 | $V_H$ a.a. 23C6 |
| 35 | $V_K$ a.a. 12C5 |
| 36 | $V_K$ a.a. 19A3 |
| 37 | $V_K.1$ a.a. 16F7 |
| 38 | $V_K.2$ a.a. 16F7 |
| 39 | $V_K.1$ a.a. 23C6 |
| 40 | $V_K.2$ a.a. 23C6 |
| 41 | $V_H$ n.t. 12C5 |
| 42 | $V_H$ n.t. 19A3 |
| 43 | $V_H$ n.t. 16F7 |
| 44 | $V_H$ n.t. 23C6 |
| 45 | $V_K$ n.t. 12C5 |
| 46 | $V_K$ n.t. 19A3 |
| 47 | $V_K.1$ n.t. 16F7 |
| 48 | $V_K.2$ n.t. 16F7 |
| 49 | $V_K.1$ n.t. 23C6 |
| 50 | $V_K.2$ n.t. 23C6 |
| 51 | $V_H$ 7-4.1 germline a.a. |
| 52 | $V_H$ 4-34 germline a.a. |
| 53 | $V_H$ 5-51 germline a.a. |
| 54 | $V_H$ 1-69 germline a.a. |
| 55 | $V_\lambda$ 2b2 germline a.a. |
| 56 | $V_K$ L6 germline a.a. |
| 57 | $V_K$ A27 germline a.a. |
| 58 | $V_K$ A10 germline a.a. |
| 59 | human CD22 (NP_001762) |
| 60 | $V_H$ CDR2 a.a. CD22.2 |
| 61 | $V_H$ a.a. CD22.2 |
| 62 | $V_H$ n.t. CD22.2 |
| 63 | $V_H$ CDR1 a.a. 4G6 |
| 64 | $V_{H1}$ CDR1 a.a.21F6 |
| 65 | $V_{H2}$ CDR1 a.a. 21F6 |
| 66 | $V_H$ CDR2 a.a. 4G6 |
| 67 | $V_{H1}$ CDR2 a.a. 21F6 |
| 68 | $V_{H2}$ CDR2 a.a. 21F6 |
| 69 | $V_H$ CDR3 a.a. 4G6 |
| 70 | $V_{H1}$ CDR3 a.a. 21F6 |
| 71 | $V_{H2}$ CDR3 a.a. 21F6 |
| 72 | $V_{K1}$ CDR1 a.a. 4G6 |
| 73 | $V_{K2}$ CDR1 a.a. 4G6 |
| 74 | $V_K$ CDR1 a.a. 21F6 |
| 75 | $V_{K1}$ CDR2 a.a. 4G6 |
| 76 | $V_{K2}$ CDR2 a.a. 4G6 |
| 77 | $V_K$ CDR2 a.a. 21F6 |
| 78 | $V_{K1}$ CDR3 a.a. 4G6 |
| 79 | $V_{K2}$ CDR3 a.a. 4G6 |
| 80 | $V_K$ CDR3 a.a. 21F6 |
| 81 | $V_H$ a.a. 4G6 |
| 82 | $V_{H1}$ a.a. 21F6 |
| 83 | $V_{H2}$ a.a. 21F6 |
| 84 | $V_{K1}$ a.a. 4G6 |
| 85 | $V_{K2}$ a.a. 4G6 |
| 86 | $V_K$ a.a. 21F6 |
| 87 | $V_H$ n.t. 4G6 |
| 88 | $V_{H1}$ n.t. 21F6 |
| 89 | $V_{H2}$ n.t. 21F6 |
| 90 | $V_{K1}$ n.t. 4G6 |
| 91 | $V_{K2}$ n.t. 4F6 |
| 92 | $V_{K2}$ n.t. 21F6 |
| 93 | $V_{K1}$ L18 germline a.a. |
| 94 | Peptide Linker |
| 95 | Peptide Linker |
| 96 | Peptide Linker |
| 97 | Peptide Linker |
| 98 | Peptide Linker |
| 99 | Peptide Linker |
| 100 | Peptide Linker |
| 101 | Peptide Linker |
| 102 | Peptide Linker |
| 103 | Peptide Linker |
| 104 | Peptide Linker |
| 105 | Peptide Linker |
| 106 | Peptide Linker |
| 107 | Peptide Linker |
| 108 | 12C5 JH6b germline |
| 109 | JL2 germline |
| 110 | JK1 germline |
| 111 | JK4b germline |

| SUMMARY OF SEQUENCE LISTING | |
|---|---|
| SEQ ID NO: | SEQUENCE |
| 112 | JK3b germline |
| 113 | JK1 germline |
| 114 | JK2 germline |
| 115 | 2-15 germline |
| 116 | JK1 germline |
| 117 | JH4b germline |
| 118 | 21F6 4-34 germline VH1 |
| 119 | 21F6 JH4b germlineVH1 |
| 120 | 21F6 4-34 germline VH2 |

| SUMMARY OF SEQUENCE LISTING | |
|---|---|
| SEQ ID NO: | SEQUENCE |
| 121 | 21F6 JH4b germline VH2 |
| 122 | 21F6 VK L6 germline |
| 123 | 21F6 VK JK4 germline |
| 124 | 4G6 VH 1-69 germline |
| 125 | 4G6 VH JH4b germline |
| 126 | 4G6 VK1 JK2 germline |
| 127 | 4G6 VK2 A27 germline |
| 128 | 4G6 VK2 JK4 germline |

We claim:

1. A method of treating a CD22-expressing B cell cancer in a subject comprising administering to the subject a monoclonal antibody or an antigen-binding portion thereof, which specifically binds to CD22, in an amount effective to treat the cancer, wherein the monoclonal antibody or antigen-binding portion thereof comprises:
    (a) a heavy chain variable region CDR1 comprising amino acids having the sequence set forth in SEQ ID NO:2;
    (b) a heavy chain variable region CDR2 comprising amino acids having the sequence set forth in SEQ ID NO:6 or SEQ ID NO:60;
    (c) a heavy chain variable region CDR3 comprising amino acids having the sequence set forth in SEQ ID NO:10;
    (d) a light chain variable region CDR1 comprising amino acids having the sequence set forth in SEQ ID NO:14;
    (e) a light chain variable region CDR2 comprising amino acids having the sequence set forth in SEQ ID NO:20; and
    (f) a light chain variable region CDR3 comprising amino acids having the sequence set forth in SEQ ID NO:26.

2. The method of claim 1, wherein the cancer is a B cell lymphoma.

3. The method of claim 2, wherein the B cell lymphoma is a non-Hodgkin's lymphoma.

4. The method of claim 1, wherein the cancer is Burkitt's lymphoma or B cell chronic lymphocytic leukemia.

5. The method of claim 1, wherein the subject is a human and the antibody binds to human CD22.

6. The method of claim 1, wherein the monoclonal antibody or antigen-binding portion thereof comprises:
    (a) a heavy chain variable region CDR1 comprising amino acids having the sequence set forth in SEQ ID NO:2;
    (b) a heavy chain variable region CDR2 comprising amino acids having the sequence set forth in SEQ ID NO:6;
    (c) a heavy chain variable region CDR3 comprising amino acids having the sequence set forth in SEQ ID NO:10;
    (d) a light chain variable region CDR1 comprising amino acids having the sequence set forth in SEQ ID NO:14;
    (e) a light chain variable region CDR2 comprising amino acids having the sequence set forth in SEQ ID NO:20; and
    (f) a light chain variable region CDR3 comprising amino acids having the sequence set forth in SEQ ID NO:26.

7. The method of claim 1, wherein the monoclonal antibody or antigen-binding portion thereof comprises:
    (a) a heavy chain variable region CDR1 comprising amino acids having the sequence set forth in SEQ ID NO:2;
    (b) a heavy chain variable region CDR2 comprising amino acids having the sequence set forth in SEQ ID NO:60;
    (c) a heavy chain variable region CDR3 comprising amino acids having the sequence set forth in SEQ ID NO:10;
    (d) a light chain variable region CDR1 comprising amino acids having the sequence set forth in SEQ ID NO:14;

(e) a light chain variable region CDR2 comprising amino acids having the sequence set forth in SEQ ID NO:20; and
(f) a light chain variable region CDR3 comprising amino acids having the sequence set forth in SEQ ID NO:26.

8. The method of claim 1, wherein the monoclonal antibody or antigen-binding portion thereof comprises:
(a) a heavy chain variable region comprising amino acids having the sequence set forth in SEQ ID NO:32 or 61; and
(b) a light chain variable region comprising amino acids having the sequence set forth in SEQ ID NO:36.

9. The method of claim 8, wherein the monoclonal antibody or antigen-binding portion thereof comprises:
(a) a heavy chain variable region comprising amino acids having the sequence set forth in SEQ ID NO:32; and
(b) a light chain variable region comprising amino acids having the sequence set forth in SEQ ID NO:36.

10. The method of claim 8, wherein the monoclonal antibody or antigen-binding portion thereof comprises:
(a) a heavy chain variable region comprising amino acids having the sequence set forth in SEQ ID NO:61; and
(b) a light chain variable region comprising amino acids having the sequence set forth in SEQ ID NO:36.

11. The method of claim 1, wherein the antibody or antigen-binding portion thereof is of an IgG1 isotype or an IgG4 isotype.

12. The method of claim 1, wherein the antibody or antigen-binding portion thereof is linked to a therapeutic agent.

13. The method of claim 12, wherein the therapeutic agent is a cytotoxin or a radioactive agent.

14. The method of claim 12, wherein the therapeutic agent is conjugated to the antibody by a chemical linker.

15. The method of claim 14, wherein the chemical linker is selected from the group consisting of peptidyl linkers, hydrazine linkers, and disulfide linkers.

16. The method of claim 1, wherein the antibody is administered subcutaneously, intravenously, intramuscularly, intradermally, or intraperitoneally.

17. The method of claim 1, further comprising administering to the subject a second anti-neoplastic agent.

18. The method of claim 1, wherein the antigen-binding portion is a Fab, Fab', F(ab')$_2$, Fd, Fv, or dAb fragment, a nanobody, a single chain Fv (scFv) or a single chain antibody.

19. The method of claim 1, wherein the antibody or antigen-binding portion thereof is a human antibody or a portion thereof.

20. The method of claim 1, wherein the antibody or antigen-binding portion thereof is a humanized antibody or a chimeric antibody, or a portion thereof.

21. The method of claim 17, wherein the second anti-neoplastic agent is an anti-CD20 antibody or an antigen-binding portion thereof.

22. The method of claim 17, wherein the second anti-neoplastic agent is an antibody that binds to CTLA-4 or an antigen-binding portion thereof.

23. The method of claim 17, wherein the second anti-neoplastic agent is an antibody that binds to PD-1 or an antigen-binding portion thereof.

24. The method of claim 17, wherein the second anti-neoplastic agent is an antibody that binds to PD-L1 or an antigen-binding portion thereof.

25. A method of treating a CD22-expressing B cell cancer in a subject, comprising administering to the subject a human IgG1 monoclonal antibody, or an antigen-binding portion thereof, which specifically binds to CD22, in an amount effective to treat the cancer, wherein the monoclonal antibody or antigen-binding portion thereof comprises:
(a) a heavy chain variable region comprising amino acids having the sequence set forth in SEQ ID NO:32 or 61; and
(b) a light chain variable region comprising amino acids having the sequence set forth in SEQ ID NO:36.

26. A method of inhibiting growth of a CD22-expressing B cell tumor cell comprising contacting the tumor cell with a monoclonal antibody or an antigen-binding portion thereof, which specifically binds to CD22 such that growth of the tumor cell is inhibited, wherein the monoclonal antibody or antigen-binding portion thereof comprises:
(a) a heavy chain variable region CDR1 comprising amino acids having the sequence set forth in SEQ ID NO:2;
(b) a heavy chain variable region CDR2 comprising amino acids having the sequence set forth in SEQ ID NO:6 or SEQ ID NO:60;
(c) a heavy chain variable region CDR3 comprising amino acids having the sequence set forth in SEQ ID NO:10;
(d) a light chain variable region CDR1 comprising amino acids having the sequence set forth in SEQ ID NO:14;
(e) a light chain variable region CDR2 comprising amino acids having the sequence set forth in SEQ ID NO:20; and
(f) a light chain variable region CDR3 comprising amino acids having the sequence set forth in SEQ ID NO:26.

27. The method of claim 26, wherein the monoclonal antibody or antigen-binding portion thereof comprises:
(a) a heavy chain variable region CDR1 comprising amino acids having the sequence set forth in SEQ ID NO:2;
(b) a heavy chain variable region CDR2 comprising amino acids having the sequence set forth in SEQ ID NO:6;
(c) a heavy chain variable region CDR3 comprising amino acids having the sequence set forth in SEQ ID NO:10;
(d) a light chain variable region CDR1 comprising amino acids having the sequence set forth in SEQ ID NO:14;
(e) a light chain variable region CDR2 comprising amino acids having the sequence set forth in SEQ ID NO:20; and
(f) a light chain variable region CDR3 comprising amino acids having the sequence set forth in SEQ ID NO:26.

28. The method of claim 26, wherein the monoclonal antibody or antigen-binding portion thereof comprises:
(a) a heavy chain variable region CDR1 comprising amino acids having the sequence set forth in SEQ ID NO:2;
(b) a heavy chain variable region CDR2 comprising amino acids having the sequence set forth in SEQ ID NO:60;
(c) a heavy chain variable region CDR3 comprising amino acids having the sequence set forth in SEQ ID NO:10;
(d) a light chain variable region CDR1 comprising amino acids having the sequence set forth in SEQ ID NO:14;
(e) a light chain variable region CDR2 comprising amino acids having the sequence set forth in SEQ ID NO:20; and
(f) a light chain variable region CDR3 comprising amino acids having the sequence set forth in SEQ ID NO:26.

29. The method of claim 26, wherein the monoclonal antibody or antigen-binding portion thereof comprises:
 (a) a heavy chain variable region comprising amino acids having the sequence set forth in SEQ ID NO:32 or 61; and
 (b) a light chain variable region comprising amino acids having the sequence set forth in SEQ ID NO:36.

30. The method of claim 29, wherein the monoclonal antibody or antigen-binding portion thereof comprises:
 (a) a heavy chain variable region comprising amino acids having the sequence set forth in SEQ ID NO:32; and
 (b) a light chain variable region comprising amino acids having the sequence set forth in SEQ ID NO:36.

31. The method of claim 29, wherein the monoclonal antibody or antigen-binding portion thereof comprises:
 (a) a heavy chain variable region comprising amino acids having the sequence set forth in SEQ ID NO:61; and
 (b) a light chain variable region comprising amino acids having the sequence set forth in SEQ ID NO:36.

32. The method of claim 26, wherein the tumor cell is a cell of a B cell lymphoma.

33. The method of claim 29, wherein the B cell lymphoma is a non-Hodgkin's lymphoma.

34. The method of claim 26, wherein the tumor cell is a Burkitt's lymphoma cell or a B cell chronic lymphocytic leukemia cell.

35. The method of claim 26, wherein the antibody or antigen-binding portion thereof is of an IgG1 isotype or an IgG4 isotype.

36. The method of claim 26, wherein the antibody or antigen-binding portion thereof is linked to a therapeutic agent.

37. The method of claim 36, wherein the therapeutic agent is a cytotoxin or a radioactive agent.

38. The method of claim 36, wherein the therapeutic agent is conjugated to the antibody by a chemical linker.

39. The method of claim 38, wherein the chemical linker is selected from the group consisting of peptidyl linkers, hydrazine linkers, and disulfide linkers.

40. The method of claim 26, wherein the antigen-binding portion is a Fab, Fab', F(ab')$_2$, Fd, Fv, or dAb fragment, a nanobody, a single chain Fv (scFv) or a single chain antibody.

41. The method of claim 26, wherein the antibody or antigen-binding portion thereof is a human antibody or a portion thereof.

42. The method of claim 26, wherein the antibody or antigen-binding portion thereof is a humanized antibody or a chimeric antibody, or a portion thereof.

* * * * *

UNITED STATES PATENT AND TRADEMARK OFFICE
CERTIFICATE OF CORRECTION

PATENT NO. : 9,499,632 B2
APPLICATION NO. : 13/772063
DATED : November 22, 2016
INVENTOR(S) : David John King It is certified that error appears in the above-identified patent and that said Letters Patent is hereby corrected as shown below:

In the Claims

Claim 33, Column 197, Line 21, delete "claim 29," and insert -- claim 32, --, therefor.

Signed and Sealed this
First Day of May, 2018

Andrei Iancu
*Director of the United States Patent and Trademark Office*

SEQUENCE LISTING

```
<160> NUMBER OF SEQ ID NOS: 114

<210> SEQ ID NO 1
<211> LENGTH: 5
<212> TYPE: PRT
<213> ORGANISM: Homo sapiens

<400> SEQUENCE: 1

Ser Tyr Ala Met Asn
1               5

<210> SEQ ID NO 2
<211> LENGTH: 5
<212> TYPE: PRT
<213> ORGANISM: Homo sapiens

<400> SEQUENCE: 2

Ser Tyr Tyr Trp Ser
1               5

<210> SEQ ID NO 3
<211> LENGTH: 5
<212> TYPE: PRT
<213> ORGANISM: Homo sapiens

<400> SEQUENCE: 3

Ser Tyr Trp Ile Gly
1               5

<210> SEQ ID NO 4
<211> LENGTH: 5
<212> TYPE: PRT
<213> ORGANISM: Homo sapiens

<400> SEQUENCE: 4

Ser Tyr Gly Ile Asn
1               5

<210> SEQ ID NO 5
<211> LENGTH: 17
<212> TYPE: PRT
<213> ORGANISM: Homo sapiens

<400> SEQUENCE: 5

Trp Ile Asn Thr Asn Thr Gly Asn Pro Thr Tyr Ala Gln Gly Phe Thr
1               5                   10                  15

Gly

<210> SEQ ID NO 6
```

```
<211> LENGTH: 16
<212> TYPE: PRT
<213> ORGANISM: Homo sapiens

<400> SEQUENCE: 6

Asp Ile Asn His Ser Gly Ser Thr Asn Tyr Asn Pro Ser Leu Lys Ser
1               5                   10                  15

<210> SEQ ID NO 7
<211> LENGTH: 17
<212> TYPE: PRT
<213> ORGANISM: Homo sapiens

<400> SEQUENCE: 7

Ile Ile Tyr Pro Gly Asp Ser Asp Thr Arg Tyr Ser Pro Ser Phe Gln
1               5                   10                  15

Gly

<210> SEQ ID NO 8
<211> LENGTH: 17
<212> TYPE: PRT
<213> ORGANISM: Homo sapiens

<400> SEQUENCE: 8

Glu Ile Ile Pro Ile Phe Gly Thr Ala Asn Tyr Ala Gln Lys Phe Gln
1               5                   10                  15

Gly

<210> SEQ ID NO 9
<211> LENGTH: 10
<212> TYPE: PRT
<213> ORGANISM: Homo sapiens

<400> SEQUENCE: 9

Leu Phe Tyr Tyr Tyr Phe Gly Met Asp Val
1               5                   10

<210> SEQ ID NO 10
<211> LENGTH: 14
<212> TYPE: PRT
<213> ORGANISM: Homo sapiens

<400> SEQUENCE: 10

Thr Phe Tyr Asp Ile Leu Thr Gly Tyr Tyr Pro Leu Gly Tyr
1               5                   10

<210> SEQ ID NO 11
<211> LENGTH: 12
<212> TYPE: PRT
<213> ORGANISM: Homo sapiens

<400> SEQUENCE: 11

Pro Thr Tyr Tyr Phe Gly Ser Val Ala Phe Asp Ile
1               5                   10

<210> SEQ ID NO 12
<211> LENGTH: 19
<212> TYPE: PRT
<213> ORGANISM: Homo sapiens

<400> SEQUENCE: 12

Asp Gln Gly Val Val Val Ala Ala Thr His Tyr Tyr Tyr Tyr Gly
1               5                   10                  15
```

Met Asp Val

<210> SEQ ID NO 13
<211> LENGTH: 14
<212> TYPE: PRT
<213> ORGANISM: Homo sapiens

<400> SEQUENCE: 13

Thr Gly Thr Ser Ser Asp Val Gly Ser Tyr Asn Leu Val Ser
1               5                   10

<210> SEQ ID NO 14
<211> LENGTH: 11
<212> TYPE: PRT
<213> ORGANISM: Homo sapiens

<400> SEQUENCE: 14

Arg Ala Ser Gln Ser Val Ser Ser Tyr Leu Ala
1               5                   10

<210> SEQ ID NO 15
<211> LENGTH: 12
<212> TYPE: PRT
<213> ORGANISM: Homo sapiens

<400> SEQUENCE: 15

Arg Ala Ser Gln Ser Val Ser Ser Ser Tyr Leu Ala
1               5                   10

<210> SEQ ID NO 16
<211> LENGTH: 11
<212> TYPE: PRT
<213> ORGANISM: Homo sapiens

<400> SEQUENCE: 16

Arg Ala Ser Gln Ser Ile Gly Ser Ser Leu His
1               5                   10

<210> SEQ ID NO 17
<211> LENGTH: 11
<212> TYPE: PRT
<213> ORGANISM: Homo sapiens

<400> SEQUENCE: 17

Arg Ala Ser Gln Ser Val Ser Ser Tyr Leu Ala
1               5                   10

<210> SEQ ID NO 18
<211> LENGTH: 11
<212> TYPE: PRT
<213> ORGANISM: Homo sapiens

<400> SEQUENCE: 18

Arg Ala Ser Gln Ser Val Ser Asn Phe Leu Ala
1               5                   10

<210> SEQ ID NO 19
<211> LENGTH: 7
<212> TYPE: PRT
<213> ORGANISM: Homo sapiens

<400> SEQUENCE: 19

Glu Val Ser Lys Arg Pro Ser
1               5

<210> SEQ ID NO 20
<211> LENGTH: 7
<212> TYPE: PRT
<213> ORGANISM: Homo sapiens

<400> SEQUENCE: 20

Asp Ala Ser Asn Arg Ala Thr
1               5

<210> SEQ ID NO 21
<211> LENGTH: 7
<212> TYPE: PRT
<213> ORGANISM: Homo sapiens

<400> SEQUENCE: 21

Gly Ala Ser Ser Arg Ala Thr
1               5

<210> SEQ ID NO 22
<211> LENGTH: 7
<212> TYPE: PRT
<213> ORGANISM: Homo sapiens

<400> SEQUENCE: 22

Tyr Ala Ser Gln Ser Phe Ser
1               5

<210> SEQ ID NO 23
<211> LENGTH: 7
<212> TYPE: PRT
<213> ORGANISM: Homo sapiens

<400> SEQUENCE: 23

Asp Ala Ser Asn Arg Ala Thr
1               5

<210> SEQ ID NO 24
<211> LENGTH: 7
<212> TYPE: PRT
<213> ORGANISM: Homo sapiens

<400> SEQUENCE: 24

Asp Ala Ser Asn Arg Ala Thr
1               5

<210> SEQ ID NO 25
<211> LENGTH: 10
<212> TYPE: PRT
<213> ORGANISM: Homo sapiens

<400> SEQUENCE: 25

Cys Ser Tyr Ala Asn Ser Ser Thr Leu Val
1               5                   10

<210> SEQ ID NO 26
<211> LENGTH: 8
<212> TYPE: PRT
<213> ORGANISM: Homo sapiens

<400> SEQUENCE: 26

Gln Gln Arg Ser Asn Trp Pro Thr
1               5

<210> SEQ ID NO 27

```
<211> LENGTH: 9
<212> TYPE: PRT
<213> ORGANISM: Homo sapiens

<400> SEQUENCE: 27

Gln Gln Tyr Gly Ser Ser Pro Pro Thr
1               5

<210> SEQ ID NO 28
<211> LENGTH: 9
<212> TYPE: PRT
<213> ORGANISM: Homo sapiens

<400> SEQUENCE: 28

His Gln Ser Ser Ser Leu Pro Tyr Thr
1               5

<210> SEQ ID NO 29
<211> LENGTH: 9
<212> TYPE: PRT
<213> ORGANISM: Homo sapiens

<400> SEQUENCE: 29

Gln Gln Arg Ser Asn Trp Pro Trp Thr
1               5

<210> SEQ ID NO 30
<211> LENGTH: 9
<212> TYPE: PRT
<213> ORGANISM: Homo sapiens

<400> SEQUENCE: 30

Gln Gln Arg Ser Asn Trp Pro Pro Thr
1               5

<210> SEQ ID NO 31
<211> LENGTH: 119
<212> TYPE: PRT
<213> ORGANISM: Homo sapiens

<400> SEQUENCE: 31

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Leu Phe Tyr Tyr Tyr Phe Gly Met Asp Val Trp Gly Gln Gly
            100                 105                 110

Thr Thr Val Thr Val Ser Ser
        115

<210> SEQ ID NO 32
<211> LENGTH: 122
<212> TYPE: PRT
<213> ORGANISM: Homo sapiens
```

-continued

```
<400> SEQUENCE: 32

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Arg Ser Phe Ser Ser Tyr
            20                  25                  30

Tyr Trp Ser Trp Ile Arg Gln Pro Pro Gly Lys Gly Leu Glu Trp Ile
        35                  40                  45

Gly Asp Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Gly Thr Phe Tyr Asp Ile Leu Thr Gly Tyr Tyr Pro Leu Gly Tyr Trp
            100                 105                 110

Gly Pro Gly Thr Leu Val Thr Val Ser Ser
        115                 120

<210> SEQ ID NO 33
<211> LENGTH: 121
<212> TYPE: PRT
<213> ORGANISM: Homo sapiens

<400> SEQUENCE: 33

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Thr Pro Thr Tyr Tyr Phe Gly Ser Val Ala Phe Asp Ile Trp Gly
            100                 105                 110

Gln Gly Thr Met Val Thr Val Ser Ser
        115                 120

<210> SEQ ID NO 34
<211> LENGTH: 128
<212> TYPE: PRT
<213> ORGANISM: Homo sapiens

<400> SEQUENCE: 34

Gln Val Gln Leu Val Gln Ser Gly Ala Glu Val Lys Lys Thr Gly Ser
1               5                   10                  15

Ser Val Lys Val Ser Cys Lys Ala Ser Gly Gly Thr Phe Ser Ser Tyr
            20                  25                  30

Gly Ile Asn Trp Val Arg Gln Ala Pro Gly Gln Gly Leu Glu Trp Met
        35                  40                  45

Gly Glu Ile Ile Pro Ile Phe Gly Thr Ala Asn Tyr Ala Gln Lys Phe
    50                  55                  60
```

```
Gln Gly Arg Val Thr Ile Thr Ala Asp Glu Ser Thr Ser Thr Val Tyr
 65                  70                  75                  80

Met Glu Leu Ser Ser Leu Arg Ala Glu Asp Thr Ala Val Tyr Tyr Cys
                 85                  90                  95

Ala Arg Asp Gln Gly Val Val Val Ala Ala Thr His Tyr Tyr Tyr
            100                 105                 110

Tyr Gly Met Asp Val Trp Gly Gln Gly Thr Thr Val Thr Val Ser Ser
            115                 120                 125
```

<210> SEQ ID NO 35
<211> LENGTH: 110
<212> TYPE: PRT
<213> ORGANISM: Homo sapiens

<400> SEQUENCE: 35

```
Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Ser Tyr
                 20                  25                  30

Asn Leu Val Ser Trp Tyr Gln Leu His Pro Gly Lys Ala Pro Lys Leu
             35                  40                  45

Met Ile Tyr Glu Val Ser Lys Arg Pro Ser Gly Val Ser Asn Arg Phe
 50                  55                  60

Ser Gly Ser Arg Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Asn Ser
                 85                  90                  95

Ser Thr Leu Val Phe Gly Gly Gly Thr Lys Leu Thr Val Leu
             100                 105                 110
```

<210> SEQ ID NO 36
<211> LENGTH: 106
<212> TYPE: PRT
<213> ORGANISM: Homo sapiens

<400> SEQUENCE: 36

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Thr
                 85                  90                  95

Phe Gly Gln Gly Thr Lys Val Glu Ile Lys
             100                 105
```

<210> SEQ ID NO 37
<211> LENGTH: 108
<212> TYPE: PRT
<213> ORGANISM: Homo sapiens

<400> SEQUENCE: 37

```
Glu Ile Val Leu Thr Gln Ser Pro Gly Thr Leu Ser Leu Ser Pro Gly
```

```
             1               5                  10                 15
Glu Arg Ala Thr Leu Ser Cys Arg Ala Ser Gln Ser Val Ser Ser Ser
                20                  25                 30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Thr Phe Gly Gln Gly Thr Lys Val Glu Ile Lys
                100                 105
```

<210> SEQ ID NO 38
<211> LENGTH: 107
<212> TYPE: PRT
<213> ORGANISM: Homo sapiens

<400> SEQUENCE: 38

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
                20                  25                  30

Leu His Trp Tyr Gln Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys His Gln Ser Ser Ser Leu Pro Tyr
                85                  90                  95

Thr Phe Gly Gln Gly Thr Lys Leu Glu Ile Lys
                100                 105
```

<210> SEQ ID NO 39
<211> LENGTH: 107
<212> TYPE: PRT
<213> ORGANISM: Homo sapiens

<400> SEQUENCE: 39

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys
                100                 105
```

<210> SEQ ID NO 40
<211> LENGTH: 107
<212> TYPE: PRT
<213> ORGANISM: Homo sapiens

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Phe
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 41
<211> LENGTH: 357
<212> TYPE: DNA
<213> ORGANISM: Homo sapiens

<400> SEQUENCE: 41
caggtgcagc tggtgcaatc tgggtctgag ttgaagaagc ctggggcctc agtgaaggtt      60
tcctgcaagg cttctggata caccttcact agttatgcta tgaattgggt gcgacaggcc    120
cctggacaag gcttgagtg gatgggatgg atcaacacca acactgggaa cccaacgtat    180
gcccagggct tcacaggacg gtttgtcttc ccttggaca cctctgtcag cacggcatat    240
ctgcagatca gcagcctaaa ggctgaggac actgccgtgt attactgtgc taggttattc    300
tactactact cggtatgga cgtctggggc aagggaccac ggtcaccgt ctcctca          357

<210> SEQ ID NO 42
<211> LENGTH: 366
<212> TYPE: DNA
<213> ORGANISM: Homo sapiens

<400> SEQUENCE: 42
caggtgcagc tacagcagtg gggcgcagga ctgttgaagc cttcggagac cctgtccctc      60
acctgcgctg tctatggtag gtccttcagt agttactact ggagctggat ccgccagccc    120
ccagggaagg gctggagtg gattggggac atcaatcata gtggaagcac caactacaac    180
ccgtccctca agagtcgagt caccatatca gtagacacgt ccaagaacca gttctccctg    240
aagctgagct ctgtgaccgc cgcggacacg gctgtgtatt actgtgcggg aacgttttac    300 gatatttga ctggttatta tcccttgg tactggggcc cgggaaccct ggtcaccgtc    360
tcctca                                                                                                      366

<210> SEQ ID NO 43
<211> LENGTH: 363
<212> TYPE: DNA
<213> ORGANISM: Homo sapiens

<400> SEQUENCE: 43
gaggtgcagc tggtgcagtc tggagcagag gtgaaaaagc ccggggagtc tctgaagatc      60

```
tcctgtaagg gttctggata caactttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca gtccatcag caccgcctac     240 ctgcagtgga gcagcctgaa ggcctcggac accgccatgt attactgtgc gaccccgacg    300
tattactttg gttcggtggc ttttgatatc tggggccaag gacaatggt caccgtctct     360 tca                                                                  363

<210> SEQ ID NO 44
<211> LENGTH: 384
<212> TYPE: DNA
<213> ORGANISM: Homo sapiens

<400> SEQUENCE: 44
caggtccagc tggtgcagtc tggggctgag gtgaaaaaga ctgggtcctc ggtgaaggtc    60
tcctgcaagg cttctggagg cacctt cagc agctatggta tcaactgggt gcgacaggcc   120
cctggacaag gcttgaatg gatgggagag atcatcccta tctttggtac agcaaactac    180
gcacagaagt tccagggcag agtcacgatt accgcggacg aatccacgag cacagtctac   240
atggagctga gcagcctgag agctgaggac acggccgtgt attactgtgc gagagatcag   300
ggtgtagtgg tggtagctgc aacccactac tactactacg gtatggacgt ctggggccaa   360
gggaccacgg tcaccgtctc ctca                                          384

<210> SEQ ID NO 45
<211> LENGTH: 330
<212> TYPE: DNA
<213> ORGANISM: Homo sapiens

<400> SEQUENCE: 45
cagtctgccc tgactcagcc tgcctccgtg tctgggtctc ctggacagtc gatcaccatc    60
tcctgcactg gaaccagcag tgatgttggg agttataacc ttgtctcctg gtaccaactg   120
cacccaggca aagcccccaa actcatgatt tatgaggtca gtaagcggcc ctcagggggtt 180 tctaatcgct tctctggctc caggtctggc aacacggcct ccctgacaat ctctgggctc   240
caggctgagg acgaggctga ttattactgc tgctcatatg caaatagtag cactttggta   300
ttcggcggag ggaccaagct gaccgtccta                                    330

<210> SEQ ID NO 46
<211> LENGTH: 318
<212> TYPE: DNA
<213> ORGANISM: Homo sapiens

<400> SEQUENCE: 46
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctacgtt cggccaaggg   300
accaaggtgg aaatcaaa                                                 318

<210> SEQ ID NO 47
<211> LENGTH: 324
<212> TYPE: DNA
```

<213> ORGANISM: Homo sapiens

<400> SEQUENCE: 47

| | |
|---|---|
| gaaattgtgt tgacgcagtc tccaggcacc ctgtctttgt ctccagggga aagagccacc | 60 |
| ctctcctgca gggccagtca gagtgttagc agcagctact tagcctggta ccagcagaaa | 120 |
| cctggccagg ctcccaggct cctcatctat ggtgcatcca gcagggccac tggcatccca | 180 |
| gacaggttca gtggcagtgg gtctgggaca gacttcactc tcaccatcag cagactggag | 240 |
| cctgaagatt ttgcagtgta ttactgtcag cagtatggta gctcacctcc gacgttcggc | 300 |
| caagggacca aggtggaaat caaa | 324 |

<210> SEQ ID NO 48
<211> LENGTH: 321
<212> TYPE: DNA
<213> ORGANISM: Homo sapiens

<400> SEQUENCE: 48

| | |
|---|---|
| gaaattgtgc tgactcagtc tccagacttt cagtctgtga ctccaaagga gaaagtcacc | 60 |
| atcacctgcc gggccagtca gagcattggt agtagcttac actggtacca gcagaaacca | 120 |
| gatcagtctc caaagctcct catcaagtat gcttcccagt ccttctcagg ggtcccctcg | 180 |
| aggttcagtg gcagtggatc tgggacagat ttcaccctca ccatcaatag cctggaagct | 240 |
| gaagatgctg cagcgtatta ctgtcatcag agtagtagtt taccgtacac ttttggccag | 300 |
| gggaccaagc tggagatcaa a | 321 |

<210> SEQ ID NO 49
<211> LENGTH: 321
<212> TYPE: DNA
<213> ORGANISM: Homo sapiens

<400> SEQUENCE: 49

| | |
|---|---|
| gaaattgtgt tgacacagtc tccagccacc ctgtctttgt ctccagggga aagagccacc | 60 |
| ctctcctgca gggccagtca gagtgttagc agctacttag cctggtacca acagaaacct | 120 |
| ggccaggctc ccaggctcct catctatgat gcatccaaca gggccactgg catcccagcc | 180 |
| aggttcagtg gcagtgggtc tgggacagac ttcactctca ccatcagcag cctagagcct | 240 |
| gaagattttg cagtttatta ctgtcagcag cgtagcaact ggccgtggac gttcggccaa | 300 |
| gggaccaagg tggaaatcaa a | 321 |

<210> SEQ ID NO 50
<211> LENGTH: 321
<212> TYPE: DNA
<213> ORGANISM: Homo sapiens

<400> SEQUENCE: 50

| | |
|---|---|
| gaaattgtgt tgacacagtc tccagccacc ctgtctttgt ctccagggga aagagccacc | 60 |
| ctctcctgca gggccagtca gagtgttagc aacttcttag cctggtacca acagaaacct | 120 |
| ggccaggctc ccaggctcct catctatgat gcatccaaca gggccactgg catcccagcc | 180 |
| aggttcagtg gcagtgggtc tgggacagac ttcactctca ccatcagcag cctagagcct | 240 |
| gaagattttg cagtttatta ctgtcagcag cgtagcaact ggcctccgac gttcggccaa | 300 |
| gggaccaagg tggaaatcaa a | 321 |

<210> SEQ ID NO 51
<211> LENGTH: 98

```
<212> TYPE: PRT
<213> ORGANISM: Homo sapiens

<400> SEQUENCE: 51

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg

<210> SEQ ID NO 52
<211> LENGTH: 97
<212> TYPE: PRT
<213> ORGANISM: Homo sapiens

<400> SEQUENCE: 52

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 53
<211> LENGTH: 98
<212> TYPE: PRT
<213> ORGANISM: Homo sapiens

<400> SEQUENCE: 53

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95
```

Ala Arg

<210> SEQ ID NO 54
<211> LENGTH: 98
<212> TYPE: PRT
<213> ORGANISM: Homo sapiens

<400> SEQUENCE: 54

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg
```

<210> SEQ ID NO 55
<211> LENGTH: 98
<212> TYPE: PRT
<213> ORGANISM: Homo sapiens

<400> SEQUENCE: 55

```
Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Ser Tyr
            20                  25                  30
Asn Leu Val Ser Trp Tyr Gln Gln His Pro Gly Lys Ala Pro Lys Leu
        35                  40                  45
Met Ile Tyr Glu Val Ser Lys Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Cys Ser Tyr Ala Gly Ser
                85                  90                  95
Ser Thr
```

<210> SEQ ID NO 56
<211> LENGTH: 95
<212> TYPE: PRT
<213> ORGANISM: Homo sapiens

<400> SEQUENCE: 56

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
```

```
                65                  70                  75                  80
Glu Asp Phe Ala Val Tyr Tyr Cys Gln Gln Arg Ser Asn Trp Pro
                    85                  90                  95
```

<210> SEQ ID NO 57
<211> LENGTH: 97
<212> TYPE: PRT
<213> ORGANISM: Homo sapiens

<400> SEQUENCE: 57

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro
```

<210> SEQ ID NO 58
<211> LENGTH: 95
<212> TYPE: PRT
<213> ORGANISM: Homo sapiens

<400> SEQUENCE: 58

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
                20                  25                  30

Leu His Trp Tyr Gln Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95
```

<210> SEQ ID NO 59
<211> LENGTH: 4
<212> TYPE: PRT
<213> ORGANISM: Homo sapiens

<400> SEQUENCE: 59

```
Gln Leu Val Gln
1
```

<210> SEQ ID NO 60
<211> LENGTH: 16
<212> TYPE: PRT
<213> ORGANISM: Homo sapiens

<400> SEQUENCE: 60

```
Asp Ile Gln His Ser Gly Ser Thr Asn Tyr Asn Pro Ser Leu Lys Ser
```

<210> SEQ ID NO 61
<211> LENGTH: 122
<212> TYPE: PRT
<213> ORGANISM: Homo sapiens

<400> SEQUENCE: 61

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Arg Ser Phe Ser Ser Tyr
            20                  25                  30

Tyr Trp Ser Trp Ile Arg Gln Pro Pro Gly Lys Gly Leu Glu Trp Ile
        35                  40                  45

Gly Asp Ile Gln His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Gly Thr Phe Tyr Asp Ile Leu Thr Gly Tyr Tyr Pro Leu Gly Tyr Trp
            100                 105                 110

Gly Pro Gly Thr Leu Val Thr Val Ser Ser
        115                 120

<210> SEQ ID NO 62
<211> LENGTH: 366
<212> TYPE: DNA
<213> ORGANISM: Homo sapiens

<400> SEQUENCE: 62
caggtgcagc tacagcagtg gggcgcagga ctgttgaagc cttcggagac cctgtccctc      60
acctgcgctg tctatggtag gtccttcagt agttactact ggagctggat ccgccagccc     120
ccagggaagg ggctggagtg gattggggac atccaacata gtggaagcac caactacaac     180
ccgtccctca agagtcgagt caccatatca gtagacacgt ccaagaacca gttctccctg     240
aagctgagct ctgtgaccgc cgcggacacg gctgtgtatt actgtgcggg aacgttttac     300
gatattttga ctggttatta tccccttggg tactggggcc cgggaaccct ggtcaccgtc     360
tcctca                                                               366

<210> SEQ ID NO 63
<211> LENGTH: 19
<212> TYPE: PRT
<213> ORGANISM: Homo sapiens

<400> SEQUENCE: 63

Tyr Tyr Tyr Tyr Gly Met Asp Val Trp Gly Gln Gly Thr Thr Val Thr
1               5                   10                  15

Val Ser Ser

<210> SEQ ID NO 64
<211> LENGTH: 12
<212> TYPE: PRT
<213> ORGANISM: Homo sapiens

<400> SEQUENCE: 64

Val Val Phe Gly Gly Gly Thr Lys Leu Thr Val Leu
1               5                   10

<210> SEQ ID NO 65
<211> LENGTH: 11
<212> TYPE: PRT
<213> ORGANISM: Homo sapiens

<400> SEQUENCE: 65

Thr Phe Gly Gln Gly Thr Lys Val Glu Ile Lys
1               5                   10

<210> SEQ ID NO 66
<211> LENGTH: 13
<212> TYPE: PRT
<213> ORGANISM: Homo sapiens

<400> SEQUENCE: 66

Asp Tyr Trp Gly Gln Gly Thr Leu Val Thr Val Ser Ser
1               5                   10

<210> SEQ ID NO 67
<211> LENGTH: 15
<212> TYPE: PRT
<213> ORGANISM: Homo sapiens

<400> SEQUENCE: 67

Ala Phe Asp Ile Trp Gly Gln Gly Thr Met Val Thr Val Ser Ser
1               5                   10                  15

<210> SEQ ID NO 68
<211> LENGTH: 11
<212> TYPE: PRT
<213> ORGANISM: Homo sapiens

<400> SEQUENCE: 68

Thr Phe Gly Gln Gly Thr Lys Val Glu Ile Lys
1               5                   10

<210> SEQ ID NO 69
<211> LENGTH: 12
<212> TYPE: PRT
<213> ORGANISM: Homo sapiens

<400> SEQUENCE: 69

Tyr Thr Phe Gly Gln Gly Thr Lys Leu Glu Ile Lys
1               5                   10

<210> SEQ ID NO 70
<211> LENGTH: 9
<212> TYPE: PRT
<213> ORGANISM: Homo sapiens

<400> SEQUENCE: 70

Asp Ile Val Val Val Val Ala Ala Thr
1               5

<210> SEQ ID NO 71
<211> LENGTH: 12
<212> TYPE: PRT
<213> ORGANISM: Homo sapiens

<400> SEQUENCE: 71

Trp Thr Phe Gly Gln Gly Thr Lys Val Glu Ile Lys
1               5                   10

-continued

<210> SEQ ID NO 72
<211> LENGTH: 13
<212> TYPE: PRT
<213> ORGANISM: Homo sapiens

<400> SEQUENCE: 72

Asp Tyr Trp Gly Gln Gly Thr Leu Val Thr Val Ser Ser
1               5                   10

<210> SEQ ID NO 73
<211> LENGTH: 366
<212> TYPE: DNA
<213> ORGANISM: Homo sapiens

<400> SEQUENCE: 73
caggtccagt tggtgcagtc tggggctgag gtgaagaagc ctgggtcctc ggtgaaggtc      60
tcctgcaagc cttctggaga caccttcagc aactatgcta tcagctgggt gcgacaggcc     120
cctggacaag gcttgagtg gatgggaagg atcatcccta tccttggtat ggctatctac     180
gcaccgaagt tccagggcag agttacgatt accgcgaca aatccacgaa cacagccttc     240
atggatctta ccagcctgta ttttgaggac acggccgtgt attactgtgc gagagcccca     300
acttactggg gatcgaagga ctactttgac tactggggcc agggaaccct ggtcaccgtc     360
tcctca                                                               366

<210> SEQ ID NO 74
<211> LENGTH: 121
<212> TYPE: PRT
<213> ORGANISM: Homo sapiens

<400> SEQUENCE: 74

Gln Val Gln Leu Val Gln Ser Gly Ala Glu Val Lys Lys Pro Gly Ser
1               5                   10                  15

Ser Val Lys Val Ser Cys Lys Pro Ser Gly Asp Thr Phe Ser Asn Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Met Ala Ile Tyr Ala Pro Lys Phe
    50                  55                  60

Gln Gly Arg Val Thr Ile Thr Ala Asp Lys Ser Thr Asn Thr Ala Phe
65                  70                  75                  80

Met Asp Leu Thr Ser Leu Tyr Phe Glu Asp Ala Val Tyr Tyr Cys Ala
                85                  90                  95

Arg Ala Pro Thr Tyr Trp Gly Ser Lys Asp Tyr Phe Asp Tyr Trp Gly
            100                 105                 110

Gln Gly Thr Leu Val Thr Val Ser Ser
        115                 120

<210> SEQ ID NO 75
<211> LENGTH: 5
<212> TYPE: PRT
<213> ORGANISM: Homo sapiens

<400> SEQUENCE: 75

Asn Tyr Ala Ile Ser
1               5

<210> SEQ ID NO 76
<211> LENGTH: 17
<212> TYPE: PRT

<213> ORGANISM: Homo sapiens

<400> SEQUENCE: 76

Arg Ile Ile Pro Ile Leu Gly Met Ala Ile Tyr Ala Pro Lys Phe Gln
1               5                   10                  15

Gly

<210> SEQ ID NO 77
<211> LENGTH: 13
<212> TYPE: PRT
<213> ORGANISM: Homo sapiens

<400> SEQUENCE: 77

Ala Pro Thr Tyr Trp Gly Ser Lys Asp Tyr Phe Asp Tyr
1               5                   10

<210> SEQ ID NO 78
<211> LENGTH: 321
<212> TYPE: DNA
<213> ORGANISM: Homo sapiens

<400> SEQUENCE: 78
gccatccagt tgacccagtc tccatcctcc ctgtctgcat ctgtaggaga cagagtcacc      60
atcacttgcc gggcaagtca ggacattagc agtggtttag cctggtatca gcagaaacca    120
gggacagctc ctaagctcct gatctatgat gcctccagtt tggaaagtgg ggtcccatca    180
aggttcagcg gcagtggatc tgggacagat ttcactctca ccatcagcag cctgcagcct    240
gacgattttg caacttatta ctgtcaacag tttaatagtt tcccgtacac ttttggccag    300
gggaccaagc tggagatcaa a                                              321

<210> SEQ ID NO 79
<211> LENGTH: 107
<212> TYPE: PRT
<213> ORGANISM: Homo sapiens

<400> SEQUENCE: 79

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Gly
                20                  25                  30

Leu Ala Trp Tyr Gln Gln Lys Pro Gly Thr Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Phe Asn Ser Phe Pro Tyr
                85                  90                  95

Thr Phe Gly Gln Gly Thr Lys Leu Glu Ile Lys
            100                 105

<210> SEQ ID NO 80
<211> LENGTH: 11
<212> TYPE: PRT
<213> ORGANISM: Homo sapiens

<400> SEQUENCE: 80

Arg Ala Ser Gln Asp Ile Ser Ser Gly Leu Ala
1               5                   10

<210> SEQ ID NO 81
<211> LENGTH: 7
<212> TYPE: PRT
<213> ORGANISM: Homo sapiens

<400> SEQUENCE: 81

Asp Ala Ser Ser Leu Glu Ser
1               5

<210> SEQ ID NO 82
<211> LENGTH: 9
<212> TYPE: PRT
<213> ORGANISM: Homo sapiens

<400> SEQUENCE: 82

Gln Gln Phe Asn Ser Phe Pro Tyr Thr
1               5

<210> SEQ ID NO 83
<211> LENGTH: 321
<212> TYPE: DNA
<213> ORGANISM: Homo sapiens

<400> SEQUENCE: 83

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacccac tttcggcgga     300
gggaccaagg tggagatcaa a                                               321
```

<210> SEQ ID NO 84
<211> LENGTH: 107
<212> TYPE: PRT
<213> ORGANISM: Homo sapiens

<400> SEQUENCE: 84

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gly Gly Thr Lys Val Glu Ile Lys
            100                 105

<210> SEQ ID NO 85
<211> LENGTH: 12
<212> TYPE: PRT
<213> ORGANISM: Homo sapiens

<400> SEQUENCE: 85

Arg Ala Ser Gln Ser Val Ser Ser Tyr Leu Ala
1               5                   10

<210> SEQ ID NO 86
<211> LENGTH: 7
<212> TYPE: PRT
<213> ORGANISM: Homo sapiens

<400> SEQUENCE: 86

Gly Ala Ser Ser Arg Ala Thr
1               5

<210> SEQ ID NO 87
<211> LENGTH: 8
<212> TYPE: PRT
<213> ORGANISM: Homo sapiens

<400> SEQUENCE: 87

Gln Gln Tyr Gly Ser Ser Pro Thr
1               5

<210> SEQ ID NO 88
<211> LENGTH: 366
<212> TYPE: DNA
<213> ORGANISM: Homo sapiens

<400> SEQUENCE: 88
caggtgcagc tacagcagtg gggcgcagga ctgttgaagc cttcggagac cctgtccctc      60
acctgcgctg tctatggtgg gtccttcagt ggtcactact ggagctggat ccgccagtcc     120
ccagggaagg ggctggagtg gattgggaa accgatcata gtggaagcac caactacaat     180
ccgtccctca agagtcgagt caccatatca atagacacgt ccaagaatca gttctccctg     240
aagctgagct ctgtgaccgc cgcggacacg gctgtgtatt actgtgcgag gacgtattac     300 gatatttga ctgattatta ccccttgac tcctggggcc agggaaccct ggtcaccgtc     360
tcctca                                                                366

<210> SEQ ID NO 89
<211> LENGTH: 122
<212> TYPE: PRT
<213> ORGANISM: Homo sapiens

<400> SEQUENCE: 89

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly His
            20                  25                  30

Tyr Trp Ser Trp Ile Arg Gln Ser Pro Gly Lys Gly Leu Glu Trp Ile
        35                  40                  45

Gly Glu Thr Asp His Ser Gly Ser Thr Asn Tyr Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Thr Tyr Tyr Asp Ile Leu Thr Asp Tyr Tyr Pro Phe Asp Ser Trp
            100                 105                 110

Gly Gln Gly Thr Leu Val Thr Val Ser Ser
        115                 120

-continued

<210> SEQ ID NO 90
<211> LENGTH: 5
<212> TYPE: PRT
<213> ORGANISM: Homo sapiens

<400> SEQUENCE: 90

Gly His Tyr Trp Ser
1               5

<210> SEQ ID NO 91
<211> LENGTH: 16
<212> TYPE: PRT
<213> ORGANISM: Homo sapiens

<400> SEQUENCE: 91

Glu Thr Asp His Ser Gly Ser Thr Asn Tyr Asn Pro Ser Leu Lys Ser
1               5                   10                  15

<210> SEQ ID NO 92
<211> LENGTH: 14
<212> TYPE: PRT
<213> ORGANISM: Homo sapiens

<400> SEQUENCE: 92

Thr Tyr Tyr Asp Ile Leu Thr Asp Tyr Tyr Pro Phe Asp Ser
1               5                   10

<210> SEQ ID NO 93
<211> LENGTH: 366
<212> TYPE: DNA
<213> ORGANISM: Homo sapiens

<400> SEQUENCE: 93
caggtgcagc tacagcagtg gggcgcagga ctgttgaagc cttcggagac cctgtccctc      60
acctgcgctg tctatggtgg gtccttcagt ggtcactact ggagctggat ccgccagtcc     120
ccagggaagg gactggagtg gattggggaa atcgatcata gtggaagcac caactacaat     180
ccgtccctca gagtcgagt caccatatca gtagacacgt ccaagaacca gttctccctg     240
aagctgagct ctgtgaccgc cgcggacacg gctatgtatt actgtgcgag gacgtattac     300 gatatttttga ctgattatta ccccttttgac tcctggggcc agggaaccct ggtcaccgtc     360
tcctca                                                                366

<210> SEQ ID NO 94
<211> LENGTH: 122
<212> TYPE: PRT
<213> ORGANISM: Homo sapiens

<400> SEQUENCE: 94

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly His
                20                  25                  30

Tyr Trp Ser Trp Ile Arg Gln Ser Pro Gly Lys Gly Leu Glu Trp Ile
            35                  40                  45

Gly Glu Ile Asp His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Met Tyr Tyr Cys Ala
            85                  90                  95

Arg Thr Tyr Tyr Asp Ile Leu Thr Asp Tyr Tyr Pro Phe Asp Ser Trp
        100                 105                 110

Gly Gln Gly Thr Leu Val Thr Val Ser Ser
        115                 120

<210> SEQ ID NO 95
<211> LENGTH: 5
<212> TYPE: PRT
<213> ORGANISM: Homo sapiens

<400> SEQUENCE: 95

Gly His Tyr Trp Ser
1               5

<210> SEQ ID NO 96
<211> LENGTH: 16
<212> TYPE: PRT
<213> ORGANISM: Homo sapiens

<400> SEQUENCE: 96

Glu Ile Asp His Ser Gly Ser Thr Asn Tyr Asn Pro Ser Leu Lys Ser
1               5                   10                  15

<210> SEQ ID NO 97
<211> LENGTH: 25
<212> TYPE: PRT
<213> ORGANISM: Homo sapiens

<400> SEQUENCE: 97

Thr Tyr Tyr Asp Ile Leu Thr Asp Tyr Tyr Pro Phe Asp Ser Trp Gly
1               5                   10                  15

Gln Gly Thr Leu Val Thr Val Ser Ser
            20                  25

<210> SEQ ID NO 98
<211> LENGTH: 321
<212> TYPE: DNA
<213> ORGANISM: Homo sapiens

<400> SEQUENCE: 98
gaaattgtgt tgacacagtc tccagccacc ctgtctttgt ctccagggga aagagccacc      60
ctctcctgca gggccagtca gagtgttagc ggctacttag cctggtacca acagaaacct     120
ggccaggctc ccaggctcct catctatgat gtatcctaca gggccactgg catcctagtc     180
aggttcagtg gcagtgggtc tgggacagac ttcactctca ccatcagcag cctagagcct     240
gaagattttg cagtttatta ctgtcagcag cgtagcaact ggcccatcac tttcggcgga     300
gggaccaagg tggagatcaa a                                              321

<210> SEQ ID NO 99
<211> LENGTH: 107
<212> TYPE: PRT
<213> ORGANISM: Homo sapiens

<400> SEQUENCE: 99

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Gly Tyr
            20                  25                  30

```
Leu Ala Trp Tyr Gln Gln Lys Pro Gly Gln Ala Pro Arg Leu Leu Ile
            35                  40                  45

Tyr Asp Val Ser Tyr Arg Ala Thr Gly Ile Leu Val Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Ile
                 85                  90                  95

Thr Phe Gly Gly Gly Thr Lys Val Glu Ile Lys
            100                 105
```

<210> SEQ ID NO 100
<211> LENGTH: 11
<212> TYPE: PRT
<213> ORGANISM: Homo sapiens

<400> SEQUENCE: 100

```
Arg Ala Ser Gln Ser Val Ser Gly Tyr Leu Ala
 1               5                   10
```

<210> SEQ ID NO 101
<211> LENGTH: 7
<212> TYPE: PRT
<213> ORGANISM: Homo sapiens

<400> SEQUENCE: 101

```
Asp Val Ser Tyr Arg Ala Thr
 1               5
```

<210> SEQ ID NO 102
<211> LENGTH: 9
<212> TYPE: PRT
<213> ORGANISM: Homo sapiens

<400> SEQUENCE: 102

```
Gln Gln Arg Ser Asn Trp Pro Ile Thr
 1               5
```

<210> SEQ ID NO 103
<211> LENGTH: 97
<212> TYPE: PRT
<213> ORGANISM: Homo sapiens

<400> SEQUENCE: 103

```
Gln Val Gln Leu Gln Gln Trp Gly Ala Gly Leu Leu Lys Pro Ser Glu
 1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg
```

<210> SEQ ID NO 104
<211> LENGTH: 14

-continued

<212> TYPE: PRT
<213> ORGANISM: Homo sapiens

<400> SEQUENCE: 104

Phe Asp Tyr Trp Gly Gln Gly Thr Leu Val Thr Val Ser Ser
1               5                   10

<210> SEQ ID NO 105
<211> LENGTH: 97
<212> TYPE: PRT
<213> ORGANISM: Homo sapiens

<400> SEQUENCE: 105

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 106
<211> LENGTH: 14
<212> TYPE: PRT
<213> ORGANISM: Homo sapiens

<400> SEQUENCE: 106

Phe Asp Tyr Trp Gly Gln Gly Thr Leu Val Thr Val Ser Ser
1               5                   10

<210> SEQ ID NO 107
<211> LENGTH: 95
<212> TYPE: PRT
<213> ORGANISM: Homo sapiens

<400> SEQUENCE: 107

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 108
<211> LENGTH: 11
<212> TYPE: PRT
<213> ORGANISM: Homo sapiens

<400> SEQUENCE: 108

Thr Phe Gly Gly Gly Thr Lys Val Glu Ile Lys
1               5                   10

<210> SEQ ID NO 109
<211> LENGTH: 98
<212> TYPE: PRT
<213> ORGANISM: Homo sapiens

<400> SEQUENCE: 109

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 110
<211> LENGTH: 15
<212> TYPE: PRT
<213> ORGANISM: Homo sapiens

<400> SEQUENCE: 110

Tyr Phe Asp Tyr Trp Gly Gln Gly Thr Leu Val Thr Val Ser Ser
1               5                   10                  15

<210> SEQ ID NO 111
<211> LENGTH: 93
<212> TYPE: PRT
<213> ORGANISM: Homo sapiens

<400> SEQUENCE: 111

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser
                85                  90

<210> SEQ ID NO 112
<211> LENGTH: 12
<212> TYPE: PRT
<213> ORGANISM: Homo sapiens

<400> SEQUENCE: 112

Tyr Thr Phe Gly Gln Gly Thr Lys Leu Glu Ile Lys

```
<210> SEQ ID NO 113
<211> LENGTH: 96
<212> TYPE: PRT
<213> ORGANISM: Homo sapiens

<400> SEQUENCE: 113

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 114
<211> LENGTH: 11
<212> TYPE: PRT
<213> ORGANISM: Homo sapiens

<400> SEQUENCE: 114

Thr Phe Gly Gly Gly Thr Lys Val Glu Ile Lys
1               5                   10
```